US011596655B2

(12) United States Patent
Colonna et al.

(10) Patent No.: US 11,596,655 B2
(45) Date of Patent: Mar. 7, 2023

(54) ACTIVATION OF NATURAL CYTOTOXICITY RECEPTOR 2 (NCR2)

(71) Applicants: Marco Colonna, St. Louis, MO (US); Alexander David Barrow, St. Louis, MO (US)

(72) Inventors: Marco Colonna, St. Louis, MO (US); Alexander David Barrow, St. Louis, MO (US)

(73) Assignee: Washington University, St. Louis, MO (US)

(*) Notice: Subject to any disclaimer, the term of this patent is extended or adjusted under 35 U.S.C. 154(b) by 391 days.

(21) Appl. No.: 16/608,708

(22) PCT Filed: Apr. 27, 2018

(86) PCT No.: PCT/US2018/030019
§ 371 (c)(1),
(2) Date: Oct. 25, 2019

(87) PCT Pub. No.: WO2018/201088
PCT Pub. Date: Nov. 1, 2018

(65) Prior Publication Data
US 2020/0046770 A1     Feb. 13, 2020

Related U.S. Application Data

(60) Provisional application No. 62/491,084, filed on Apr. 27, 2017.

(51) Int. Cl.
*A61K 35/17*     (2015.01)
*C07K 14/725*    (2006.01)
*C07K 16/28*     (2006.01)

(52) U.S. Cl.
CPC .......... *A61K 35/17* (2013.01); *C07K 14/7051* (2013.01); *C07K 16/2803* (2013.01); *C07K 2319/03* (2013.01)

(58) Field of Classification Search
CPC ................ A61K 35/17; A61K 39/0011; A61K 2039/505; A61K 2039/5156;
(Continued)

(56) References Cited

U.S. PATENT DOCUMENTS 4,241,046 A     12/1980     Papahadjopoulos et al.
4,394,448 A     7/1983      Szoka, Jr. et al.
(Continued)

FOREIGN PATENT DOCUMENTS

JP     6842688 B2 *   3/2018 ......... A61K 39/0011
WO    2005105848 A1   11/2005
(Continued)

OTHER PUBLICATIONS

Wang, Z., et al. (2010) Emerging roles of PDGF-D signaling pathway in tumor development and progression Biochim Biophys Acta 1806 (1); 122-130 (Year: 2010).*
(Continued)

*Primary Examiner* — Joanne Hama
*Assistant Examiner* — Audrey L Buttice
(74) *Attorney, Agent, or Firm* — Polsinelli PC

(57) ABSTRACT

Among the various aspects of the present disclosure is the provision of methods and compositions for modulating the Natural Cyotoxicity Receptor 2 (NCR2).

6 Claims, 84 Drawing Sheets
(65 of 84 Drawing Sheet(s) Filed in Color)
Specification includes a Sequence Listing.

(58) Field of Classification Search
CPC ........ A61K 2039/5158; C07K 14/7051; C07K 16/2803; C07K 2319/03; A61P 35/04; A61P 35/00
See application file for complete search history.

(56) References Cited

U.S. PATENT DOCUMENTS

| | | | |
|---|---|---|---|
| 4,529,561 | A | 7/1985 | Hunt et al. |
| 4,755,388 | A | 7/1988 | Heath et al. |
| 4,828,837 | A | 5/1989 | Uster et al. |
| 4,925,661 | A | 5/1990 | Huang |
| 4,954,345 | A | 9/1990 | Muller |
| 4,957,735 | A | 9/1990 | Huang |
| 5,043,164 | A | 8/1991 | Huang et al. |
| 5,064,655 | A | 11/1991 | Uster et al. |
| 5,077,211 | A | 12/1991 | Yarosh |
| 5,264,618 | A | 11/1993 | Felgner et al. |
| 2002/0164710 | A1 | 11/2002 | Eriksson et al. |
| 2010/0310504 | A1 | 12/2010 | Lowe et al. |
| 2016/0207989 | A1 † | 7/2016 | Short |
| 2016/0311907 | A1 | 10/2016 | Brogdon et al. |

FOREIGN PATENT DOCUMENTS

| | | | | |
|---|---|---|---|---|
| WO | 2007039507 | A2 | 4/2007 | |
| WO | WO-2007059234 | A1 * | 5/2007 | ............ C07K 16/22 |
| WO | 2015197582 | A1 | 12/2015 | |
| WO | WO 2015188119 | A1 * | 12/2015 | ............ A01N 63/00 |
| WO | 2016019300 | A1 | 2/2016 | |
| WO | 2016044605 | A1 † | 3/2016 | |
| WO | 2016164580 | A1 | 10/2016 | |
| WO | 2017029511 | A1 † | 2/2017 | |
| WO | 2018201088 | A1 | 11/2018 | |

OTHER PUBLICATIONS

Kasahara, Y., et al (2016) A Novel NKp44-Based Chimeric Antigen Receptor That Targets Multiple Types of Cancer Blood 128 (22) : 3517 (Year: 2016).*
Gersuk, G.M., et al (1988) Inhibition of Human Natural Killer Cell Activity by Platelet-Derived Growth Factor the Journal of Immunology 141(11); 4031-4038 (Year: 1988).*
Vieillard, V., et al (2014) NKp44L a new tool for fighting cancer OncoImmunology 3, e27988, 1-2 (Year: 2014).*
Reiners, K.S., et al (2013) Soluble ligands for NK cell receptors promote evasion of chronic lymphocytic leukemia cells from NK cell anti-tumor activity Blood 121(18): 3658-3665 (Year: 2013).*
Gersuk, G.M., et al (1991) Inhibition of Human Natural Killer Cell Activity by Platelet-Derived Growth Factor (PDGF) Scand. J. Immunol 33; 521-532 (Year: 1991).*
Takeda, K. et al., "IFN-γ production by lung NK cells is critical for the natural resistance to pulmonary metastasis of B16 melanoma in mice" J. Leukoc. Biol., Oct. 2011, pp. 777-785, vol. 90 (Year: 2011).*
Larochelle, W. et al., "Platelet-derived Growth Factor D: Tumorigenicity in Mice and Dysregulated Expression in Human Cancer," Cancer Res., May 2002, pp. 2468-2473, vol. 62.
Lee, J. et al., "Aptamer therapeutics advance," Curr. Opin. Chem. Biol., Jun. 2006, pp. 282-289, vol. 10, No. 3.
Lee, D. et al., "The Future Is Now: Chimeric Antigen Receptors as New Targeted Therapies for Childhood Cancer," Clin. Cancer Res., 2012, pp. 2780-2790, vol. 18, No. 10.
Lee, J-Y. et al., "A genome-wide association study of a coronary artery disease risk variant," J. Hum. Genet., 2013, pp. 120-126, vol. 58.
Lefrancois, L. et al., "Isolation of Mouse Small Intestinal Intraepithelial Lymphocytes, Peyer's Patch, and Lamina Propria Cells," Curr. Protoc. Immunol., 1996, pp. 3.19.1-3.19.16, vol. 17, Unit 3.19, John Wiley & Sons, Inc.
Li, X. et al., "Novel PDGF family members: PDGF-C and PDGF-D," Cytokine Growth Factor Rev., 2003, pp. 91-98, vol. 14.
Li, H. et al., "Fast and accurate short read alignment with Burrows-Wheeler transform," Bioinformatics, 2009, pp. 1754-1760, vol. 25, No. 14.
Li, H. et al., "The Sequence Alignment/Map format and SAMtools," Bioinformatics, 2009, pp. 2078-2079, vol. 25, No. 16.
Li, S. et al., "The NK Receptor NKp30 Mediates Direct Fungal Recognition and Killing and Is Diminished in NK Cells from HIV-Infected Patients," Cell Host Microbe, Oct. 2013, pp. 387-397, vol. 14.
Lin, Y-C. et al., "Genome dynamics of the human embryonic kidney 293 lineage in response to cell biology manipulations," Nat. Commun., 2014, pp. 1-12, vol. 5, No. 4767.
Link, A. et al., "Beyond toothpicks: new methods for isolating mutant bacteria," Nat. Rev. Microbiol., Sep. 2007, pp. 680-688, vol. 5.
Lipinski, C. "Drug-like properties and the causes of poor solubility and poor permeability," J. Pharmacol. Toxicol. Methods, 2000, pp. 235-249, vol. 44.
Liu, C. et al., "Plasmacytoid dendritic cells induce NK cell-dependent, tumor antigen-specific T cell cross-priming and tumor regression in mice," J. Clin Invest., 2008, pp. 1165-1175, vol. 118, No. 3.
Lokker, N. et al., "Platelet-derived Growth Factor (PDGF) Autocrine Signaling Regulates Survival and Mitogenic Pathways in Glioblastoma Cells: Evidence That the Novel PDGF-C and PDGF-D Ligands May Play a Role in the Development of Brain Tumors," Cancer Res., Jul. 2002, pp. 3729-3735, vol. 62.
Maher, L., "DNA Triple-Helix Formation: An Approach to Artificial Gene Repressors?," BioEssays, Dec. 1992, pp. 807-815, vol. 14, No. 12.
Nakamura, K. et al., "Characterization of mouse melanoma cell lines by their mortal malignancy using an experimental metastatic model," Life Sci., 2002, pp. 791-798, vol. 70.
Nazarenko, I. et al., "PDGF and PDGF receptors in glioma," Ups. J. Med. Sci., 2012, pp. 99-112, vol. 117.
Nikpay, M. et al., "A comprehensive 1000 Genomes-based genome-wide association meta-analysis of coronary artery disease," Europe PMC Funders Group Author Manuscript, Apr. 1, 2016, pp. 1-28, published in final edited form as: Nat. Genet., Oct. 2015, pp. 1121-1130, vol. 47, No. 10.
Nirschl, C. et al., "IFNγ-Dependent Tissue-Immune Homeostasis Is Co-opted in the Tumor Microenvironment," Cell, Jun. 2017, pp. 127-141, vol. 170.
Oi, V. et al., "Immunoglobulin gene expression in transformed lymphoid cells," PNAS, Feb. 1983, pp. 825-829, vol. 80.
Park, J. et al., "Gene Variants in Angiogenesis and Lymphangiogenesis and Cutaneous Melanoma Progression," Cancer Epidemiol Biomarkers Prev., 2013, pp. 827-834, vol. 22, No. 5.
Park, S. et al., "Mercapturic Acids Derived from the Toxicants Acrolein and Crotonaldehyde in the Urine of Cigarette Smokers from Five Ethnic Groups with Differing Risks for Lung Cancer," PLoS One, 2015, pp. 1-17, vol. 10, No. 6, e0124841.
Peden, J. et al., "A genome-wide association study in Europeans and South Asians identifies five new loci for coronary artery disease," Nat. Genet., Apr. 2011, pp. 339-444, vol. 43, No. 4, with Online Methods, 2 pgs.
Pushparaj, P. et al., "Short Interfering RNA (siRNA) as a Novel Therapeutic," Clinical and Experimental Pharmacology and Physiology, 2006, pp. 504-510, vol. 33, with Retraction, Clinical and Experimental Pharmacology and Physiology, 2013, p. 305, vol. 40.
Raulet, D. et al., "Regulation of ligands for the NKG2D activating receptor," NIH Public Access Author Manuscript, Nov. 25, 2014, pp. 1-34, published in final edited form as: Annu. Rev. Immunol., 2013, pp. 413-441, vol. 31.
Reigstad, L. et al., Structural and functional specificities of PDGF-C and PDGF-D, the novel members of the platelet-derived growth factors family, FEBS J., 2005, pp. 5723-5741, vol. 272.
Reynolds, A. et al., "Rational siRNA design for RNA interference," Nat. Biotechnol., 2004, pp. 326-330, vol. 22, No. 3.

(56) References Cited

OTHER PUBLICATIONS

Robinette, M. et al., "Transcriptional programs define molecular characteristics of innate lymphoid cell classes and subsets," Nat. Immunol., Mar. 2015, pp. 306-317, vol. 16, No. 3.
Rosental, B. et al., "Proliferating Cell Nuclear Antigen Is a Novel Inhibitory Ligand for the Natural Cytotoxicity Receptor NKp44," J. Immunol., 2011, pp. 5693-5702, vol. 187.
Sagner, G. et al., "Rapid filter assay for the detection of DNA polymerase activity: direct identification of the gene for the DNA polymerase from Thermus aquaticus," Gene, 1991, pp. 119-123, vol. 97, Elsevier.
Schneider, U. et al., "Characterization of EBV-Genome Negative 'Null' and 'T' Cell Lines Derived From Children With Acute Lymphoblastic Leukemia and Leukemic Transformed Non-Hodgkin Lymphoma," Int. J. Cancer, 1977, pp. 621-626, vol. 19.
Shim, A. et al., "Structures of a platelet-derived growth factor/propeptide complex and a platelet-derived growth factor/receptor complex," PNAS, Jun. 2010, pp. 11307-11312, vol. 107, No. 25.
Sivori, S. et al., "Involvement of natural cytotoxicity receptors in human natural killer cell-mediated lysis of neuroblastoma and glioblastoma cell lines," J Neuroimmunol., 2000, pp. 220-225, vol. 107, Elsevier Science B.V.
Soule, H. et al., "A Human Cell Line From a Pleural Effusion Derived From a Breast Carcinoma," J. Natl. Cancer Inst., Nov. 1973, pp. 1409-1416, vol. 51, No. 5.
Studier, W., "Protein production by auto-induction in high-density cultures," Protein Expr. Purif., 2005, pp. 207-234, vol. 41, Elsevier Inc.
Szatmari, T. et al., "Detailed characterization of the mouse glioma 261 tumor model for experimental glioblastoma therapy," Cancer Sci., Jun. 2006, pp. 546-553, vol. 97, No. 6.
UniProtKB/Swiss-Prot Accession O95944.2 (NCTR2_HUMAN), "Natural cytotoxicity triggering receptor 2," May 24, 2004; 15 pgs.
UniProtKB/Swiss-Prot Accession Q9GZPO (PDGFD_HUMAN), "Platelet-derived growth factor D," Sep. 19, 2006; 15 pgs.
Ustach, C. et al., "Platelet-Derived Growth Factor D Is Activated by Urokinase Plasminogen Activator in Prostate Carcinoma Cells," Mol Cell. Biol., Jul. 2005, pp. 6279-6288, vol. 25, No. 14.
Ustach, C. et al., "A Novel Signaling Axis of Matriptase/PDGF-D/beta-PDGFR in Human Prostate Cancer," Cancer Res., 2010, pp. 9631-9640, vol. 70, No. 23.
Vieillard, V. et al., "NK cytotoxicity against CD4+ T cells during HIV-1 infection: A gp41 peptide induces the expression of an NKp44 ligand," PNAS, Aug. 2005, pp. 10981-10986, vol. 102, No. 31.
Vitale, M. et al., "NKp44, a Novel Triggering Surface Molecule Specifically Expressed by Activated Natural Killer Cells, Is Involved in Non-Major Histocompatibility Complex-restricted Tumor Cell Lysis," J. Exp. Med., Jun. 1998, pp. 2065-2072, vol. 187, No. 12, The Rockefeller University Press.
Wu, Q. et al., "Emerging roles of PDGF-D in EMT progression during tumorigenesis," NIHPublic Access Author Manuscript, Oct. 1, 2014, pp. 1-16, published in final edited form as: Cancer Treat. Rev., Oct. 2013, pp. 640-646, vol. 39, No. 6.
Xu, L. et al., "Blocking Platelet-Derived Growth Factor-D/Platelet-Derived Growth Factor Receptor beta Signaling Inhibits Human Renal Cell Carcinoma Progression in an Orthotopic Mouse Model," Cancer Res., 2005, pp. 5711-5719, vol. 65, No. 13.
Yang, T.-Y. et al., "Comparison of genome-wide DNA methylation in urothelial carcinomas of patients with and without arsenic exposure," Environ. Res., 2014, pp. 57-63, vol. 128.
Yucesoy, B. et al., "Genome-Wide Association Study Identifies Novel Loci Associated With Diisocyanate-Induced Occupational Asthma," Toxicol. Sci., 2015, pp. 192-201, vol. 146, No. 1.
Ahola-Olli, A. et al., "Genome-wide Association Study Identifies 27 Loci Influencing Concentrations of Circulating Cytokines and Growth Factors," Am. J. Hum. Genet., Jan. 2017, pp. 40-50, vol. 100.
Andrae, J. et al., "Role of platelet-derived growth factors in physiology and medicine," Genes Dev., 2008, pp. 1276-1312, vol. 22.
Arase, H. et al., "Direct Recognition of Cytomegalovirus by Activating and Inhibitory NK Cell Receptors," Sci., May 2002, pp. 1323-1326, vol. 296, No. 5571.
Barrow, A. et al., "OSCAR is a collagen receptor that costimulates osteoclastogenesis in DAP12-deficient humans and mice," J. Clin Invest., 2011, pp. 3505-3516, vol. 121, No. 9.
Barrow, A. et al., "OSCAR Is a Receptor for Surfactant Protein D That Activates TNF-a Release from Human CCR2 + Inflammatory Monocytes," J. Immunol., 2015, pp. 3317-3326, vol. 194.
Bast, R. et al., "Reactivity of a Monoclonal Antibody with Human Ovarian Carcinoma," J. Clin. Invest., Nov. 1981, pp. 1331-1337, vol. 68.
Baychelier, F. et al., "Identification of a cellular ligand for the natural cytotoxicity receptor NKp44," Blood, 2013, pp. 2935-2942, vol. 122, No. 17.
Bergsten, E. et al., "PDGF-D is a specific, protease-activated ligand for the PDGF beta-receptor," Nat. Cell Biol., May 2001, pp. 512-516, vol. 3.
Bezbradica, J. et al., "Role of ITAM signaling module in signal integration," Curr. Opin. Immunol., Feb. 2012, pp. 58-66, vol. 24, No. 1.
Blake, S. et al., "Molecular Pathways: Targeting CD96 and TIGIT for Cancer Immunotherapy," Clin. Cancer Res., 2016, pp. 5183-5188, vol. 22, No. 21.
Boles, K. et al., "The tumor suppressor TSLC1/NECL-2 triggers NK-cell and CD8+ T-cell responses through the cell-surface receptor CRTAM," Blood, 2005, pp. 779-786, vol. 106.
Boor, P. et al., "Patients with IgA nephropathy exhibit high systemic PDGF-DD levels," Nephrol. Dial. Transplant., 2009, pp. 1-8.
Braumuller, H. et al., "T-helper-1-cell cytokines drive cancer into senescence," Nature, 2013, pp. 361-365, vol. 494, No. 7437.
Cantoni, C. et al., "NKp44, a Triggering Receptor Involved in Tumor Cell Lysis by Activated Human Natural Killer Cells, Is a Novel Member of the Immunoglobulin Superfamily," J. Exp. Med., Mar. 1999, pp. 787-795, vol. vol. 189, No. 5.
Carrega, P. et al., "NCR(+) ILC3 concentrate in human lung cancer and associate with intratumoral lymphoid structures," Nat. Commun., 2015, pp. 1-13, vol. 6, No. 8280.
Cella, M. et al., "A human natural killer cell subset provides an innate source of IL-22 for mucosal immunity," Nature, Feb. 2009, pp. 722-725, vol. 457.
Cella, M. et al., "Expansion of human NK-22 cells with IL-7, IL-2, and IL-1beta reveals intrinsic functional plasticity," PNAS, Jun. 2010, pp. 10961-10966, vol. 107, No. 24.
Chang, C.-C. et al., "Immune Selection of Hot-Spot beta2-Microglobulin Gene Mutations, HLA-A2 Allospecificity Loss, and Antigen-Processing Machinery Component Down-Regulation in Melanoma Cells Derived from Recurrent Metastases following Immunotherapy," J. Immunol., 2005, 174, 1462-1471.
Chen, J. et al., "PDGF-D contributes to neointimal hyperplasia in rat model of vessel injury," Biochem. Biophys. Res. Commun., 2005, pp. 976-983, vol. 329, No. 3.
Cornelis, M. et al., "Genome-wide association study of selenium concentrations," Hum. Mol. Genet., 2015, pp. 1469-1477, vol. 24, No. 5.
Dadi, S. et al., "Cancer Immunosurveillance by Tissue-Resident Innate Lymphoid Cells and Innate-like T Cells," Cell, Jan. 2016, pp. 365-377, vol. 164.
Dechamethakun, S. et al., "Associations between the CDKN2A/B, ADTRP and PDGFD Polymorphisms and the Development of Coronary Atherosclerosis in Japanese Patients," J. Atheroscler. Thromb. 2014, pp. 680-690, vol. 21, No. 7.
Deschodt-Lanckman, M. et al., "Degradation of Alpha-Melanocyte Stimulating Hormone (Alpha-MSH) by Calla/Endopeptidase 24.11 Expressed by Human Melanoma Cells in Culture," Int. J. Cancer, 1990, pp. 1124-1130, vol. 46, Wiley-Liss, Inc.
Deuel, T. et al., "Expression of a Platelet-Derived Growth Factor-Like Protein in Simian Sarcoma Virus Transformed Cells," Sci., 1983, pp. 1348-1350, vol. 221, No. 4618.
Deuel, T., "Anaplastic lymphoma kinase: 'Ligand Independent Activation' mediated by the PTN/RPTPbeta/zeta signaling pathway," Biochim. Biophys. Acta, 2013, pp. 2219-2223, vol. 1834, Elsevier B.V.

(56) References Cited

OTHER PUBLICATIONS

Dillon, C. et al., "RNAI as an Experimental and Therapeutic Tool to Study and Regulate Physiological and Disease Processes," Annu. Rev. Physiol., 2005, pp. 147-173, vol. 67.

Divaris, K., "Exploring the genetic basis of chronic periodontitis: a genome-wide association study," Hum. Mol. Genet., 2013, pp. 2312-2324, vol. 22, No. 11.

Dolcetti, R. et al., "Interplay among viral antigens, cellular pathways and tumor microenvironment in the pathogenesis of EBV-driven lymphomas," Sem. Cancer Biol., 2013, pp. 441-456, vol. 23P.

Dykxhoorn, D. et al., "The Slient Revolution: RNA Interference as Basic Biology, Research Tool, and Therapeutic," Annu. Rev. Med., 2005, pp. 401-423, vol. 56.

Eisenberg, V. et al., "Targeting Multiple Tumors Using T-Cells Engineered to Express a Natural Cytotoxicity Receptor 2-Based Chimeric Receptor," Frontiers Immunol., Sep. 2017, pp. 1-11, vol. 8, No. 1212.

Elhai, J. et al., "Conjugal Transfer of DNA to Cyanobacteria," Methods in Enzymology, 1988, pp. 747-754, vol. 167, Academic Press, Inc.

Fanning, G. et al., "Gene-Expressed RNA as a Therapeutic: Issues to Consider, Using Ribozymes and Small Hairpin RNA as Specific Examples," RNA Towards Medicine, Erdmann et al. (eds.), Handb. Exp. Pharmacol., 2006, pp. 289-303, vol. 173, Springer-Verlag Bedin Heidelberg, Germany.

Feuerstein, A., "Celldex Brain Tumor Vaccine Fails Pivotal Clinical Trial," TheStreet, Mar. 7, 2016, 3 pgs., available at: https://www.thestreet.com/investing/stocks/celldex-brain-tumor-vaccine-fails-pivotal-clinical-trial-13484143.

Fuchs, A. et al., "Paradoxic inhibition of human natural interferon-producing cells by the activating receptor NKp44," Blood, Sep. 2005, pp. 2076-2082, vol. 106, No. 6.

Fuchs, A. et al., "Intraepithelial Type 1 Innate Lymphoid Cells Are a Unique Subset of IL-12- and IL-15-Responsive IFN-y-Producing Cells," Immunity, Apr. 2013, pp. 769-781, vol. 38.

Gajewski, T. et al., "Innate and adaptive immune cells in the tumor microenvironment," Nat. Immunol., Oct. 2013, pp. 1014-1022, vol. 14, No. 10.

Ghadessy, F. et al., "Directed evolution of polymerase function by compartmentalized self-replication," PNAS, 2001, pp. 4552-4557, vol. 98, No. 8.

Glatzer, T. et al., "RORyt+ Innate Lymphoid Cells Acquire a Proinflammatory Program upon Engagement of the Activating Receptor NKp44," Immunity, Jun. 2013, pp. 1223-1235, vol. 38.

Gong, J-H. et al., "Characterization of a Human Cell Line (NK-92) with Phenotypical and Functional Characteristics of Activated Natural Killer Cells," Leukemia, Apr. 1994, pp. 652-658, vol. 8, No. 4.

Gonzalez, R. et al., "Screening the mammalian extracellular proteome for regulators of embryonic human stem cell pluripotency," PNAS, Feb. 2010, pp. 3552-3557, vol. 107, No. 8.

Gorer, P., "Studies in Antibody Response of Mice to Tumour Inoculation," Br. J. Cancer, Oct. 1950, pp. 372-379, vol. 4.

Groh, V. et al., "Tumour-derived soluble MIC ligands impair expression of NKG2D and T-cell activation," Nature, Oct. 2002, pp. 734-738, vol. 419.

Hedrick, S. et al., "The Fine Specificity of Antigen and la Determinant Recognition by T Cell Hybridoma Clones Specific for Pigeon Cytochrome c," Cell, Aug. 1982, pp. 141-152, vol. 30.

Helene, C. et al., "Control of Gene Expression by Triple Helix-Forming Oligonucleotides. The Antigene Strategy," Ann. N.Y. Acad. Sci., Oct. 1992, pp. 27-36, vol. 660, No. 1.

Ho, J. et al., "H5-Type Influenza Virus Hemagglutinin Is Functionally Recognized by the Natural Killer-Activating Receptor NKp44," J. Virol., Feb. 2008, pp. 2028-2032, vol. 82, No. 4.

Huang, W. et al., "Dynamic Regulation of Platelet-derived Growth Factor D (PDGF-D) Activity and Extracellular Spatial Distribution by Matriptase-mediated Proteolysis," J. Biol Chem., Apr. 2015, pp. 9162-9170, vol. 290, No. 14.

International Search Report and Written Opinion dated Jul. 9, 2018 from related Patent Application No. PCT/US2018/030019; 10 pgs.

Irwin, J. et al., "ZINC—A Free Database of Commercially Available Compounds for Virtual Screening," NIH Public Access Author Manuscript, Feb. 3, 2006, pp. 1-11, published in final edited form as: J. Chem. Inf. Model, 2005, pp. 177-182, vol. 45, No. 1.

Kitamura, T. et al., "Retrovirus-mediated gene transfer and expression cloning: Powerful tools in functional genomics," Exp. Hematol., 2003, pp. 1007-1014, vol. 31.

Kline, J. et al., "Clinical development of mAbs to block the PD1 pathway as an immunotherapy for cancer," Curr. Opin. Investig. Drugs, 2010, pp. 1354-1359, vol. 11, No. 12.

Takeda, IFN-y production by lung NK cells is critical for the natural resistance to pulmonary metastasis of B16 melanoma in mice, Journal of Leukocyte Biology, Oct. 2011, vol. 90, pp. 777-785.

David et al., "Detection of protein aggregates in brain and cerebrospinal fluid derived from multiple sclerosis patients," Front Neurol, vol. 5, Article 251, pp. 1-7 (Dec. 2014).†

Moudgil et al., "Cytokines in autoimmunity: role in induction, regulation, and treatment," J Interferon Cytokine Res, vol. 31, Issue No. 10, pp. 695-703 (Sep. 2011).†

Chandra, "Role of amyloid from a multiple sclerosis perspective: a literature review," Neuroimmunomodulation, vol. 22, Issue No. 6, pp. 343-346 (Mar. 2015).†

Zhang et al., "High shed antigen levels within tumors: an additional barrier to immunoconjugate therapy," Clin Cancer Res, vol. 14, Issue No. 24, pp. 7981-7986 (Dec. 2008).†

Boor et al., "Patients with IgA nephropathy exhibit high systemic PDGF-DD levels," Nephrol Dial Transplant, vol. 24 Issue No. 9, pp. 2755-2762 (Apr. 2009).†

\* cited by examiner
† cited by third party

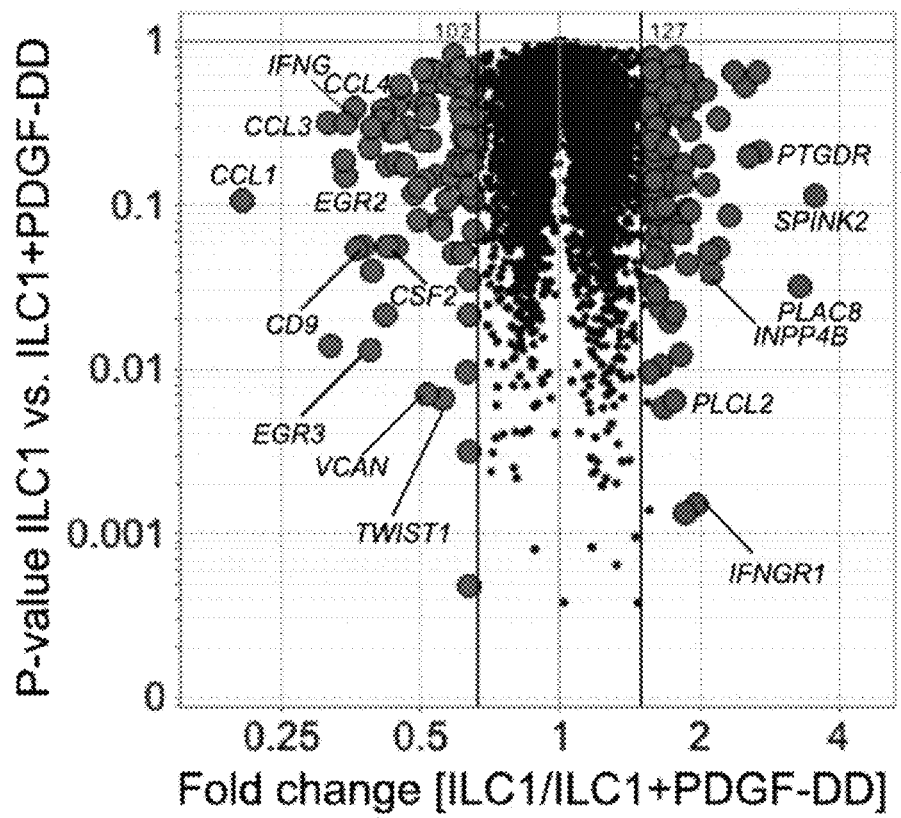
Fig. 4E
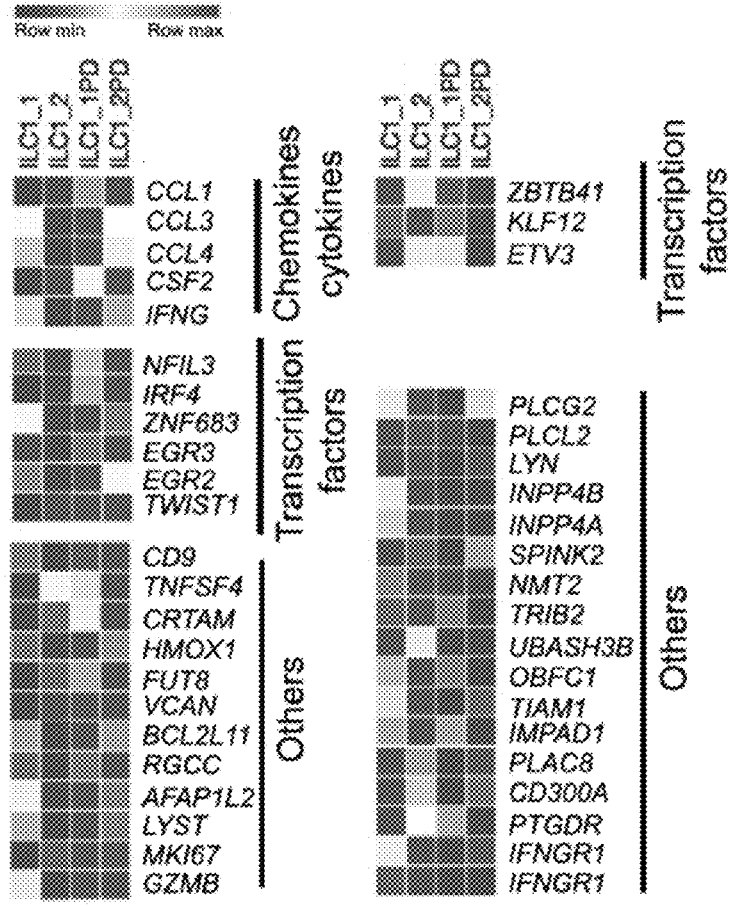

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 1
gtggcaagag ctgagcatcg                                            20

<210> SEQ ID NO 2
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 2
gccccaagtt aggggggtgac                                           20

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 3
gcttgtgtga gtgagtggcg                                            20

<210> SEQ ID NO 4
<211> LENGTH: 20
<212> TYPE: DNA
<213> ORGANISM: Artificial Sequence
<220> FEATURE:
```

```
<223> OTHER INFORMATION: SYNTHESIZED

<400> SEQUENCE: 4
ctctgctgga ctggcgatct                                              20

<210> SEQ ID NO 5
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 5
tgctcgtctg gtggtgagtg                                              20

<210> SEQ ID NO 6
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 6
ctctggccga ttcccctctg                                              20

<210> SEQ ID NO 7
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 7
ggcgagcaag gcttggaaac                                              20

<210> SEQ ID NO 8
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 8
cccgccacct atggactcac                                              20

<210> SEQ ID NO 9
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 9
ggctaagagg ggccatcacg                                              20

<210> SEQ ID NO 10
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 10
atcattctcc aggctctcag gcacaatcca                                   30
```

```
<210> SEQ ID NO 11
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 11
catggtgaca gtgaagaagc cagcatcagg                                      30

<210> SEQ ID NO 12
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 12
cccgccacct atggactcac                                                 20
```

ACTIVATION OF NATURAL CYTOTOXICITY RECEPTOR 2 (NCR2)

CROSS REFERENCE TO RELATED APPLICATIONS

This application claims the benefit of International Patent Application number PCT/US2018/030019, filed Apr. 27, 2018, which claims the benefit of U.S. Provisional Application No. 62/491,084, filed Apr. 27, 2017, the disclosures of which are hereby incorporated by reference in their entirety

FIELD OF THE INVENTION

The present disclosure generally relates to methods and compositions for activation of NKp44 in the use of cancer therapeutics, infectious disease and autoimmune disorders.

BACKGROUND OF THE INVENTION

Immunotherapy is generally a method of treating diseases which comprises activating the immune system of a patient by various means or introducing immune cells activated outside the body of a patient into the body of the patient. Different types of immunotherapy including an immune cell therapy, a peptide/DNA vaccine therapy, a cytokine therapy, and an antibody therapy have been developed.

Natural killer (NK) and innate lymphoid cells (ILCs) lack highly variable antigen-specific receptors yet express multiple germ line-encoded receptors that recognize ligands associated with pathogens and cellular stress. Such receptors transmit activating intracellular signals by recruiting the protein tyrosine kinases Syk or ZAP70, either directly or through the adaptors DAP12 and FcRγ. These immunoreceptor tyrosine-based activation motif (ITAM) signaling pathways are similar to those induced by antigen-specific receptors. However, physiological ligands of many of these receptors have remained elusive. Therefore, there is a need to identify novel molecular mechanisms for use in a immunotherapeutic.

BRIEF DESCRIPTION OF THE FIGURES

The application file contains at least one drawing executed in color. Copies of this patent application publication with color drawing(s) will be provided by the Office upon request and payment of the necessary fee.

(FIG. 2A) A secretome library screen with NKp44-GFP reporter cells identified 30 proteins (red) as putative NKp44 ligands including PDGF-D (y axis, screen 1; x axis, screen 2). NFS, normalized fluorescence signal. (FIG. 2B) GFP expression from NKp44-GFP reporter cells incubated with dilution series of the top 30 secretome library hits (PDGF-D, red; protein hits 1-29, black). Plate immobilized anti-NKp44 (blue) and anti-NKp30 (green) mAbs were used as positive and negative controls, respectively. (FIG. 2C) Schematic of PDGFD, PDGF-D, and PDGF-DD isoforms: signal peptide (SP, white); CUB domain (blue); growth factor domain (GFD, red); black triangle, protease cleavage site; black lines, disulfide bonds. (FIG. 2D and FIG. 2E) Recombinant PDGF-D (FIG. 2D) and PDGF-DD (FIG. 2E) induce activation of NKp44-GFP reporter cells that is blocked by anti-PDGF-D (FIG. 2D and FIG. 2E). (FIG. 2F) NKp44-Fc binds to recombinant PDGF-DD but not PDGF-D in solid phase. BSA, recombinant Chikungunya virus (CHIK) E2 protein and IL-17A were used as negative controls. Recombinant CUB-TEV-PDGFD contains a TEV cleavage site between CUB and GFD. (FIG. 2G) Dose-dependent GFP expression from NKp44-GFP reporter cells stimulated with PDGF-DD. (FIG. 2H) PDGF-DD has 3.3±0.4 AM affinity for NKp44 as determined by surface plasmon resonance (SPR). (FIG. 2I) PDGF-DD, but not PDGF-D, binds NKp44 by SPR. PDGF-D or PDGF-DD binding were investigated in the solid phase and NKp44 in the mobile phase (2-fold dilution series from 36 AM to 36 nM). A subset of the concentrations tested is shown.

(FIG. 3A) PDGF-DD induces calcium signaling in NK92 cells, which is blocked by anti-NKp44 mAb. (FIG. 3B) IL-2 cultured NK cells were stimulated with PDGF-DD for the indicated time points and phosphorylated AKT, ERK1/2, and FOXO3A and total ERK1/2 determined by immunoblotting. (FIG. 3C and FIG. 3D) PDGF-DD stimulates dose-dependent NK cell secretion of IFN-γ (FIG. 3C) and TNF-a (FIG. 3D). NK cells were kept in IL-2 medium throughout the assay. (FIG. 3E and FIG. 3F) IFN-γ (FIG. 3E) and TNF-α (FIG. 3F) secretion by PDGF-DD-stimulated NK cells derived from either normal donor (Norm) or DAP12-deficient (D12) patient. Induction of IFN-γ and TNF-α is blocked by anti-NKp44 (FIG. 3E and FIG. 3F). In the absence of PDGF-DD, IFN-γ and TNF-α can be induced by cross-linking NKp44 with Ga M+a-NKp44 as surrogate NKp44 ligand (FIG. 3E and FIG. 3F). (FIG. 3G) Representative dotplots of intracellular IFN-γ and TNF-α staining of PDGF-DD-stimulated IL-2-cultured NK cells from normal (Norm) or DAP12-deficient (D12) donors (percentage expression indicated in each quadrant). PMT was used as positive control. (FIG. 3H) Representative histograms of NKp44 surface expression on IL-2-cultured NK cells from normal (Norm) or DAP12-deficient (D12) donors before and after PDGF-DD stimulation. (FIG. 3I) Volcano plot and heatmap analysis of RNA-seq transcriptional profile induced by PDGF-DD in 4 NK cell donors. Transcripts in red were upregulated at least 1.5-fold by PDGF-DD (NK;1-4_PD) versus unstimulated NK cells (NK;1-4), those in blue were similarly downregulated. (FIG. 3J) Top 10 highest scoring IPA cellular immune response pathways generated from transcripts differentially expressed (±1.5-fold) in PDGF-DD-stimulated NK cells as in (FIG. 3I). Ratios in columns indicate total PDGF-DD-regulated genes to the total number of genes in each pathway. Error bar represents mean±SEM (****$p<0.0001$).

FIG. 4A, FIG. 4B, FIG. 4C, FIG. 4D, FIG. 4E and FIG. 4F show PDGF-DD/NKp44 interaction induces cytokine secretion by ILC3 and ILC1. (FIG. 4A) Representative histograms of intracellular TNF-a content of freshly isolated tonsil ILC3s stimulated with PDGF-DD and/or IL-23 (percentage cytokine-positive cells is indicated in each histogram). (FIG. 4B) Percentage of TNF-a secreting cells in PDGF-DD stimulated tonsil ILC3s from 6 different donors. (FIG. 4C and FIG. 4D) ILC1 derived in vitro by IL-2-induced conversion of tonsil ILC3 secrete IFN-y (FIG. 4C) and TNF-a (FIG. 4D) following stimulation with the indicated PDGF-DD concentrations (ng/mL). Anti-NKp44 but not control anti-NKp46 mAb blocks cytokine secretion (FIG. 4C and FIG. 4D). (FIG. 4E) Volcano plot and heatmap analysis of transcripts differentially expressed between PDGF-DD-stimulated (ILC1_1/2PD) versus unstimulated tonsilar ILC1 (ILC1_1/2) isolated from two different donors. Transcripts represented in red were upregulated at least 1.5-fold in PDGF-DD-stimulated versus unstimulated ILC1, and those in blue were similarly downregulated. (FIG. 4F) Top 5 highest scoring IPA cellular immune response pathways generated from transcripts differentially expressed (±1.5-fold) in PDGF-DD stimulated tonsil ILC1. Ratios in columns indicate total PDGF-DD-regulated genes to the total number of genes in each pathway.

(FIG. 5A) Meljuso melanoma cells were cultured with TC supernatants from NK cells stimulated with either PDGF-DD plus IgG1 ($NK^{DD+IgG}$ sup) or PDGF-DD plus anti-NKp44 ($NK^{DD+\alpha NKp44}$ sup) or recombinant IFN-y and TNF-a. Representative dotplots (left) show BrdU incorporation (y axis) and 7-AAD staining for total DNA content (x axis). The percentages of cells in different stages of the cell cycle (G1, S, and G2/M) are indicated in each gate. Cells in the different stages of the cell cycle are quantified (right). (FIG. 5B and FIG. 5C) Colo38 (FIG. 5B) or Meljuso (FIG. 5C) melanoma cells were cultured in either NKDD+IgG sup, NKDD+aNKp44 sup or complete medium, washed, then re-plated in complete medium and the percentage (%) growth relative to control medium recorded for 3 passages. (FIG. 5D) Colo38 cells were cultured in either complete medium or NKDD+IgG sup with (+) or without anti-IFN-γ and anti-TNF-α (Abs) before washing and passaging in complete medium as described above. (FIG. 5E-G) Cells were pre-cultured in either NKDD+IgG sup, NKDD+αNKp44 sup, or complete medium, washed, then re-plated in complete medium and the secretion of IL-8 for Colo38 (FIG. 5E) and Meljuso (FIG. 5F) or the secretion of IL-6 for Colo38 (FIG. 5G) measured in the culture medium at the end of the first passage. (FIG. 5H) Representative dotplots of CADM1 (assessed by CRTAM-Fc binding), CD112, CD155, and CD95 (Fas) expression from Colo38 cells exposed to NKDD+IgG sup or NKDD'"NKP44 sups (24 hr). (FIG. 5I) RNA-seq profiles of human melanoma (Colo38 and Meljuso), breast cancer (MCF7) and ovarian cancer (OVCA) cell lines exposed to either NKDD+IgG sup or NKDD+aNKP44 sup (48 hr). Transcripts in red were upregulated at least 1.5-fold and those in blue were similarly downregulated. Error bar represents mean±SEM. *p<0.001; **p<0.0001; ns, not significant.

(FIG. 6A and FIG. 6B) PDGF-D expression in tissue sections in a case of GBM (FIG. 6A), as determined by immunohistochemistry (representative of 5 cases). Arrowheads indicate PDGF-D' proliferating blood vessels (FIG. 6B). Scale bar, 100 μM. (FIG. 6C) Expression of signature core cytokine and chemokine genes by NK cells from different donors kept in medium alone (Unstim), or stimulated with PDGF-DD or PMA/i. (FIG. 6D) Expression of signature core cell-cycle genes in different tumor cells exposed to medium alone, NKDD+'-NKp44 sup, or NKDD+ IgG sup. (FIG. 6E) Correlation data for individual cytokine and chemokine genes (y axis) in the core signatures of PDGF-DD-activated NK cells versus NCR2 expression (x axis) extracted for TCGA GBM. Each dot represents a tumor case (n=539 patients). The statistical significance of the correlation was determined using the Pearson's correlation coefficient. A red linear regression line is shown in each plot. (FIG. 6F) Infiltration of NKp44' (red) and CD3e+ (green) lymphocytes in tissue sections of a GBM case (representative of 8) including a case of gliosarcoma, as assessed by immunofluorescence. Scale bar, 20 μM. (FIG. 6G) Correlation data for NCR2 (y axis) versus NCR3 (x axis) expression in the TCGA GBM cohort. (FIG. 6H) Correlation data for individual cell-cycle genes (y axis) in core signatures of growth-arrested tumor cells versus NCR2 expression (x axis) extracted for TCGA GBM. (FIG. 6I and FIG. 6J) Kaplan-Meier survival curves for the first (Q1) and fourth quartile (Q4) of the canonical cytokine (FIG. 6I) and canonical cell-cycle (FIG. 6J) variates of NCR2 expression, respectively.

(FIG. 7A) Representative dotplots of NKp44 expression in CD3-NK1.1" NK cells (NK), CD31'1K1.1" NKT cells (NKT), and CD31'1K1.1-T lymphocytes (T) isolated from spleen and mesenteric lymph nodes (mLN) of NCR2-tg (founder #1) and non-tg mice. The percentages of cells are indicated in each gate. (FIG. 7B) NKp44 expression on NK cells from spleens of NCR2-tg and non-tg mice activated in vitro with IL-2 and IL-15±IL-15 and TNF-a. (FIG. 7C) GFP expression of B16F10 melanoma cells stably transduced with pMX-IRES-eGFP retroviral vector (B16-pMX) or pMX-IRES-eGFP-encoding PDGFD (B16-PDGFD). (FIG. 7D and FIG. 7E) TC supernatants from B16-PDGFD cells (B16-PDGFD sup) elicit IFN-y (FIG. 7D) and TNF-a (FIG. 7E) secretion from human NK cells, which is blocked by anti-PDGF-D or anti-NKp44 (FIG. 7D and FIG. 7E). (FIG. 7F) Quantification (left) and representative photos (right) of surface lung metastases formed in NCR2-tg or non-tg littermate mice injected with B16-PDGFD cells. (FIG. 7G) Mean tumor area (.11V1 2) and representative histochemical images of lung metastases from NCR2-tg (n=6) or non-tg (n=7) mice injected with B16-PDGFD cells. Scale bar, 100 μM. (FIG. 7H and FIG. 7I) Day 17 quantitative RT-PCR of lfng (FIG. 7H) and Tnf (FIG. 7I) transcripts in lungs of NCR2-tg and non-tg mice injected with B16-PDGFD cells. (FIG. 7J) Day 17 surface lung metastases in NCR2-tg injected with B16-PDGFD cells and treated with either control or anti-NKp44 antibodies. (FIG. 7K) Day 17 surface lung metastases in NCR2-tg and non-tg mice injected with B16-pMX control cells.

(FIG. 8A) NK cell expression of NKp44 and CD96 in the lungs of NCR2-tg and non-tg mice. (FIG. 8B) Representative plots of NK cells from day 17 lungs and mLN of NCR2-tg mice injected with B16-PDGFD cells showing expression of NKp44, CD96, PD-1, or TIGIT. (FIG. 8C) Percentages of NKp44' NK cells expressing CD96, PD-1, or TIGIT in day 17 lungs and mLN of NCR2-tg mice injected with B16-PDGFD cells. (FIG. 8D) The CD96 ligand CD155 and CD95 are upregulated on B16F10 cells stimulated with IFN-y and TNF-a. (FIG. 8E) Quantification of day 17 surface lung metastases from NCR2-tg and non-tg mice injected with B16-PDGFD cells and treated with anti-CD96 mAb or control antibodies. (FIG. 8F) Tumor volumes from NCR2-tg or non-tg mice injected subcutaneously with B16-PDGFD cells and treated with CpG-ODN or left untreated (arrows indicate intratumoral CpG-ODN injections). (FIG. 8G and FIG. 8H) Representative dotplots (FIG. 8G) and percentages (FIG. 8H) of NKp44" cells in NK cells isolated from B16-PDGFD tumors of NCR2-tg or non-tg mice treated with CpG-ODN or left untreated.

(FIG. 9A) Generation of EL4 cell-line clones stably overexpressing PCNA. Transfection of constructs encoding nuclear PCNA into tumor cell-lines was proposed to induce cell-surface PCNA expression (Rosental et al., 2011). EL4 cells were transduced with retrovirus-containing TC supernatants generated from the transfection of phoenix amphotropic packaging cells with a pMX-PCNA-IRES-eGFP retroviral vector and five single-cell clones that stably overexpress high levels of GFP were selected (EL4-PCNA cells). The mean fluorescent intensity (MFI) of GFP expression for each clone is displayed. (FIG. 9B) PCNA is not expressed on the cell surface of parental EL4 cells (left histograms) or EL4-PCNA cell clones (right histograms) as determined by staining with anti-PCNA mAb. The percentages of PCNA+ cells are indicated. Anti-Thy1.2 was used as positive control for cell surface staining. (FIG. 9C) EL4-PCNA cell clones do not activate NKp44-GFP reporter cells. 105 NKp44-GFP reporter cells were mixed 1:1 with either EL4 or EL4-PCNA cell clones and incubated for 16 hr before determining GFP expression from NKp44-GFP cells by flow cytometry. PDGF-DD was used to stimulate NKp44-GFP reporter cells assay positive control (+PDGF-DD). Percentages of GFP+NKp44-GFP reporter cells are indicated. (FIG. 9D) Influenza virus HA does not interact with NKp44. CHO cells were transiently transfected with expression plasm ids encoding either the Hong Kong/97 H5 (HK/97), Vietnam/04 H5 (Viet/04) or WSN/33 H1 influenza virus type A HAs (kindly provided by Adolfo Garcia-Sastre). Binding of anti-HA antibodies (left histograms) and NKp44-Fc (right histograms) to transfected CHO cells was determined by flow cytometry. As negative controls, CHO cells were either mock transfected with pcDNA3.1 or left untransfected. The MFI of HA expression for each transfection is displayed (left histograms) and the percentages of cells staining for cell surface NKp44-Fc are indicated (right histograms). (FIG. 9E) CHO cells transfected with influenza HAs do not activate NKp44-GFP reporter cells. 105 NKp44-GFP reporter cells were mixed 1:1 with CHO cells transfected with plasmids encoding the different influenza HAs in 96-well plates and incubated for 16 hr before GFP expression from NKp44-GFP reporter cells was determined by flow cytometry. As negative controls, CHO cells were either mock transfected or left untransfected. PDGF-DD was used to stimulate NKp44-GFP reporter cells as a positive control. Percentages of GFP+NKp44-GFP reporter cells are indicated. (FIG. 9F and FIG. 9G) The HIV gp41 peptide described by Vieillard et al. does not upregulate an NKp44 ligand (NKp44L) on human CD4+ T cells. Human CD4+ T cells from two different donors (d1, d2) were pulsed for 16 hr with (+) or without (−) the HIV gp41-derived peptide (HIV gp41) that was reported to upregulate an NKp44L (Vieillard et al. 2005), later identified as the nuclear antigen MLLS (Baychelier et al., 2013). NKp44-Fc binding to CD4+ T cells (FIG. 9F) or GFP expression from NKp44-GFP reporter cells mixed 1:1 for 16 hr with CD4+ T cells (FIG. 9G) either unpulsed or pulsed with HIV gp41 peptide. PDGF-DD was used to stimulate NKp44-GFP reporter cells as a positive control. The percentage of NKp44-Fc+ cells in each quadrant (FIG. 9F) and the percentage of GFP+NKp44- GFP reporter cells (FIG. 9G) are indicated. (FIG. 9H) Jurkat T cells do not activate NKp44-GFP reporter cells. NKp44-GFP reporter cells were mixed for 16 hr with (1:1) or without Jurkat T cells, which were reported to express MLLS on the cell surface (Baychelier et al., 2013) before GFP expression was measured by flow cytometry. PDGF-DD was used to stimulate NKp44-GFP reporter cells as a positive control. The percentage of GFP+ NKp44-GFP reporter cells are indicated.

(FIG. 10A) Polyclonal NK cells cultured in IL-2 medium were stained either with isotype control mAbs or mAbs to CD3, CD56 in combination with mAbs to NKp44, PDGFRα or PDGFRβ. CD3-CD56' human NK cells express NKp44 but not PDGFRa or PDGFRP. Percentage expression is indicated in each gate. (FIG. 10B) PDGF-DD stimulates dose-dependent NK cell surface CD107a expression. (FIG. 10C) Cell surface CD107a expression by PDGF-DD-stimulated NK cells. Upper panels, representative dotplots and percentage expression in each gate; lower panel, quantification. Cell surface CD107a is blocked by soluble anti-NKp44. In the absence of PDGF-DD, CD107a expression was induced by mAb-mediated cross-linking of NKp44 (a-NKp44+goat anti-mouse−GaM). Induction of CD107a by PMA/i was used as positive control. (FIG. 10D) Generation of a TEV cleavable PDGF-D construct (CUB-TEV-PDGFD). After expression and purification from 293F cells, CUB-TEV-PDGFD proteins were incubated with (+TEV) or without (−TEV) TEV protease at 30° C. for 0 or 24 hours (h). Samples were then boiled in SDS-PAGE loading buffer with (+) or without (−) DTT before resolving on 4%-10% SDS-PAGE gels (Molecular mass, kD). (FIG. 10E) IFN-y and TNF-a secretion by NK cells is enhanced by TEV cleavage of CUB-TEV-PDGFD. Recombinant PDGF-DD was added to some cultures as positive control. Cleavage of CUB-TEV-PDGFD by proteases in serum containing medium likely explains cytokine production by NK cells in wells stimulated with CUB-TEV-PDGFD without TEV protease. (FIG. 10F) The enhanced secretion of IFN-y and TNF-a by NK cells stimulated with CUB-TEV-PDGFD TEV wells is blocked by anti-NKp44 and anti-PDGF-D mAbs.

(FIG. 13A-I) Sections from normal tissues are derived from: (FIG. 13A) stomach, (FIG. 13B) skin, (FIG. 13C) colon, (FIG. 13D) bladder, (FIG. 13E) lung, (FIG. 13F) kidney, (FIG. 13G) prostate, (FIG. 13H) pancreas, and (FIG. 13I) testis. Reactivity is evident in tissue epithelial compartments (brown staining). Scale bar, 100 µM. (FIG. 13J-X) Sections from human carcinomas are from different primary sites including: (FIG. 13J) head and neck, (FIG. 13K, FIG. 13L) lung, (FIG. 13M) bladder, (FIG. 13N, FIG. 13O) colon, (FIG. 13P) breast, (FIG. 13Q) ovarian cancer, (FIG. 13R, FIG. 13S) primary melanoma, (FIG. 13T-X) melanoma metastasis to the (FIG. 13T, FIG. 13U) skin, (FIG. 13V) lung, (FIG. 13W) lymph nodes and (FIG. 13X) brain. All sections were stained with anti-PDGF-D antibody. Scale bar, 100 µM.

(FIG. 14A and FIG. 14B) Representative dotplots (FIG. 14A) and quantification (FIG. 14B) of NKp44 expression in CD3-NK1.1" (NK) cells isolated from the spleen and mesenteric lymph nodes (mLN) of a second NCR2-tg founder line (founder #2). The percentages of cells are indicated in each gate. (FIG. 14C and FIG. 14D) Representative dotplots (FIG. 14C) and quantification (FIG. 14D) of NKp44 expression in ILC1/NK cells, ILC2, CCR6" ILC3, NKp46" ILC3, and NKp46-CCR6-(DN) ILC3 isolated from the small intestine of NCR2-tg mice. The percentages of cells are indicated in each gate. Lamina propria mononuclear cells were stained for T-bet, RORyt, GATA3, NKp46, NK1.1, CCR6, lineage markers (CD3, CD19, CD5) and analyzed by flow cytometry. Cells were gated on Lineage-cells. ILC1/NK: T-berNK1.1"GATA3-RORyt–; ILC2: GATArT-bet-RORyt–; ILC3: RORyt+GATA3int. (FIG. 14E and FIG. 14F) TC supernatants from B16-pMX control cells B16-pMX sup do not stimulate IFN-y (E) or TNF-c4 (FIG. 14F) secretion from two different NK cell donors unless 250 ng/mL recombinant PDGF-DD (+PDGF-DD) is added as a positive control for NK cell activation. (FIG. 14G) Quantification (upper panel) and representative photos (lower panel) of lung surface metastases from non-tg and NCR2-tg (founder #2) at Day 17 post-injection with 2×105 B16F10 cells stably expressing PDGFD (B16-PDGFD). (FIG. 14H) Mean tumor area (.1M2) and representative histochemical images of lung metastases from non-tg (n=7) and NCR2-tg (founder #2; n=10) mice injected with B16-PDGFD cells.

DETAILED DESCRIPTION OF THE INVENTION

Figure 1:
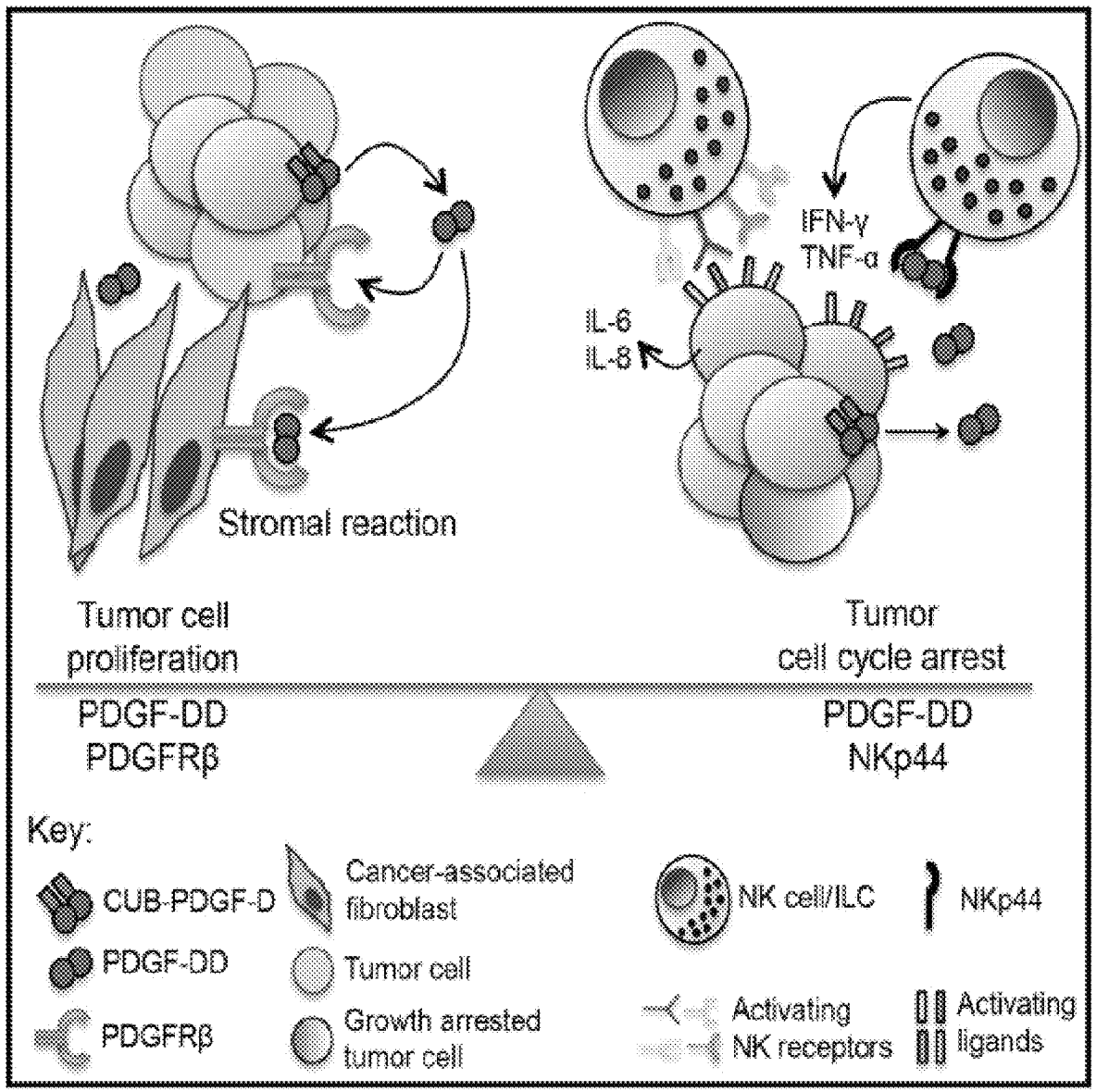
FIG. 1 depicts PDGF-DD is secreted by tumor cells and is a stimulatory ligand for human NK cells and ILC through binding to NKp44 thereby activating the secretion of cytokines which trigger tumor cell-cycle arrest.

The present disclosure is based, at least in part, on the discovery that PDGF-DD activated NKp44-expressing cells act as immune modulators capable of anti-tumoral activity. As described herein, PDGF-DD stimulated cytokine secretion by NK cells and ILCs (IFN-γ and TNF-α), and PDGF-DD stimulation enhances IFN-γ and TNF-α and IL-6 production by pDCs in vitro. In one aspect, the compositions and methods as described herein can be used to augment anti-cancer therapies by promoting the activation of NKp44-expressing NK cells, e.g., pDCs or ILCs. In another aspect, the compositions and methods as described herein can be used to improve vaccine responses through stimulating enhanced cytokine production by NKp44-expressing NK cells, pDCs or ILCs (adjuvant properties). In still another aspect, the compositions and methods as described herein can be used to block the biological activity of NKp44-expressing cells (e.g. cytokine secretion) due to the NKp44-PDGF-DD axis in inflammatory and autoimmune diseases. In still another aspect, the compositions and methods as described herein can be used for treating cancer or autoimmune disorders using the CAR-T cells as described herein.

The use of "or" means "and/or" unless stated otherwise. Furthermore, the use of the term "including," as well as other forms, such as "includes" and "included," is not limiting.

Generally, nomenclatures used in connection with, and techniques of, cell and tissue culture, molecular biology, immunology, microbiology, genetics and protein and nucleic acid chemistry and hybridization described herein are those well-known and commonly used in the art. Enzymatic and staining reactions and purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also those well-known and commonly used in the art.

The immunotherapeutic compositions and methods of their use are described in further detail below.

(I) Immunotherapeutic Compositions (a) PDGF-DD

In some embodiments, the present disclosure provides compositions comprising PDGF-DD, including functional homologs, derivatives and fragments thereof. In some embodiments, the PDGF-DD of the invention comprises the amino acid sequence as set forth in UniProtKB/Swiss-Prot: accession Q9GZP0.1, herein incorporated by reference. The platelet-derived growth factor (PDGF) family encompasses four polypeptides that assemble into five dimeric isoforms (PDGF-AA, PDGF-BB, PDGF-AB, PDGF-CC, and PDGF-DD) and engage two receptor tyrosine kinases, PDGFRα and PDGFRβ, which are mainly expressed on cells of mesenchymal origin. In accordance with the present disclosure it was discovered NKp44 recognizes PDGF-DD and engagement of NKp44 by PDGF-DD triggered immune secretion of proinflammatory cytokines and chemokines. In one aspect, it was discovered that PDGF-DD was identified as a cancer-expressed ligand for the orphan NK cell receptor, NKp44. As shown herein, a new method to stimulate cytokine secretion of NKp44-expressing (NKp44+) cells via soluble PDGF-DD binding to the activating NKp44 receptor is described as follows: (i) PDGF-DD stimulated Nk cell secretion of IFN-γ and TNF-α and other cytokines that block tumor cell proliferation and lead to the upregulation of tumor expressed ligands for cytotoxic NK cell receptor (e.g. Fas, PVR/CD115) by tumor cells; (ii) PDGF-DD enhanced the secretion of large amount of type-I interferon (IFN-I) and stimulated the production of TNF-α and IL-6 by NKp44+ plasmacytoid dendritic cells (pDCs); and (iii) PDGF-DD stimulated the production of IFN-γ and TNF-α by ILC1 and TNF-α by ILC3.

In some embodiments, compositions of the present disclosure comprising PDGF-DD, including functional homologs, derivatives and fragments thereof may further comprise a PDGFRβ antagonist. PDGFRβ signaling has been documented in a wide range of human cancer. The PDGFRβ antagonist may be any known in the art which blocks or prevents signaling mediated through PDGFRβ. For instance, by way of non-limiting example, suitable PDGFRβ antagonists include imatinib, sunitinib, and sorafenib. In some embodiments, a compound with the ability to antagonize PDGFRβ may include, without limitation, a compound, a drug, a small molecule, a peptide, a nucleic acid molecule, a protein, an antibody, a lipid, a carbohydrate, a sugar, a lipoprotein and combinations thereof. A nucleic acid molecule may be an antisense oligonucleotide, a small interfering RNA (siRNA), a ribozyme, a small nuclear RNA (snRNA), a long noncoding RNA (LncRNA), or a nucleic acid molecule which forms triple helical structures. Such compounds can be isolated from nature (e.g., isolated from organisms) or they can be produced in a laboratory (e.g., recombinantly or synthetically). Also encompassed are compounds that are combinations of natural and synthetic molecules. Methods to isolate or produce recombinant or synthetic candidate compounds are known to those skilled in the art.

A PDGF-DD composition of the invention may be a pharmaceutical composition for use in activating NKp44-expressing cells. In some embodiments, PDGF-DD activation of NKp44-expressing cells occurs in vitro, in vivo or ex vivo. In some embodiments, pharmaceutical compositions comprising PDGF-DD are used to inhibit or prevent the development of an infectious disease or to treat a cancer in a subject. "Preventing or inhibiting the development of an infectious disease" as used herein, refers to the situation wherein the occurrence of the infectious disease is prevented or the onset of the infectious disease is delayed, or the spread of an existing infection is reversed. In some embodiments, an infectious disease results from infection with an infectious organism. As used herein, "infectious organisms" or "infectious disease organisms" can include, but are not limited to, for example, bacteria, viruses, fungi, parasites and protozoa. Various infectious organisms are encompassed by the methods and compositions provided herein. In some embodiments, the composition comprising PDGF-DD inhibits growth, or induces death of an infectious disease organism.

In an aspect, the disclosure provides a pharmaceutical composition comprising a PDGF-DD and a PDGFRβ antagonist that is used to treat cancer in a subject. In some embodiments, the cancer is a PDGF-DD secreting cancer.

(b) NKp44

The NCR2 gene encodes the NKp44 receptor. As discussed herein, NKp44 is an orphan receptor expressed by some immune cells that provides protection against infectious disease and cancer. In some embodiments, the NKp44 of the disclosure comprises the amino acid sequence as set forth in UniProtKB/Swiss-Prot: accession 095944.2, herein incorporated by reference. The present disclosure has identified PDGF-DD as a ligand for NKp44. PDGF-DD binding to NKp44 activates the secretion of various cytokines. Thus, the present disclosure provides a new mechanism of NKp44-mediated control of immune cells that may augment current therapies. For example, PDGF-DD stimulation can enhance the secretion of inflammatory cytokines by NKp44+NK cells, pDCs and ILCs. Thus, the NKp44-PDGF-DD axis could also be used as an adjuvant to enhance immune responses.

In another aspect, inhibiting or reducing NKp44 activity in a subject may be used to reduce immune responses in a subject. In some embodiments, a NKp44 antagonist may be used to treat an autoimmune disorder in a subject. For instance, non-limiting examples of suitable autoimmune disorders include lupus, multiple sclerosis, inflammatory bowel disease, psoriasis, celiac disease, Graves' disease, myasthenia gravis, Guillain-Barr like syndrome, Behcet's disease, Thyroiditis, cerebral vaculitis, post-infusion purpura, chronic inflammatory demyelinating polyneuropathy, Sjogren's syndrome, ticks and obsessive-compulsive disorder triggered by infection, stiff-man syndrome, Eaton-Lambert syndrome, Goodpasture syndrome, dermatomyositis, polymyositis, thrombocytopenia, warm type autoimmune hemolytic anemia, systemic vasculitic syndromes, West syndrome, Lennox-Gastaut syndrome, acute renal failure, asthma, chronic fatigue syndrome, diabetes mellitus, inclusion body myositis, rheumatoid arthritis, recurrent spontaneous abortion, euthyroid ophthalmopathy, and immune mediated neutropenia. An NKp44 antagonist according to the invention may be a compound capable of downregulating or inhibiting NKp44. Such a compound may include, without limitation, a compound, a drug, a small molecule, a peptide, a nucleic acid molecule, a protein, an antibody, a lipid, a carbohydrate, a sugar, a lipoprotein and combinations thereof. A nucleic acid molecule may be an antisense oligonucleotide, a small interfering RNA (siRNA), a ribozyme, a small nuclear RNA (snRNA), a long noncoding RNA (LncRNA), or a nucleic acid molecule which forms triple helical structures. Such compounds can be isolated from nature (e.g., isolated from organisms) or they can be produced in a laboratory (e.g., recombinantly or synthetically). Also encompassed are compounds that are combinations of natural and synthetic molecules. Methods to isolate or produce recombinant or synthetic candidate compounds are known to those skilled in the art.

In an embodiment, NKp44 nucleic acid expression may be measured to identify a compound that downregulates or inhibits NKp44. For example, when NKp44 nucleic acid expression is decreased in the presence of a compound relative to an untreated control, the compound decreases the expression of NKp44. In a specific embodiment, NKp44 mRNA may be measured to identify a compound that decreases the expression of NKp44.

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In another embodiment, NKp44 protein expression may be measured to identify a compound that downregulates or inhibits the expression of NKp44. For example, when NKp44 protein expression is decreased in the presence of a compound relative to an untreated control, the compound decreases the expression of NKp44. In a specific embodiment, NKp44 protein expression may be measured using immunoblot.

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In an embodiment, NKp44 activity may be measured to identify a compound that downregulates or inhibits NKp44. For example, expression of NKp44 mediated secretion of cytokines (e.g. INF-γ and/or TNF-α) may be measured. In an embodiment, a compound that downregulates or inhibits NKp44 may reduce the amount of expression of proinflammatory cytokines from NKp44-expressing cells.

(c) Adjuvant Compositions

The adjuvant composition of the present disclosure preferably comprises PDGF-DD, including functional derivatives and fragments thereof. In other embodiments, the adjuvant composition further comprises at least one of the following: saline, immunomodulators, small molecules, cytokines, sterols including cholesterol, alcohol, a saponin, and sodium hydroxide.

The saline component can be any solution of sodium chloride and water suitable for use in an adjuvant composition. Typically, saline refers to a solution of 0.90% w/v of NaCl, about 300 mOsm/L or 9.0 g per liter, however, saline for purpose of the present disclosure is not limited to this solution. In a particularly preferred embodiment, the saline solution is Dulbecco's Phosphate Buffered Saline without Calcium or Magnesium (Cellgro Catalog No. 21-CV).

In some embodiments, the saline solution is present in an amount of from about 50% to about 98% of the adjuvant composition of the present disclosure by volume, where amounts such as 60% to 98%, 70% to 98%, 80% to 98%, 90% to 98%, 55%, 60%, 65%, 70%, 75%, 80%, 85%, 86%, 87%, 88%, 89%, 90%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 94%, 95%, 96%, 97%, and 98% are envisioned. In a particularly preferred embodiment, saline is present in the adjuvant composition of the present disclosure in an amount of about 92% by volume.

The alcohol component may be selected from the group consisting of ethanol, isopropanol, butanol, and combinations thereof. In some embodiments, ethanol is used. In some embodiments, the alcohol is present in an amount of from about 0.01% to about 3% of the adjuvant composition of the present disclosure, by volume, where values such as 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.6%. 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned.

Further, ranges incorporating any two of the described values are also envisioned. For example, 0.01% to 1%, 0.01% to 2%, 0.3% to 1%, 0.3% to 1.5%, 0.03% to 0.07%, 0.05% to 2.4%, and 1% to 1.6% are all covered in by the present disclosure. The alcohol is useful for solubilizing the saponin, for example Quil A and much or most (at least 10%, 20%, 30%, 40%, 50%, 60%, 70%, or more) dries off leaving the final concentration of the alcohol in the final product very low.

The saponin for purposes of the present disclosure can be any selected from the class of saponins. Generally, saponins are a class of chemical compounds found in particular abundance in various plant species. Preferably, they are amphipathic glycosides grouped phenomenologically by the soap-like foaming they produce when shaken in aqueous solutions, and structurally by having one or more hydrophilic glycoside moieties combined with a lipophilic triterpene derivative. In a preferred embodiment, the saponin is purified or semi-purified and lyophilized. Preferably, the saponin is an extract from the cortex of the South American tree, Quillaja saponaria Molia.

In some embodiments, the saponin is present in the adjuvant composition of the present disclosure in an amount of about 0.001% to about 0.5%, where values such as 0.001%, 0.002%, 0.003%, 0.004%, 0.005%, 0.006%. 0.007%, 0.008%, 0.009%, 0.01%, 0.015%, 0.02%, 0.025%, 0.03%, 0.035%, 0.04%, 0.045%, 0.05%, 0.06%, 0.07%, 0.08%, 0.09%, 0.1%, 0.15%, 0.2%, 0.25%, 0.3%, 0.35%, 0.4%, 0.45% and 0.5% are envisioned. Further, ranges including any two discreet values described above are also envisioned. For example, the saponin may be present in the adjuvant composition of the present disclosure in an amount from about 0.003% to about 0.01%, about 0.003% to about 0.05%, about 0.01% to about 0.03%, about 0.1%, to about 0.5%, about 0.07% to about 0.2%, and the like.

The adjuvant composition of the present disclosure may include a sterol. Any sterol will work for purposes of the present disclosure, including those that occur in plants, animals, and fungi. The sterol is preferably taken from a plant source, however, the sterol may be selected from but not limited to, phytosterols, zoosterols, cholesterol, campesterol, sitosterol, stigmasterol, ergosterol, and combinations thereof. In an aspect, the sterol is a phytosterol, more preferably cholesterol, preferably of non-animal origin. The cholesterol can be any cholesterol source suitable for use in an adjuvant composition. The cholesterol is preferably derived from animals or plants, most preferably, the cholesterol is plant derived.

In some embodiments, the cholesterol is present in the adjuvant composition of the present disclosure in an amount of from about 0.001% to about 3% by volume, where values such as 0.005% to 0.05%, 0.008% to 0.008%, 0.002%, 0.003%, 0.004%, 0.005%, 0.006%. 0.007%, 0.008%, 0.009%, 0.01%, 0.02%, 0.03%, 0.04%, 0.05%, 0.06%. 0.07%, 0.08%, 0.09%, 0.1%, 0.2%, 0.3%, 0.4%, 0.5%, 0.6%. 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. Further, ranges including any two of these volumes are also envisioned. In a particularly preferred embodiment, the cholesterol is present in an amount of about 0.01% by volume.

The adjuvant composition of the present disclosure preferably comprises a component that neutralizes the pH of the composition to a pH from about 6 to about 8, more preferably a pH of 7. Any conventional neutralizer can be use, but preferably, the neutralizer is selected from the group consisting of sodium hydroxide, potassium hydroxide, and ammonium hydroxide. In an aspect, the component that neutralizes the pH of the solution is sodium hydroxide.

In some embodiments, the component that neutralizes the pH of the adjuvant composition is present in an amount of about 0.1% to about 10%, where values such as 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, and 10% are envisioned. Additionally, any range incorporating two of these values is also envisioned including, but not limited to 2% to 8%, 2% to 6%, 3% to 8%, 4% to 6%, 1.5%, 2%, 2.5%, 3%, 3.5%, 4%, 4.5%, 5%, 5.5%, 6%, 6.5%, 7%, 7.5%, 8%, 8.5%, 9%, and 9.5%.

The adjuvant composition of the present disclosure may include any immunomodulator, small molecule or cytokine known in the art to be useful in adjuvant compositions. For example, synthetic oligodeoxynucleotides (ODNs) containing unmethylated CpG motifs trigger cells that express Toll-like receptor 9 (including human plasmacytoid dendritic cells and B cells) to mount an innate immune response characterized by the production of Th1 and proinflammatory cytokines. When used in vaccine adjuvants, CpG ODNs improve the function of professional antigen-presenting cells and boost the generation of humoral and cellular vaccine-specific immune responses. These effects are optimized by maintaining ODNs and vaccine in close proximity. Preclinical studies indicate that CpG ODNs improve the activity of vaccines targeting infectious diseases and cancer. Clinical trials demonstrate that CpG ODNs have a good safety profile and increase the immunogenicity of coadministered vaccines. In some embodiments, the adjuvant composition may include a TLR9 ligand. In an aspect, the adjuvant composition may include a DNA virus or cancer virotherapy.

A method of making the adjuvant composition of the present disclosure is also provided. In one form of the method, the method preferably comprises the steps of combining the components of the adjuvant composition, preferably via emulsion, and adding a composition that neutralizes the pH of the adjuvant composition.

In a further embodiment of the present disclosure, the method for making the adjuvant composition of the present disclosure comprises the steps of admixing a lipophile, polymer of acrylic or methacrylic acid, and saline to form a composition. A further embodiment of the present disclosure additionally provides for the step of performing at least one emulsion before the pH of the first composition is adjusted.

The present disclosure also provides for a vaccine composition. The vaccine composition preferably comprises the adjuvant composition of the present disclosure and an antigen(s). The amount of the adjuvant composition of the present disclosure and the amount of antigen, as well as the antigen production technology depend on the administration method selected. Those of skill in the art will be able to determine the appropriate ratio for such administration methods. The adjuvant composition is present in an amount of from about 1% to about 30%, by volume, of the total volume of the vaccine composition, where values and ranges such as 1% to 25%, 1% to 20%, 1% to 15%, 15% to 30%, 10% to 20%, 10% to 25%, 10% to 20%, 15% to 25%, 20% to 30%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, and 30% are envisioned. In a particularly preferred embodiment, the adjuvant composition is present in an amount of about 20% by volume.

The adjuvants of the present invention are shelf-stable alone or when admixed with one or more antigens. Preferably, the shelf life of the adjuvant of the present invention is shelf stable for at least 4 months, more preferably, for at least 5 months, more preferably, for at least 6 months, for at least 12 months, for at least 18 months, and for at least 24 months, for at least 36 months where ranges such as 6-18 months, 6-24 months, 6-36, 12-24 months, 12-36 months, 18-24 months, and 18-36 months are envisioned. Preferably, the adjuvants of the present invention are shelf stable for these durations at ambient temperatures. Preferably, the temperature range is about 16° C. to about 26° C.

(d) CAR-T Cells

One aspect of the present disclosure encompasses chimeric antigen receptor (CAR)-T cells (also referred to as artificial T-cell receptors, chimeric T-cell receptors, or chimeric immunoreceptors) which target soluble ligands. The phrase "chimeric antigen receptor (CAR)," as used herein, refers to a recombinant fusion protein that has an antigen-specific extracellular domain coupled to an intracellular domain. Chimeric antigen receptor molecules are distinguished by their ability to both bind ligands and transduce activation signals via their intracellular domain. A CAR-T cell is a T cell that expresses a chimeric antigen receptor. The extracellular and intracellular portions of the chimeric antigen receptor (CAR) are discussed in more detail below.

The ligand specific extracellular domain of a chimeric antigen receptor of the present disclosure is designed to recognize soluble ligands. As used herein, the term "soluble ligand", refers to a water soluble peptide secreted from a cell which is capable of transmitting a signal or directly producing a change inside of a cell. A ligand specific extracellular domain suitable for use in a CAR of the present disclosure may be any ligand-binding polypeptide, a wide variety of which are known in the art. In one embodiment, the ligand specific extracellular domain binds to a platelet derived growth factor, for example, PDGF-DD. In some instances, the ligand-binding domain is an extracellular domain of a receptor which binds to the ligand. In one embodiment, the ligand-binding domain comprises the extracellular domain of NKp44. In some instances, the ligand-binding domain is a single chain Fv (scFv). Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing V.alpha.V.beta.) are also suitable for use.

Suitable ligands include those secreted by a tumor cells or are associated with an autoimmune disorder. For instance, by way of non-limiting example, bone morphogenic proteins (BMPs), colony-stimulating factors (e.g. m-CSF, G-CSF, GM-CSF), epidermal growth factor (EGF), fibroblast growth factor (FGFs), glial derived neurotrophic factor family of ligands, granulocyte-macrophage colony stimulating factor, hepatocyte growth factor, hepatoma-derived growth factor, insulin-like growth factors, interleukins, interferons, keratinocyte growth factors, neurotrophins, platelet-derived growth factors, tumor necrosis factor, transforming growth factors, and vascular endothelial growth factors and the like are suitable ligands secreted by tumor cells or associated with an autoimmune disorder. In one embodiment, a CAR-T cell of the present disclosure comprises an extracellular domain of a chimeric antigen receptor that specifically binds to a bone morphogenic protein. In another embodiment, a CAR-T cell of the present disclosure comprises an extracellular domain of a chimeric antigen receptor that specifically binds to a colony-stimulating factor. In yet another embodiment, a CAR-T cell of the present disclosure comprises an extracellular domain of a chimeric antigen receptor that specifically binds to a epidermal growth factor. In still another embodiment, a CAR-T cell of the present disclosure comprises an extracellular domain of a chimeric antigen receptor that specifically binds to a transforming growth factor. In still yet another embodiment, a CAR-T cell of the present disclosure comprises an extracellular domain of a chimeric antigen receptor that specifically binds to a fibroblast growth factor. In still yet another embodiment, a CAR-T cell of the present disclosure comprises an extracellular domain of a chimeric antigen receptor that specifically binds to a hepatoma-derived growth factor. In still yet another embodiment, a CAR-T cell of the present disclosure comprises an extracellular domain of a chimeric antigen receptor that specifically binds to a platelet-derived growth factor. In still yet another embodiment, a CAR-T cell of the present disclosure comprises an extracellular domain of a chimeric antigen receptor that specifically binds to PDGF-DD.

As described above, in one embodiment the ligand is PDFG-DD. For instance, by way of non-limiting example, PDGF-DD may be expressed by a melanoma, glioblastoma, gastrointestinal stromal tumor or a carcinoma including, lung, ovary, breast, bladder, colon, prostate, stomach, kidney, or head and neck. CAR-T cells of the present disclosure may be used to target tumor cells that express PDGF-DD.

In another aspect, in one embodiment the CAR-T cells of the invention bind a soluble ligand associated with an autoimmune disorder. Suitable autoimmune disorders are those as described herein, including, in non-limiting examples lupus, celiac disease, diabetes mellitus type 1, Graves' disease, inflammatory bowel disease, multiple sclerosis, psoriasis, rheumatoid arthritis, and systemic lupus erythematosus.

The soluble ligand-specific extracellular domain of a chimeric antigen receptor recognizes and specifically binds a soluble ligand, typically a secreted ligand from a tumor cell or a secreted ligand associated with an autoimmune disorder. A soluble ligand-specific extracellular domain specifically binds a ligand when, for example, it binds the ligand with an affinity constant or affinity of interaction (KD) between about 0.1 pM to about 10 μM, preferably about 0.1 pM to about 1 μM, more preferably about 0.1 pM to about 100 nM. Methods for determining the affinity of interaction are known in the art.

A chimeric antigen receptor also comprises an intracellular domain, which may provide a signal to the T cell upon antigen binding to the antigen-specific extracellular domain. The intracellular signaling domain of a chimeric receptor of the invention is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular domain" refers to the portion of a protein that transduces the effector function signal and directs the cell to perform a specialized function. While usually the entire intracellular domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular domain is thus meant to include any truncated portion of the intracellular domain sufficient to transduce the effector function signal. Examples include the zeta chain of the T-cell receptor or any of its homologs (e.g., eta, delta, gamma, or epsilon), MB 1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins may be used, such as Fc.gamma.RIII and Fc.epsilon.RI. While usually the entire intracellular domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular domain is thus meant to include any truncated portion of the intracellular domain sufficient to transduce the effector function signal.

Typically, the antigen specific extracellular domain is linked to the intracellular domain of the chimeric antigen receptor with a transmembrane domain. A transmembrane domain traverses the cell membrane, anchors the CAR to the T cell surface, and connects the extracellular domain to the intracellular signaling domain, thus impacting expression of the CAR on the T cell surface. Chimeric antigen receptors may also further comprise one or more costimulatory domain and/or one or more spacer. A costimulatory domain is derived from the intracellular signaling domains of costimulatory proteins that enhance cytokine production, proliferation, cytotoxicity, and/or persistence in vivo. A spacer connects (i) the antigen-specific extracellular domain to the transmembrane domain, (ii) the transmembrane domain to a costimulatory domain, (iii) a costimulatory domain to the intracellular domain, and/or (iv) the transmembrane domain to the intracellular domain. For example, inclusion of a spacer domain between the antigen-specific extracellular domain and the transmembrane domain may affect flexibility of the antigen-binding domain and thereby CAR function. Suitable transmembrane domains are known in the art.

Methods for CAR design, delivery and expression in T cells, and the manufacturing of clinical-grade CAR-T cell populations are known in the art. See, for example, Lee et al., Clin. Cancer Res., 2012, 18(10): 2780-90, hereby incorporated by reference in its entirety. For example, the engineered CARs may be introduced into T cells using retroviruses, which efficiently and stably integrate a nucleic acid sequence encoding the chimeric antigen receptor into the target cell genome. Other methods known in the art include, but are not limited to, lentiviral transduction, transposon-based systems, direct RNA transfection, and CRISPR/Cas systems (e.g., type I, type II, or type III systems using a suitable Cas protein such Cas3, Cas4, Cas5, Cas5e (or CasD), Casio, Cas6e, Cas6f, Cas7, Cas8a1, Cas8a2, Cas8b, Cas8c, Cas9, Cas10, Casl Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966, etc.).

CAR-T cells may be generated from any suitable source of T cells known in the art including, but not limited to, T cells collected from a subject. The subject may be the patient with cancer or a subject of the same species as the subject. The collected T cells may be expanded ex vivo before transduction with a CAR to generate a CAR-T cell using methods commonly known in the art.

In an aspect the CAR for a PDGF-DD specific CAR cell may be generated by cloning an extracellular domain of NKp44 into a $3^{rd}$ generation CAR backbone with CD28 and 4-1BB internal signaling domains. An extracellular hCD34 domain may be added after a P2A peptide to enable both detection of CAR following viral transduction and purification using anti-hCD34 magnetic beads.

The engineered CARs may be introduced into T cells using retro viral receptors to produce the CAR-T cells.

The use of autologous T cells for the generation of CAR-T cells, while possible, may present unique challenges. The hosts that need therapy may be undergoing treatment for malignancies; this treatment may have affected the number and function of T cells of the host, which reduces the efficient generation of sufficient number of T cells that may be engineered into CAR-T cells. Thus to avoid risk, T cells from another healthy donor (donor subject), may be used to generate CAR-T cells for allogeneic therapy. The T cells for allogeneic therapy may be collected from a single subject or multiple subjects. Methods of collecting blood cells, isolating and enriching T cells, and expanding them ex vivo may be by methods known in the art.

An allogeneic transplant, such as a T cell therapy, may trigger Graft versus Host Disease (GvHD). GvHD may occur when the allogeneic cells transplanted recognize the host cells as foreign and mount an immune response against the host cells. A T cell therapy system that does not trigger GvHD may be preferred. One way to prevent GvHD is by disrupting the native T cell receptor (TCR) signaling in the CAR-T cells. It may be possible to disrupt TCR signaling in the CAR-T cells by modifying a part of the TCR receptor, such as the TCR receptor alpha chain (TRAC). TRAC modification may block TCR mediated signaling. TRAC modification may thus permit the safe use of allogeneic T cells as the source of CAR-T cells without inducing life-threatening GvHD.

(e) Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature (Tm) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: Tm=81.5° C.+16.6(log 10[Na+])+0.41(fraction G/C content)−0.63(% formamide)−(600/I). Furthermore, the Tm of a DNA:DNA hybrid is decreased by 1-1.5°C for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

An immunotherapeutic composition of the present disclosure may optionally comprise one or more additional drug(s) or therapeutically active agent(s) in addition to a composition described above. An immunotherapeutic composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

(II) Pharmaceutical Compositions

Another aspect of the present disclosure provides pharmaceutical compositions. The pharmaceutical compositions comprise at least one immunotherapeutic composition described in Section I and at least one pharmaceutical acceptable excipient.

The pharmaceutically acceptable excipient may be a perfusion solution, a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Perfusion Solution

In some embodiments, the excipient may be a perfusion solution. Perfusion solutions generally consist of saline solutions of varying osmolality, with certain solutions being better for specific organs. The skilled artisan can readily determine desired components of a perfusion solution which are selected in an organ specific manner. Non-limiting examples of suitable perfusion solutions include EuroCollins, UW (Viaspan, Celsior, Custodiol, IGL-1 and Belzer UW.

(ii) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(iii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

(iv) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(v) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(vi) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vii) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(viii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(ix) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(x) Lubricant

In a further embodiment, the excipient may be a lubricant. Non-limiting examples of suitable lubricants include minerals such as talc or silica; and fats such as vegetable stearin, magnesium stearate, or stearic acid.

(xi) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xii) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xiii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(a) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising at least one immunotherapeutic composition as described herein is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of at least one immunotherapeutic composition as described herein in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, at least one immunotherapeutic composition as described herein may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying at least one immunotherapeutic composition as described herein may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of the immunotherapeutic composition as described herein, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatters of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. At least one immunotherapeutic composition as described herein may be encapsulated in a microemulsion by any method generally known in the art.

In yet another embodiment, at least one immunotherapeutic composition as described herein may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(ii) Dosage

Dosages of the pharmaceutical compositions can vary between wide limits, depending upon the disease or disorder to be treated, the age of the subject, and the condition of the subject to be treated. In an embodiment, the amount of the immunotherapeutic composition as described herein in the pharmaceutical composition is an amount to provide a therapeutic or prophylactic effect.

(iii) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas, and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

(III) Methods

In an aspect, the present disclosure provides immunotherapeutic compositions as described herein for use in vitro, in vivo, or ex vivo. In an aspect, the present disclosure provides methods of reducing immunopathological disorders including autoimmune disorders, or for treating cancer in a subject. Suitable immunotherapeutic compositions are disclosed herein, for instance those described in Section I.

According to an aspect of the invention a pharmaceutical composition comprising PDGF-DD as described herein is used to activate NKp44-expressing cells for adoptive therapy for cancer and infectious diseases. The method generally comprises contacting a NKp44-expressing cell with a pharmaceutical composition comprising PDGF-DD, wherein NKp44 activity is increased compared to a control composition. In some embodiments, the method comprising contacting the NKp44-expressing cells in vivo by administering a pharmaceutical composition comprising PDGF-DD to the subject, wherein the NKp44 activity is measured by the secretion of pro-inflammatory cytokines, so that the cancer or infectious disease is treated. For example, when NKp44 mediated signaling is activated in the presence of PDGF-DD relative to an untreated control, the NKp44-expressing cells increase the expression of cytokines. In another aspect, the method comprising contacting the NKp44-expressing cells ex vivo by contacting NKp44-expressing cell with a pharmaceutical composition comprising PDGF-DD and administering the activated NKp44 expressing cells to the subject, wherein the NKp44 activated cells are measured by an increase expression of cytokines compared to an untreated control, so that the cancer or infectious disease is treated.

According to another aspect of the invention a pharmaceutical composition comprising at least one NKp44 antagonist described herein used as an anti-inflammatory agent or to treat an autoimmune disorder. Thus, the NKp44 antagonist as described herein may be used in a method to treat or prevent an inflammatory disorder. An "inflammatory disorder", as used herein, is a condition that is characterized by inflammation. The injury may be caused by physical, chemical, or biological agents. The response may involve secretion of cytokines, including chemokines, and migration of leukocytes to the site of injury. The method generally comprises administering to a subject a pharmaceutical composition comprising a therapeutically effective amount of at least one NKp44 antagonist. In some embodiments, the inflammatory disorder is characterized by accumulation of inflammatory cytokines. In some embodiments, the method comprising administering a composition comprising at least one NKp44 antagonist to the subject, wherein the NKp44 antagonist inhibits NKp44 mediated secretion of pro-inflammatory cytokines, so that the inflammatory or autoimmune condition is relieved. For example, when NKp44 mediated signaling is decreased in the presence of NKp44 antagonist relative to an untreated control, the NKp44 antagonist decreases the expression of pro-inflammatory cytokines for NKp44-expressing cells.

(a) Method of Using an Adjuvant Composition Comprising PDGF-DD

The present disclosure additionally provides for a method of vaccinating animals or humans. Suitable vaccine compositions are those described in Section I(x). The method preferably comprises the step of administering the vaccine composition of the present disclosure to a recipient thereof. Alternatively, the method of the present disclosure comprises the steps of combining the adjuvant of the present disclosure with an antigen to form a composition and administering the composition to an animal or human in need thereof. The antigen is one typically utilized in an immunogenic composition or vaccine composition and is preferably capable of providing an immune response in the recipient. The recipient is preferably a human or animal. In an embodiment where the recipient is an animal, the animal is preferably selected from the group consisting of pigs, cows, horses, dogs, cats, sheep, mules, monkeys, companion animals, and other mammals.

The antigen, for purposes of the vaccine composition of the present disclosure, can be any antigen or combination of antigens suitable to induce an immunogenic response in a recipient. The recipient may be an animal or a human. The antigen for use in this invention may be any desired antigen falling within the definition set forth above. Antigens are commercially available or one of skill in the art is capable of producing them. In some preferred forms, the antigenic moiety making up the vaccine can be either a modified-live or killed microorganism, or a natural product purified from a microorganism or other cell including, but not limited to, tumor cell, a synthetic product, a genetically engineered protein, peptide, polysaccharide or similar product, or an allergen. The antigenic moiety can also be a subunit of a protein, peptide, polysaccharide or similar product. The antigen may also be the genetic antigens, i.e., the DNA or RNA that engenders an immune response. Representative of the antigens that can be used according to the present invention include, but are not limited to, natural, recombinant or synthetic products derived from viruses, bacteria, fungi, parasites and other infectious agents in addition to autoimmune diseases, hormones, or tumor antigens which might be used in prophylactic or therapeutic vaccines and allergens. The viral or bacterial products can be components which the organism produced by enzymatic cleavage or can be components of the organism that were produced by recombinant DNA techniques that are well known to those of ordinary skill in the art. Because of the nature of the invention and its mode of delivery it is very conceivable that the invention would also function as a delivery system for drugs, such as hormones, antibiotics and antivirals.

Examples of antigens suitable for use in the vaccine composition of the present disclosure, include, but are not limited to antigens derived from infectious organisms. As understood by those of skill in the art and the usefulness of the vaccine with any type of antigen, all variations of the antigen including whole organisms, macro molecules, subunits, nucleic acids, expressed proteins, and combinations thereof are contemplated by the present disclosure.

The method of vaccinating of the present disclosure preferably includes administration of the composition comprising the adjuvant of the present disclosure and an antigen, where administration is needleless or through injection. More preferably, the administration method is selected from the group consisting of topical, intramuscular, nasal, oral, transdermal, mucosal, and subcutaneous. The adjuvant composition of the present disclosure provides for an advantage in needleless administration methods, where the administration utilizes skin-absorption of antigens, therefore, in a preferred embodiment, the administration method is transdermal or mucosal. In a further embodiment, the administration for purposes of the method of the present disclosure is via a needleless administration method, such as a vaccine gun; however, the method of the present disclosure is not limited to this embodiment. The present invention is not limited to vaccine guns, as any needleless administration method will work. Needleless administration methods include, but are not limited to, vaccine guns, transdermal patches, aerosols, mucosal administration methods, skin adhesion methods, dry particle projectiles, wet projectiles, gold/inert particle guns, and pneumatic guns.

(b) Method of Using CAR-T cells

In an aspect, soluble ligand targeting CAR-T cells may be administered to treat a cancer. In one embodiment, CAR-T cells that target soluble ligands may be administered to a subject with a cancer that secretes the ligand.

In another aspect, soluble ligand targeting CAR-T cells may be administered to treat an autoimmune disorder.

In an aspect the subject administered CAR-T cell may be a human subject. In another aspect the subject treated by CAR-T cells may be any mammalian subject. T cells that are engineered into CAR-T cells for allogeneic CAR-T cell therapy may be collected from a single donor or multiple donor subjects.

In an aspect, the CAR-T cells may be administered to a subject by an intravenous route, for instance, by an intravenous infusion. The CAR-T cells may be administered in a single dose or in multiple doses. The CAR-T cells may be injected in a pharmaceutical composition suitable for intravenous administration. Suitable pharmaceutical compositions for IV administration are known in the art. A pharmaceutical composition of the present disclosure may further comprise additional components. For instance, such components may be used to sustain the viability and/or activity of injected CAR-T cells. In one embodiment, the CAR-T cell composition may include IL-2 to sustain the CAR-T cells.

The cancers that may be treated by the CAR-T cells are cancers which secrete soluble ligands. The malignancies may be characterized by the expression of particular ligands by the cancer cells. For instance, by way of non-limiting example, PDGF-DD may be expressed by a melanoma, glioblastoma, gastrointestinal stromal tumor or a carcinoma including lung, ovary, breast, bladder, colon, prostate, stomach, kidney, or head and neck. In an aspect CAR-T cell therapy may be accompanied by other therapies for malignancy such as chemotherapy or radiation therapy. In certain aspects, the cancer is a breast cancer, lung cancer, head and neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer, ovarian cancer, leukemia or skin cancer. In one aspect, the subject has previously been treated for a cancer or has previously had a tumor surgically removed.

For instance, non-limiting examples of suitable autoimmune disorders that may be treated by the CAR-T cells of the disclosure include lupus, multiple sclerosis, inflammatory bowel disease, psoriasis, celiac disease, Graves' disease, myasthenia gravis, Guillain-Barr like syndrome, Behcet's disease, Thyroiditis, cerebral vaculitis, post-infusion purpura, chronic inflammatory demyelinating polyneuropathy, Sjogren's syndrome, ticks and obsessive-compulsive disorder triggered by infection, stiff-man syndrome, Eaton-Lambert syndrome, Goodpasture syndrome, dermatomyositis, polymyositis, thrombocytopenia, warm type autoimmune hemolytic anemia, systemic vasculitic syndromes, West syndrome, Lennox-Gastaut syndrome, acute renal failure, asthma, chronic fatigue syndrome, diabetes mellitus, inclusion body myositis, rheumatoid arthritis, recurrent spontaneous abortion, euthyroid ophthalmopathy, and immune mediated neutropenia.

The CAR-T cells may be administered in effective doses. The effective dose may be either one or multiple doses, and are sufficient to produce the desired therapeutic effect. A typical dose of CAR-T cells may range from about $1 \times 10^5$-$5 \times 10^7$ cells/Kg body weight of subject receiving therapy. The effective dose may be calculated based on the stage of the malignancy, the health of the subject, and the type of malignancy. In the situation where multiple doses are administered, that dose and the interval between the doses may be determined based on the subject's response to therapy.

An "effective dose" or "effective amount" as used herein, means an amount which provides a therapeutic or prophylactic benefit.

The term "therapeutic effect" as used herein, refers to a biological effect which can be manifested by a decrease in the number of cancer cells, an increase in life expectancy, or amelioration of various physiological symptoms associated with the malignant condition.

In some embodiments, the methods of the invention provide immunotherapeutic compositions of the present invention used in combination with one or more of a nonsteroidal anti-inflammatory agent, a steroidal anti-inflammatory agent, an immune suppressant, an antihistamine, an antirheumatic drug and a biological preparation such as infliximab, adalimumab, tocilizumab, etc. Non-limiting examples of suitable nonsteroidal anti-inflammatory agents may include indomethacin, ibuprofen, diclofenac, and aspirin. Non-limiting examples of suitable steroidal anti-inflammatory agents may include dexamethasone, betamethasone, prednisolone, and triamcinolone. Non-limiting examples of suitable immunosuppressants may include tacrolimus, cyclosporine, and sirolimus. Non-limiting examples of suitable antihistamines may include diphenhydramine, chlorpheniramine, triprolidine, promethazine, alimemazine, hydroxyzine, cyproheptadine, fexofenadine, olopatadine, epinastine, loratadine, cetirizine, bepotastine, and mequitazine. Non-limiting examples of suitable antirheumatic drugs may include bucillamine, salazosulfapyridine, and methotrexate.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for Examples

Natural killer (NK) and innate lymphoid cells (ILCs) lack highly variable antigen-specific receptors yet express multiple germ line-encoded receptors that recognize ligands associated with pathogens (Arase et al., 2002; Li et al., 2013) and cellular stress (Raulet et al., 2013). Such receptors transmit activating intracellular signals by recruiting the protein tyrosine kinases Syk or ZAP70, either directly or through the adaptors DAP12 and FcRγ. These immunoreceptor tyrosine-based activation motif (ITAM) signaling pathways are similar to those induced by antigen-specific receptors (Bezbradica and Medzhitov, 2012). The human NKp44 receptor (encoded by NCR2) is expressed by activated NK cells (Vitale et al., 1998), innate lymphoid cells of group 1 (ILC1) (Fuchs et al., 2013) and group 3 (ILC3) (Cella et al., 2009), and plasmacytoid dendritic cells (Fuchs et al., 2005), signals through DAP12, and has been implicated in the recognition of transformed cells (Cantoni et al., 1999; Carrega et al., 2015; Sivori et al., 2000; Vitale et al., 1998). NKp44 has no mouse ortholog. NKp44 ligands have previously been reported (Baychelier et al., 2013; Ho et al., 2008; Rosental et al., 2011; Vieillard et al., 2005) but their physiological relevance in vivo thus far remains elusive.

The platelet-derived growth factor (PDGF) family encompasses four polypeptides that assemble into five dimeric isoforms (PDGF-AA, PDGF-BB, PDGF-AB, PDGF-CC, and PDGF-DD) and engage two receptor tyrosine kinases, PDGFRα and PDGFRβ, which are mainly expressed on cells of mesenchymal origin (Andrae et al., 2008). PDGFR signaling contributes to the embryonal development of multiple organs and blood vessels and promotes wound healing in the adult. Cancer cells frequently produce PDGFs, which trigger autocrine and paracrine PDGFR signaling and promote tumor growth, proliferation, stromal recruitment, angiogenesis, epithelial-mesenchymal transition, and metastasis. A homolog of cellular PDGF encoded by the simian sarcoma virus v-sis oncogene also promotes neoplastic transformation through PDGFR (Deuel et al., 1983).

By screening a human secretome protein library with an NKp44-GFP reporter cell line, we found that NKp44 recognizes PDGF-DD, which has been shown to stimulate neoplastic transformation and tumor growth through PDGFRβ (LaRochelle et al., 2002; Li and Eriksson, 2003; Reigstad et al., 2005; Wu et al., 2013; Xu et al., 2005). Engagement of NKp44 by PDGF-DD triggered NK cell secretion of interferon gamma (IFN-γ), tumor necrosis factor alpha (TNF-α), and other proinflammatory cytokines and chemokines, which in turn induced the downregulation of tumor cell-cycle genes and tumor growth arrest. Meta-analysis of a publicly available database of gene expression profiles for different human cancers revealed a remarkable positive correlation between NCR2 expression, upregulation of PDGF-DD induced NK cell cytokine genes, and downregulation of tumorcell-cycle genes, along with greater survival in glioblastoma (GBM). In vivo analysis of NCR2-transgenic mice demonstrated that NKp44 limits the dissemination of PDGF-DD-expressing tumor cells, which was enhanced by checkpoint blockade with anti-CD96 or by CpG-oligonucleotide (ODN) treatment. Therefore, PDGF-DD not only supports tumor growth and stromal expansion through PDGFRβ but also facilitates recognition of tumor cells by innate immune cells through NKp44.

Methods for Examples
Experimental Model and Subject Details
Mice

Mice were of mixed sexes. Mice within experiments were age and sex matched. All mice were between 8-12 weeks of age at the time of use. Mice used in this study were NCR2-tg and non-tg littermate mice. Mice were housed under specific pathogen free conditions. Mice did not undergo any procedures prior to their stated use. Sex matched littermate mice were randomly assigned to experimental groups for anti-CD96 and CpG 2216 DNA treatments. All studies performed on mice were done in accordance with the Institutional Animal Care and Use Committee at Washington University in St. Louis, which approved all protocols used in this study.

Human Tissues and Primary Cells

All human tissues and cells (normal and cancer) used in this study were obtained under the approval of the institutional review boards of Washington University in St Louis and the University of Brescia, respectively. Informed consent was obtained from all patients for the use of all human tissue and cells used in this study. Tonsils were obtained from children undergoing elective tonsillectomy (Children's Hospital, Washington University School of Medicine). Peripheral blood products were obtained from the pheresis unit of the Washington University School of Medicine Center of Advanced Medicine. Tonsilar lymphocyte suspensions and peripheral blood mononuclear cells (PBMC) were prepared as previously described (Cella et al., 2009, 2010). Briefly, CD56± cells were enriched from PBMC and tonsil lymphocytes by magnetic cell sorting using CD56 MicroBeads (Miltenyi Biotec). NK cells and ILC subsets were sorted from CD56± cells, as previously reported (ueiia et al., 2010). Human CD4± T cells were enriched from PBMC by magnetic cell sorting using CD4 MicroBeads (Miltenyi Biotec). Mouse lamina propria leukocytes were prepared as previously described (Lefrancois and Lycke, 2001). Formalin-fixed paraffin-embedded (FFPE) human tissues used for this study were retrieved from the archive of the Department of Pathology (ASST Spedali Civili di Brescia, University of Brescia, Brescia Italy) and included reactive lymphoid organs (tonsils and lymph nodes) and normal non-lymphoid tissue (colon, stomach, thyroid, salivary gland, breast, lung, liver, pancreas, skin, kidney, bladder, testis, prostate). PDGF-D analysis was also screened on a set of seventy-five human neoplasms (FFPRE blocks) including primary (13 cases) and metastatic (22 cases) melanoma, glioblastomas (5 cases), gastrointestinal stromal tumor (4 cases) and a set of carcinomas from different sites including lung (5 cases), ovary (2 cases), breast (2 cases), bladder (2 cases), colon (5 cases), prostate (6 cases), stomach (2 cases), kidney (5 cases), head and neck (2 cases). NKp44 staining was performed on frozen material from 10 cases of glioblastoma (6 cases, University of Brescia; four, Washington University in St. Louis), which included one case of gliosarcoma GBM variant (Washington University in St. Louis).

Cell Lines

NKp30- and NKp44-GFP reporter cells were maintained in 10% FBS in RPMI 1640 supplemented with sodium pyruvate, GlutaMAX, and penicillin/streptomycin. NKp30- and NKp44-GFP reporter cells were based on the 2B4 NFAT-GFP cells developed by Arase et al. (Arase et al., 2002). The sex of the mouse from which the 2B4 T cell hybridoma was derived has not been reported (_J2; Hedrick et al., 1982). Colo38 is a human female malignant melanoma cell line (Chang et al., 2005). Meljuso is a human female cutaneous melanoma cell line (Deschodt-Lanckman et al., 1990). OVCA is a human female ovarian serous adenocarcinoma cell line (Bast et al., 1981). MCF7 is a human female breast carcinoma cell line (Soule et al., 1973). NK92 is a human male NK cell lymphoblastic leukemia/lymphoma cell line (Gong et al., 1994). Jurkat is a human male T lymphoblastic leukemic line (Schneider et al., 1977). B16F10 is a male mouse melanoma cell-line (Nakamura et al., 2002). J558L is a mouse plasma cell myeloma cell line. The sex of the mouse from which the J558L myeloma cell line was derived has not been reported (Oi et al., 1983). EL4 is a mouse thymic lymphoma cell-line (Gorer. 1950). The sex of the mouse from which the EL4 cell line was derived has not been reported. The Phoenix amphotropic packaging cell-line and HEK293F are derivatives of the human female embryonic kidney (HEK) 293 cell-line et al., 2014). CHO is a female Chinese hamster ovary cell-line.

Method Details
Preparation of NCR2 Transgenic Mice

The RP11-380E17 BAC (~300 kb) was chosen because it encoded the complete human NCR2 gene on chromosome 6p21.1 in addition to sufficient upstream (~142 kb) and downstream (~142kb) sequence to include all the necessary elements required for correct expression of NKp44. The RP11-380E17 BAC clone was purchased from Invitrogen, isolated and purified using the QIAGEN Maxiprep kit. PCR using the following primers located in genomic regions covering NCR2: 5 kb upstream (Forward, 5'-GTGGCAAGAGCTGAGCATCG-3' SEQ ID NO: 1; Reverse, 5'-GCCCCAAGTTAGGGGGTGAC-3' SEQ ID NO: 2), the ATG (Forward, 5'-GCTTGTGTGAGT-GAGTGGCG-3' SEQ ID NO: 3; Reverse, 5'-CTCTGCTGGACTGGCGATCT-3' SEQ ID NO:4), mid-gene (Forward, 5'-TGCTCGTCTGGTGGTGAGTG-3' SEQ ID NO: 5; Reverse, 5'-CTCTGGCCGATTCCCCTCTG-3' SEQ ID NO: 6), Stop codon (Forward, 5'-GGCGAGCAAGGCTTGGAAAC-3 SEQ ID NO: 7; Reverse, 5'-CCCGCCACCTATGGACTCAC-3' SEQ ID NO: 8), and 5 kb downstream (Forward, 5'-GGCTAAGAGGGGCCATCACG-3' SEQ ID NO: 9; Reverse, 5'-AGGATACAGGGGCAGGTGTTG-3' SEQ ID NO: 10), served to screen for positive BAC clones containing the complete NCR2 gene ready for pronuclear injection. Purified BAC DNA was then used to generate BAC transgenic mice on a CBA/C57BL/6J background in the Washington University School of Medicine Mouse Transgenic and Gene Targeting Core Facility using standard transgenic methods. PCR on tail-snip DNA using human-specific primers corresponding to an internal site on the transgene (Forward, 5'-ATCATTCTCCAGGCTCTCAGGCACAATCCA-3' SEQ ID NO: 11; Reverse, 5'-CATGGTGACAGTGAAGAAGCCAGCATCAGG-3' SEQ ID NO: 12) confirmed that the BAC had fully integrated. We used 2 transgenic founders to establish 2 independent transgenic lines for further characterization. We then crossed each of these lines further onto the C57BL/6J background to obtain mice homozygous for Klrb1 (encoding the NK1.1 antigen) at the C57BL/6J Natural Killer Receptor (NKR) locus. Mice were maintained on a standard 12 hour light/dark cycle with food and water available ad libitum. All procedures were conducted in strict accordance with the NIH Guide for the Care and Use of Laboratory Animals and all studies performed on mice were approved by the Washington University in St. Louis Institutional Animal Care and Use Committee.

Screening of the GNF Secretomics Library

A cell line with GFP reporter readout driven by NFAT-responsive promoter elements that stably expresses an integrated construct encoding a fusion protein of the NKp44 extracellular and transmembrane domains with the intracellular cytoplasmic tail of CDK (NKp44-GFP reporter cells) was generated for screening a library of secreted proteins (Gonzalez et al., 2010) for NKp44 ligands. Engagement of the chimeric NKp44-CD3i; receptor results in GFP expression. GFP reporter cells expressing a fusion protein consisting of the NKp30 extracellular and transmembrane domains with the intracellular cytoplasmic tail of CDg (NKp30-GFP reporter cells) were also generated. Library proteins were coated onto a 384-well tissue culture Fq treated plate in duplicate at 5-fold dilution from a stock in a final volume of 25 µUwell. Stock solutions varied in concentration ranging from −0.1 to −50 µM. The proteins were allowed to adsorb overnight at 4° C. The following day, protein coated plates were washed with 80 µL of PBS and NKp44 or NKp30 reporter cells, previously cultured to 70% confluence in T175 flasks, were seeded into protein coated plates at a density of 35,000 cells per well in 50 µL volume of culture medium. After 24 hours incubation at 37° C., 5 µL/well of a 2 ilg/mL DAPI dilution was added to each well for detection of dead cells, bringing the final volume/well to 55 µL. Flow cytometry was used to acquire GFP and DAPI signal from each well. Candidate proteins were retested in the same 384 well format using serial dilutions from library stocks as indicated. The GNF Secretomics library (Gonzalez et al., 2010) screened contains purified versions of known and predicted mouse and human secreted proteins as well as extracellular domains of single pass transmembrane proteins. Anti-NKp44 and anti-NKp30 were immobilized to plates using goat anti-mouse Ig and used as positive and negative controls, respectively. Results of initial screen are expressed as normalized fluorescence signal (NFS).

Immobilization of Antibodies, Proteins and Peptides

2% BSA, or 5 ug/mL of proteins or antibodies were immobilized in 100 µL PBS onto TC or ELISA plates, as previously described (Barrow et al., 2011). Briefly, all wells were washed 3 times in Tris buffered saline (10 mM Tris-HCl pH 7.5, 150 mM NaCl)+0.05% Tween-20 (TBS-T) to remove excess proteins before blocking in 5% BSA in TBS-T for 1 hour at 37° C. prior to performing binding assays.

Solid-Phase Binding Assay

Solid-phase binding assays were performed as previously described (Barrow et al., 2015). After blocking, NKp44-Fc fusion protein was diluted in 100 µL of TBS-T+0.1% BSA and incubated for 1 hour at room temperature (RT) in ELISA plate wells coated with the different proteins. Wells were then washed five times in TBS-T before incubating with 100 µL 1:5000 HRP-conjugated goat anti-human Ig (Southern Biotech) in 100 µL of TBS-T for 1 hour at RT. Wells were then washed a further five times in TBS-T before developing with O-Phenylenediamine dihydrochloride and the absorbance at 492 nM recorded using a plate reader. BSA, recombinant Chikungunya virus (CHIK) E2 protein and IL-17A were used as negative controls. Recombinant CUB-TEV-PDGFD contains a TEV cleavage site between CUB and GFD.

Calcium Imaging Using Flexstation III

NK92 cells were loaded with 1 µM Fura-2 AM in Ringer's buffer (135 mM NaCl, 5 mM KCl, 1 mM CaCl2, 1 mM MgCl2, 5.6 mM Glucose, and 10 mM HEPES, pH 7.4) for 40 min in the dark, washed, and then plated in 96-well plates at a density of 105 cells/well with primary antibodies. Fura-2 excitation ratios were measured by alternatively exciting the dye at 340 and 380 nm, at a frequency of −1 image pair every 4 s and collecting emission at 510 nm using Flexstation III (Molecular Devices) equipped with SoftMax Pro 5 software (Molecular Devices). Recombinant PDGF-DD was injected after 180 s to a final concentration of 1 µg/mL.

Immunoblotting

IL-2 cultured NK cells were serum-starved in RPMI 1640 medium for two hours at 37° C. prior to stimulation with 250 ng/mL PDGF-DD for the indicated time points. Following PDGF-DD stimulation, NK cells were placed on ice, washed once in ice cold PBS before resuspending in ice cold lysis buffer (50 mM Tris pH 8.0, 150 mM NaCl, 1% Triton X-100) containing 1 mM PMSF, 1 mM Na3VO4, leupeptin and apoprotinin (1 µg/mL each), and lx phosphatase inhibitor cocktail 3 (Sigma Aldrich Cat. Number P0044) on ice for 10 mins. After centrifugation at 13,000 rpm for 15 mins at 4° C. to pellet cellular debris, sample supernatants were removed and 4×SDS-PAGE loading buffer (200 mM Tris-HCl pH 6.8, 8% sodium dodecyl sulfate, 0.4% bromophenol blue, 40% glycerol and 400 mM dithiothreitol) added. Lysates were heated to 95° C. for 10 minutes and run on a 4%-12% bis-tris gel (Nupage). Proteins were transferred to nitrocellulose and blocked for 1 hour at RT in 5% BSA in TBS-T. Membranes were incubated in primary antibody overnight at 4° C. Membranes were subsequently washed and incubated in Goat anti-rabbit HRP (Southern Biotech) for 1 hour at RT, washed, and developed using SuperSignal West Pico Chemiluminescent Substrate.

Plasmids

Human PDGFD (residues E184-R370) and NKp44 (residues G18-S130 including a C-terminal His6 tag) were cloned into the NdeI and NotI restriction sites of the pET21 bacterial expression vector. Full-length PDGFD (residues 1-370), with or without an internal Tobacco Etch Virus (TEV) protease recognition sequence preceding the cytokine domain (R254), a C-terminal TEV protease site and His6 tag, was cloned downstream of the CMV promoter in the IRES-RFP mammalian expression vector pFM-1.2. The NKp44 ectodomain and transmembrane region was cloned in frame with human CDg into the pEF6N5-H is mammalian expression vector. The NKp44 extracellular domain was cloned into the pHuIgG1 vector to make the resulting NKp44-Fc vector containing the exons for the hinge, CH2 and CH3 regions of human IgG1, the guanosine phosphotransferase gene conferring resistance to mycophenolic acid, and the K promoter for expression in mouse myeloma, as described before (Boles et al., 2005). Cloning of the CRTAM-Fc fusion protein to detect expression of NecI-2, has been described before (Boles et al., 2005). Full-length human PDGFD or PCNA were cloned into the EcoRI and NotI sites of the pMX-IRES-eGFP retroviral expression vector, respectively.

Generation of Stable Cell-Lines

GFP reporter cells were generated by electroporation of the NKp44-CD3i; fusion construct or NKp30-CD3i; fusion constructs, respectively, and selection of stable clones with Blasticidin. J558L myeloma cells were electroporated with NKp44-Fc vector and secreting transfectants selected in mycophenolic acid xanthine (Sigma-Aldrich). For the generation of stable B16F10 and EL4 cells, the Phoenix amphotropic retroviral packaging cell-line was transfected with either pMX-IRES-eGFP or pMX-IRES-eGFP (Kitamura et al., 2003) encoding either PDGFD or PCNA, respectively.

Cells were infected with the resulting amphotropic retroviruses and single-cell clones stably expressing similar levels of GFP selected in the presence of puromycin.

Recombinant Proteins

Human PDGFD (E184-R370) and NKp44 (G18-S130) were expressed in BL21 (DE3) codon plus *E. coli* cells by autoinduction (Studier, 2005). The proteins were refolded from inclusion bodies denatured in 7 M guanidinium hydrochloride, 30 mM 13-mercaptoethanol centrifuged for 10 min at 4° C. and diluted to 2 M guanidinium hydrochloride in 50 mM sodium acetate pH 5.2. The supernatant was filtered and refolded by rapid, serial dilution (1 mL injections, hourly) in 1 liter of refolding buffer (400 mM L-arginine, 100 mM Tris-base pH 8.3, 2 mM EDTA, 0.5 mM oxidized glutathione, 5 mM reduced glutathione, and 0.2 mM phenylmethanesulfonyl fluoride) at 4° C. The recombinant proteins were concentrated using a stirred cell concentrator with YM10 membrane (Millipore), centrifuged to remove aggregates and purified on an S-75 size exclusion chromatography column equilibrated in 20 mM HEPES pH 7.4 and 150 mM NaCl, 0.01% sodium azide. Full-length PDGFD and TEV cleavable PDGFD proteins were transiently expressed in serum-free HEK293F suspension cells and purified by Ni-NTA agarose affinity (QIAGEN) and Superdex 200 gel filtration chromatography, cleaved where appropriate by the addition of TEV protease, and samples at 0 and 24 hours were analyzed by SDS-PAGE. Recombinant PDGF-DD used for in vitro cell stimulations was purchased from R&D systems. NKp44-Fc fusion protein was purified from J558L TC supernatants, as previously described.

Surface Plasmon Resonance

Affinity analysis was performed using SPR (BIAcore T100, GE Company) at 25° C. in 10 mM HEPES, 150 mM NaCl, 3 mM EDTA and 0.05% v/v surfactant P20. PDGFD, PDGF-DD or a control protein (IL17A or Chikungunya E2 glycoprotein) was immobilized (500-1000 Response Units) onto a CM5 chip (GE healthcare) using amine-coupling chemistry. Bacterial expressed NKp44 (residues 18-130 with a C-terminal His6 tag) was injected at a flow rate of 20 µL/m in at concentrations ranging from 0.036 µM to 36.8 µM for 5 minutes to saturate binding and then allowed to dissociate for 20 minutes. Under these conditions, regeneration of the chip surface was not necessary. The observed binding curves were double referenced to a control protein (human IL-17A or Chikungunya E2 glycoprotein) as well as buffer in the absence of NKp44. Curves were analyzed by a steady-state fit for a 1:1 interaction, and a nonlinear least-squares fit was used to evaluate the fit of the curve to the observed data.

Cell Culture

Unless indicated otherwise stated, all cells were cultured in a 5% $CO_2$ incubator at 37° C. All primary cells and cell-lines were cultured in RPMI 1640 (Sigma-Aldrich) supplemented with kanamycin sulfate, sodium pyruvate, GlutaMAX, non-essential amino-acids and 10% serum (complete medium), and either 10% fetal bovine serum (FBS) for primary cells or 10% bovine calf serum (BCS) for tumor cell-lines with the exception of J558L cells stably expressing NKp44-Fc that were cultured in complete RPMI 1640 medium containing 1% BCS. NK92 and primary mouse and human NK cells were cultured with IL-2 (10 ng/mL). CD3-CD19-NKp44+CCR6+ tonsillar cells were cultured with human IL-2 (10 ng/mL) and IL-113 (10 ng/mL) for 21 days prior to stimulation. For microarray analysis, CD3-CD19-NKp44+CD103+ILC1 were expanded in IL-2 (10 ng/mL, Peprotech) for 10 days prior to stimulation.

Reporter Cell Assays

NKp44-GFP reporter cells (105) were mixed 1:1 with target cells or directly stimulated with proteins in 96-well plates for 16 h before immunostaining with APC-conjugated anti-NKp44 antibodies and the expression of GFP subsequently analyzed by flow cytometry.

Generation of Cytokine-Conditioned TC Supernatant

IL-2 cultured human NK cells were incubated with 250 ng/mL PDGF-DD (R&D Systems) in 24-well plates for 16 h in the presence of 1 µg/mL IgG1 ($NK^{DD+IgG}$ sup) or blocking anti-NKp44 3.43.14 mAb ($NKDD^{DD+\alpha-NKp44}$ sup). After 16 h, TC supernatants were pooled, centrifuged and filtered to remove cellular debris, and then stored at −80° C. until further use. B16-pMX and B16-PDGFD stable cell-lines were cultured in 6-well plates for 72 h. After 72 h, TC supernatants were centrifuged, filtered and then stored at +4° C. until further use.

Tumor Cell Cycle Analysis

For analysis of the cell cycle by flow cytometry, Meljuso, cells were cultured in 1:2 NK cell-conditioned TC supernatants ($NK^{DD+IgG}$ sup or $NK^{DD+\alpha-NKp44}$ sup) or complete RPMI 1640 medium with 10 ng/mL each of human IFN-γ and TNF-α (Peprotech) for 48 h. Meljuso cells were pulsed with 1 mM BrdU prior to removal from TC plates using trypsin/1 mM EDTA. Single cell suspensions were then washed twice to remove excess BrdU prior to staining with 7-aminoactinomycin D (7-AAD) and APC-conjugated antibodies to BrdU using the Becton Dickinson APC BrdU Flow kit, according to the manufacturer's instructions and then analyzed by flow cytometry. Electronic gates were set according to each stage of the cell cycle and the percentage of events in each gate is indicated.

Tumor Growth Inhibition Assays

Meljuso and Colo38 cancer cell-lines were cultured in complete medium or 1:2 NK cell-conditioned TC supernatants ($NK^{DD+IgG}$ sup or $NK^{DD+\alpha-NKp44}$ sup) for 48 h and 72 h, respectively, with or without 2 µg/mL of blocking antibodies to IFN-γ and TNF-α in 12-well plates. Cells were removed using a trypsin/EDTA solution to generate single-cell suspensions and washed twice in complete medium before enumerating the number of live cells by trypan blue exclusion using a hemacytometer (Thermofisher Scientific). A total of $4 \times 10^4$ cells per well were then cultured in 24-well plates in 1 mL complete RPMI 1640 medium in the absence of cytokines. At the end of each passage, TC supernatants were removed for the detection of inflammatory cytokines and chemokines, and the total number of cells per well enumerated by trypan blue exclusion before re-plating at $4 \times 10^4$ cells per well in 24-well for the next passage. The number of cells at the end of each passage (as determined by confluence/cell density in control wells) was recorded for a total of 3 passages and the percentage growth relative to control medium determined.

Sorting of ILC Subsets

Enriched tonsilar CD56± cells were stained with PerCP-Cy5.5-conjugated antibodies to CD3 and CD19, PE-conjugated anti-NKp44, and biotin-conjugated antibody to CCR6 followed by APC-conjugated streptavidin, and FITC-conjugated anti-CD103 and sorted on a FAGS Aria II (BD Biosciences) into CD3-CD19-NKp44+CCR6+ cells (NKp44+ ILC3) and CD3-CD19-NKp44+CD103+ cells (NKp44+CD103+ILC1). Purities of sorted populations were typically above 99%.

NK Cell Treatments

Unless indicated otherwise, NK cells were stimulated with 250 ng/mL recombinant PDGF-DD (R&D Systems) or 1 mg/mL CUB-TEV-PDGFD or neat B16F10 TC supernatants with or without addition of soluble blocking antibodies (5 mg/mL) for 16 h in all assays. For CD107a degranulation assays, CD3-CD56+ NK cells (500,000 cells) were stimulated in 96-well round bottom plates. FITC-conjugated anti-CD107a antibody was added at the start of the culture. Cells were cultured for 5 hours with 2 mM monensin (Sigma Aldrich) added after the first hour of culture. NK cells were then stained with APC-conjugated mAb to CD56 prior to flow cytometry. For intracellular cytokine staining, NK cells were stimulated in 96-well flat bottom plates. Cells were cultured for 8 h with 2 mM monensin added after two hours of culture, before surface staining with PE-conjugated anti-NKp44 and PE-Cy7-conjugated anti-CD56 followed by staining for intracellular cytokines with APC-conjugated antibodies to IFN-g and FITC-conjugated antibodies to TNF-a. For analysis of the upregulation of cell surface NKp44 on mouse NK cells, splenocytes were isolated from NCR2-tg and non-tg mice and, following red blood cell lysis, cultured in 10 ng/mL each of human IL-2 and IL-15 (both Peprotech) for a total of four days with some splenocyte cultures additionally stimulated with 4 ng/mL mouse IL-1b and 10 ng/mL mouse TNF-a (both Peprotech) for 2 days before immunostaining staining with APC-conjugated antibody to NK1.1, FITC-conjugated antibody to mouse CD3 and PE-Cy7-conjugated antibody to NKp44 and DAPI and cell surface NKp44 expression on live (DAPI-) CD3-NK1.1+ NK cells determined by flow cytometry.

ILC1 and ILC3 Treatments

Unless indicated otherwise, ILCs were stimulated with 250 ng/mL PDGF-DD with or without soluble blocking antibodies (5 mg/mL) for 16 h for all assays. For detection of intracellular cytokines in ILC3, enriched CD56+ tonsilar cells were stimulated with 250 ng/mL PDGF-DD for 6 h with 2 mM monensin added after the two hours of culture, before either surface staining with APC-conjugated anti-NKp44 and the expression of intracellular cytokines detected with PE-conjugated antibodies to IL-22 and FITC-conjugated antibodies to TNF-a (as in FIG. 4A) or surface staining with PerCP-Cy5.5-conjugated antibodies to CD3 and CD19, APC-conjugated anti-NKp44, PE-Cy7-conjugated anti-CD56, BV421-conjugated anti-CCR6 and BV605-conjugated anti-CD103 and the expression of intracellular cytokine detected with FITC-conjugated antibodies to TNF-a (as in FIG. 4B).

Detection of Cancer Cell Surface Ligands for NK Cell Receptors

Colo38 and Meljuso cells were cultured with 1:2 NK cell-conditioned TC supernatants (NKDD+IgG sup or NKDD+a-NKp44 sup) in 12-well TC plates for 48 h before cells were removed using PBS/1 mM EDTA and stained with FITC-conjugated antibodies to CD95/Fas and PE-conjugated antibodies to CD112 and either biotin-conjugated antibodies to CD155/PVR or CRTAM-Fc followed by biotin-conjugated anti-human IgG. Biotin-conjugates were detected with APC-conjugated streptavidin. B16F10 cells were cultured with 10 ng/mL of either murine TNF-a, IFN-g, or TNF-a and IFN-g (both Peprotech) for 48 h prior to staining with FITC-conjugated antibodies to CD95/Fas and biotin-conjugated antibodies to CD155 followed by APC-conjugated streptavidin and propidium iodide. Cells were washed and cell surface expression of the different antigens on live (PI-) cells determined by flow cytometry. Percentage expression is indicated in each gate or quadrant. HIV gp41 peptide stimulation of human CD4+ T cells Human CD4+ T cells were enriched from peripheral blood by magnetic cell sorting using CD4 MicroBeads (Miltenyi Biotec) and $10^5$ human CD4+ T cells were stimulated with or without 5 mg/mL of HIV gp41-derived peptide in 200 mL complete RPMI 1640 (Vieillard et al., 2005). After 16 h incubation, CD4+ T cells were immunostained with 10 mg/mL NKp44-Fc followed biotin-conjugated anti-human IgG and APC-conjugated streptavidin and FITC-conjugated anti-CD4 and then analyzed by flow cytometry. The percentage expression is indicated in each gate.

Analysis of Cellular Cytokine Secretion

IL-2 cultured NK cells or converted tonsil ILC3 (IL-2 and IL-1b) were stimulated in 96-well plates ($10^5$ cells/well) with or without blocking antibodies and the secretion of IFN-γ and TNF-α in the TC supernatants determined using the Th1/Th2/Th17 cytometric bead array (BD Biosciences). In some experiments, IFN-γ and TNF-α were induced by cross-linking NKp44 with GαM+α-NKp44 as a surrogate NKp44 ligand. NK cells and ILCs were kept in cytokine-containing medium throughout the assay. PMA/ionomycin was included in some experiments as positive control for cytokine secretion. In tumor cell growth inhibition assays, the secretion of IL-6 and IL-8 by tumor cell-lines at the end of each passage was determined using the Human Inflammatory cytokine CBA (BD Biosciences). The concentration of IL-6 or IL-8 present was normalized relative to the cell number following each passage.

Microarray and Data Analysis

Tonsilar ILC1 cells were sorted from two donors as previously described (Cella et al., 2010; Fuchs et al., 2013). Briefly, expanded tonsil ILC1 were stimulated with or without 250 ng/mL PDGF-DD for 16 h before RNA isolation using the RNeasy Plus Micro Kit (QIAGEN), amplified, and hybridized to the Affymetrix Human Gene (v.1.0) ST arrays. RNA yields from each subset were comparable. Array data were analyzed as previously described (Robinette et al., 2015). Pathway analysis of microarray data was performed using IPA software (QIAGEN).

RNA-Seq and Data Analysis

Figure 3A:
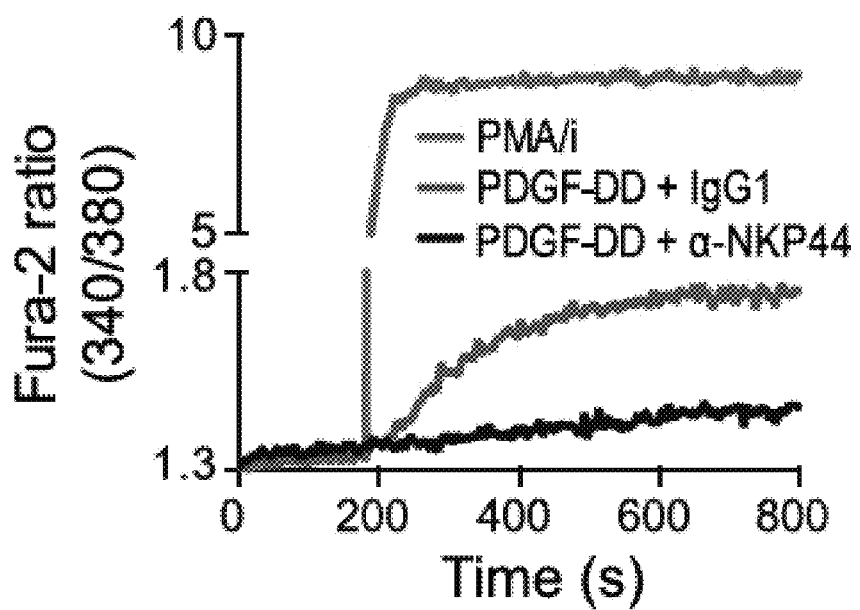
FIG. 3A, FIG. 3B, FIG. 3C, FIG. 3D, FIG. 3E, FIG. 3F, FIG. 3G, FIG. 3H, FIG. 3I and FIG. 3J show PDGF-DD triggers cytokine secretion pathways in NK cells via NKp44 and DAP12.
Figure 3B:
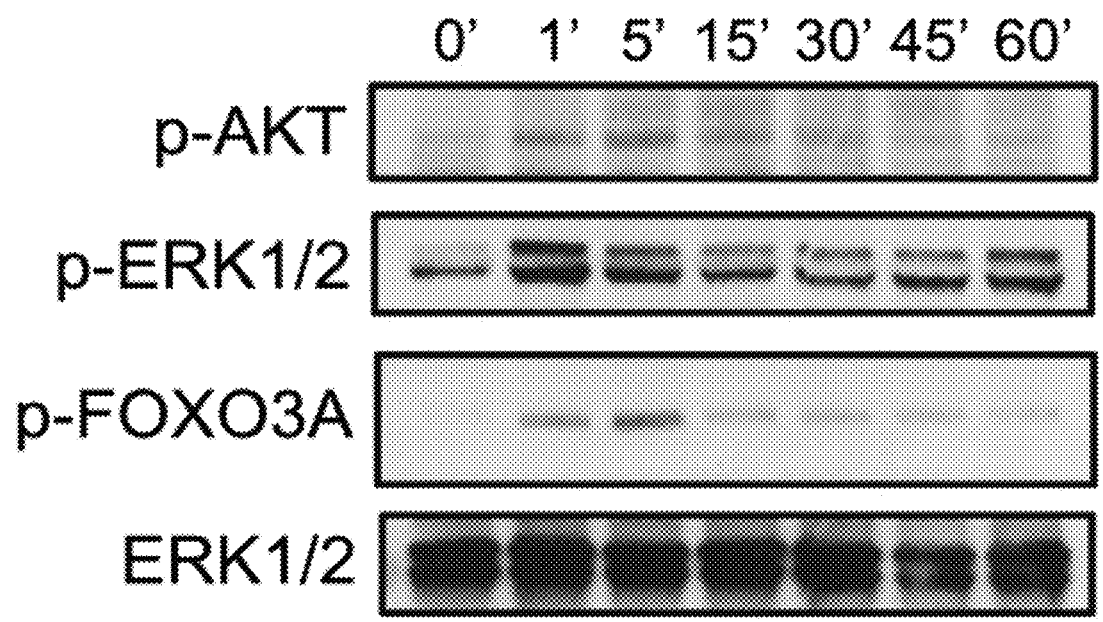
Figure 3C:
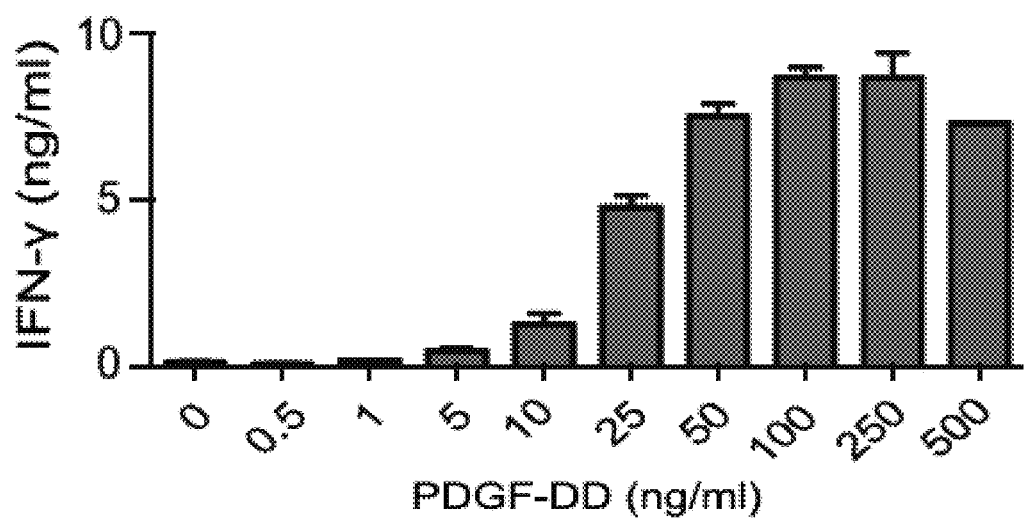
Figure 3D:
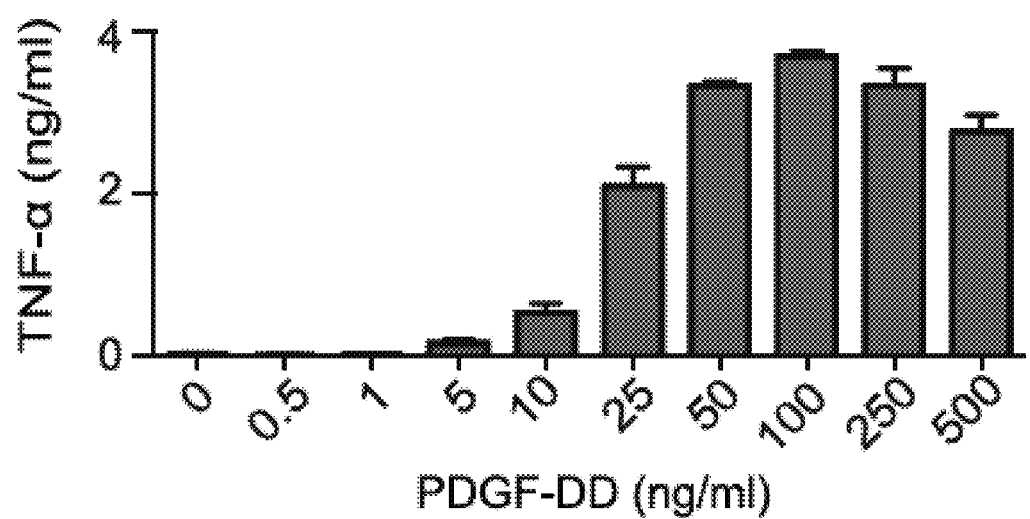
Figure 3E:
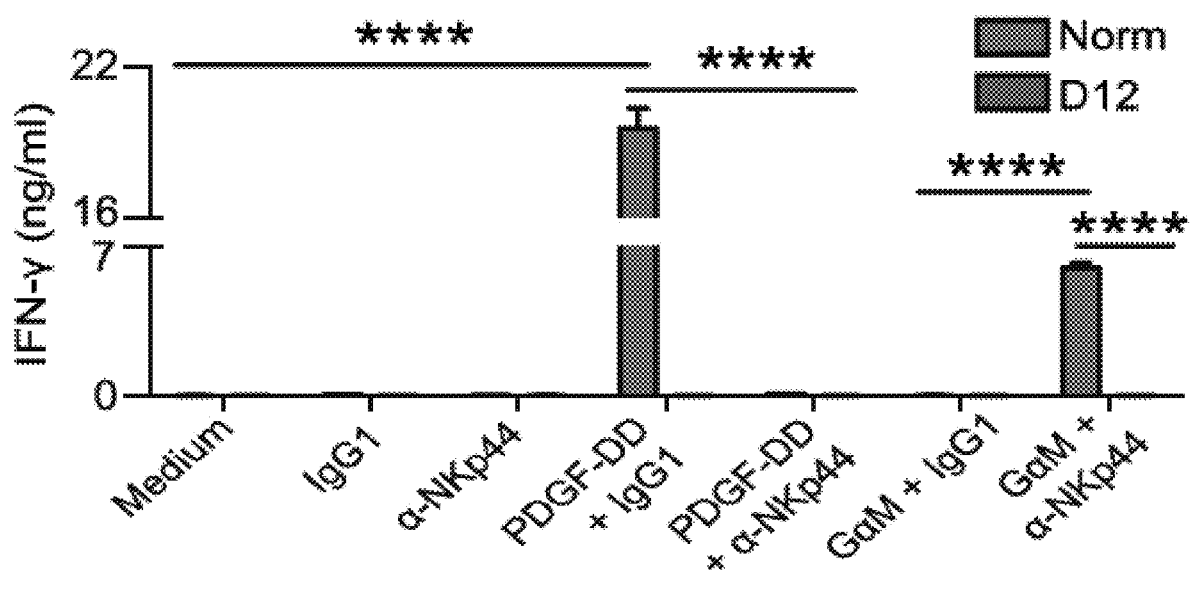
Figure 3F:
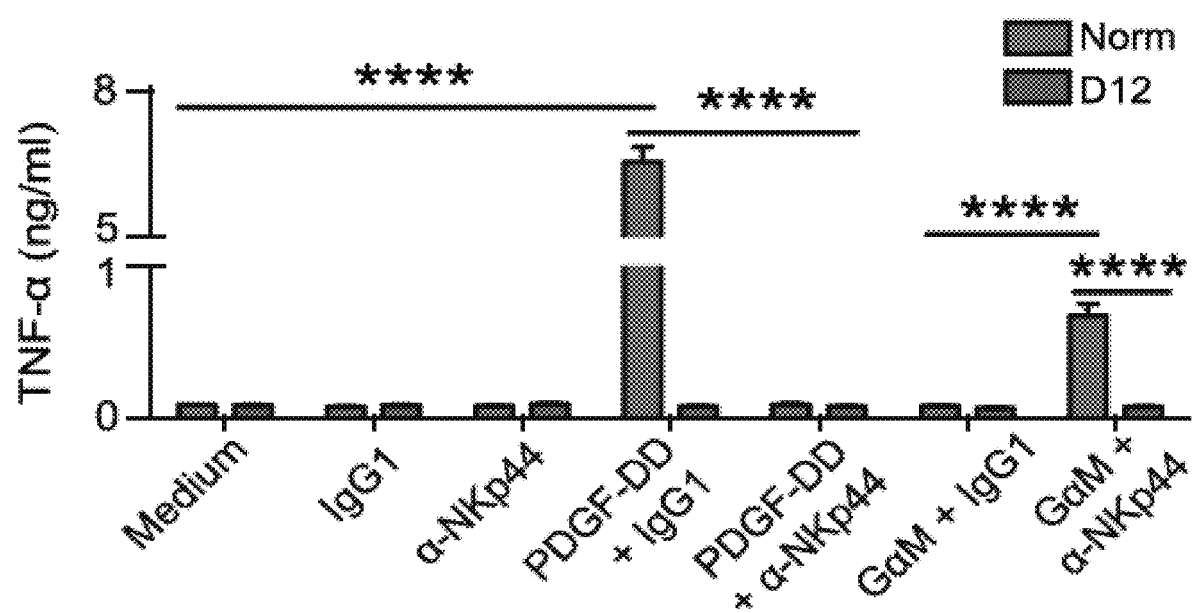
Figure 3G:
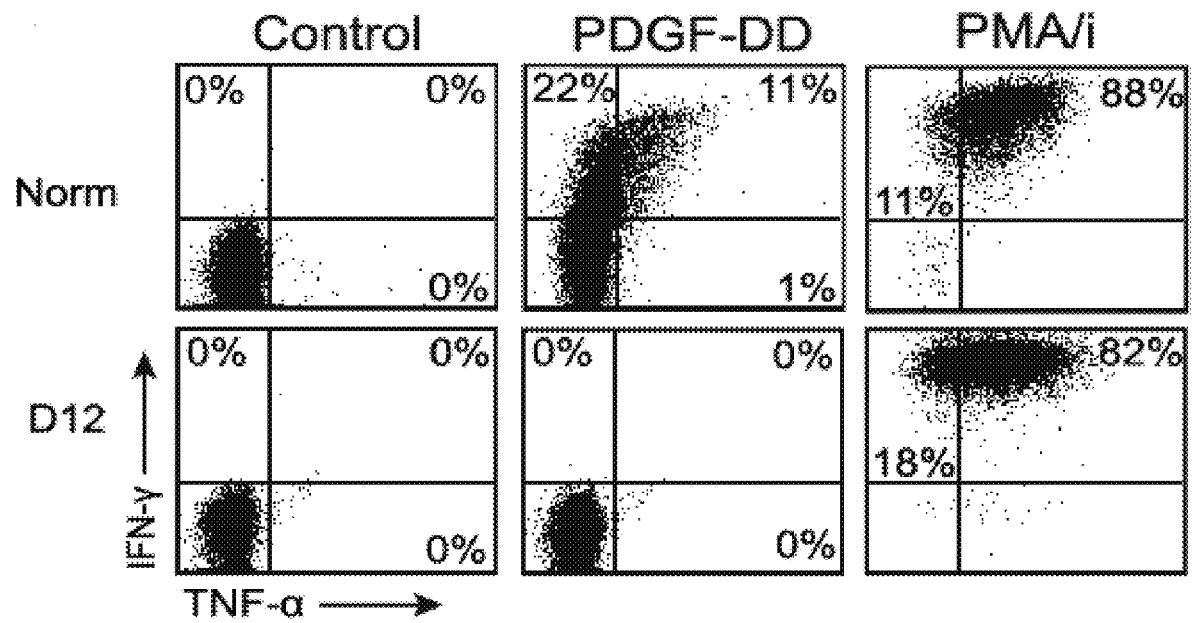
Figure 3H:
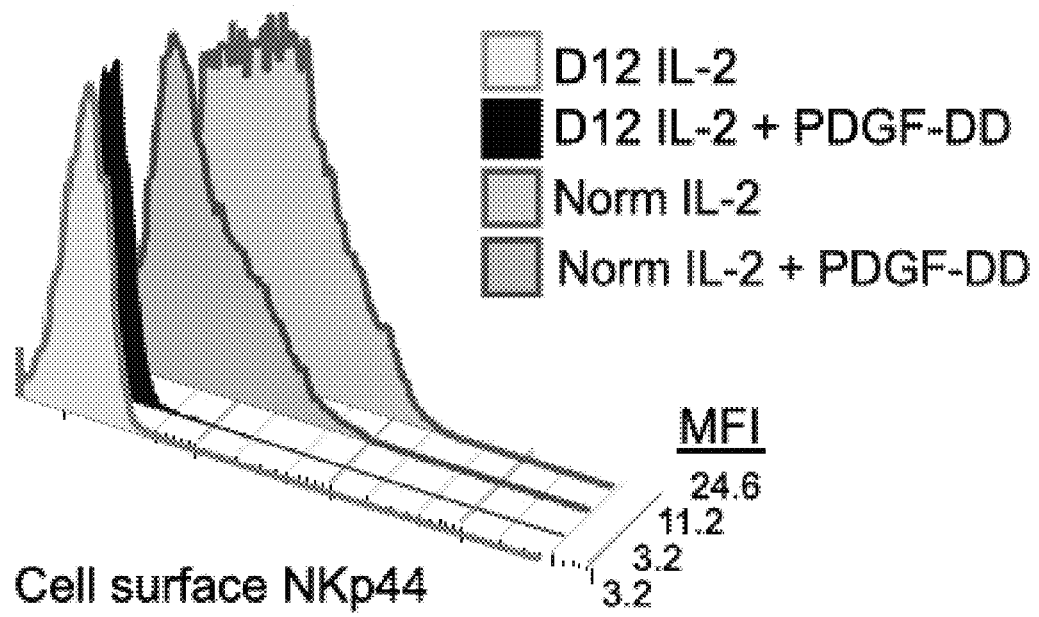
Figure 3I:
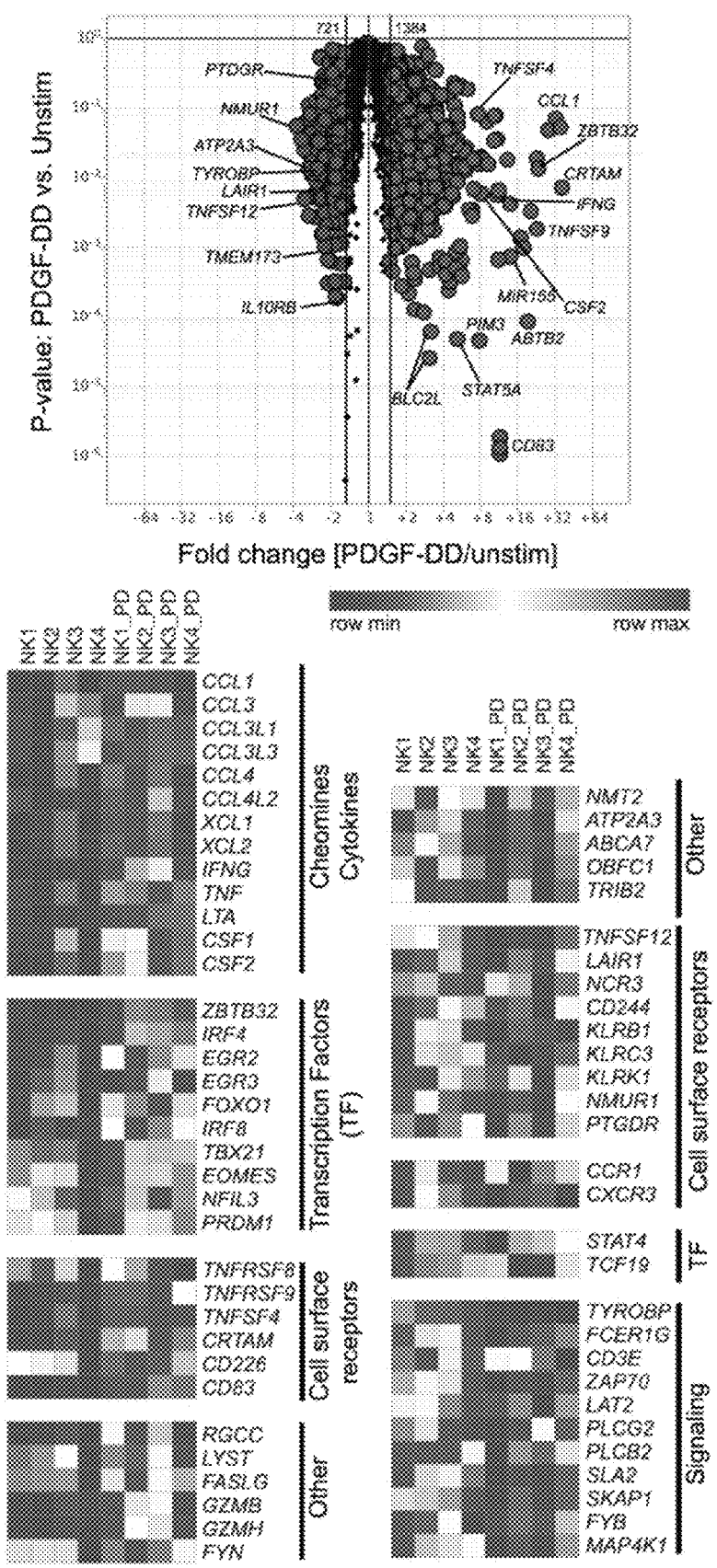

Confluent Colo38 and Meljuso (both melanoma), OVCA (ovarian) and MCF7 (breast) cancer cell-lines were cultured with 1:2 NK cell conditioned TC supernatants (NKDD+IgG sup or NK DD-Fa-NKP44 s up), or complete medium in 12-well TC plates (~0.5-1.0×106 cells) for 48 h before RNA isolation. IL-2 cultured NK cells ($1×10^6$) from four different donors were stimulated with 250 ng/mL PDGF-DD or PMA/ionomycin or left unstimulated in 12-well plates for 8 h before RNA isolation. Total RNA was isolated from NK cells and cancer cell-lines using Trizol followed by QIAGEN RNAeasy columns. 500 ng total RNA was used to make Illumina libraries using the TruSeq Stranded Total RNA library prep kit. Libraries were sequenced on an Illumina HiSeq 1000, single-end 50 bp run, to a sequencing depth of between 28 million and 60 million mapped reads per sample. Reads were aligned to a transcriptome file with BWA v0.5.9 (Li and Durbin, 2009), and the number of reads aligning to each transcript counted with SAMtools. These counts were converted to Reads per Million (RPM) by dividing each count by the total number of mapped reads for that sample, and multiplying by $10^6$. Gene expression signatures were derived from RNA-seq data using the RPM values of the transcripts for each NK cell donor (FIG. 3I). The up- or down-regulation of a transcript in response to PDGF-DD stimulation was determined according to the following criteria. First, a background level of gene expression was established in unstimulated NK cells from the four different donors cultured in IL-2. Transcripts in PDGF-DD-stimulated NK cells with at least eight RPM and at least two-fold expression over unstimulated NK cells were declared to be upregulated in that sample. Similarly, transcripts from PDGF-DD-stimulated NK cells with background expression of at least eight RPM and at most half the expression in unstimulated NK cells were declared to be downregulated.

Finally, gene expression was declared to be upregulated upon stimulation with PDGF-DD, if upregulated in at least three of the donor samples, and downregulated, if downregulated in at least two donors. Using gene expression data for each cancer cell-line (FIG. 5I; MCF, Meljuso, OVCA, or Colo38), the upregulation or downregulation of a gene in response to treatment with TC supernatants from PDGF-DD-stimulated NK cells ($NK^{DD+IgG}$ sup) was determined according to criteria analogous to that used for the stimulation of NK cells with PDGF-DD or PMA/i described above, where the background expression of a transcript was established by taking the geometric mean of its RPM in media or upon stimulation with control TC supernatants from NK cells stimulated with PDGF-DD but with the addition of anti-NKp44 blocking mAbs ($NK^{DD+\alpha NKp44}$ sup). Pathway analysis of RNA-seq data was performed using IPA software (QIAGEN).

Analysis of TCGA Datasets

TOGA GBM mRNA gene expression data obtained using the Affymetrix HT Human Genome U133a microarray platform (n=539 patients) was downloaded through the UCSC data portal (xenabrowser.net) and matched to the gene expression data (FIG. 5C and FIG. 5D). 7 of 9 cytokine genes (FIG. 5C) and 27 of 34 cell cycle genes (FIG. 5D) were matched with the GBM cohort. Scatterplots were generated plotting a cytokine or cell cycle gene with NCR2. Simple linear regression lines were fitted with correlation between two genes gauged by the Pearson correlation coefficient. The canonical correlation analysis (CCA), a dimension reduction statistical technique, was performed to investigate the overall correlation between a set of genes with NCR2. For CCA, each of the cytokine and cell cycle gene were at centered to have zero mean. A canonical cytokine variate was constructed as the linear combination of the set of centered cytokine genes and a canonical cell cycle variate as the linear combination of the centered cell cycle genes such that the resulting canonical cytokine and cell cycle variate each showed maximized positive correlation with NCR2. The canonical correlation between the constructed canonical cytokine variate with NCR2 and the canonical cell cycle variate with NCR2 were finally reported as a measure of potential absolute magnitude of the overall correlation between NCR2 with the set of cytokine genes and cell cycle genes. The canonical variates are always derived from CCA as being positively correlated with NCR2. The direction of each individual gene's associated linear coefficient, however, indicate the positive or negative correlation direction with the canonical covariate and thus with NCR2.

Tissue Immunostaining

For PDGF-D immunostaining of normal and cancer tissues, 4 µM thick sections were deparaffinized with xylene and rehydrated with decreasing concentrations of ethanol. Tissue sections were incubated with rabbit anti-PDGF-D antibody (dilution 1:250) after appropriate antigen retrieval (microwave oven; 2×5 minutes at max Watt and 3×5 minutes at 750 Watt in EDTA buffer pH 8.0) and revealed by Labeled Polymer-HRP followed by DAB. Immunostained sections were photographed using the DP-70 Olympus digital camera mounted on the Olympus BX60 microscope. For NKp44 immunostaining of GBM, 7 µM frozen sections were dried overnight before fixing in ice cold acetone for 10 mins followed by rehydration in PBS. Slides were blocked in 10% goat serum in PBS before incubating with anti-NKp44 and anti-CD38 antibodies followed by Alexa 488-conjugated anti-mouse IgG1 and Alexa 568-conjugated anti-mouse IgG2a secondary antibodies supplemented with DAPI. Immunostained sections were imaged on a Zeiss LSM880 Laser Scanning Confocal Microscope. Images were then processed with Zen 2.1 (Zeiss).

Tumor Cell Injections

Adherent B16-pMX or B16-PDGFD stable cells were removed from TC plates using a Trypsin/1 mM EDTA solution and washed twice in PBS before twice passing through a 100 µM cell filter and resuspended in PBS, and 200 µL containing a total of $2 \times 10^5$ cells injected into the tail vein of either NCR2-tg or non-tg littermate mice, respectively. After 17 days, total surface lung metastases were counted. To establish subcutaneous tumors in mice, $2 \times 10^6$ cells in 200 µL of PBS were implanted into the rear hind flanks of mice. Tumor growth was monitored by measurement of tumor size with a caliper every other day. Tumor volume was determined by the formula: length×width2/2. At the experimental end point, mice were sacrificed, and tumors were removed and processed for flow cytometric analysis.

Measurement of Lung Tumor Area

Formalin-fixed and paraffin embedded mouse lung tissues were sectioned at 3-4 µM and the slides stained with hematoxylin and eosin (H & E). H & E Slides were digitalized using an Aperio ScanScope CS Slide Scanner (Aperio Technologies) at 40× magnification. Individual tumors were manually selected using Aperio ImageScope (Leica Biosystems Imaging); a software that automatically provides the value of every selected tumor area in µM2 as output.

Quantitative RT-PCR

Total RNA was isolated with TRIzol Reagent (Invitrogen) and single-strand cDNA synthesized using SuperScript III reverse transcriptase kit (Invitrogen). Real-time PCR was performed using SYBR Green real-time PCR master mix (Thermo-Fisher) using a StepOnePlus detection system (Applied Biosystems). Primers were to mouse interferon-γ and TNF-α and cyclophilin was used as house-keeping gene.

General Statistical Methods

Data in figures are presented as mean±SEM. Statistical significance was determined using GraphPad Prism 7.0. Statistical differences were determined by two-tailed Student's t test (between two groups) and a one-way ANOVA among multiple groups and a p-value of <0.05 was considered significant.

Example 1: PDGF-DD Is a Ligand for NKp44

Figure 2A:
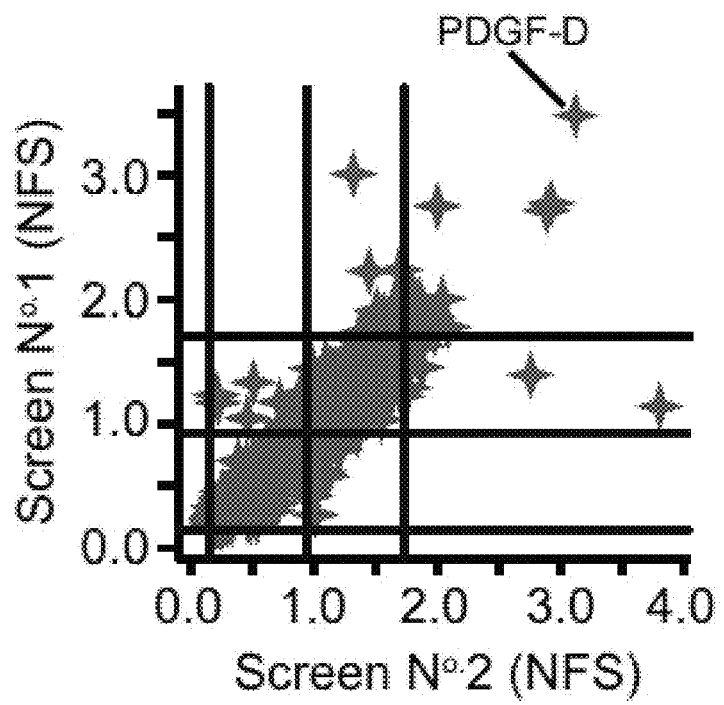
FIG. 2A, FIG. 2B, FIG. 2C, FIG. 2D, FIG. 2E, FIG. 2F, FIG. 2G, FIG. 2H and FIG. 2I show PDGF-DD is a ligand for NKp44.
Figure 2B:
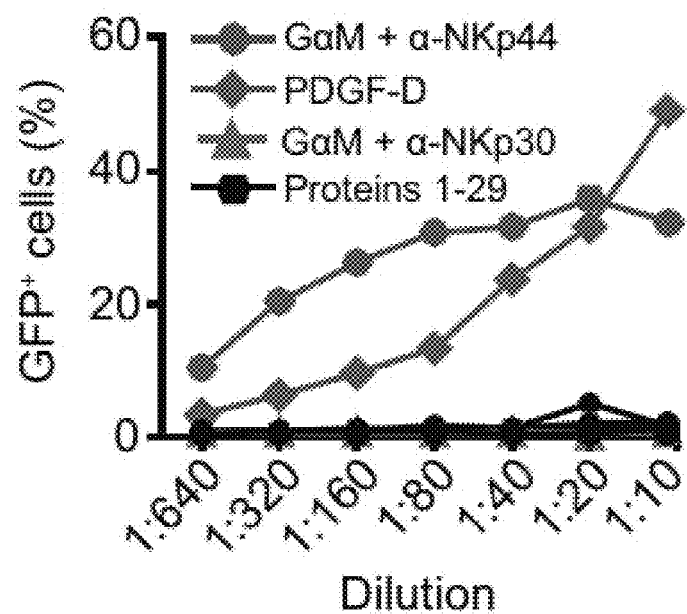
Figure 2C:
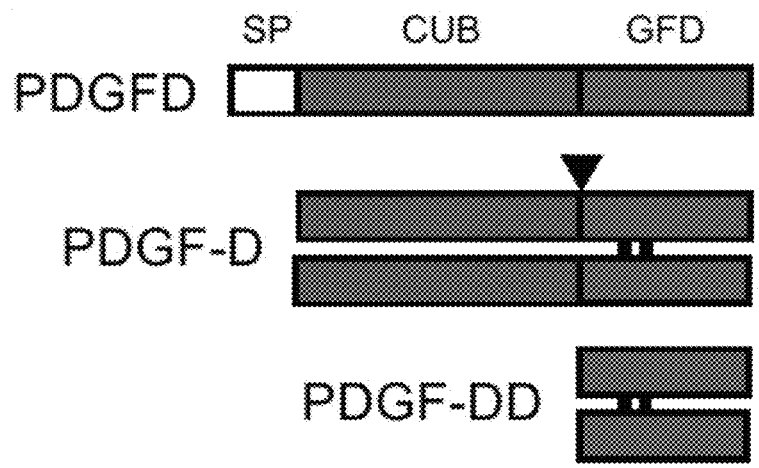
Figure 2D:
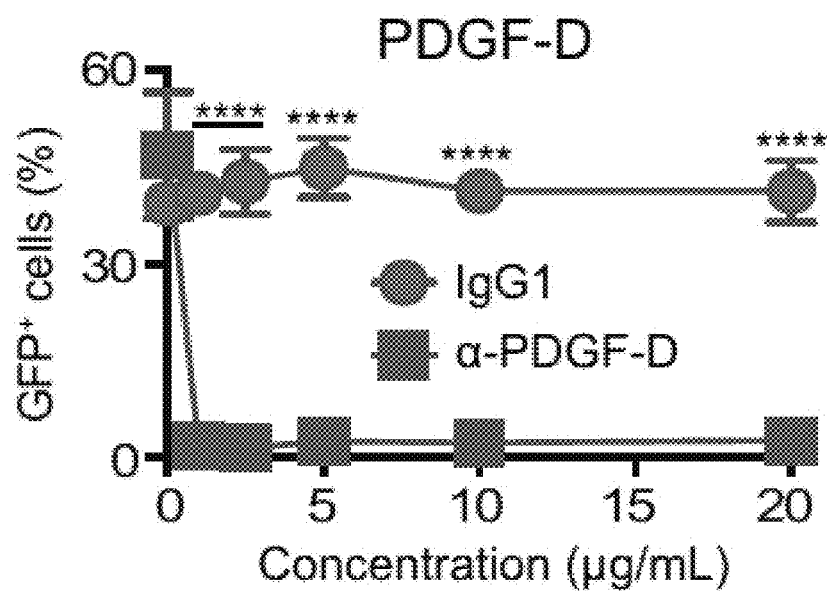
Figure 2E:
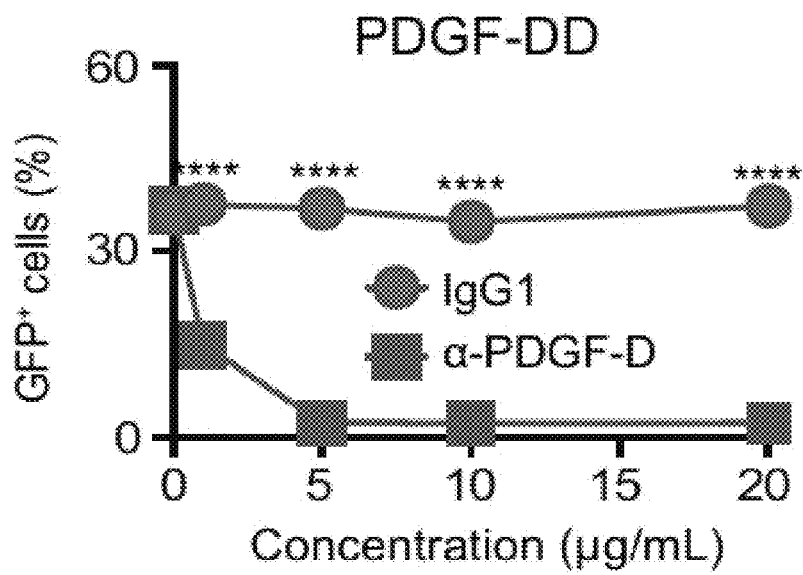
Figure 2F:
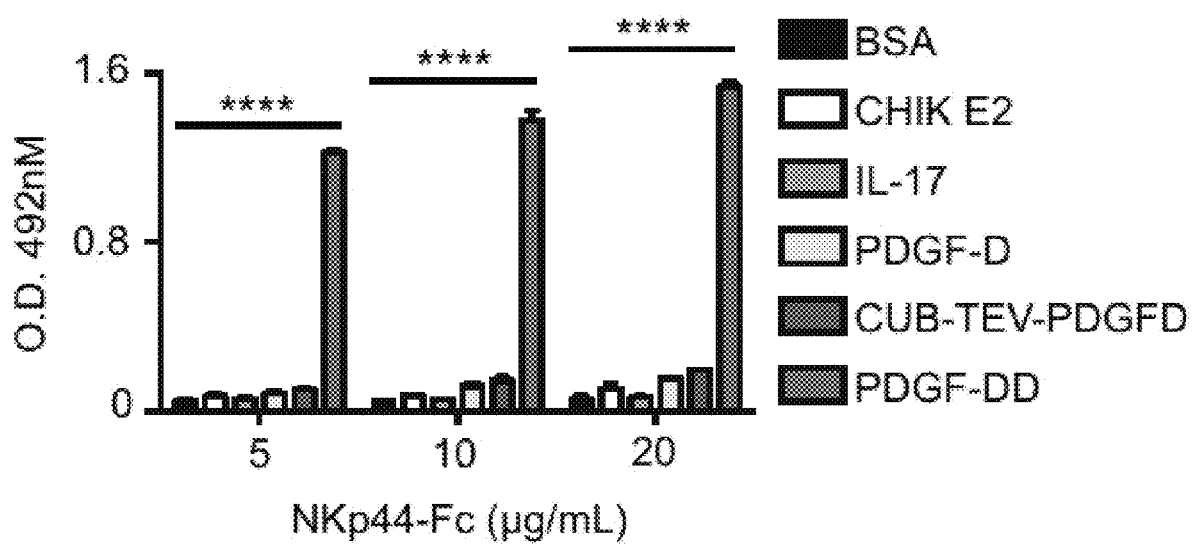
Figure 2G:
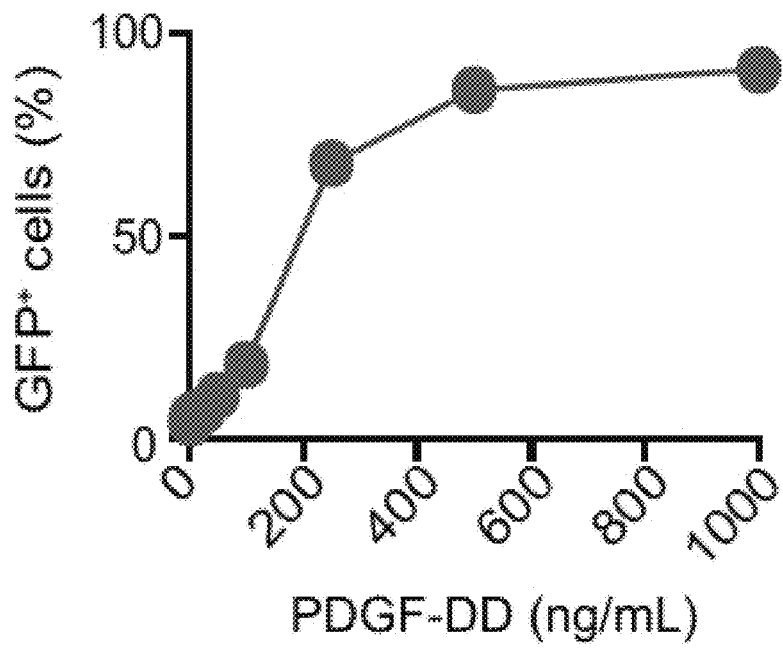
Figure 2H:
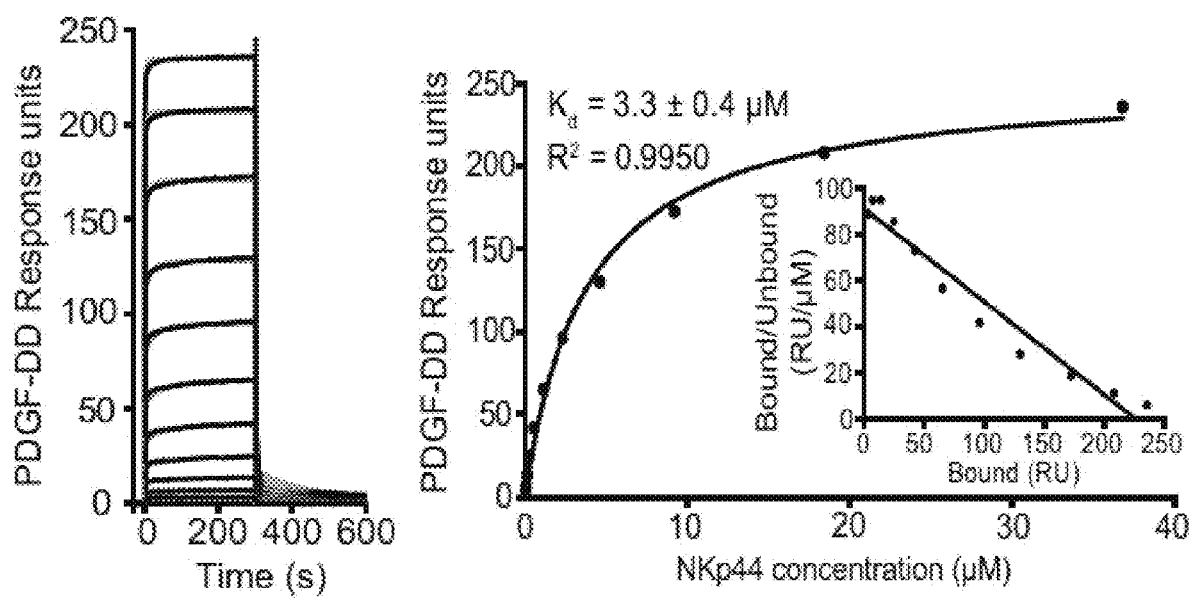
Figure 2I:
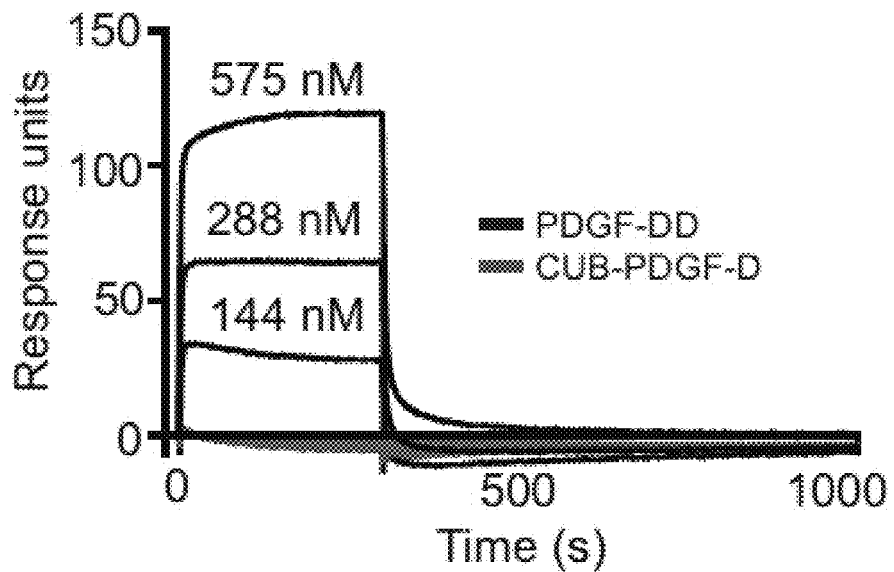
Figure 9A:
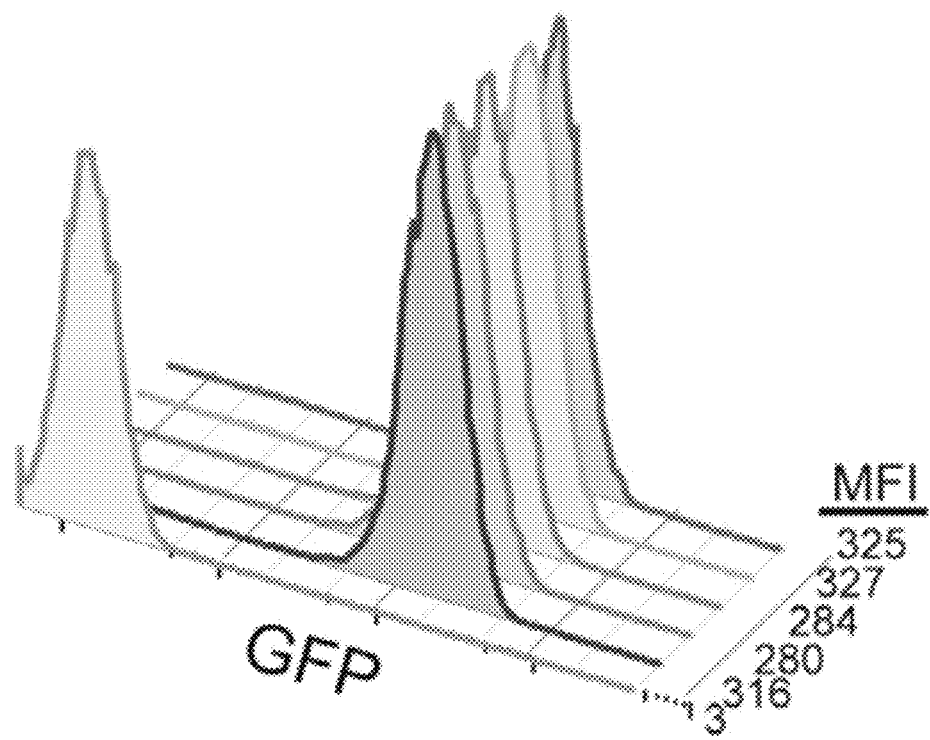
FIG. 9A, FIG. 9B, FIG. 9C, FIG. 9D, FIG. 9E, FIG. 9F, FIG. 9G and FIG. 9H show NKp44 Does Not Interact with PCNA, Influenza Virus Hemagglutinins, or the Putative NKp44 Ligand Upregulated by an HIV gp41 Derived Peptide.
Figure 9A:
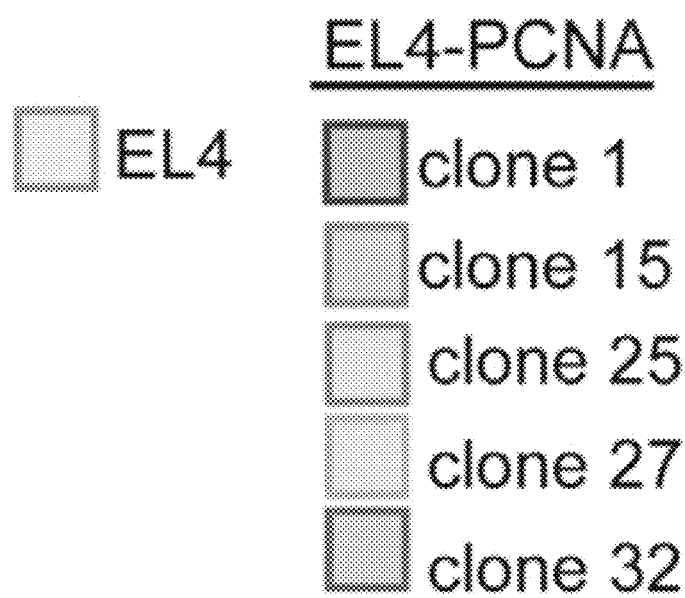
Figure 9B:
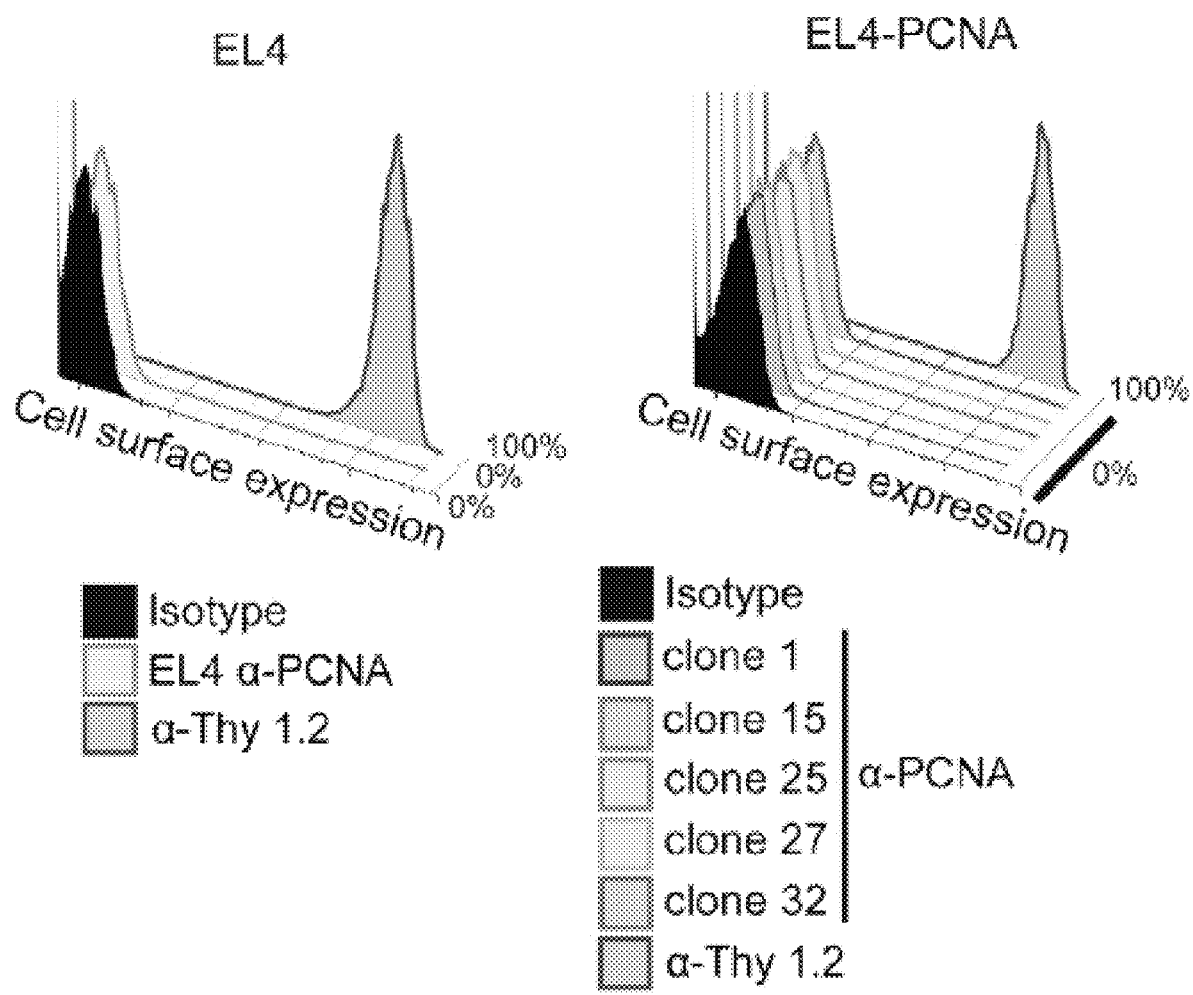
Figure 9C:
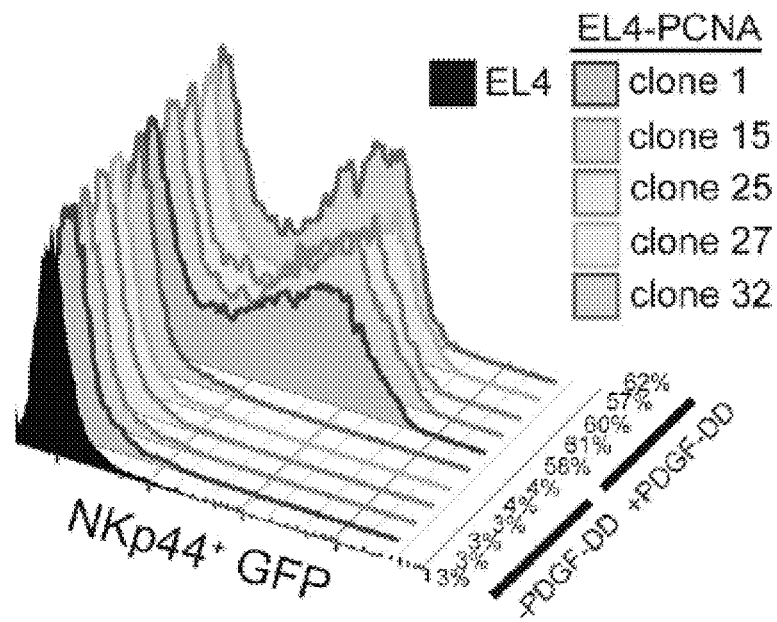
Figure 9D:
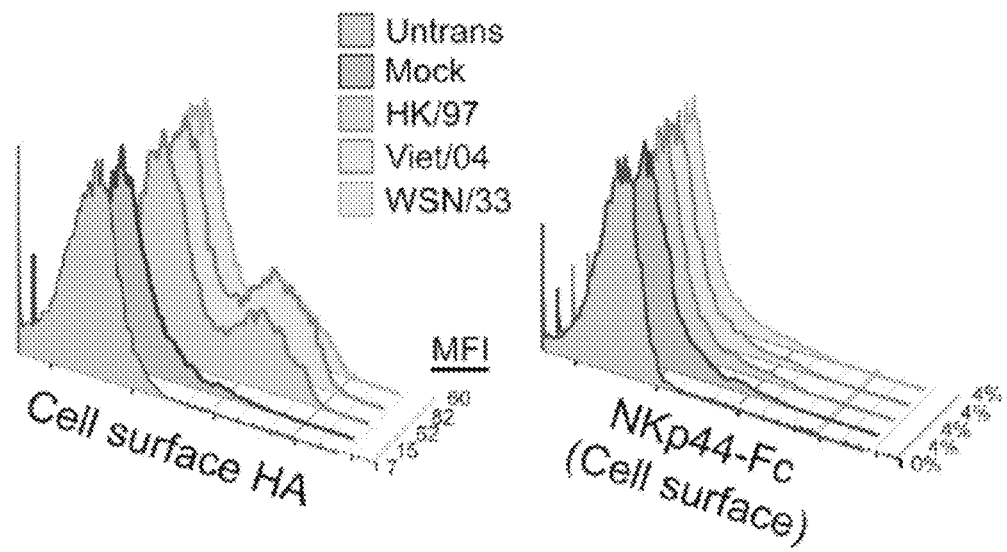
Figure 9E:
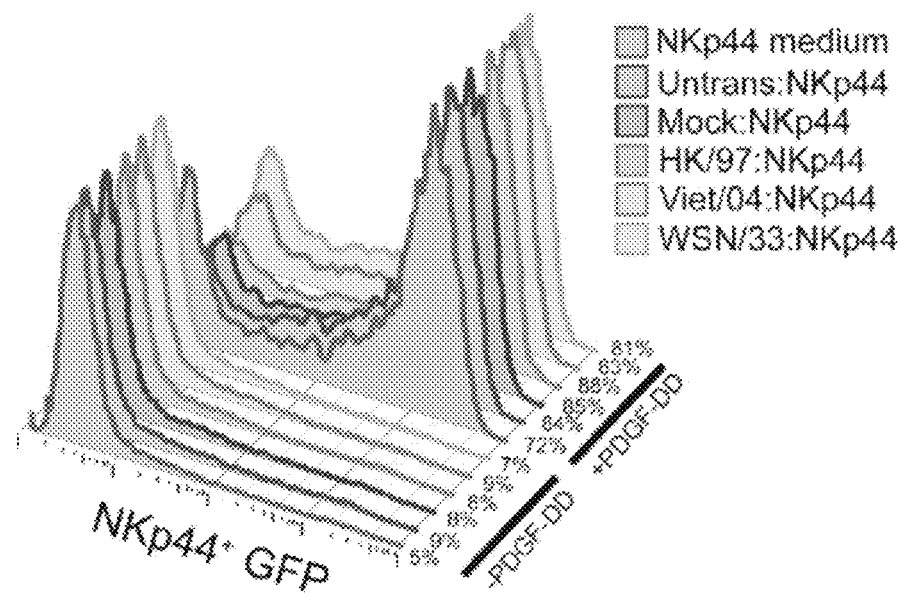
Figure 9F:
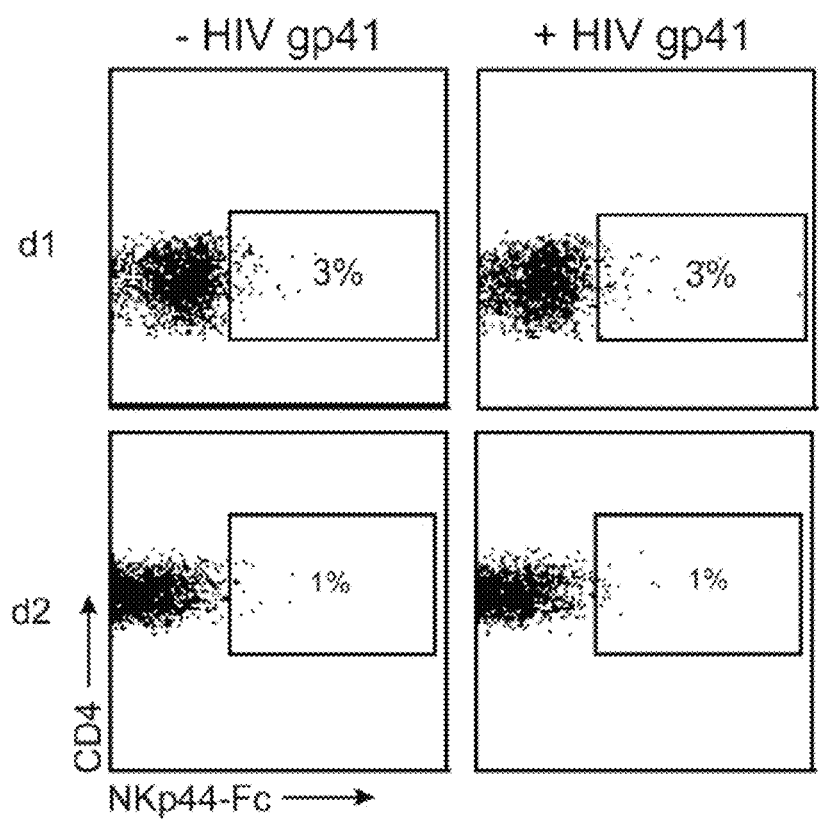
Figure 9G:
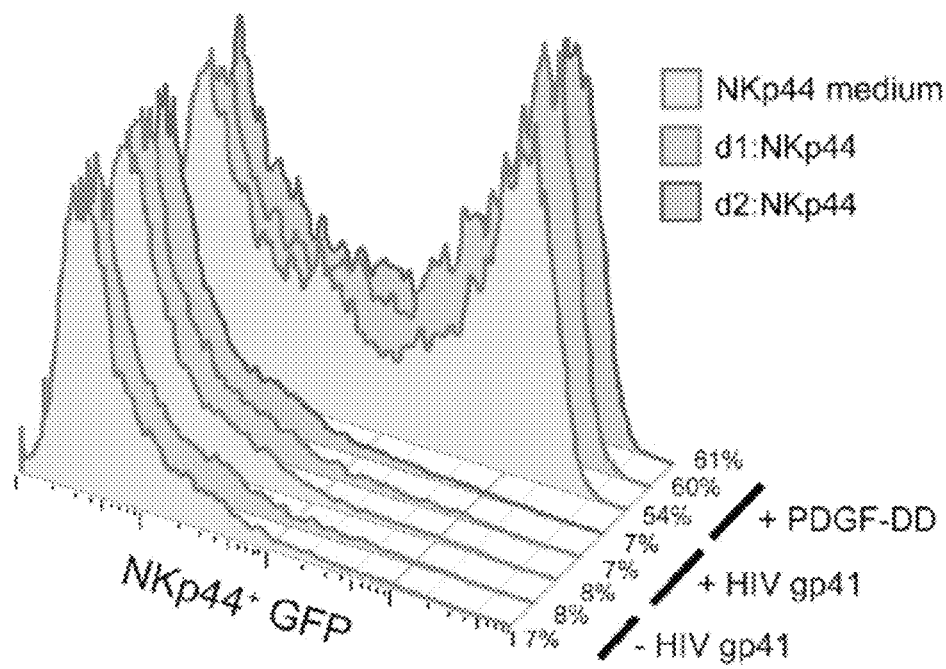
Figure 9H:
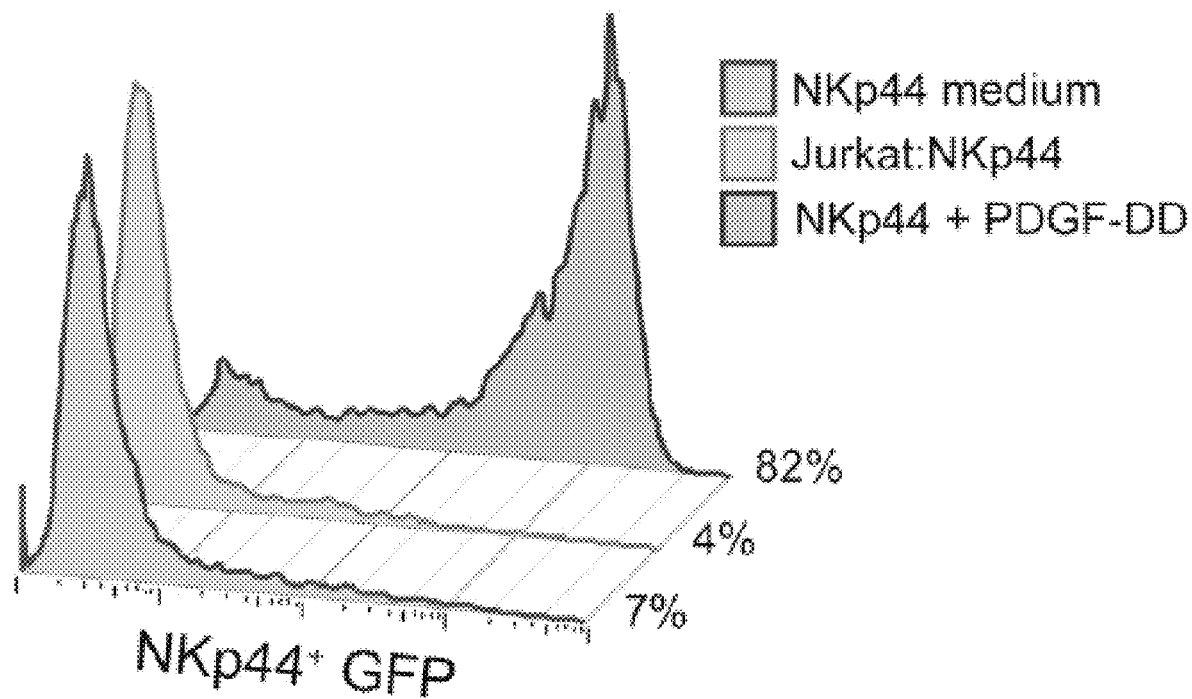

Physiological ligands of NKp44 have remained elusive for almost 20 years. To address this outstanding question, we performed an unbiased screen of a secretome protein library containing ~4,000 purified human- and mouse-secreted proteins or ectodomains of single-pass transmembrane proteins for NKp44 ligands (Gonzalez et al., 2010). To perform the screen, we transfected a chimeric receptor consisting of the human NKp44 extracellular and transmembrane domains fused to the CDK intracellular signaling domain (first generation CAR) into a reporter cell line that expresses GFP under the control of NFAT-responsive elements. Ligand engagement of the NKp44-CD3ζ fusion protein in the reporter cells leads to $Ca_{2+}$ mobilization and consequently NFAT transactivation of GFP expression (Arase et al., 2002). NKp44-GFP reporter cells were seeded into wells coated with individual secretome library proteins and GFP expression detected by flow cytometry (FIG. 2A). The top 30 secreted protein hits from the screen were individually re-tested and among these PDGF-D was validated as a putative NKp44 ligand (FIG. 2B). PDGF-D is a member of the PDGF family that signals through PDGFRβ (Andrae et al., 2008; Reigstad et al., 2005; Li and Eriksson, 2003). PDGF-D differs from PDGF-A and PDGF-B in having an unusual N-terminal domain known as complement subcomponent C1r/C1s, Uegf, and Bmp1 (CUB) domain (FIG. 2C) (Bergsten et al., 2001). PDGF-D is secreted as a dimer and must undergo extracellular proteolytic processing of the CUB domain by proteases, such as urokinase plasminogen activator and matriptase (Bergsten et al., 2001; Huang and Kim, 2015; Ustach and Kim, 2005; Ustach et al., 2010), to liberate active homodimeric PDGF-DD that binds to and activates PDGFRβ signaling (FIG. 2C). NKp44-GFP reporter cells expressed GFP when cultured in serum-containing medium with either recombinant PDGF-D (FIG. 2D) or the processed PDGF-DD form (FIG. 2E). Corroborating the specificity of these interactions, a monoclonal antibody (mAb) against PDGF-D blocked NKp44-GFP reporter activation by PDGF-D and PDGF-DD (FIGS. 2D and 2E). However, a chimeric protein consisting of the NKp44 ectodomain fused to the Fc domain of human IgG (NKp44-Fc) specifically bound to PDGF-DD but not to PDGF-D by solid phase binding assay, demonstrating that NKp44 effectively binds to active PDGF-DD (FIG. 2F). PDGF-D most likely activates NKp44-GFP reporter cells because it is processed by serum proteases contained in the culture medium. PDGF-DD-induced activation of NKp44-GFP reporter cells was dose-dependent and saturated at high PDGF-DD concentrations (FIG. 2G). Biacore analysis determined that PDGF-DD has a 3.3±0.4 µM affinity for the Ig superfamily (IgSF) domain of NKp44 (FIG. 2H), within the known range of the PDGF/PDGFR interactions (Shim et al., 2010), and confirmed that NKp44 does not bind to unprocessed PDGF-D (FIG. 2I). NKp44 ligands (NKp44L) have been proposed, such as viral hemagglutinins (Ho et al., 2008), and the nuclear proteins proliferating cell nuclear antigen (PCNA) (Rosental et al., 2011) and mixed-lineage leukemia protein 5 (MLLS) (Baychelier et al 2013; Vieillard et al., 2005). We did not detect NKp44 interaction with either EL4 cells overexpressing PCNA (FIGS. 9A and 9C), or CHO cells transfected with three different influenza virus hemagglutinins (FIGS. 9D and 9E) using NKp44-Fc binding and/or activation of NKp44-GFP reporter cells. Similarly, no interaction of NKp44 was detected with human CD4± T cells stimulated with an HIV gp41-derived peptide, which purportedly induces cell-surface expression of MLLS (FIGS. 9F and 9G), or with Jurkat T cells that were reported to express cell-surface MLLS (FIG. 9H) (Baychelier et al., 2013). Potential low-affinity interactions of NKp44 with these putative ligands and their physiological relevance remain unclear. Altogether, these results show that the proteolytically processed "active" PDGF-DD growth factor is a bona fide ligand for NKp44.

Example 2: PDGF-DD Triggers NK Cell Activation and Cytokine Secretion Via NKp44

Figure 10A:
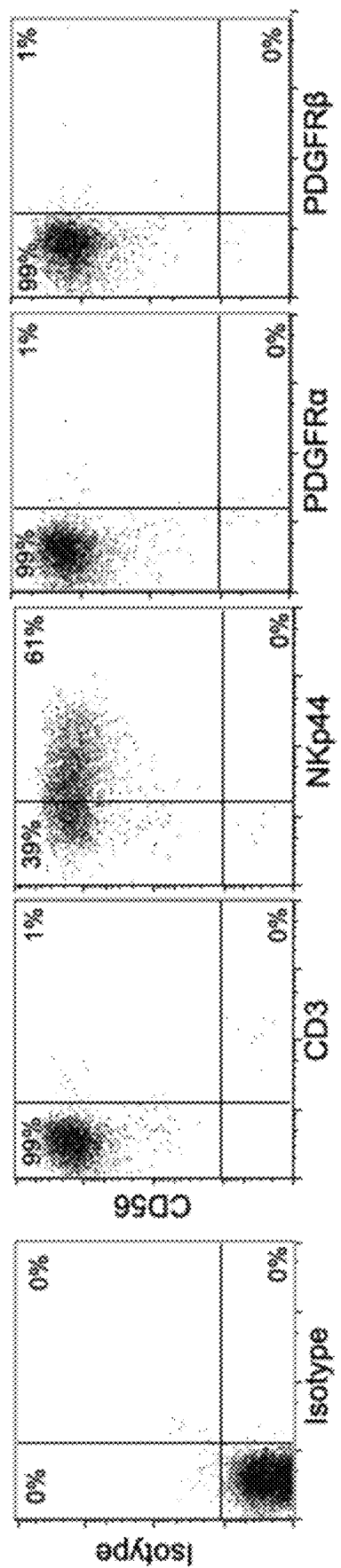
FIG. 10A, FIG. 10B, FIG. 10C, FIG. 10D, FIG. 10E and FIG. 10F show expression of NKp44 and PDGFR-α/β in Human NK Cells.

We first investigated whether PDGF-DD evokes ITAM signaling in human NK cells. The human NK cell line NK92 expresses NKp44. PDGF-DD induced $Ca^{2+}$ mobilization in NK92, which was blocked by anti-NKp44 (FIG. 3A). Furthermore, PDGF-DD induced phosphorylation of AKT, ERK, and its downstream target FOXO3A in primary human NK cells (FIG. 3B). Because activated human NK cells express the NKp44/DAP12 receptor complex, but not PDGFRα or PDGFRβ (FIG. 10A), we conclude that PDGF-DD binding to NKp44 triggers ITAM signaling in human NK cells.

Figure 10B:
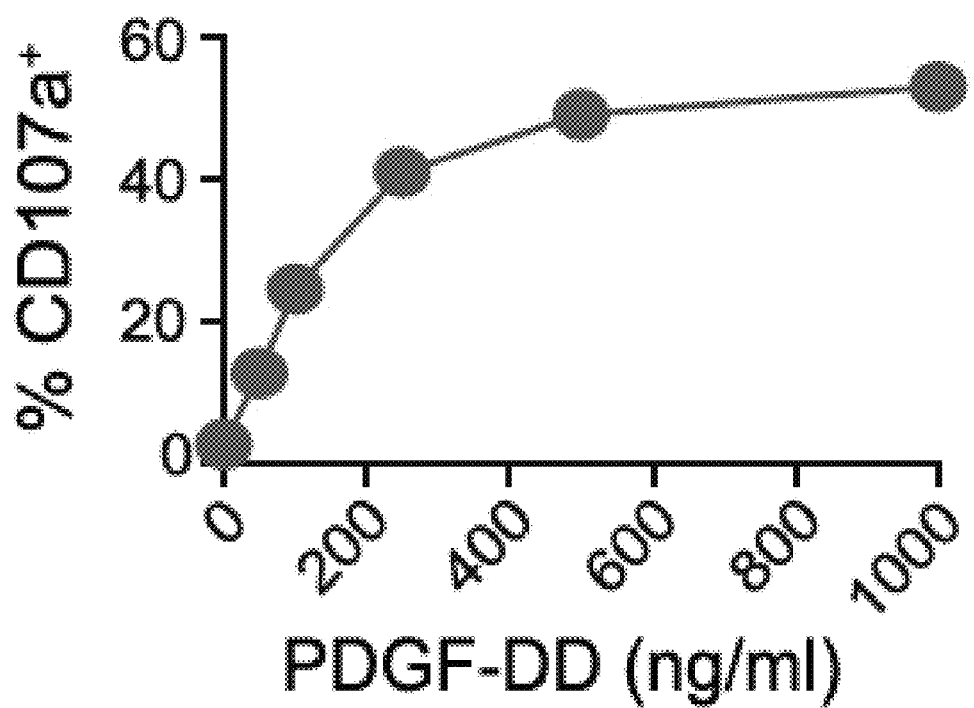
Figure 10C:
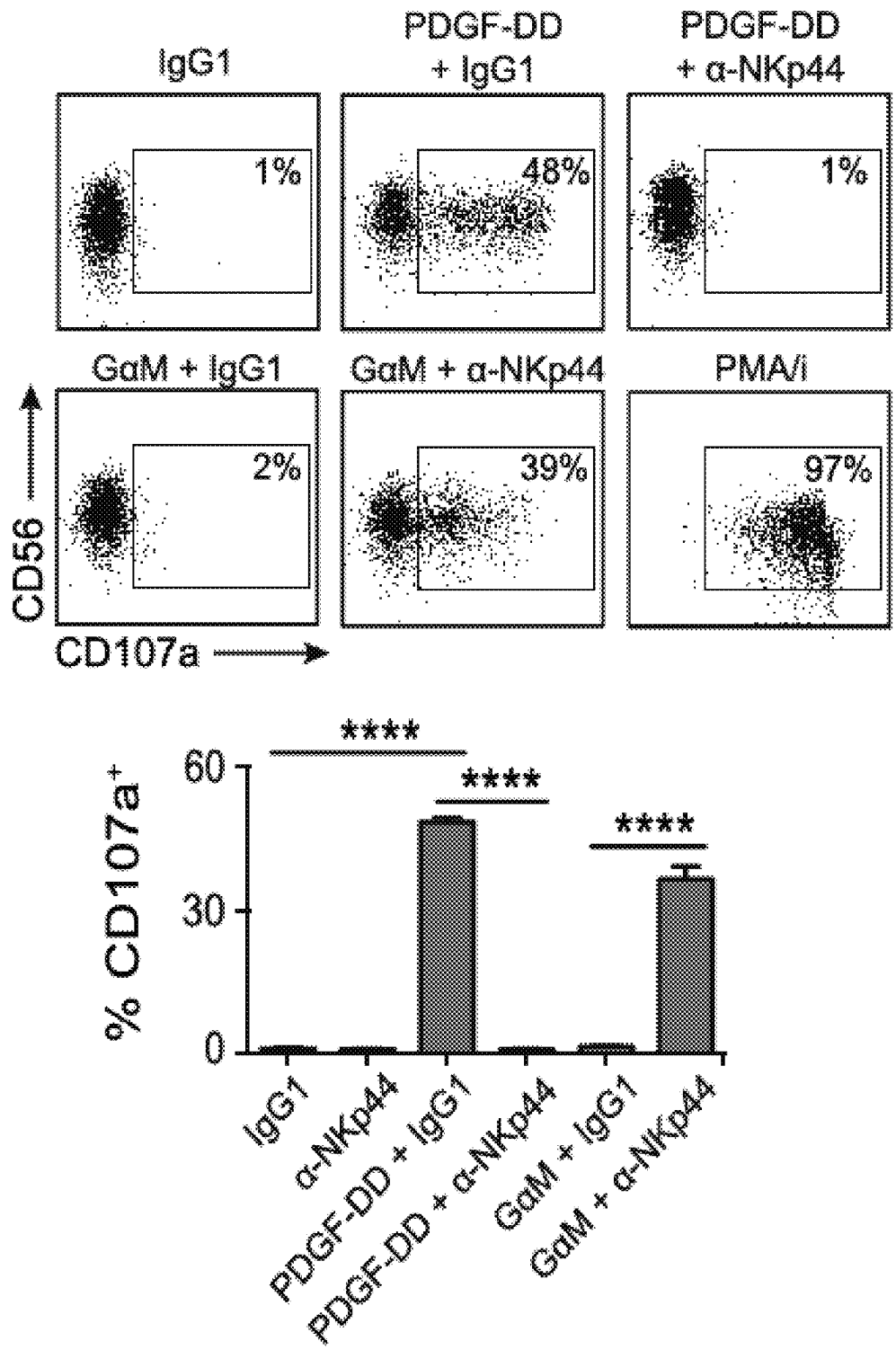

We next determined the impact of PDGF-DD-NKp44 interactions on NK cell functions. Incubation of IL-2-activated NKp44+ NK cells from normal donors with increasing concentrations of PDGF-DD induced dose-dependent cell surface expression of CD107a (FIG. 10B), which is indicative of cytokine secretion and/or the release of lytic granules. Induction of CD107a expression was blocked by anti-NKp44 (FIG. 10C), corroborating that PDGF-DD acted via NKp44 and not through other receptors. Similar induction of CD107a was observed when NK cells were stimulated with an NKp44 surrogate ligand (i.e., anti-NKp44 antibody cross-linked with a secondary antibody) (FIG. 10C). Although PDGF-DD clearly induced cell surface expression of CD107a, forced expression of PDGF-DD in target cell lines normally resistant to NK cell killing was insufficient to elicit NK cell cytotoxicity and only modestly enhanced antibody-dependent cellular cytotoxicity, which relies on activation of FcγRIII (CD16) on NK cells by an antibody bound to target cells (data not shown). These results are consistent with previous studies showing that NKp44 promotes target cell lysis only in combination with other activating receptors (Sivori et al., 2000; Vitale et al., 1998).

Figure 3J:
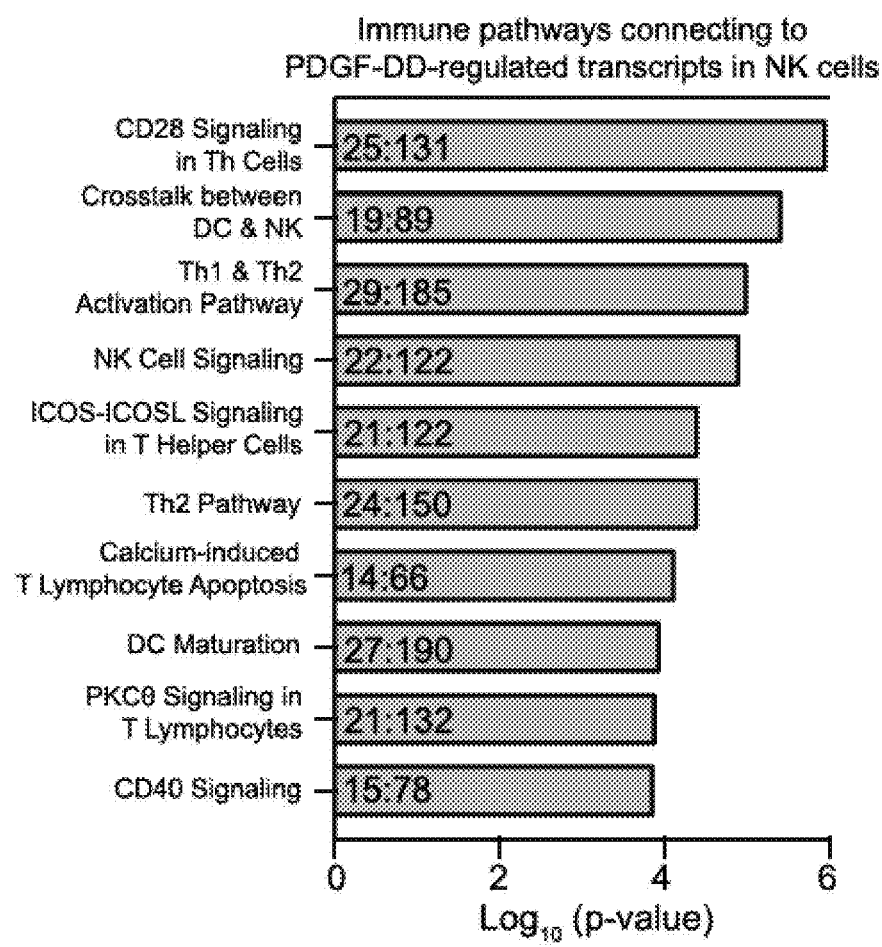
Figure 10D:
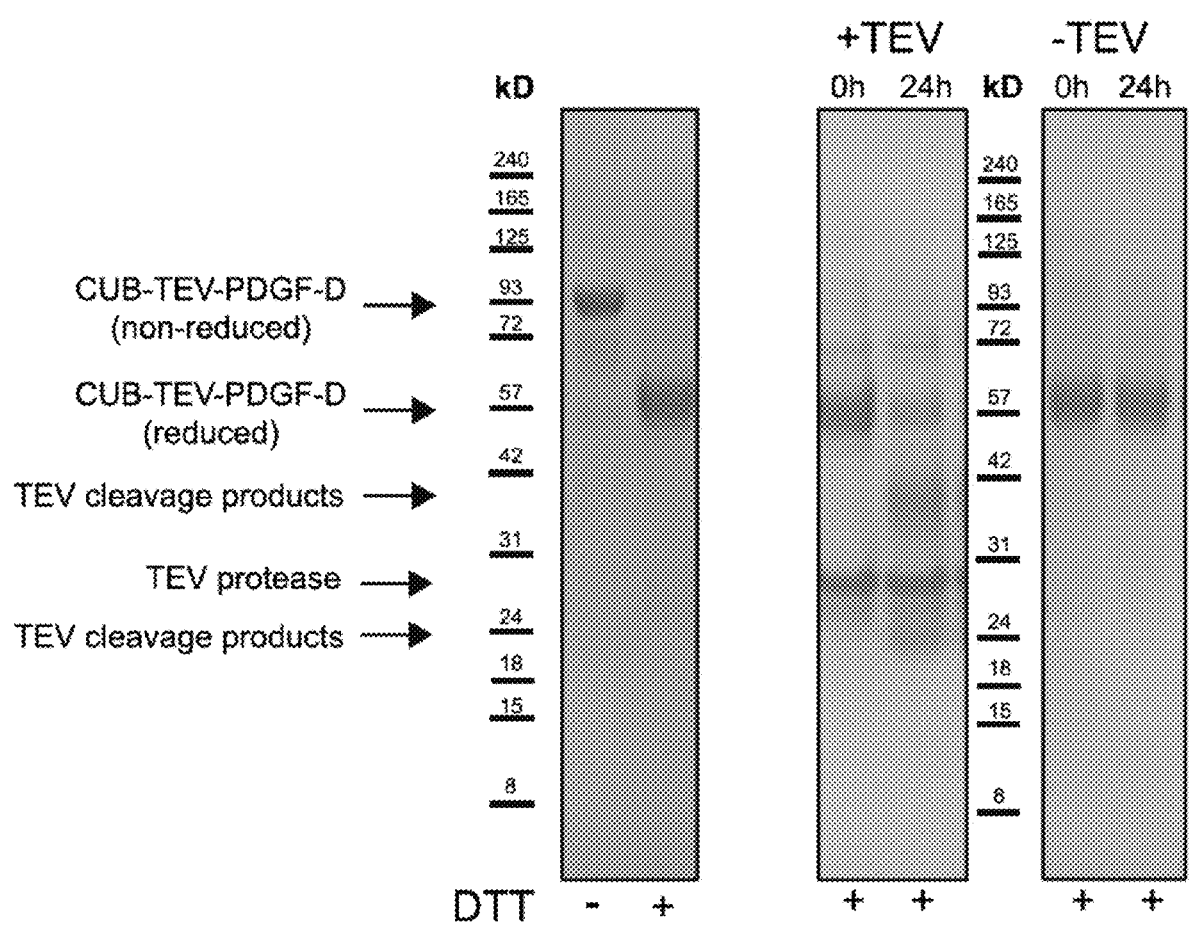
Figure 10E:
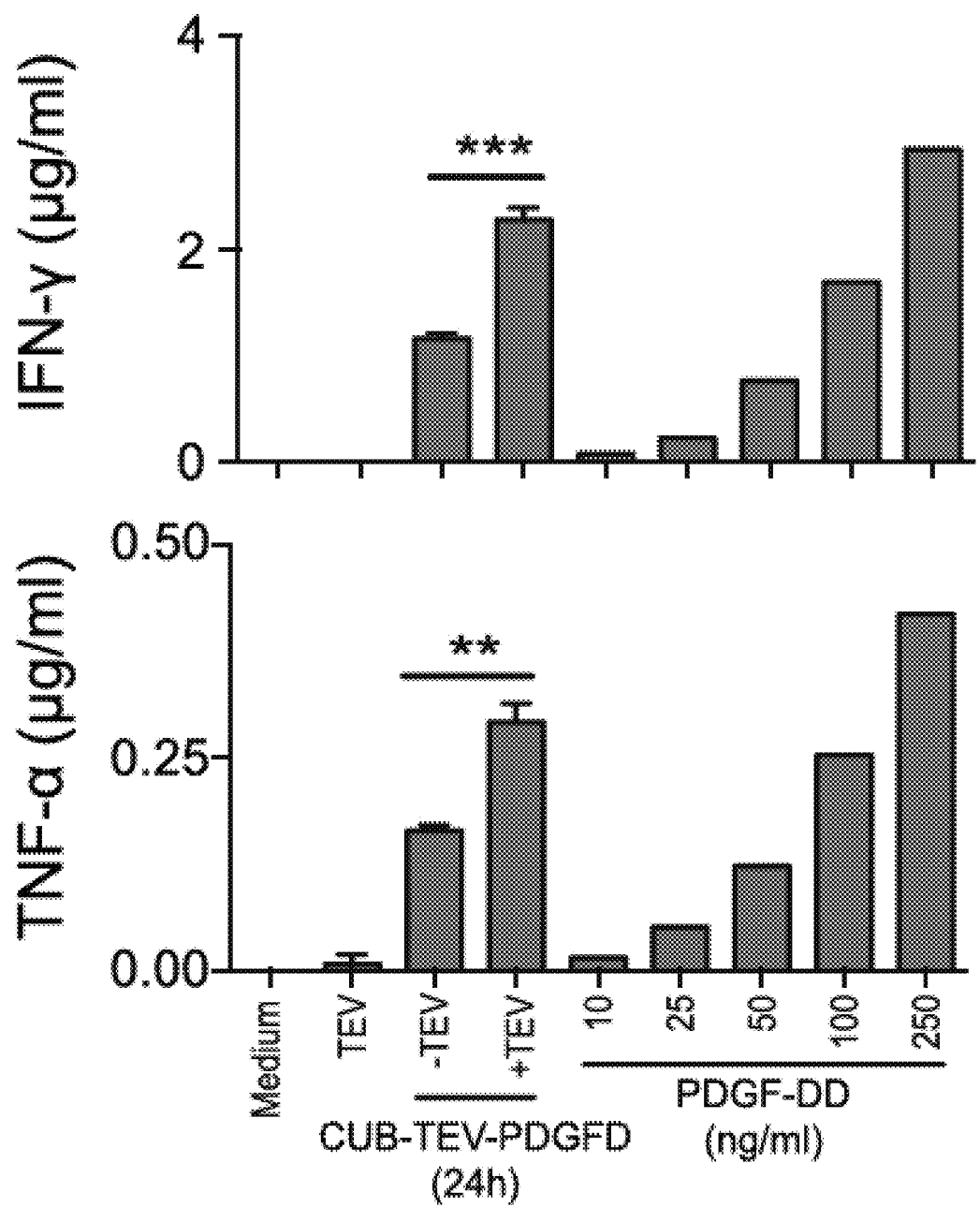
Figure 10F:
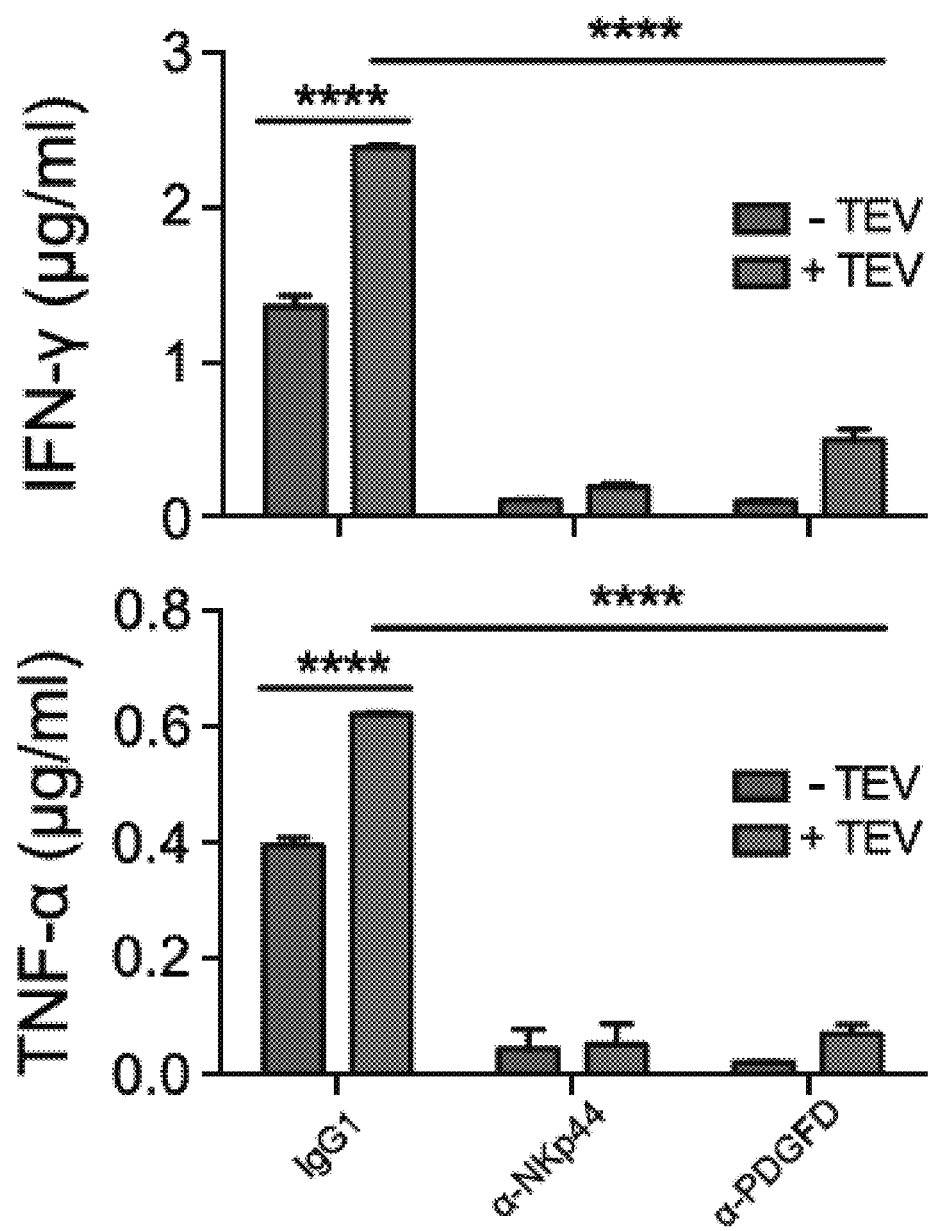

In contrast, PDGF-DD alone was sufficient to induce robust and dose-dependent IFN-γ and TNF-α secretion by interleukin (IL)-2-activated NKp44± NK cells (FIGS. 3C and 3D), which was blocked by anti-NKp44 (FIGS. 3E and 3F), further supporting specific PDGF-DD/NKp44 interaction. Induction of IFN-γ and TNF-α was also obtained by stimulating NK cells using antibody mediated cross-linking of NKp44 as surrogate ligand (FIGS. 3E and 3F). PDGF-DD stimulated the secretion of IFN-γ and TNF-α from NK cells derived from normal donors but not from an individual carrying a homozygous deletion of the TYROBP gene that encodes for DAP12 (FIGS. 3E and 3F). These DAP12-deficient NK cells lack cell surface expression of NKp44 as well as all DAP12-associated receptors (Fuchs et al. 2005). Intracellular staining for IFN-γ and TNF-α revealed that PDGF-DD stimulation of normal NK cells, but not DAP12-deficient NK cells, induced IFN-γ-producing cells as well as bifunctional cells secreting both IFN-γ and TNF-α (FIG. 3G). Cell surface staining for NKp44 of PDGF-DD-stimulated NK cells showed downregulation of NKp44 (FIG. 3H), probably reflecting ligand-induced internalization of this receptor. To provide further evidence that active PDGF-DD induces NK cell cytokine secretion, we engineered a construct encoding a full-length PDGF-D protein with a tobacco etch virus (TEV) protease cleavage site (CUB-TEV-PDGFD) in front of the growth factor domain. Incubation of CUB-TEV-PDGFD with TEV protease released active PDGF-DD (FIG. 10D), which effectively induced NK cell secretion of IFN-γ and TNF-α (FIGS. 10E and 10F). CUB-TEV-PDGFD was in part active, probably because CUB-TEV-PDGFD is cleaved into PDGF-DD by serum proteases during the time required to perform the assay. We asked how PDGF-DD impacts global gene expression in NK cells by RNA sequencing (RNA-seq) of unstimulated and PDGF-DD stimulated NK cells from four different donors. Collectively, induction of 1,384 unique transcripts and downregulation of 721 transcripts was evident in the transcriptional profiles of PDGF-DD-activated NK cells compared to unstimulated NK cells (FIG. 3I). Induced genes encoded IFN-γ, TNF-α, and other proinflammatory cytokines including LTa and GM-CSF, as well as chemokines, such as CCL3, CCL4, CCL4L2, XCL1, and XCL2 (FIG. 3I). Transcripts encoding cell surface markers of activation, such as TNFSF4 and TNFRSF9 (CD134L and CD137), and transcription factors involved in ITAM signaling, cellular activation, and proliferation, such as IRF4, EGRs, and EOMES, were also upregulated (FIG. 3I). Downregulated genes encoded components of the ITAM signaling pathways, suggesting a feedback mechanism in which the functional activation of ITAM signaling mediators is paralleled by their reduced transcription. Ingenuity pathway analysis (IPA) of PDGF-DD induced transcriptional changes corroborated the induction of pathways involved in NK cell and T cell activation, proliferation, and survival as well as IFN-γ signaling (FIG. 3J). Thus, PDGF-DD binding and signaling through the NKp44/DAP12 receptor complex leads to pronounced NK cell activation characterized by secretion of proinflammatory cytokines and chemokines Example 3: PDGF-DD Triggers Cytokine Secretion in ILC3 and ILC1

Figure 4A:
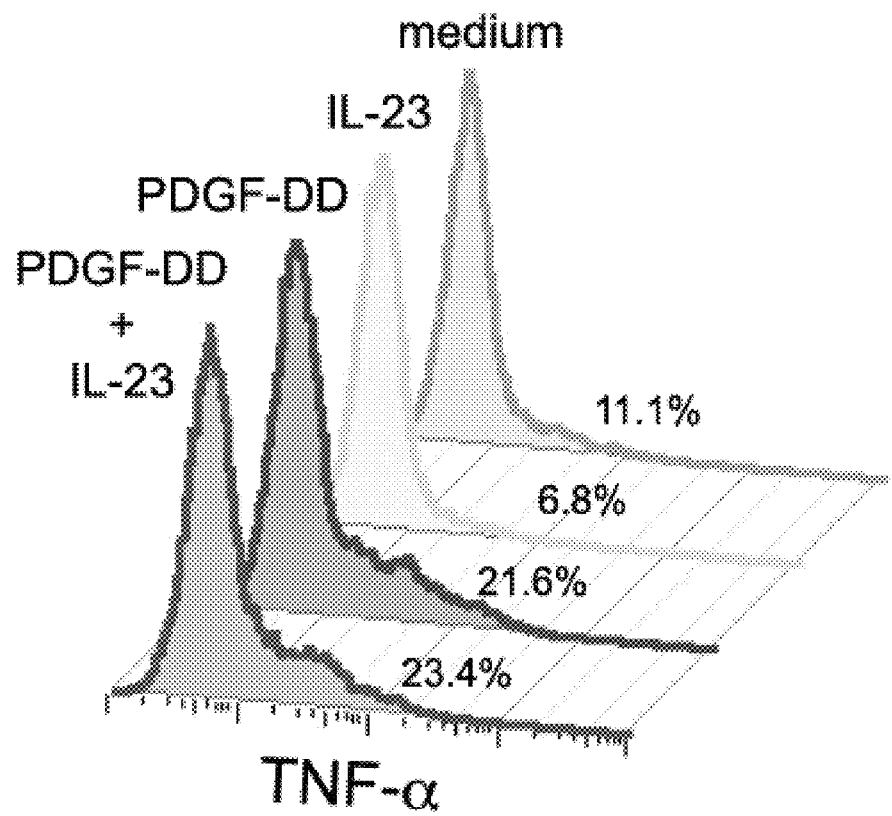
Figure 4B:
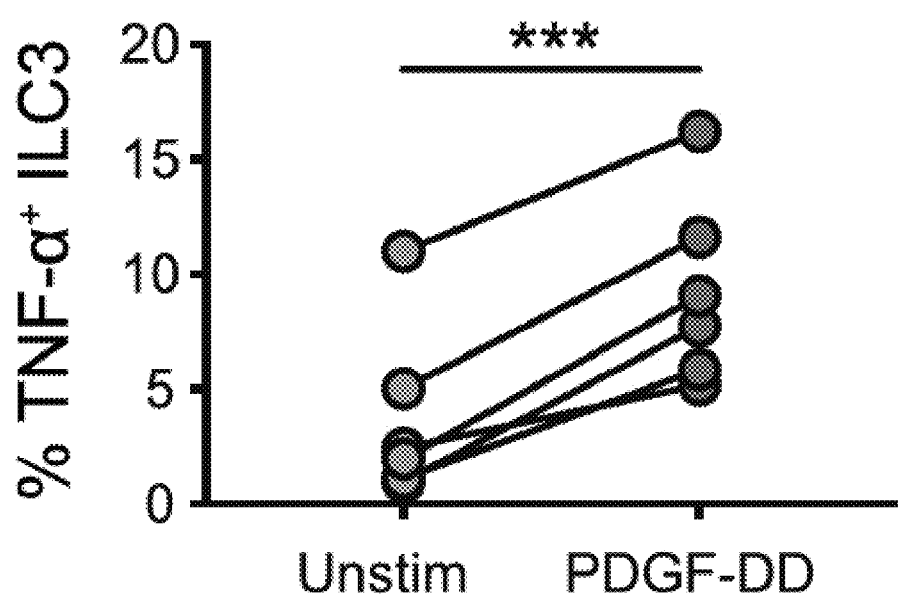
Figure 4C:
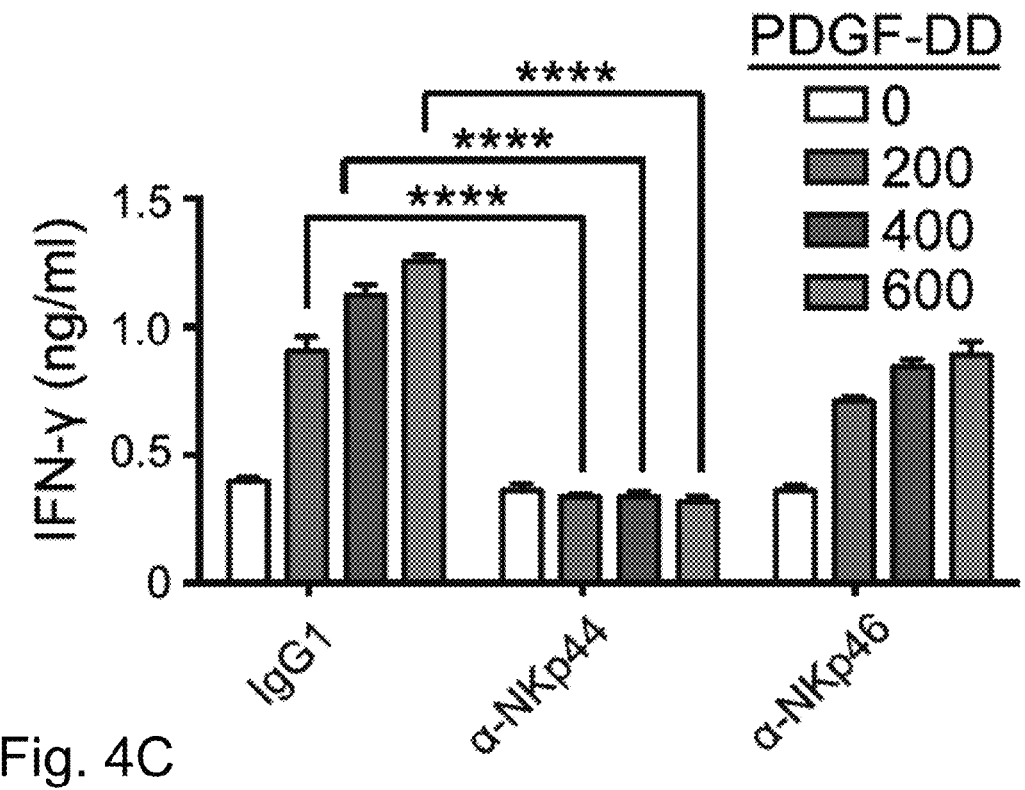
Figure 4D:
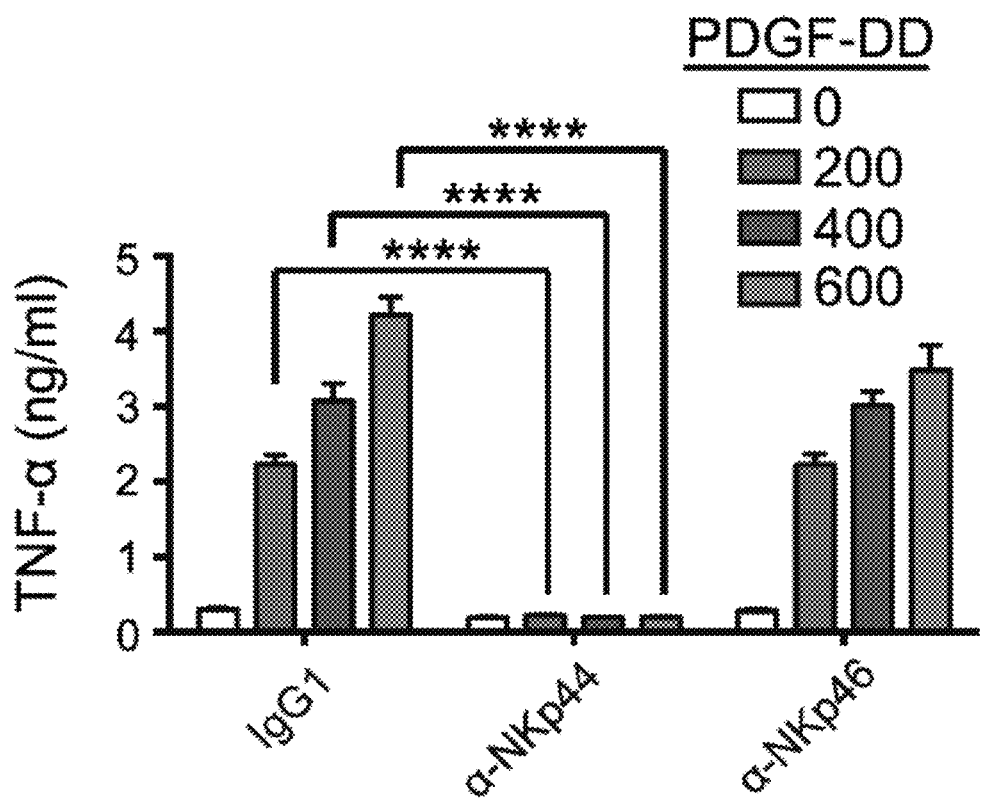
Figure 4F:
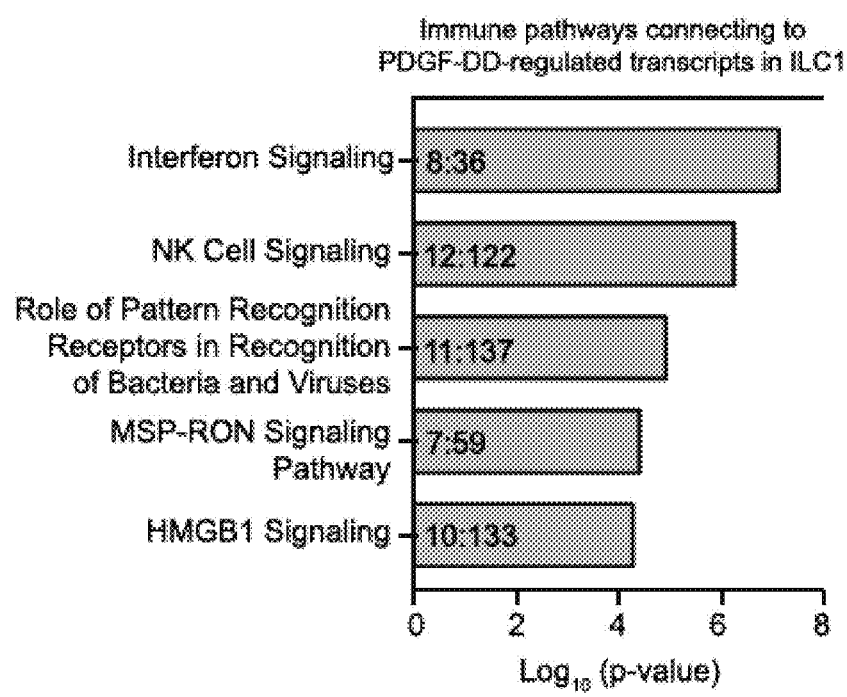
Figure 11:
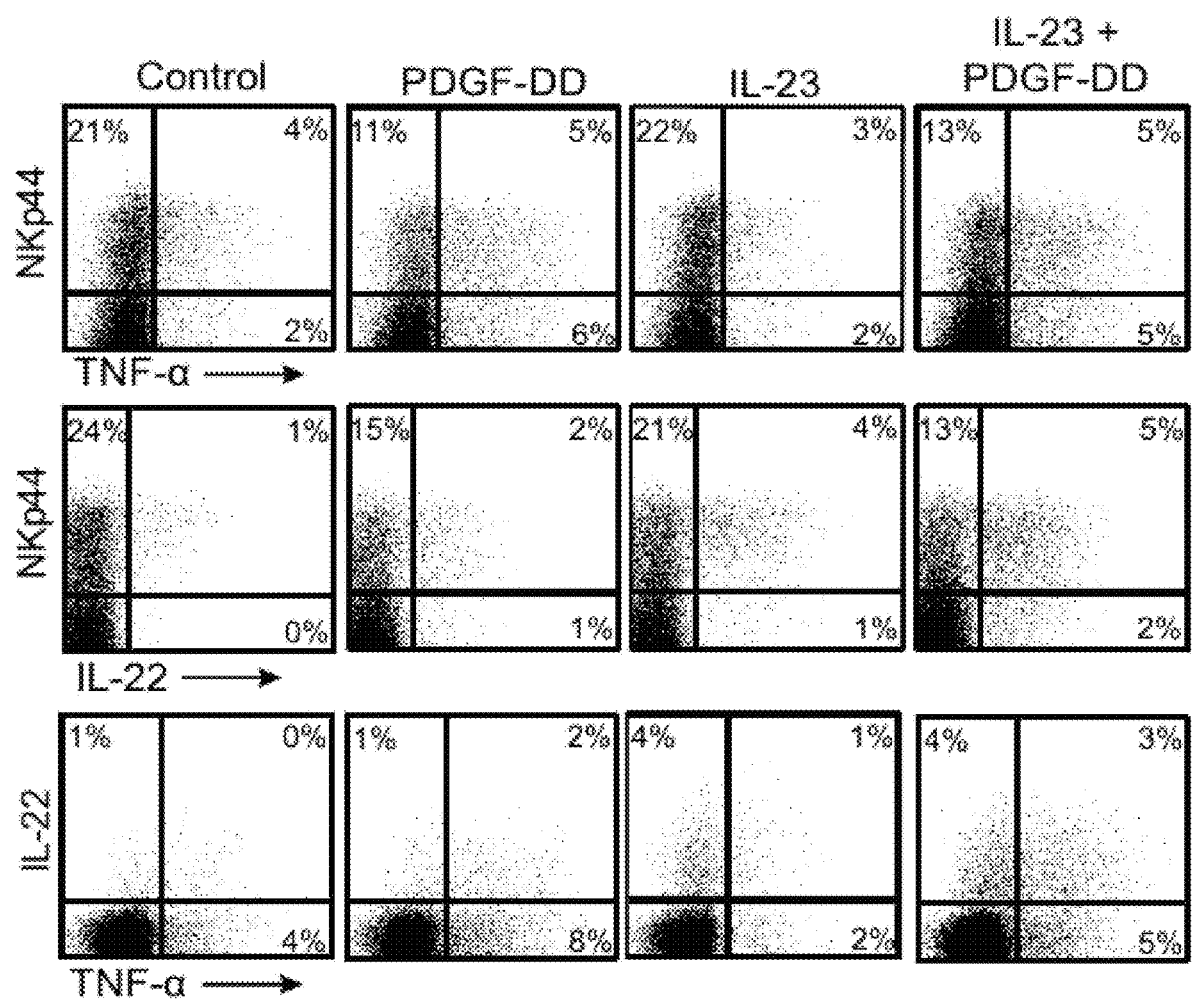
FIG. 11 shows PDGF-DD Binding to NKp44 Induces TNF-a Secretion by ILC3. Representative dotplots of intracellular TNF-a and IL-22 content and cell surface NKp44 from freshly isolated tonsil ILC3 stimulated with PDGF-DD and/or IL-23. The percentage of cytokine-positive cells is indicated in each quadrant.

We sought to test whether PDGF-DD also activated human ILC3 and intraepithelial ILC1, because these cells were initially revealed through their distinctive expression of NKp44 in mucosal tissues (Cella et al., 2009 Fuchs et al., 2013) and have been implicated in cancer immunosurveillance (Carrega et al., 2015; Dadi et al., 2016). Although NKp44+ ILC3 isolated from tonsil can produce IL-22, GM-CSF, and TNF-α, PDGF-DD selectively induced TNF-α (FIGS. 4A, 4B, and 11). IL-23 induced IL-22, as reported (Cella et al., 2009), while concurrent PDGF-DD and IL-23 stimulation did not further increase TNF-α or IL-22 production (FIG. 4A, 4B, and 11). This result corroborates the observation that stimulation of NKp44 in ILC3 with a specific mAb as a surrogate ligand selectively induces TNF-α (Glatzer et al., 2013). We also determined the impact of PDGF-DD on ILC3 cultured in vitro with IL-16 and IL-2, a condition that converts ILC3 into IFN-γ-producing ILC1-like cells (Cella et al., 2010). PDGF-DD promoted secretion of both IFN-γ (FIG. 4C) and TNF-α (FIG. 4D) in a dose-dependent fashion that was blocked by anti-NKp44, but not a control antibody. We finally tested the impact of PDGF-DD on the transcriptome of tonsilar intraepithelial ILC1 expanded in vitro with IL-2. In comparison to unstimulated ILC1, PDGF-DD induced the expression of 127 genes and downregulation of 102 genes (FIG. 4E). PDGF-DD-induced genes were similar to those induced in NK cells, including IFNG, CCL1, CCL3, CCL4, and IRF4 (FIG. 4E). IPA of PDGF-DD-induced changes in ILC1 gene expression profiles confirmed the involvement of lymphocyte activation and IFN-γ signaling pathways (FIG. 4F). We conclude that PDGF-DD induces an NKp44-dependent proinflammatory gene program in ILC3, converted ILC3, and intraepithelial ILC1.

Example 4: PDGF-DD-Activated NK Cells Induce Tumor Cell Growth Arrest

Figure 5A:
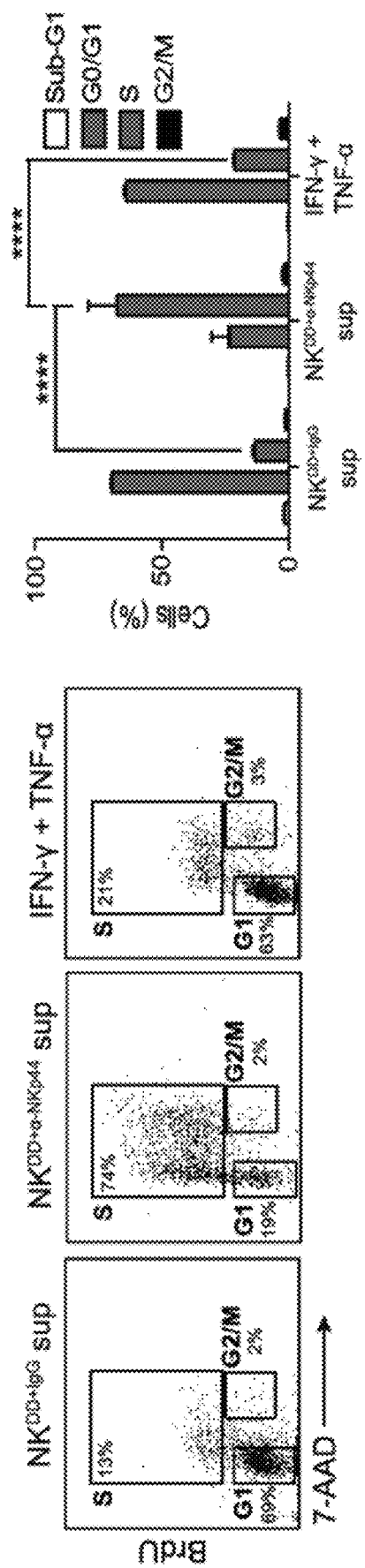
FIG. 5A, FIG. 5B, FIG. 5C, FIG. 5D, FIG. 5E, FIG. 5F, FIG. 5G, FIG. 5H and FIG. 5I show PDGF-DD binding to NKp44 induces NK cell secretion of cytokines that mediate tumor growth arrest.
Figure 5B:
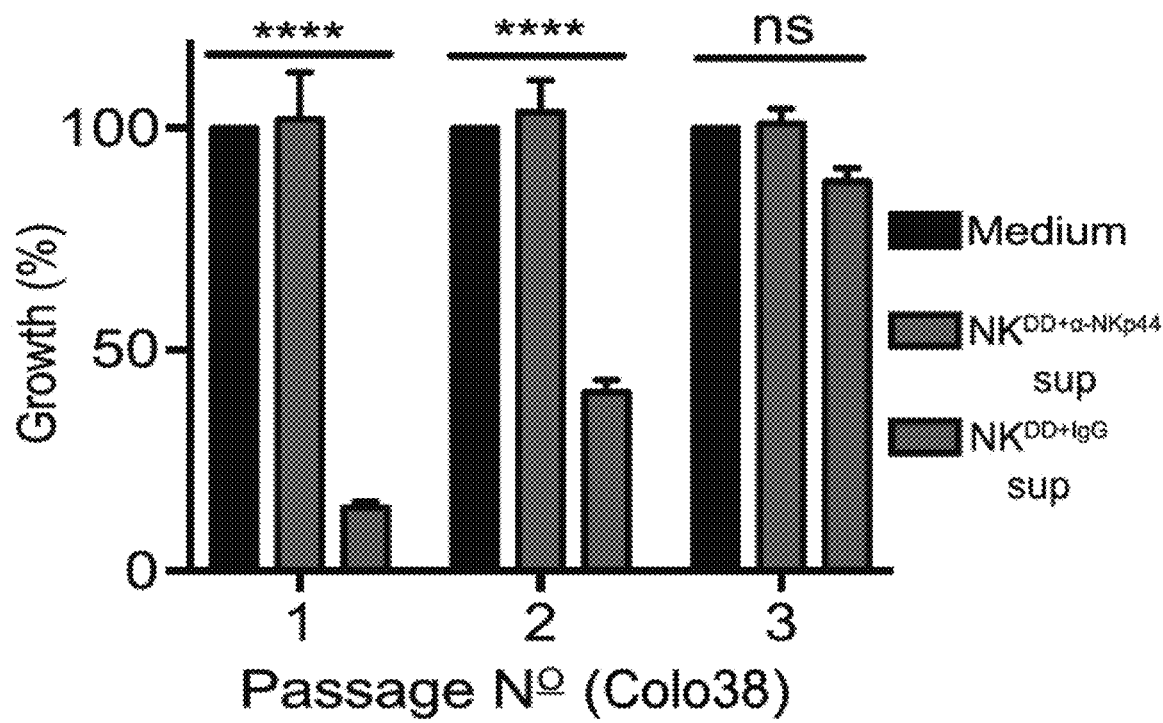
Figure 5C:
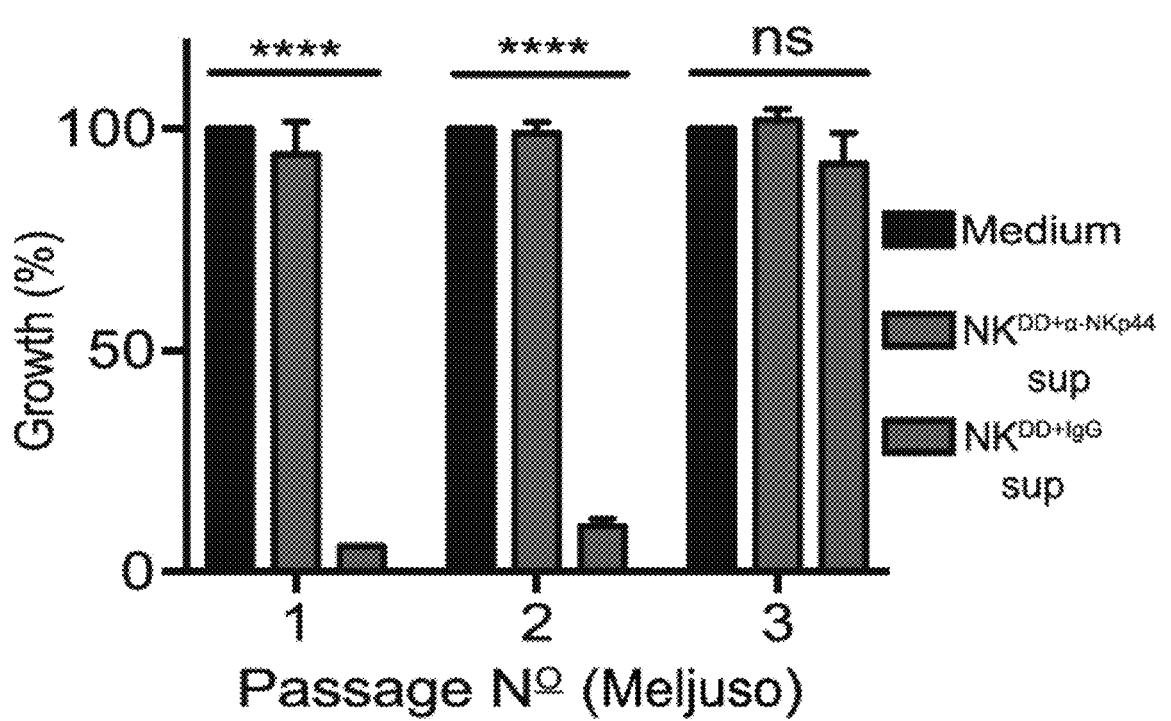
Figure 5D:
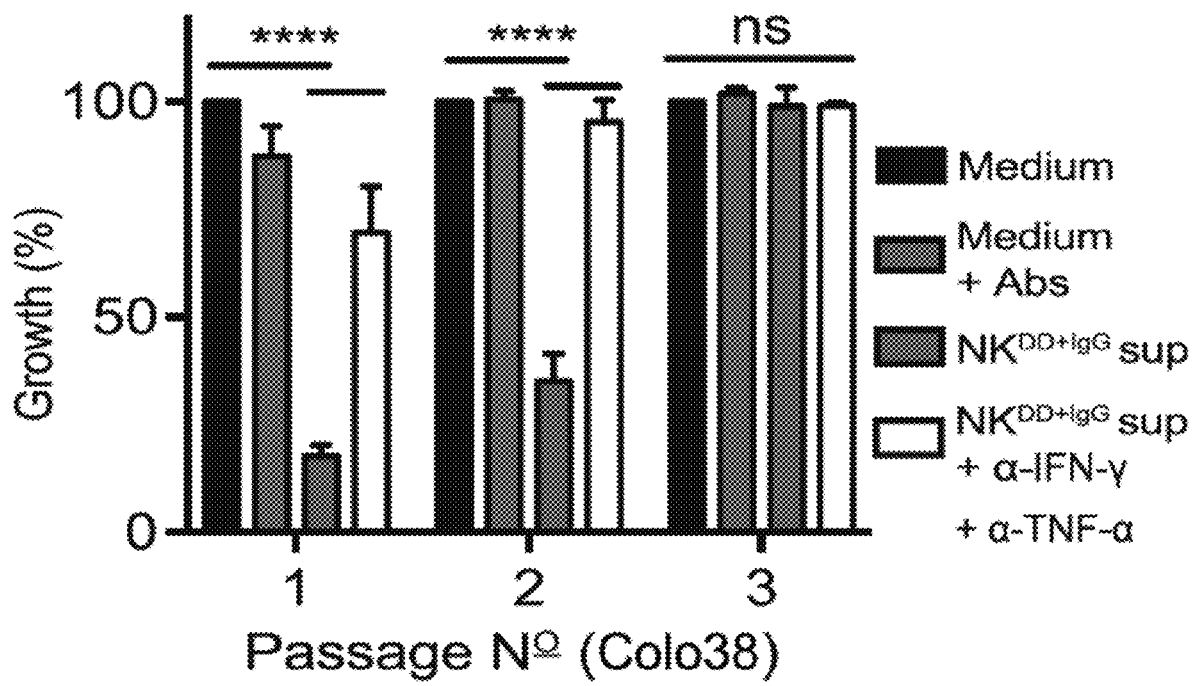

We next investigated the impact of the PDGF-DD/NKp44 interactions on tumor cells. It has been shown that CD4+ Th1 cells can induce tumor cell growth arrest through the secretion of IFN-γ and TNF-α (Braumuller et al., 2013). Because PDGF-DD/NKp44interactions induced IFN-γ and TNF-α secretion by NK cells, ILC3 and ILC1, we tested the hypothesis that this interaction might promote cell-cycle arrest in tumor cell lines. Melanoma cell lines treated with tissue culture (TC) supernatants from NK cells stimulated with PDGF-DD plus control IgG (NK$^{DD+IgG}$ sup) proliferated less and had more cells arrested in G1 than did cells treated with TC supernatants from NK cells stimulated with PDGF-DD plus a blocker of NKp44 (NK$^{DD+\alpha NKp44}$ sup) (FIG. 5A). Tumor cell growth arrest even persisted through one or two addition I cell passages after replacing NK$^{DD+IgG}$ sup with complete growth medium lacking cytokines (FIGS. 5B and 5C). The growth inhibitory effect of NK$^{DD+IgG}$ sup was neutralized by the addition of mAbs to IFN-γ and TNF-α (FIG. 5D). Thus, cytokine-containing NK$^{DD+IgG}$ sup instigate a transient suppression of tumor cell growth.

Figure 5E:
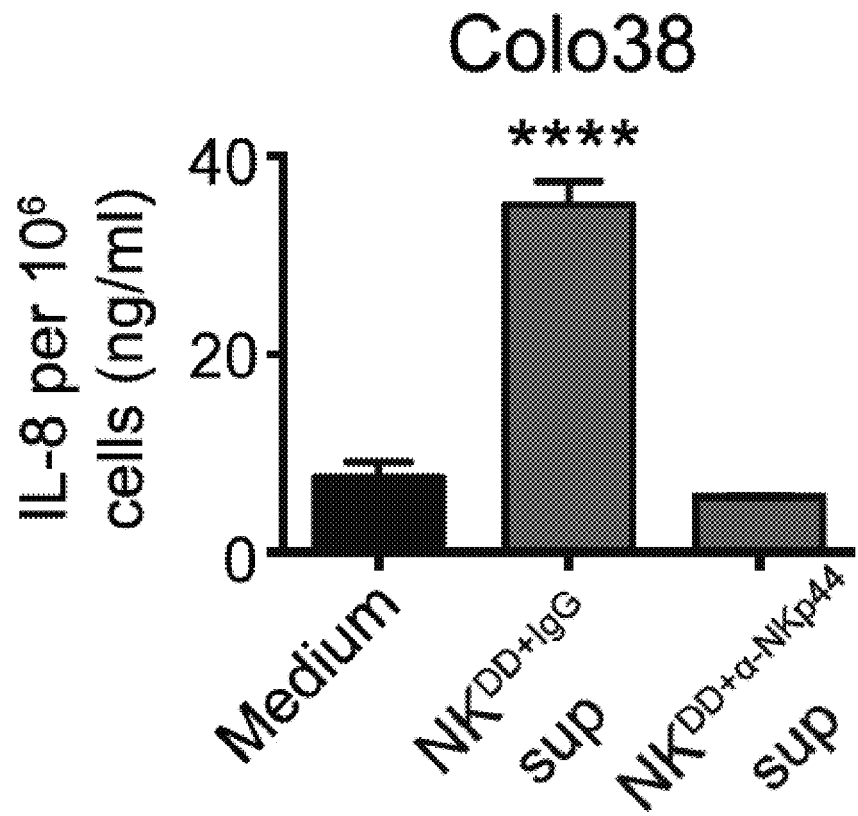
Figure 5F:
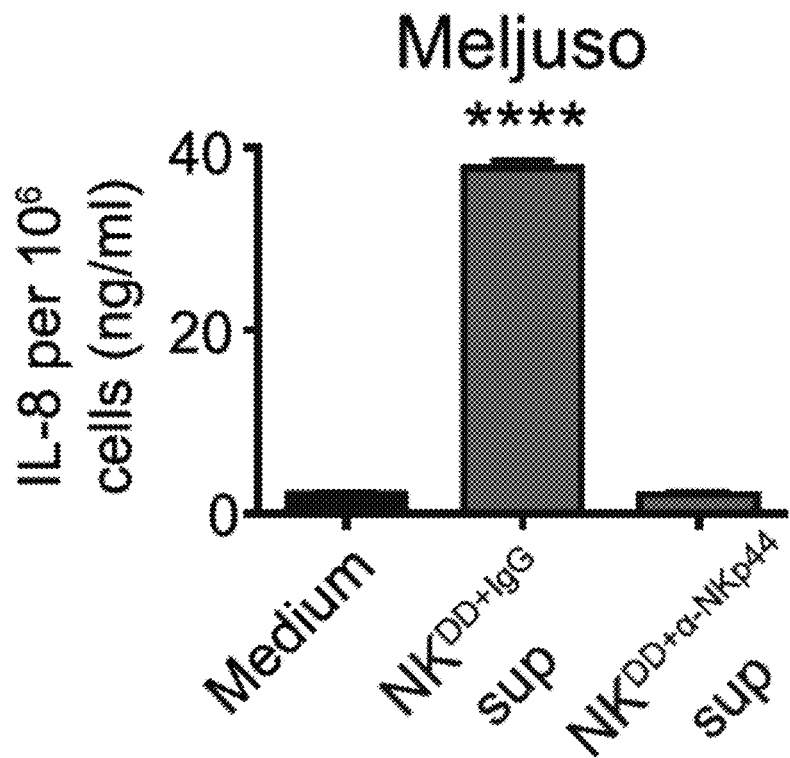
Figure 5G:
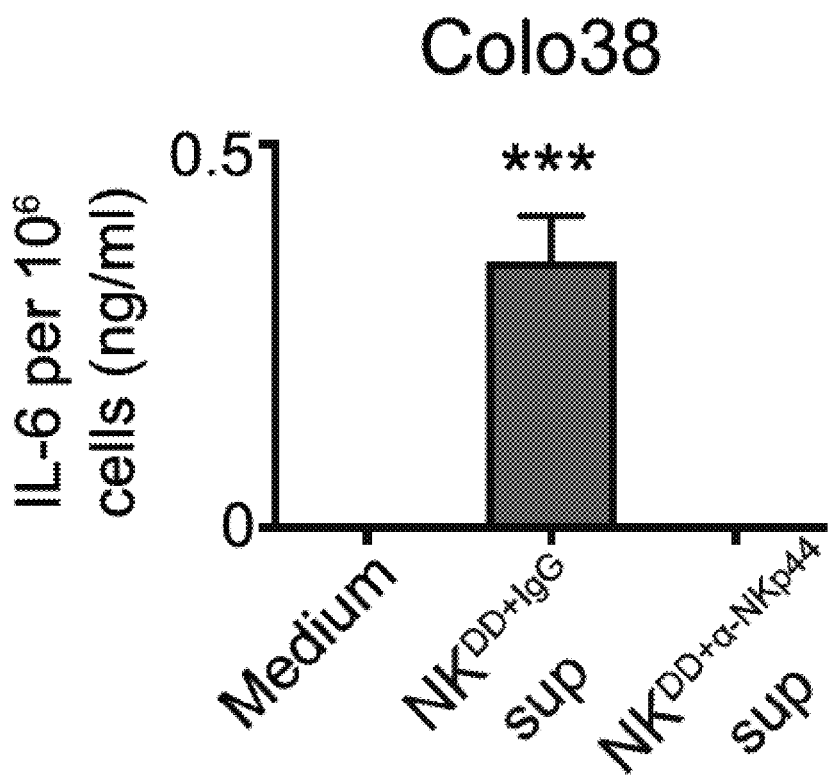
Figure 5H:
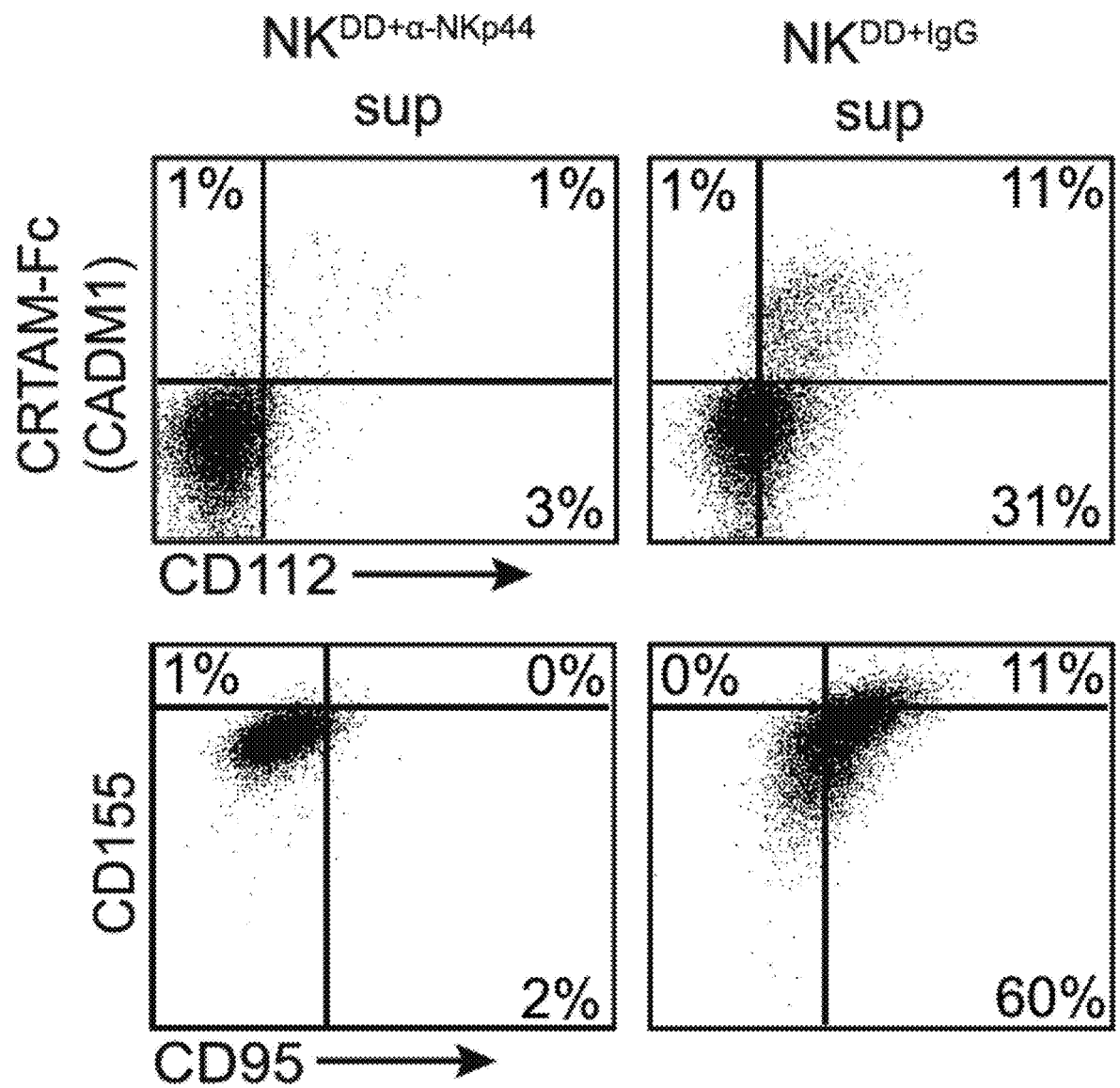
Figure 5I:
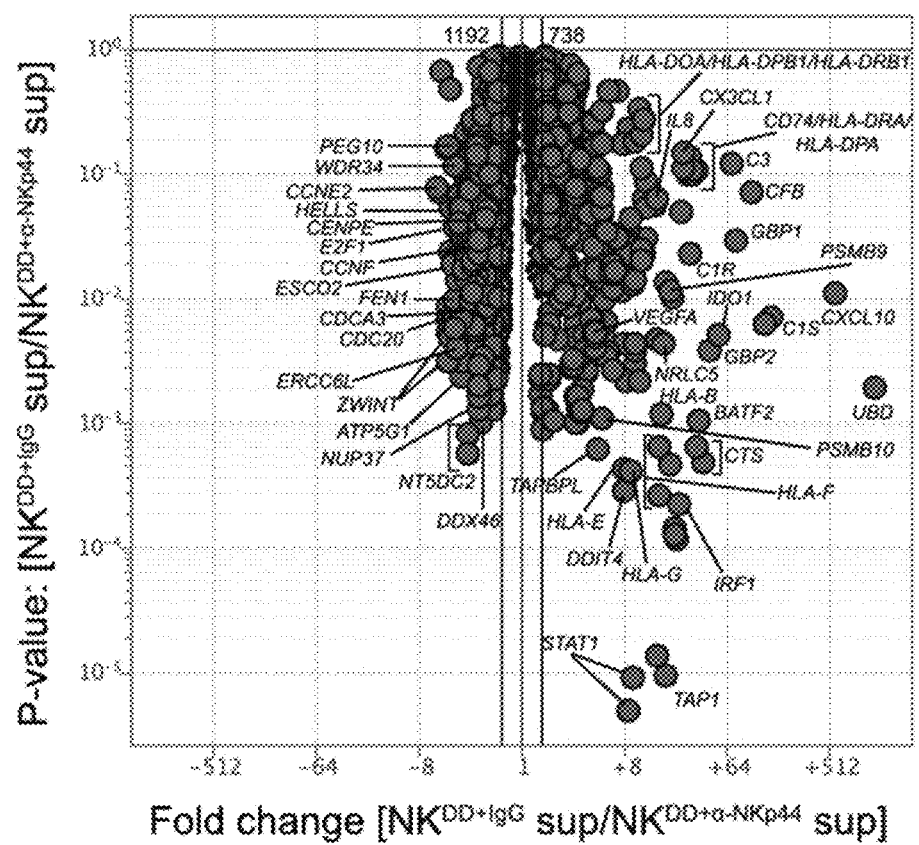
Figure 5I:
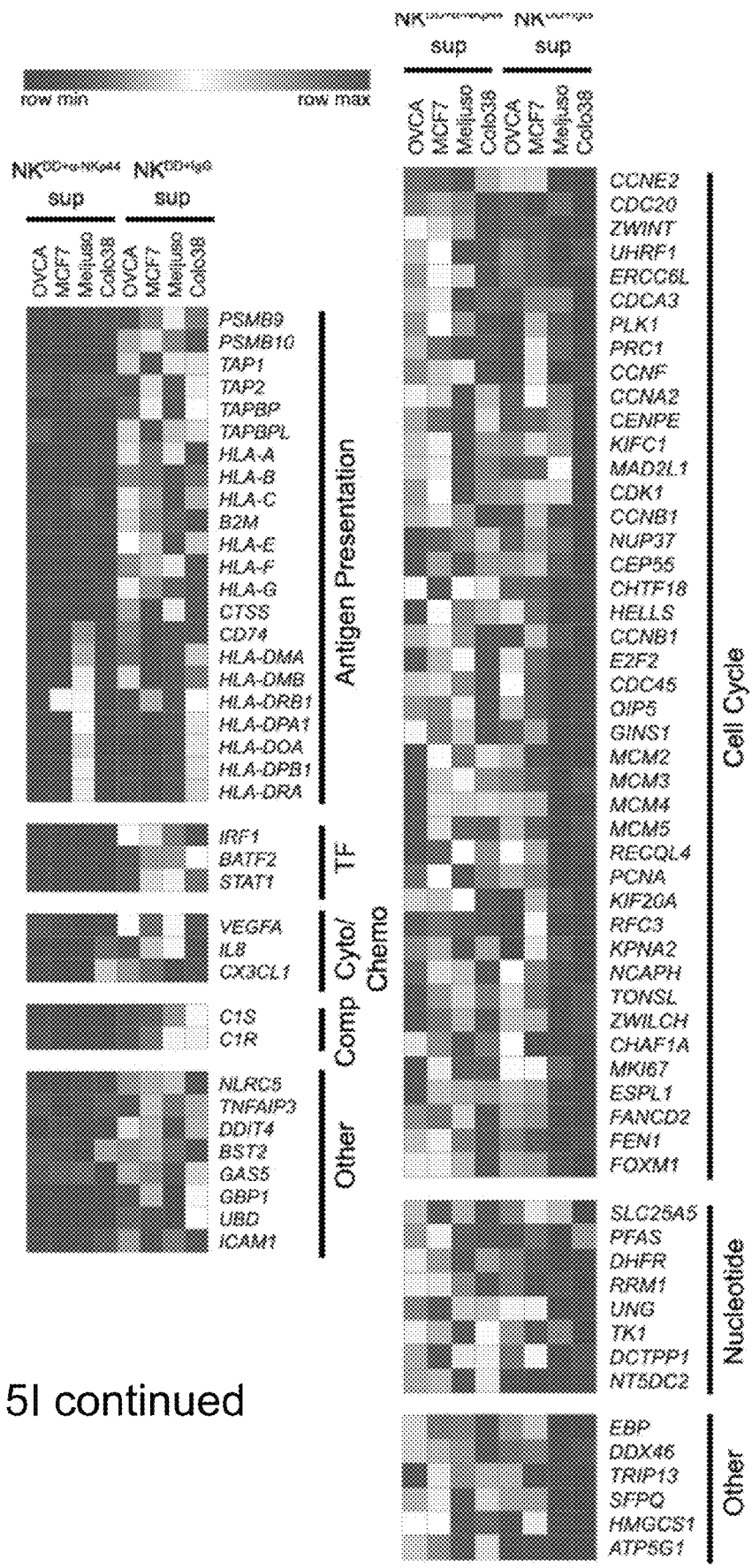

Although arrested in G1, tumor cells treated with NK$^{DD+IgG}$ sup remained metabolically active. They secreted more IL-8 (FIGS. 5E and 5F) and IL-6 (FIG. 5G), which may induce the recruitment of inflammatory cells. Tumor cells treated with NK$^{DD+IgG}$ sup upregulated CADM1, CD112, and CD155, which can either activate or inhibit NK cell-mediated lysis through engagement of the NK cell receptors CRTAM (that binds CADM1) and CD226/CD96/TIGIT (all of which bind CD112 and/or CD155) (FIG. 5H) (Blake et al., 2016). Additionally, tumor cells upregulated CD95 (Fas) (FIG. 5H) that can cause apoptosis upon encountering NK cells expressing CD95L (FasL).

Figure 12:
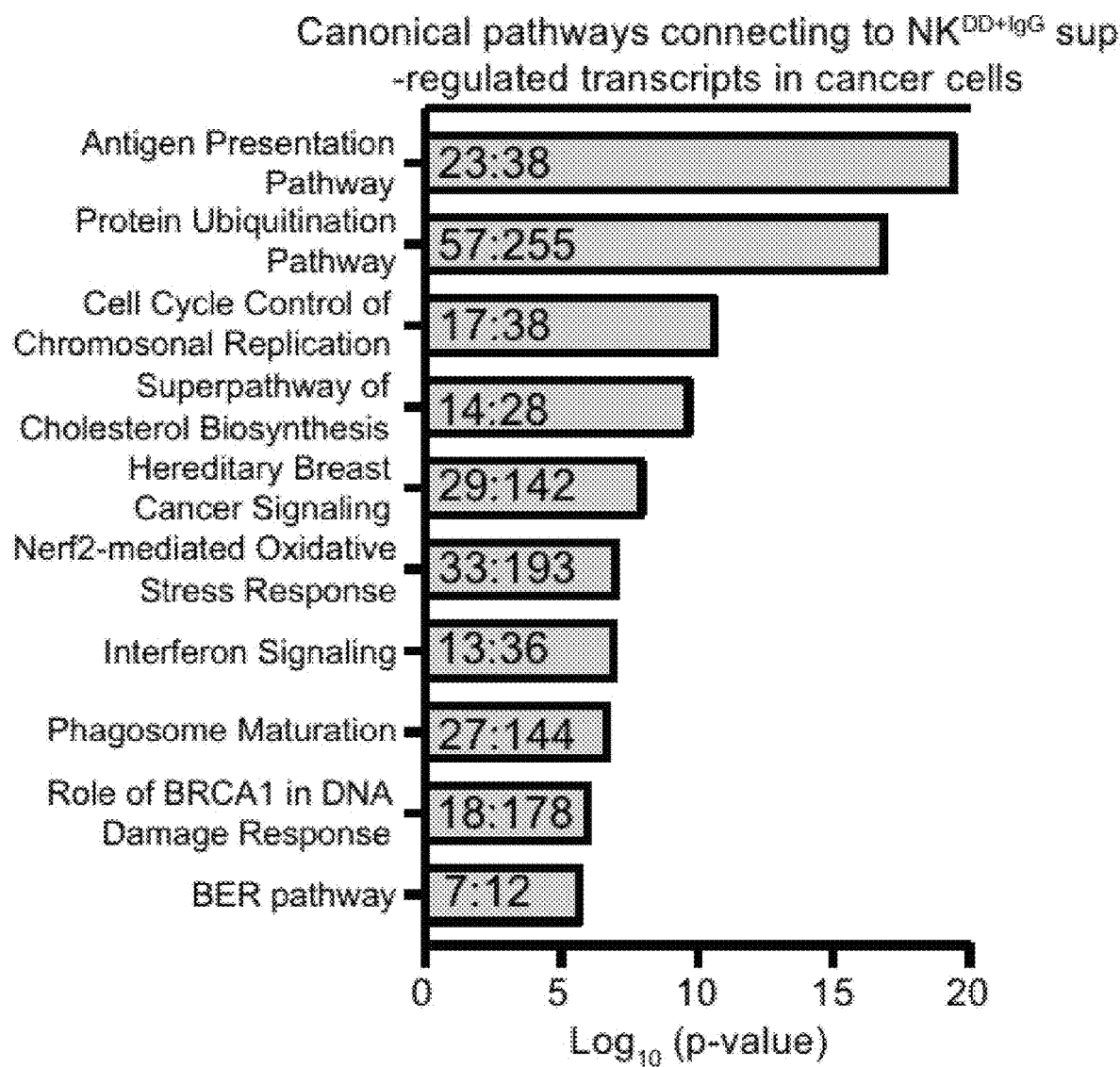
FIG. 12 shows ingenuity pathway analysis of growth-arrested cancer cell Lines Exposed to TC supernatants from PDGF-DD-activated NK cells. Top 10 highest scoring IPA canonical pathways generated from transcripts differentially expressed (±1.5-fold) in cancer cells cultured in NKDD+ IgG sup versus control NKDD+aNKp44 sup. Ratios in columns indicate total NKDD+IgG upregulated genes to the total number of genes in each pathway.

Finally, we examined global gene expression in tumor cell lines treated with either NK$^{DD+IgG}$ sup or NK$^{DD+\alpha NKp44}$ sup by RNA-seq. NK$^{DD+IgG}$ sup induced the expression of numerous unique transcripts (738), many of which reflected the impact of IFN-γ and TNF-α, such as various IFN-γ-inducible components of the antigen presentation pathway (FIG. 4I). 18 and CD155 were also upregulated. Transcripts that were downregulated in comparison to unstimulated cells (1,192) included many cell-cycle genes (FIG. 4I). IPA analysis confirmed that treatment of cancer cells with TC supernatants from PDGF-DD-activated NK cells induced pathways involving IFN-γ signaling, antigen presentation, and cell-cycle control of chromosomal replication (FIG. 12). Altogether, these data show that tumor cells exposed to PDGF-DD-induced NK cell-secreted cytokines undergo cell-cycle arrest but also express inflammatory cytokines, chemokines, and cell-surface ligands that can broadly influence the immune response to tumors.

Figure 6A:
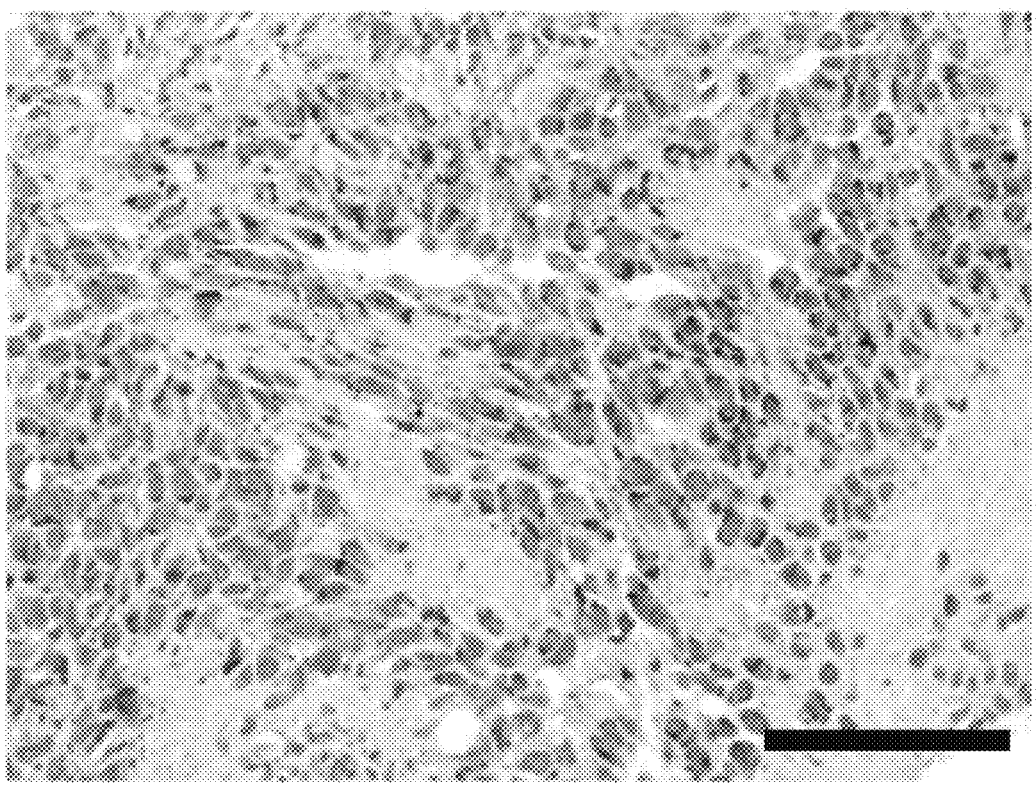
FIG. 6A, FIG. 6B, FIG. 6C, FIG. 6D, FIG. 6E, FIG. 6F, FIG. 6G, FIG. 6H, FIG. 6I, and FIG. 6J show core signatures of PDGF-DD-Activated NK cells and growth-arrested tumor cells correlate with NCR2 Expression in TCGA GBM Cohort.
Figure 6B:
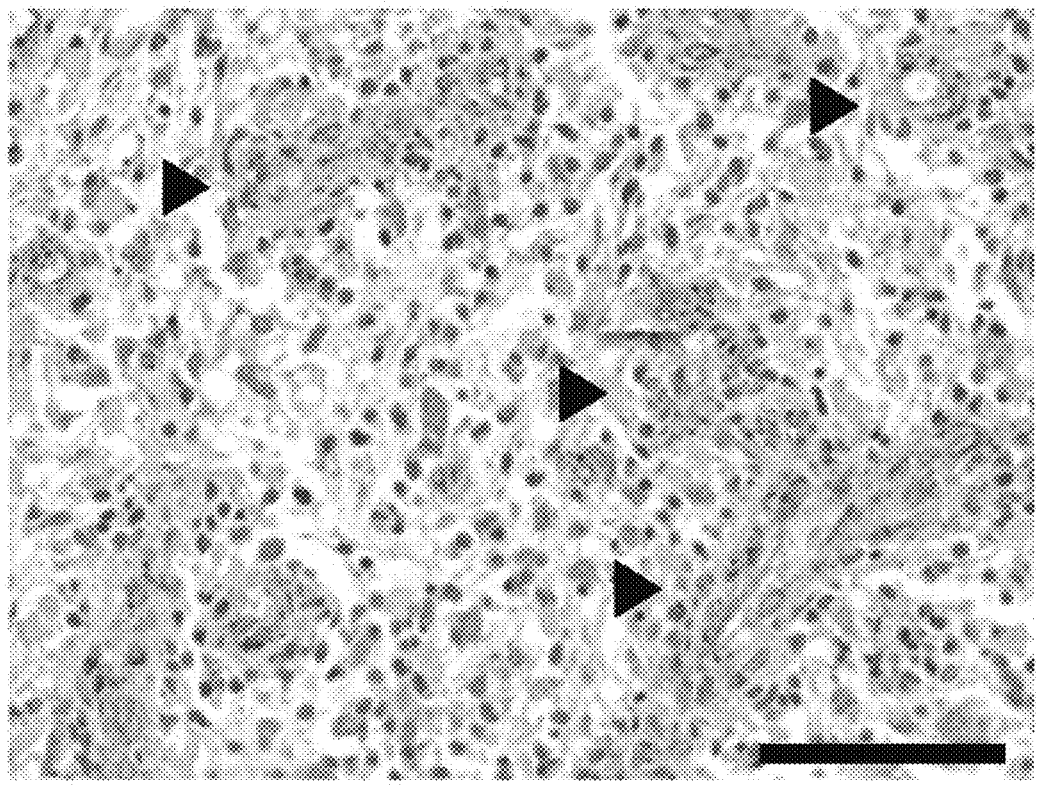
Figure 13A:
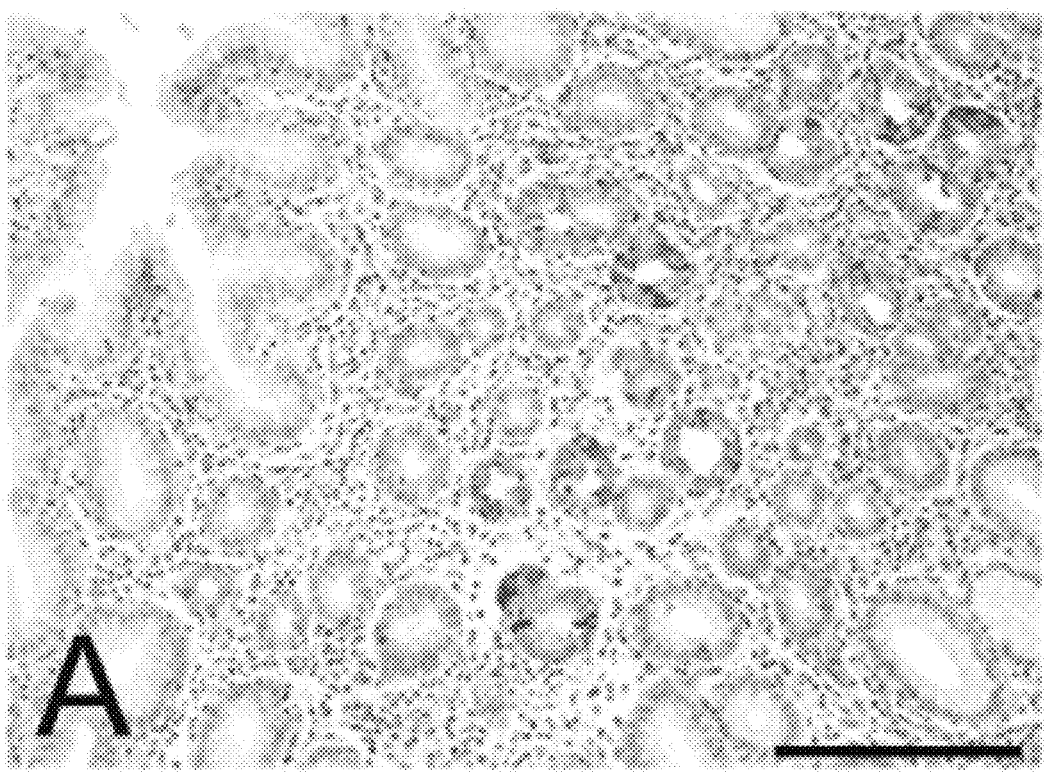
FIG. 13A, FIG. 13B, FIG. 13C, FIG. 13D, FIG. 13E, FIG. 13F, FIG. 13G, FIG. 13H, FIG. 13I, FIG. 13J, FIG. 13K, FIG. 13L, FIG. 13M, FIG. 13N, FIG. 13O, FIG. 13P, FIG. 13Q, FIG. 13R, FIG. 13S, FIG. 13T, FIG. 13U, FIG. 13V, FIG. 13W and FIG. 13X show the expression of PDGF-D in normal and cancerous Human Tissues.
Figure 13B:
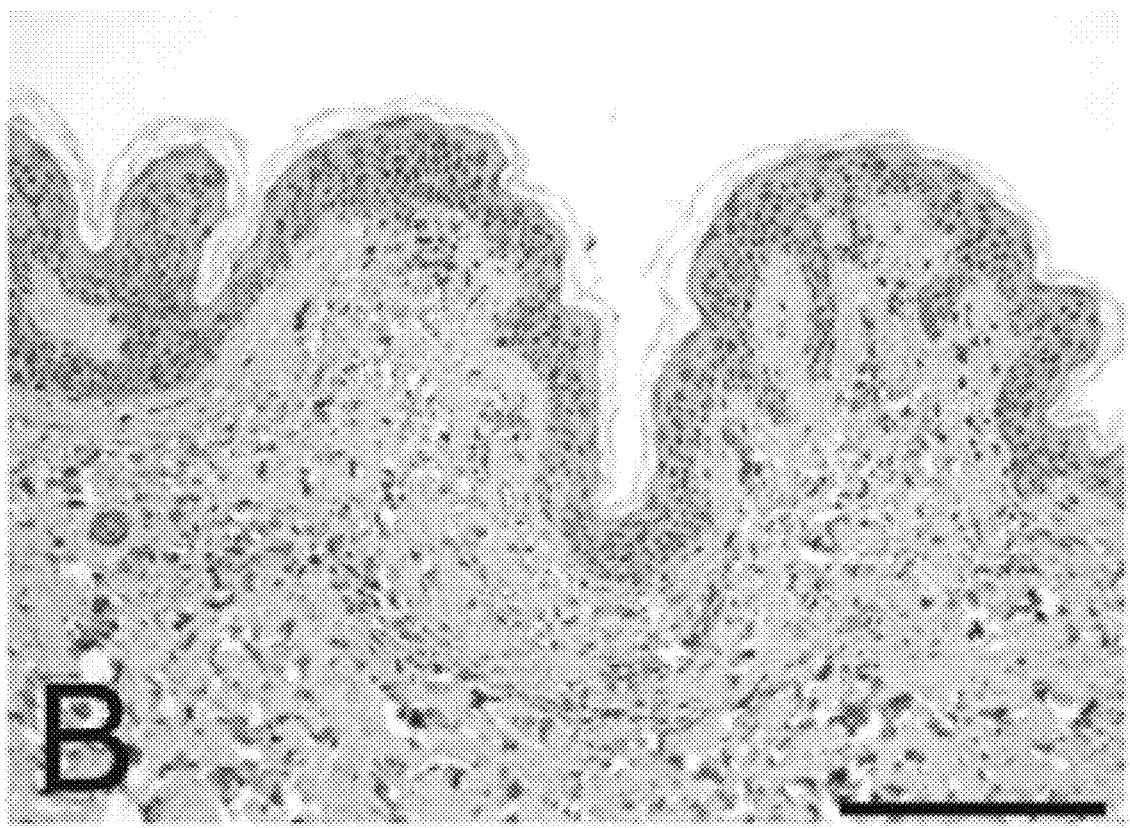
Figure 13C:
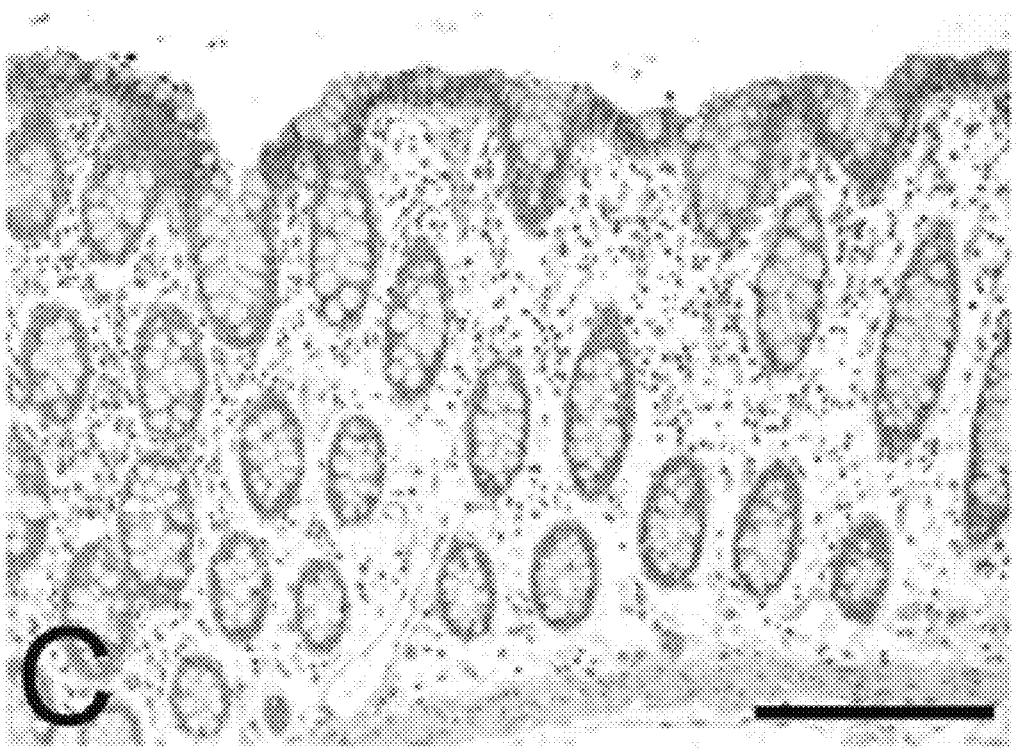
Figure 13D:
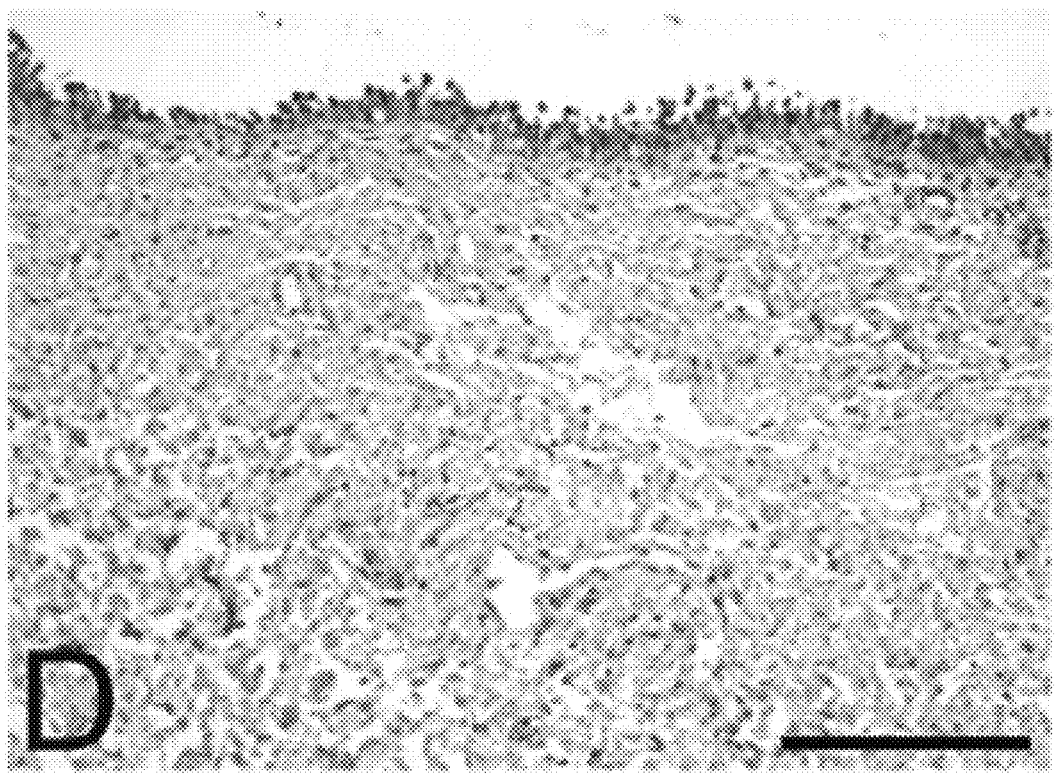
Figure 13E:
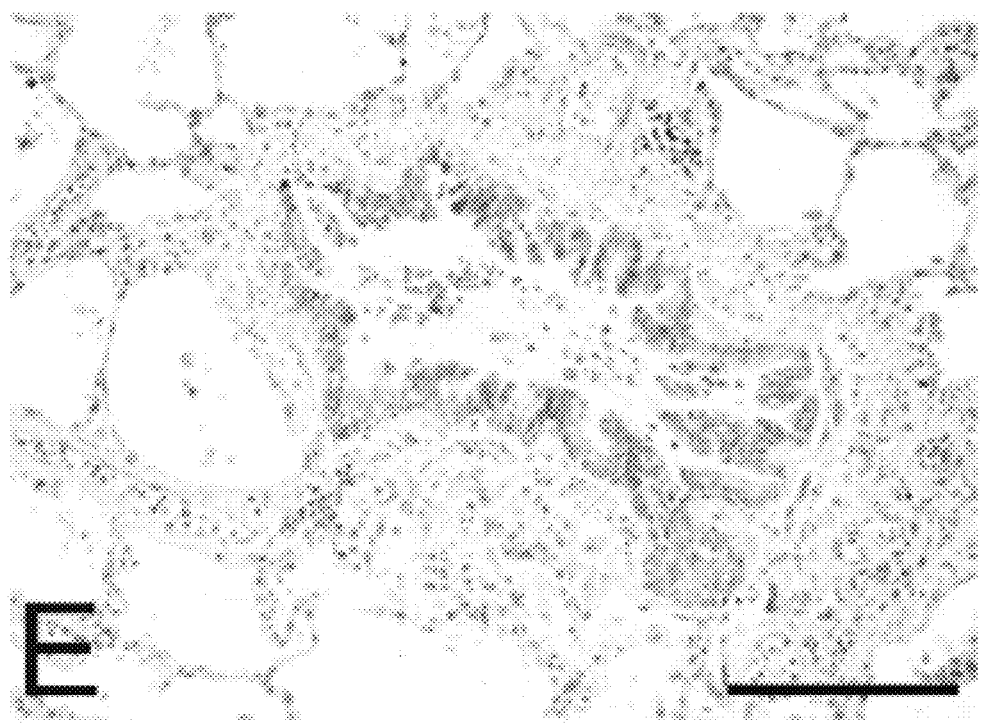
Figure 13F:
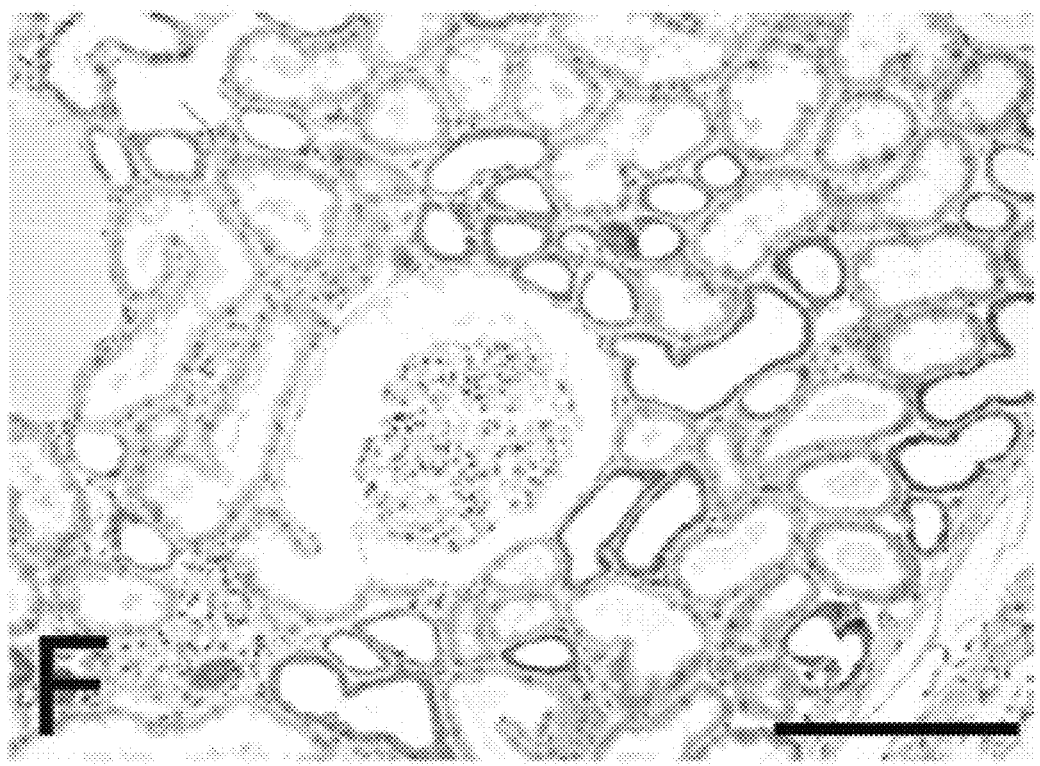
Figure 13G:
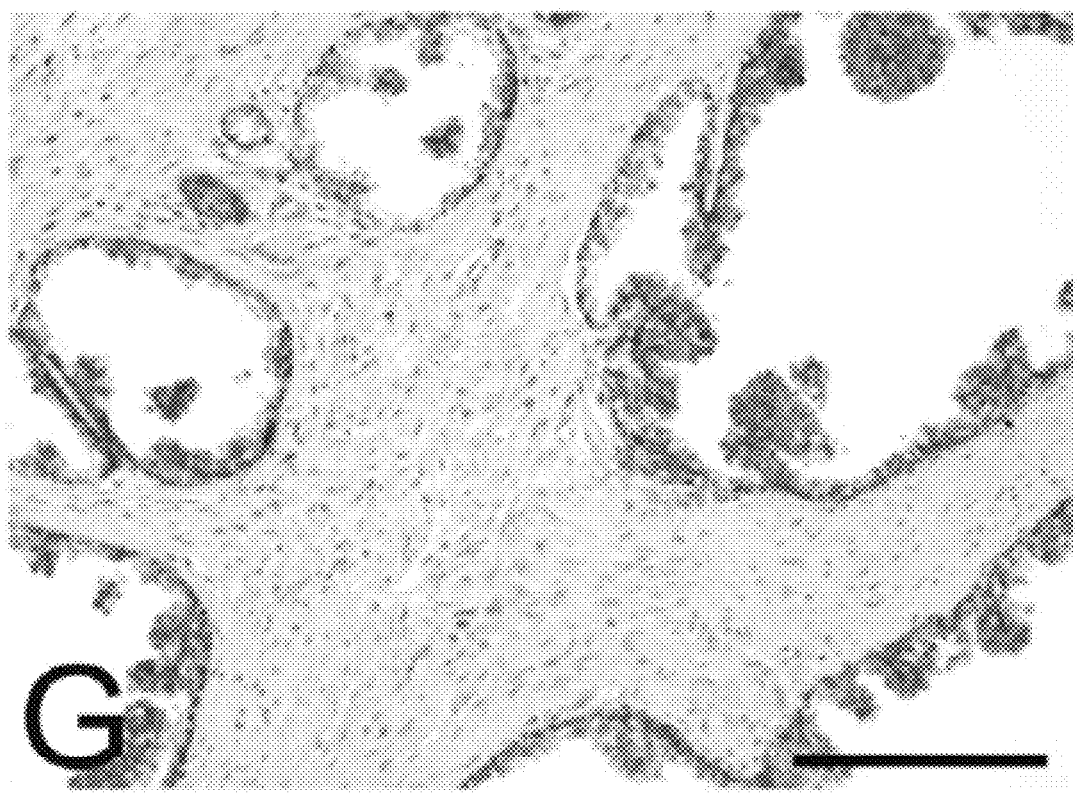
Figure 13H:
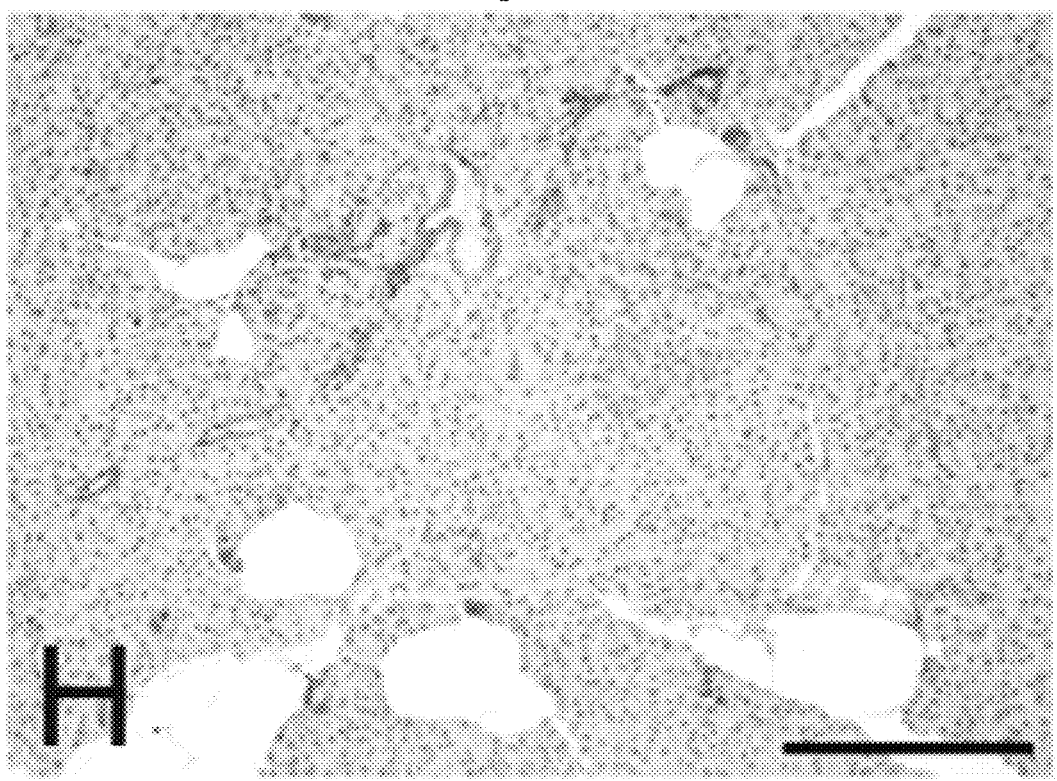
Figure 13I:
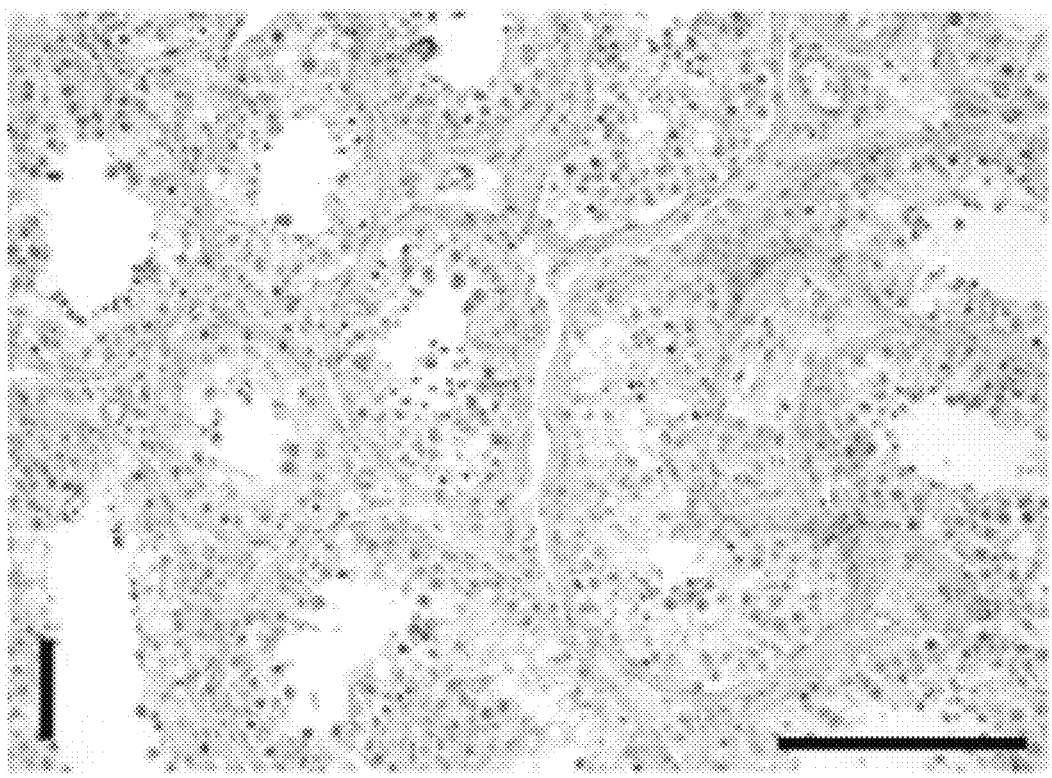
Figure 13J:
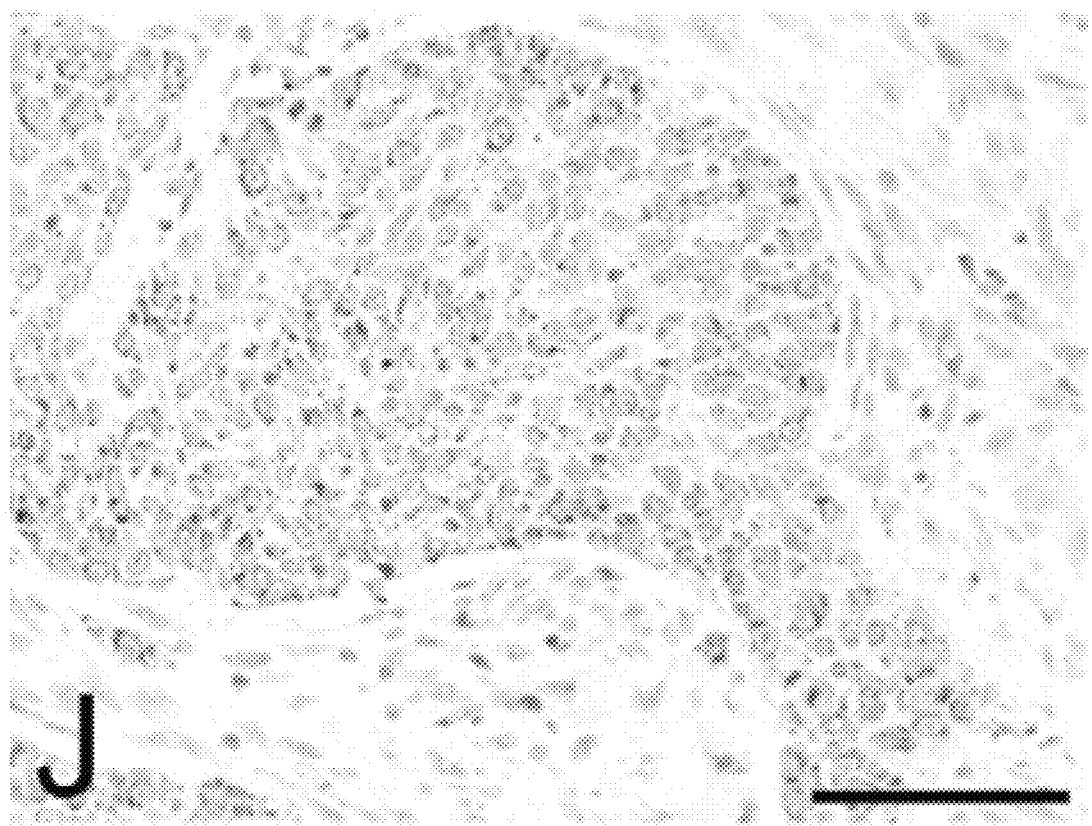
Figure 13K:
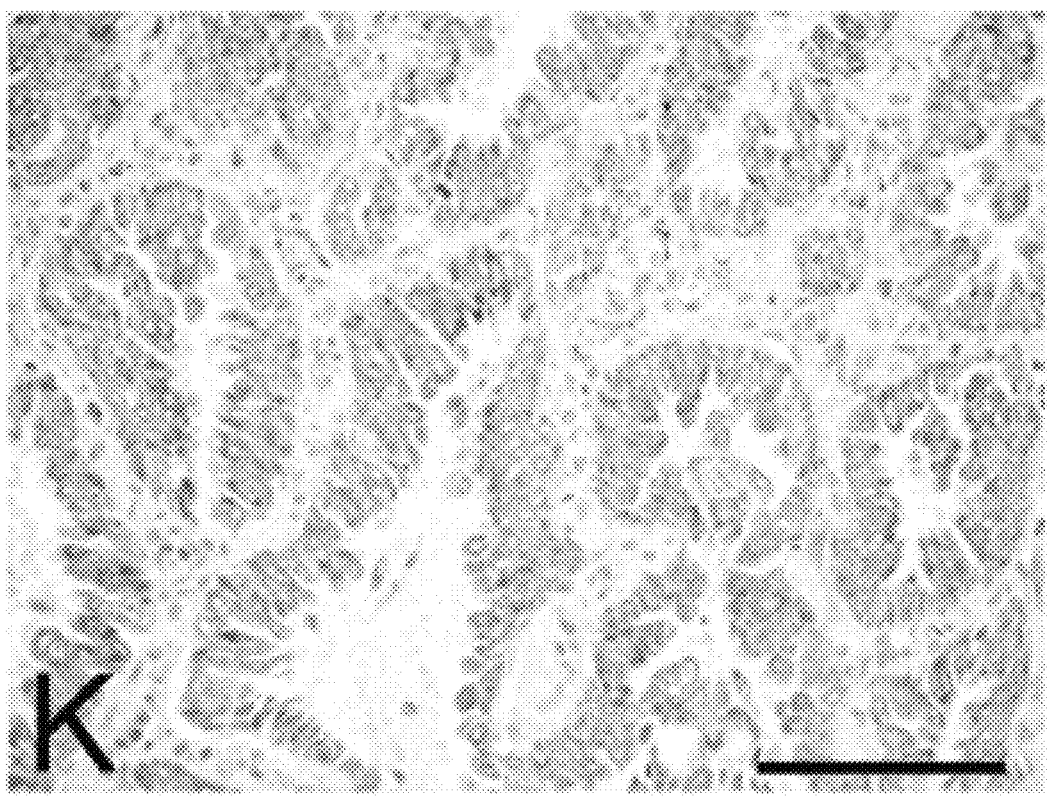
Figure 13L:
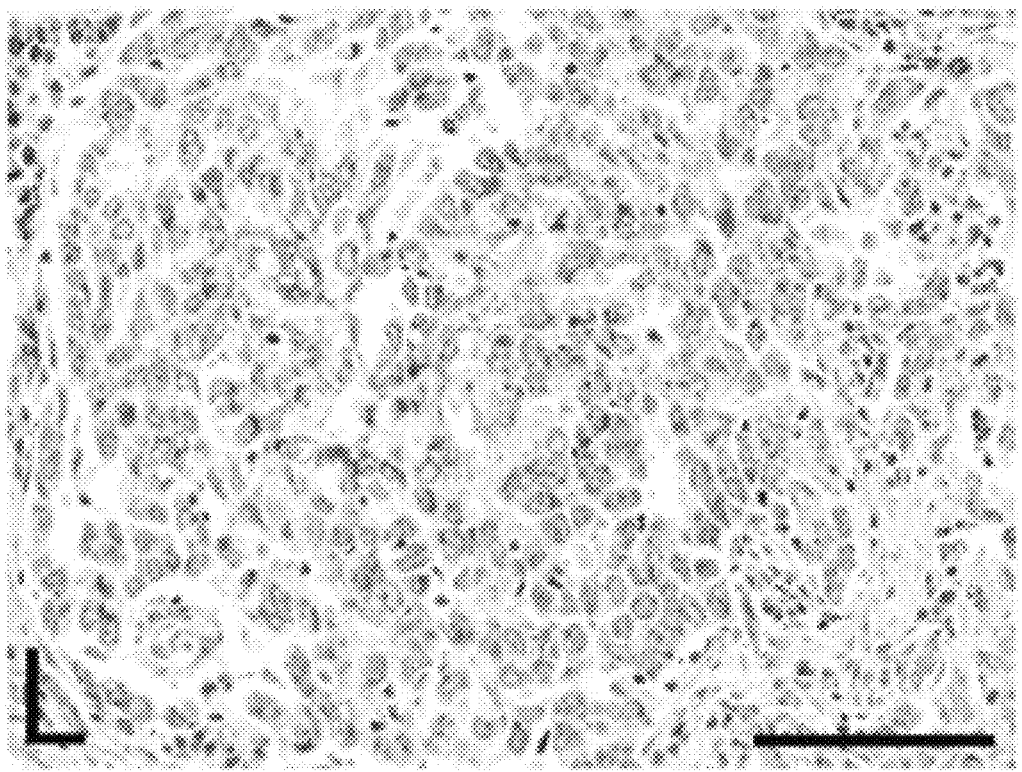
Figure 13M:
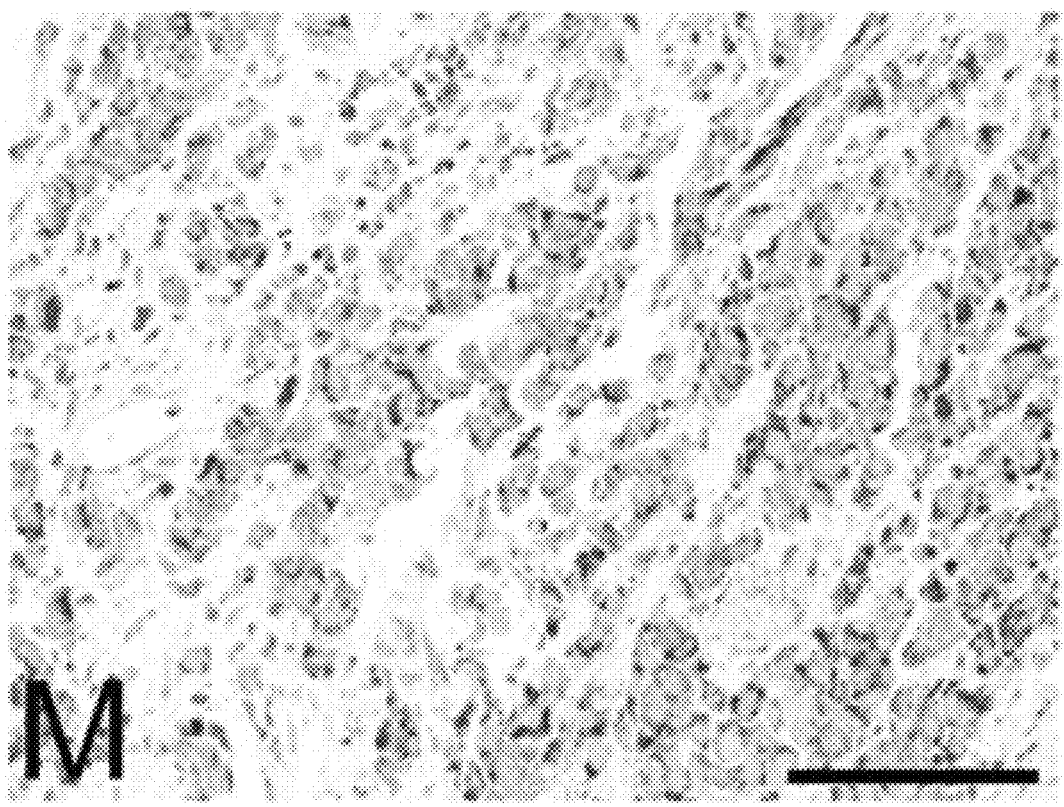
Figure 13N:
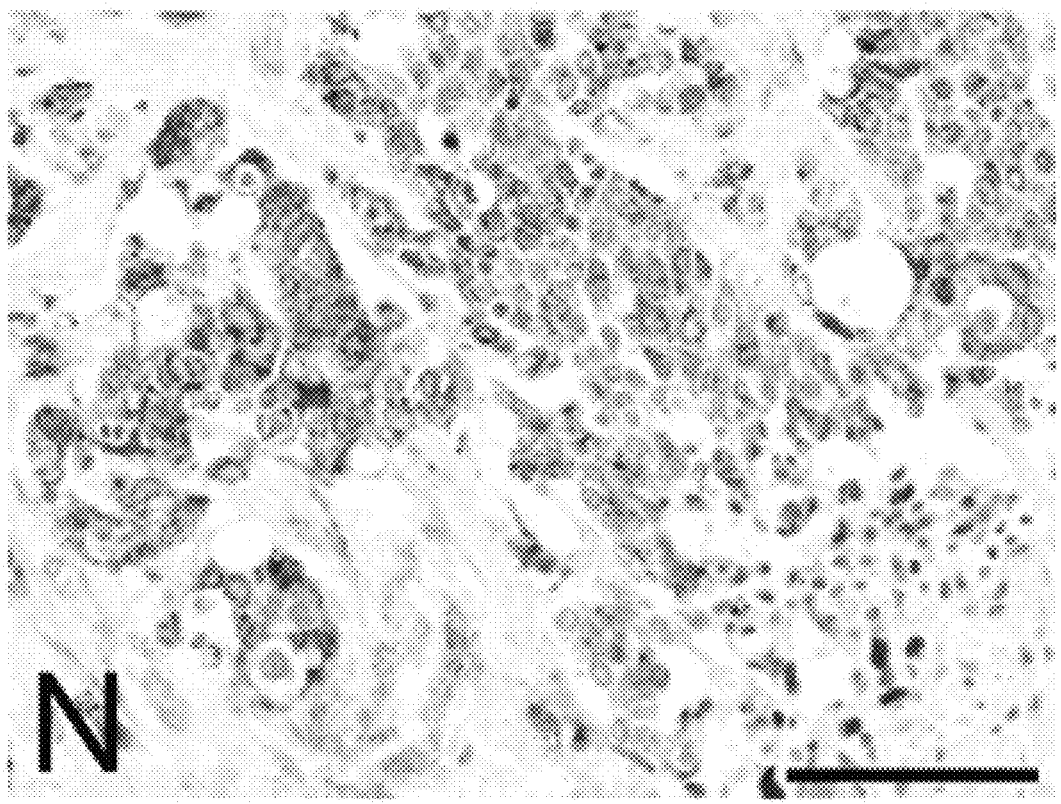
Figure 13O:
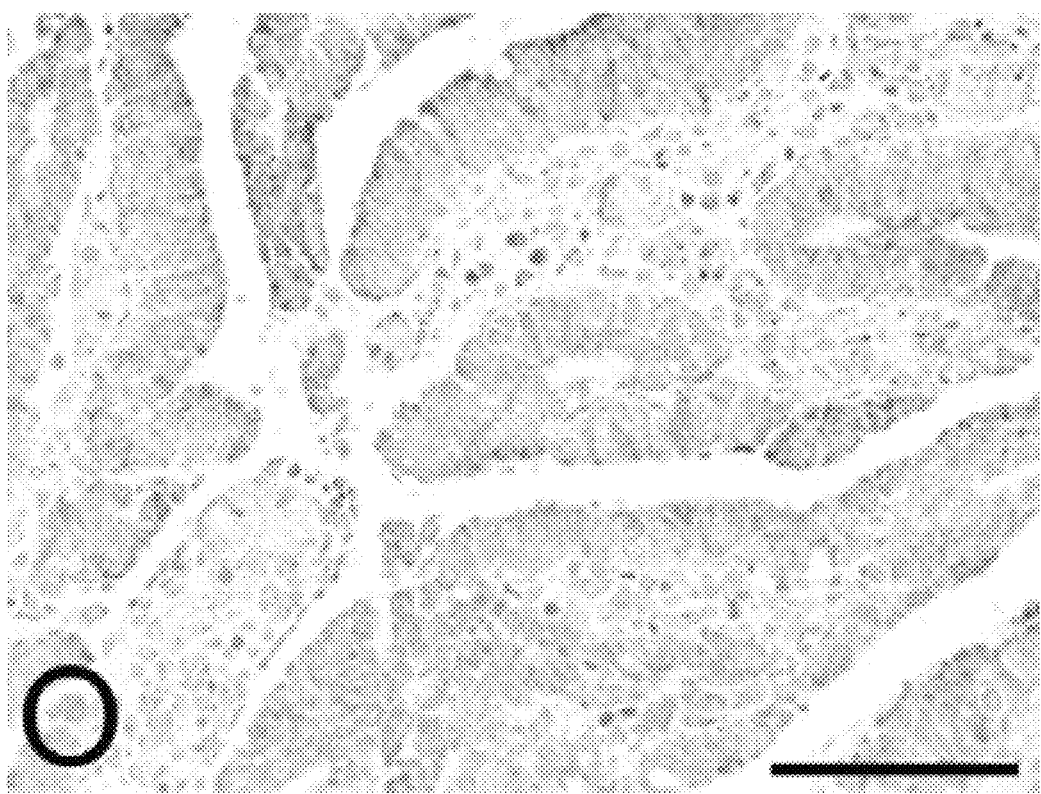
Figure 13P:
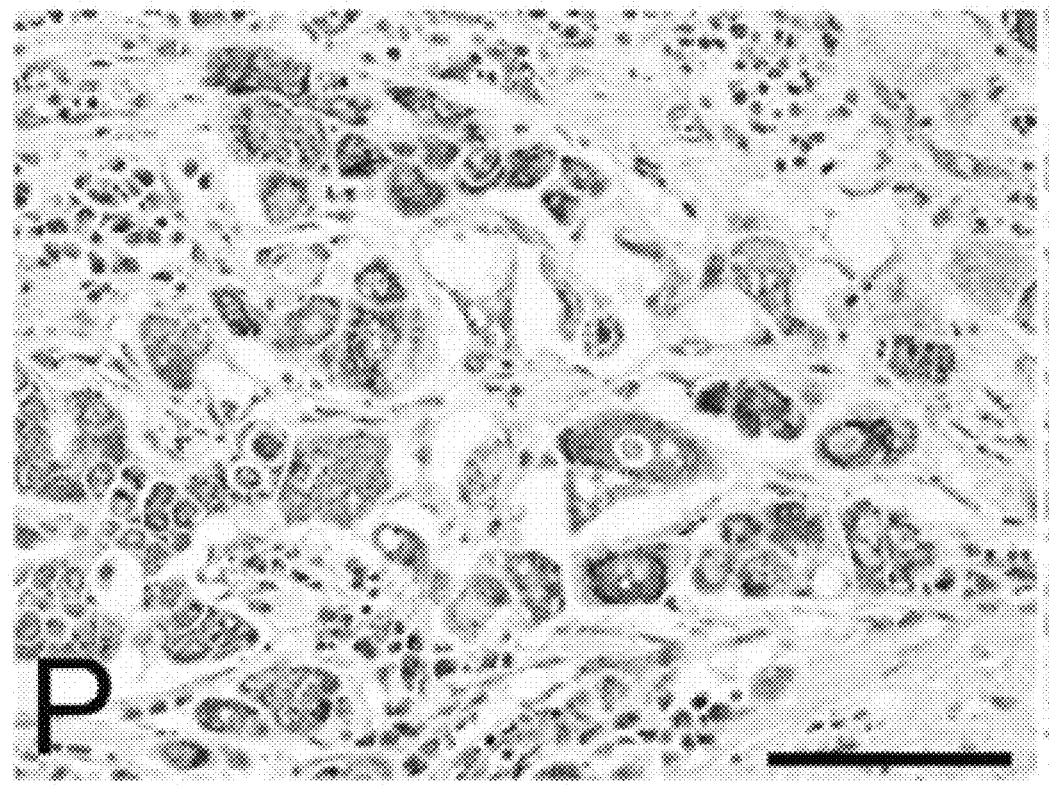
Figure 13Q:
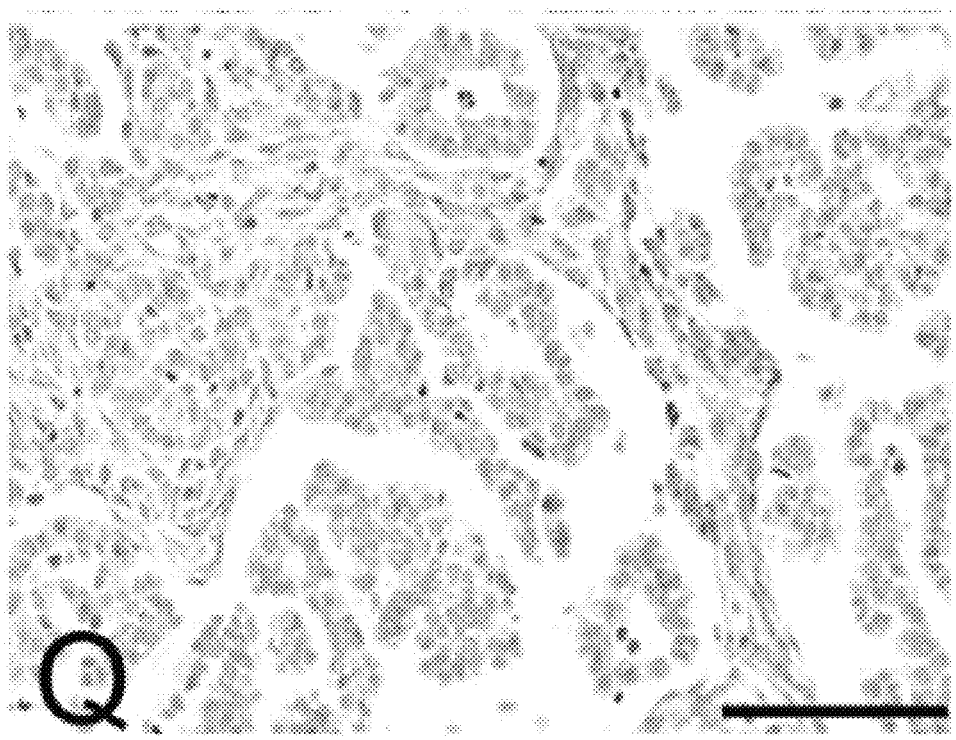
Figure 13R:
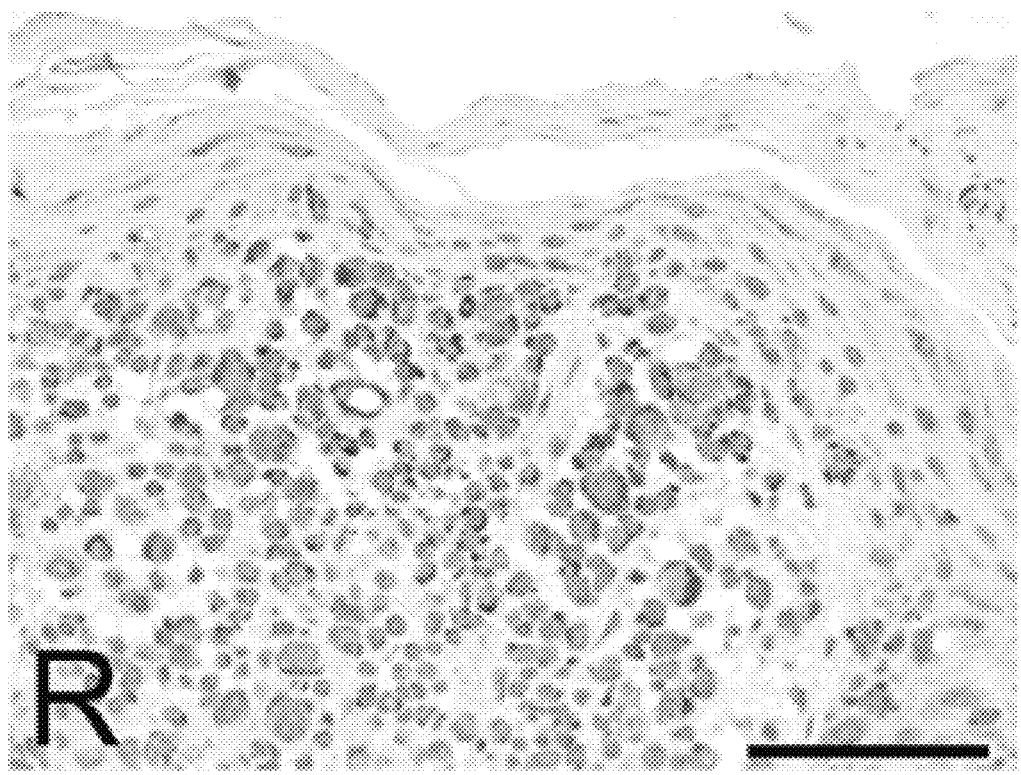
Figure 13S:
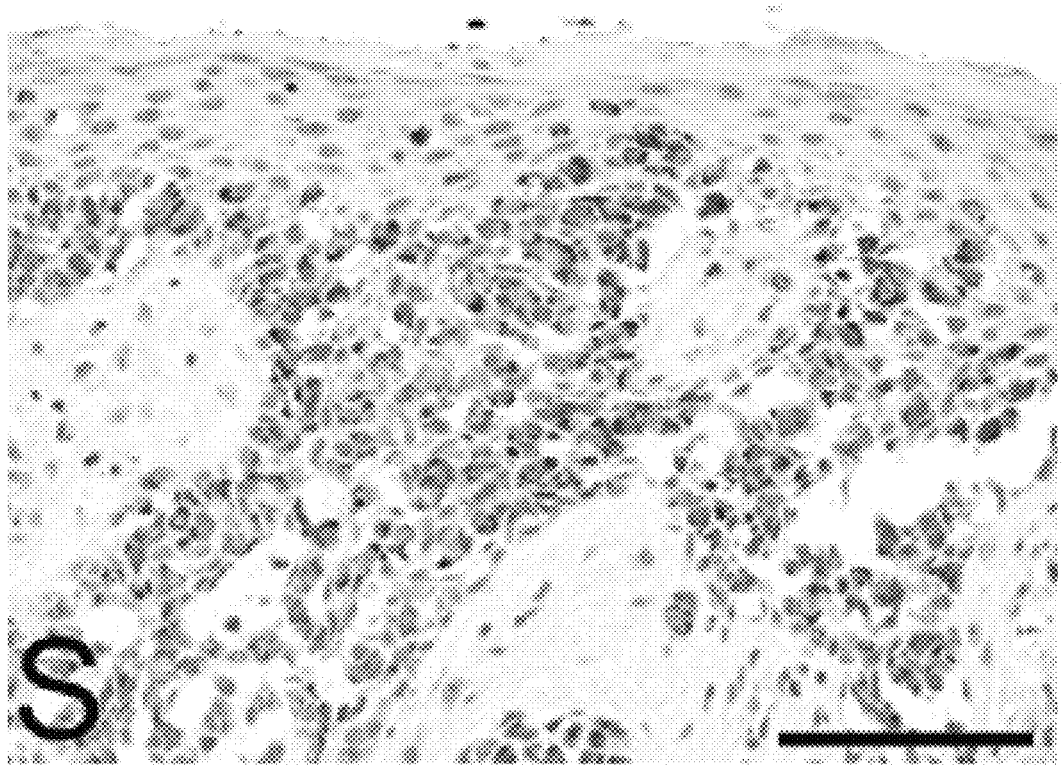
Figure 13T:
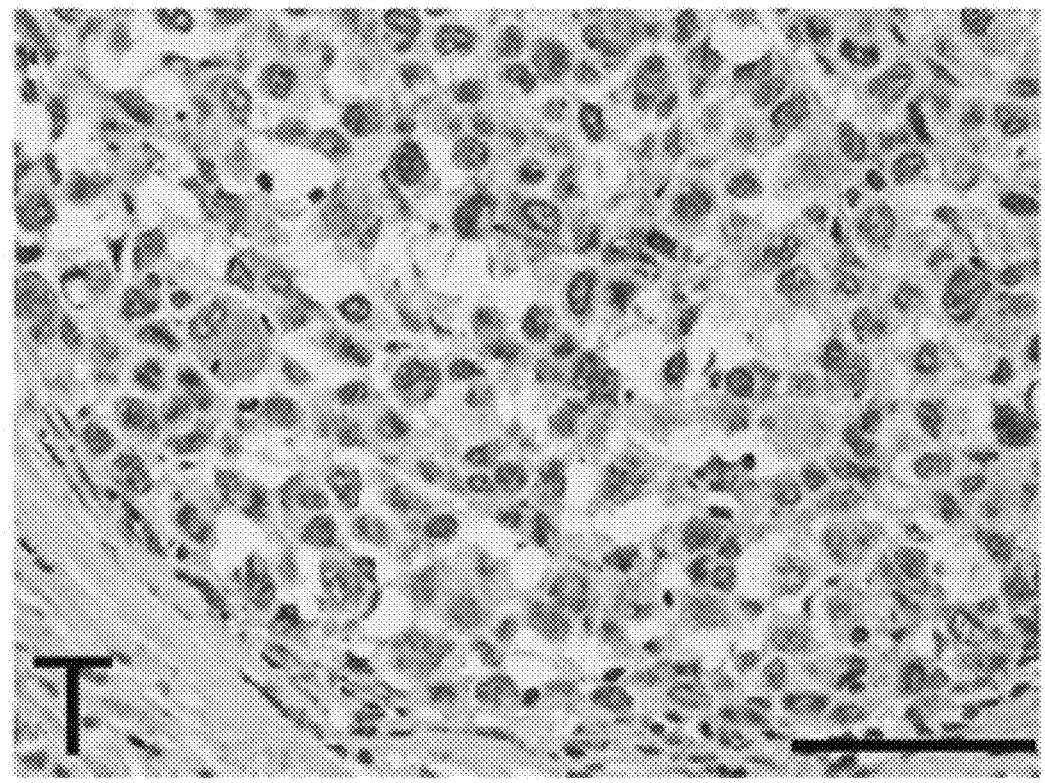
Figure 13U:
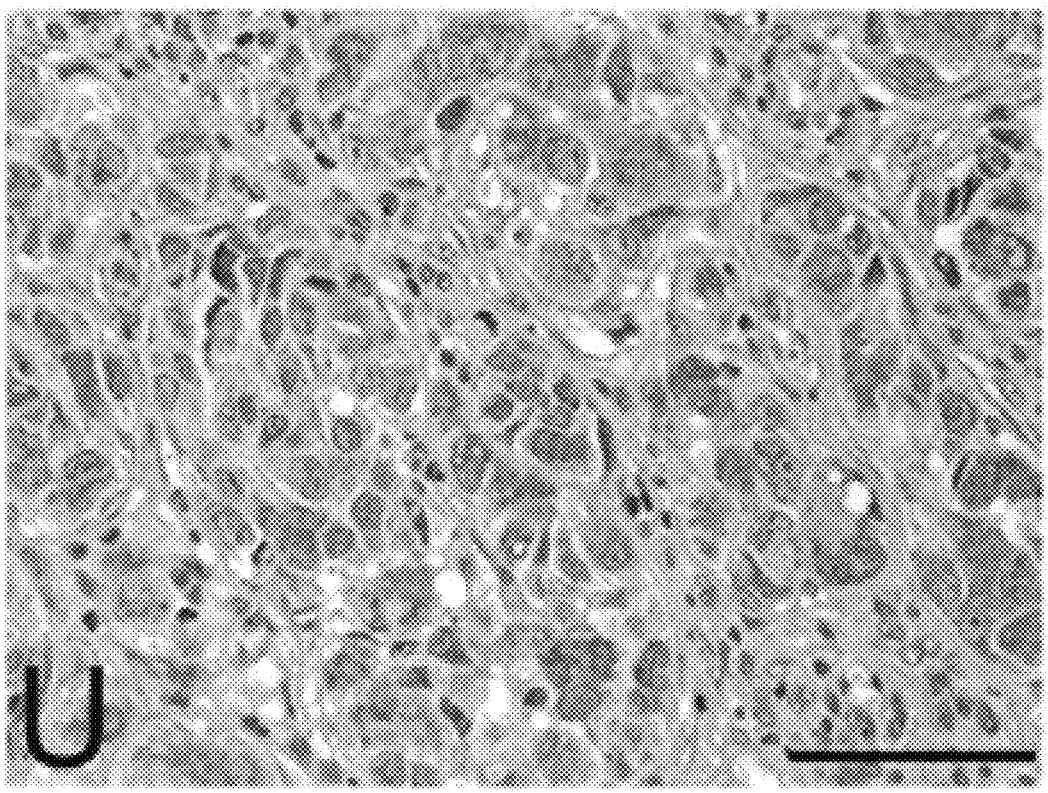
Figure 13V:
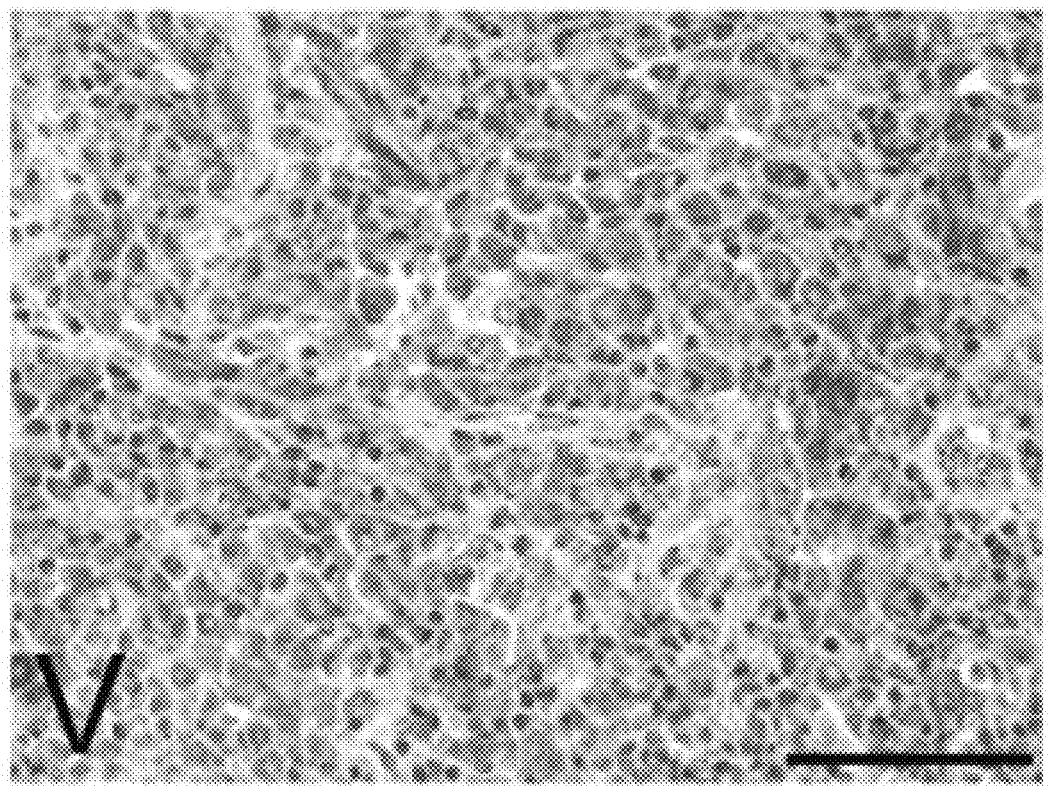
Figure 13W:
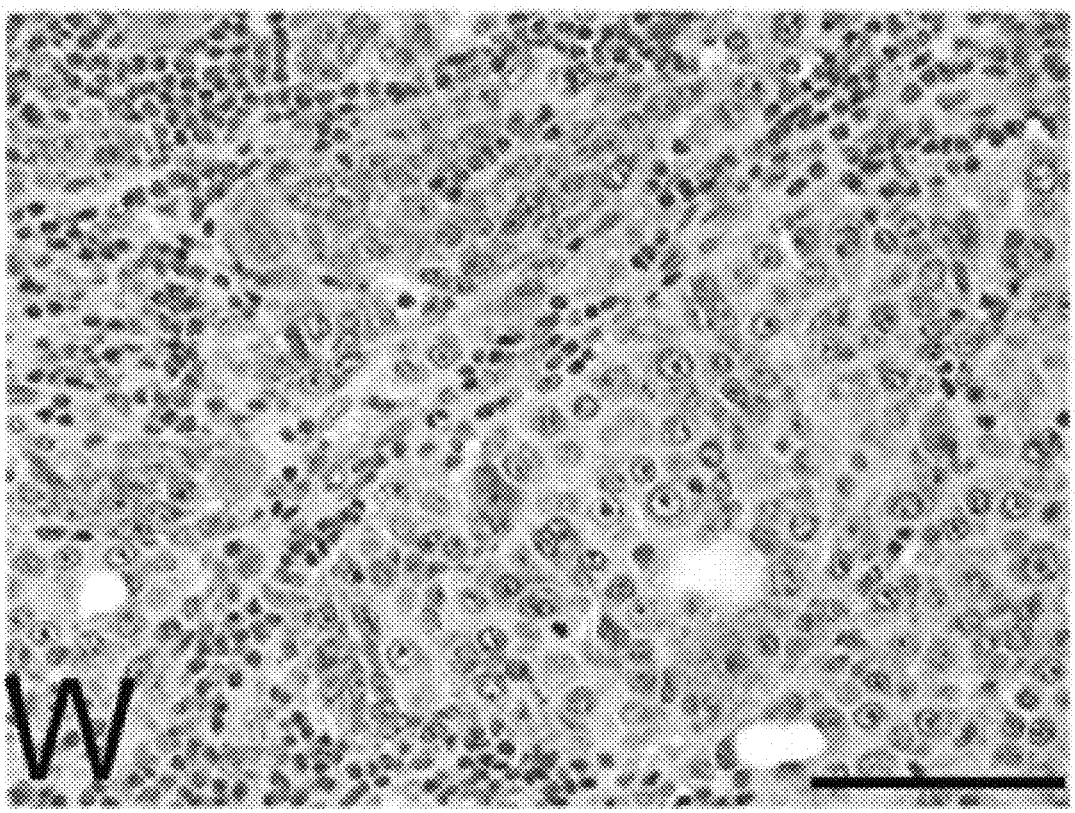
Figure 13X:
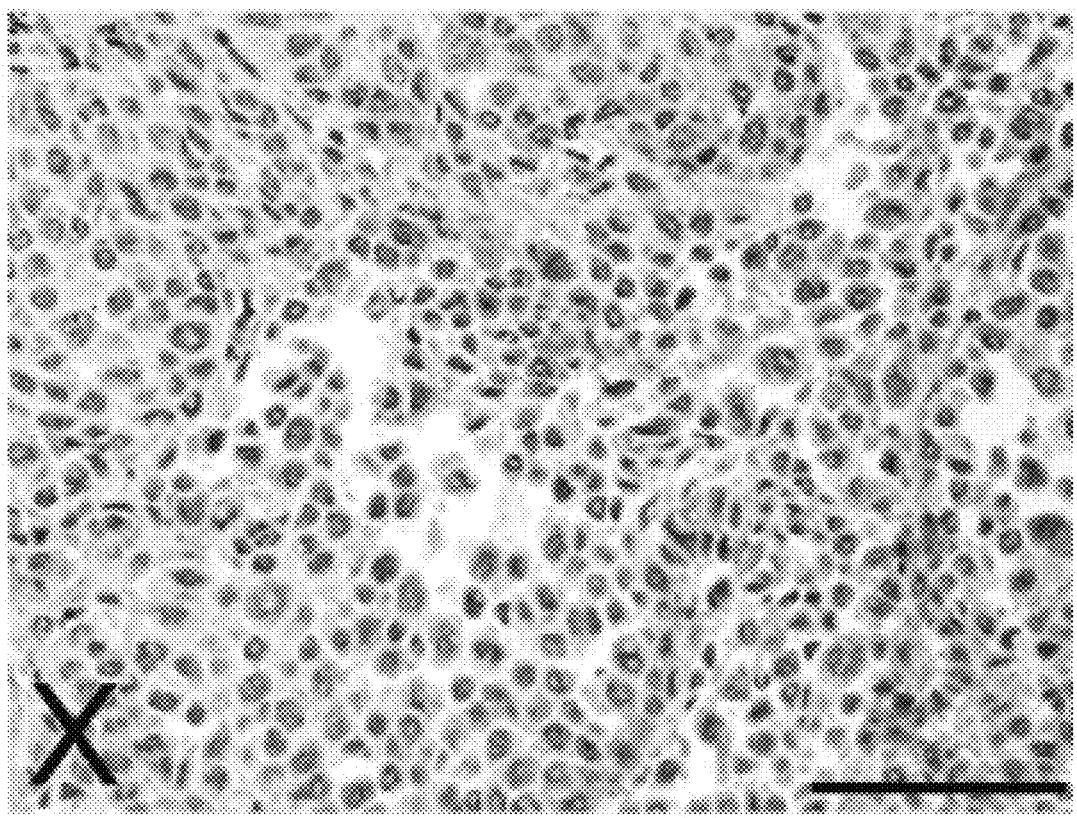

Example 5: Expression of NKp44 Correlates with Distinct Cytokine and Cell-Cycle Gene Expression Signatures in GBM We sought to determine the potential impact of the PDGF-DD/NKp44 interaction in clinical settings. Multiple human tumors, including lung, ovarian, renal, brain, prostate, breast, and pancreatic cancer, have been shown to express PDGFD mRNA (LaRochelle et al., 2002; Lokker et al., 2002), while a marked increase of PDGF-D protein was reported in lung and ovarian cancer (LaRochelle et al., 2002). We extended PDGF-D protein analysis to normal and tumor tissues. In normal tissues, PDGF-D was mainly produced in some epithelial cells and, to a lesser extent, in vascular endothelial cells and a few other cells of the vascular tunica media (FIG. 13A-13I; data not shown). Strong PDGF-D expression was detected in tumor cells of carcinomas of head, neck, lung, bladder, colon, breast, ovarian cancer, and melanomas (FIG. 13J-13X). PDGF-D was expressed in GBM (FIG. 6A) and was highly associated with vascular proliferation (FIG. 6B). Thus, PDGF-D is expressed in cancer cells and/or stroma of many human tumors with aggressive features.

Figure 6C:
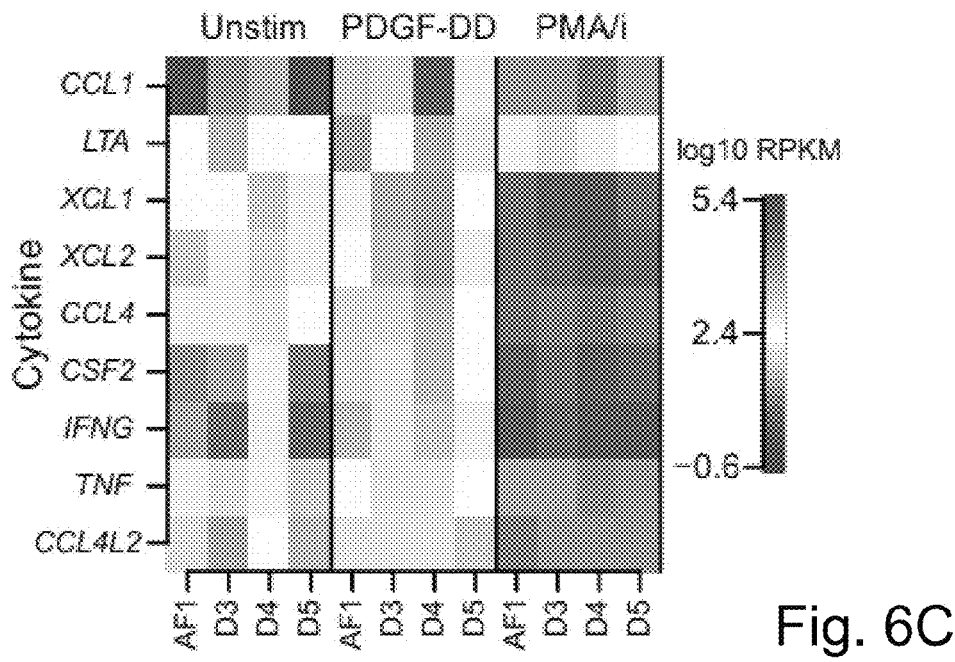
Figure 6D:
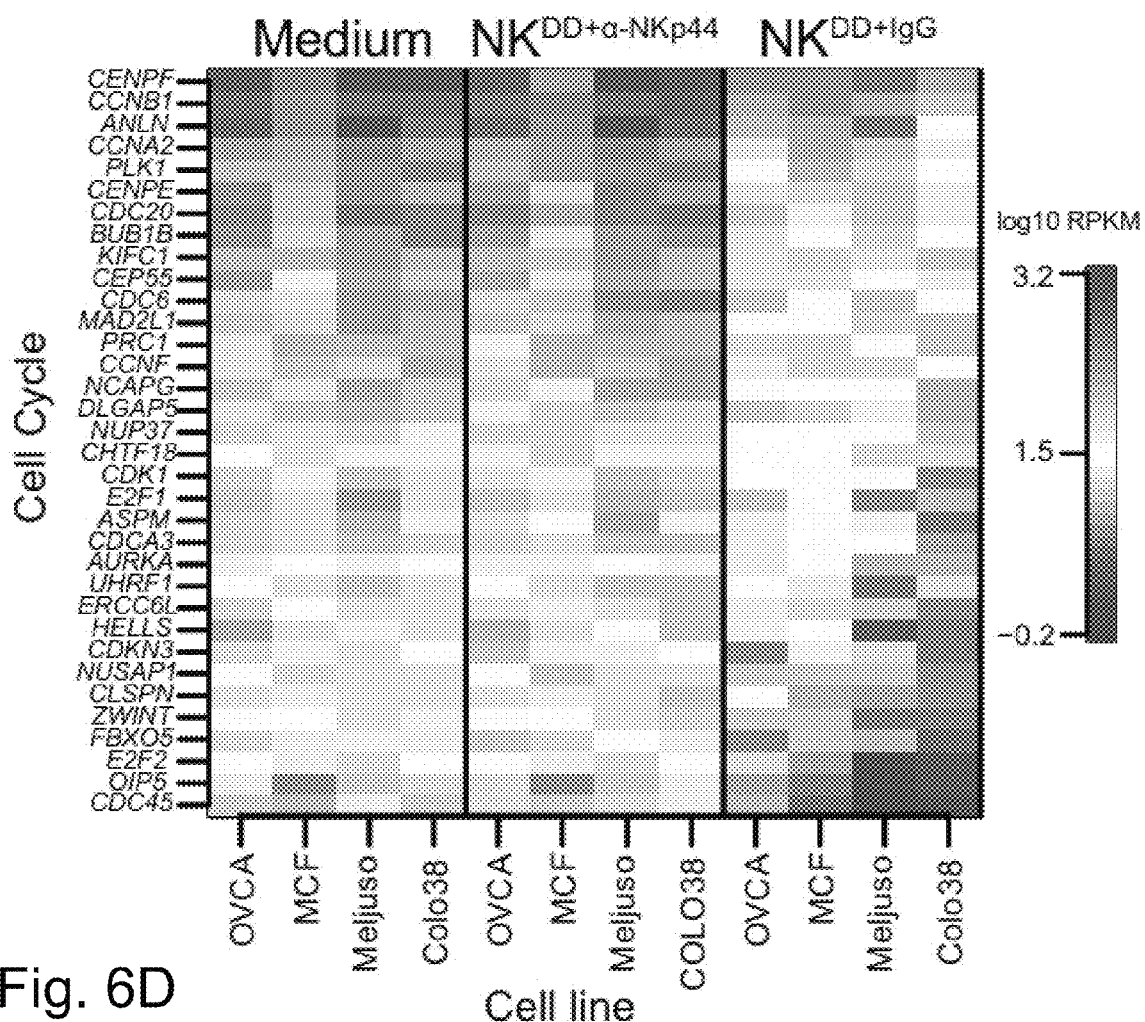
Figure 6E:
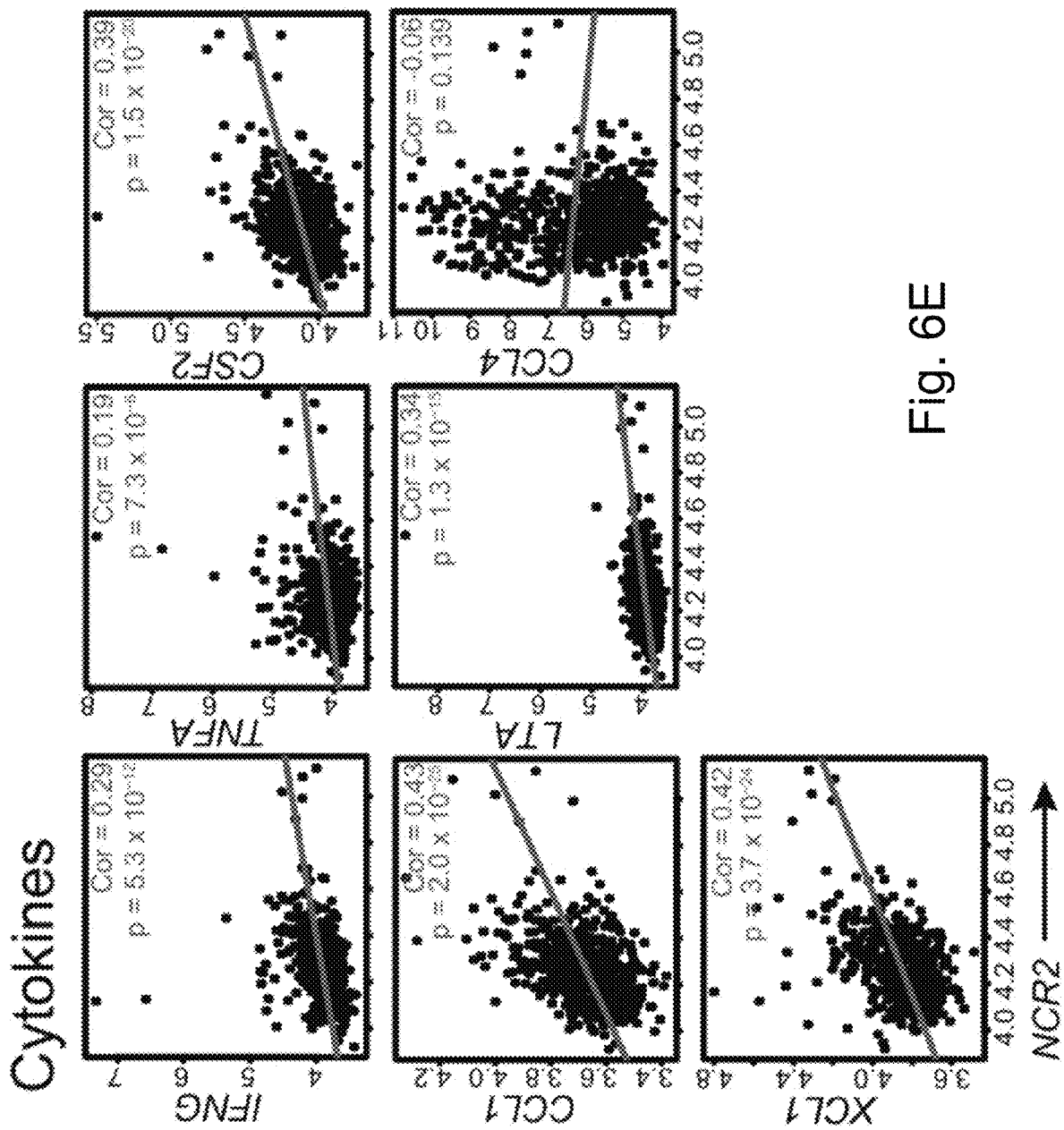
Figure 6F:
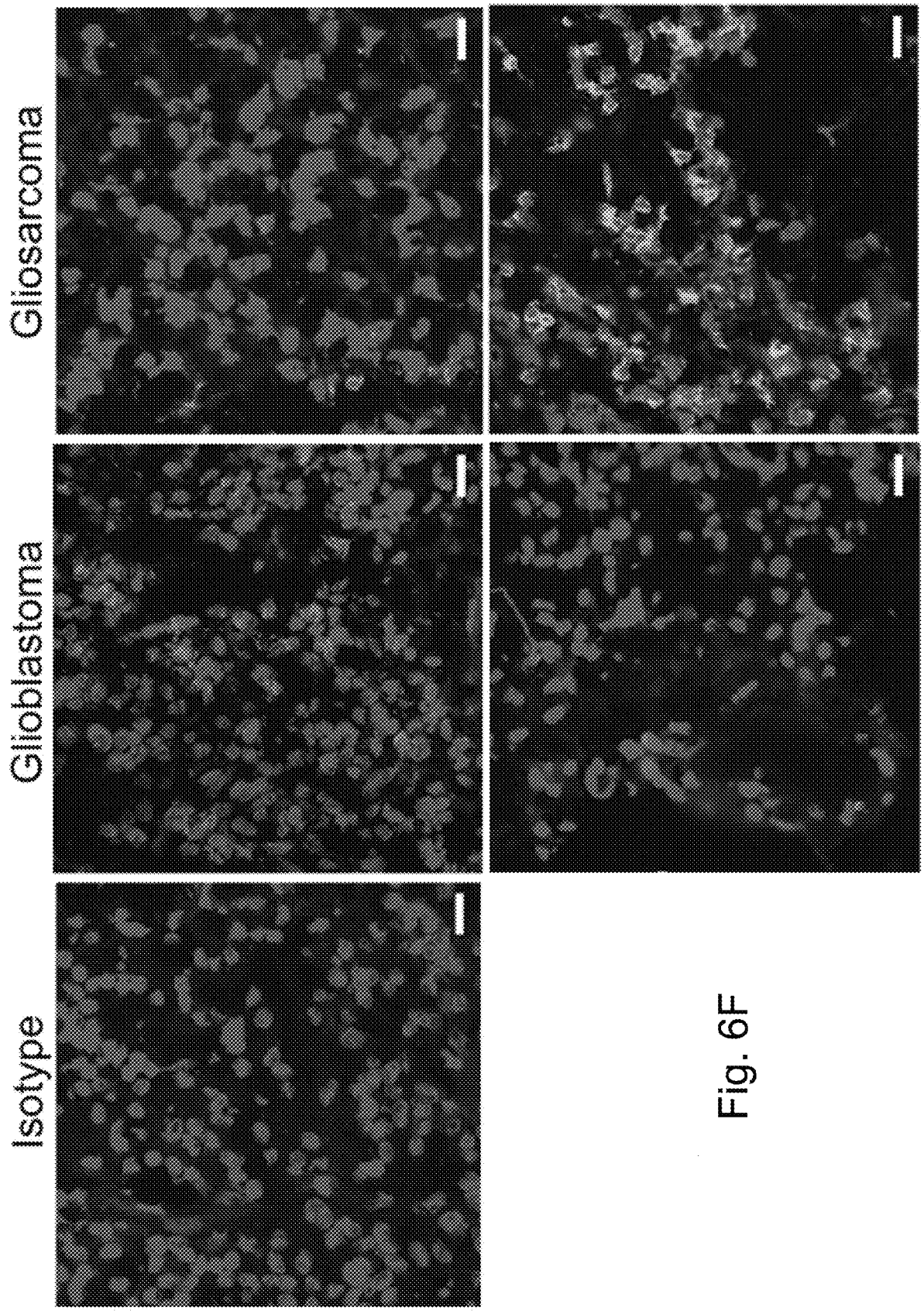
Figure 6G:
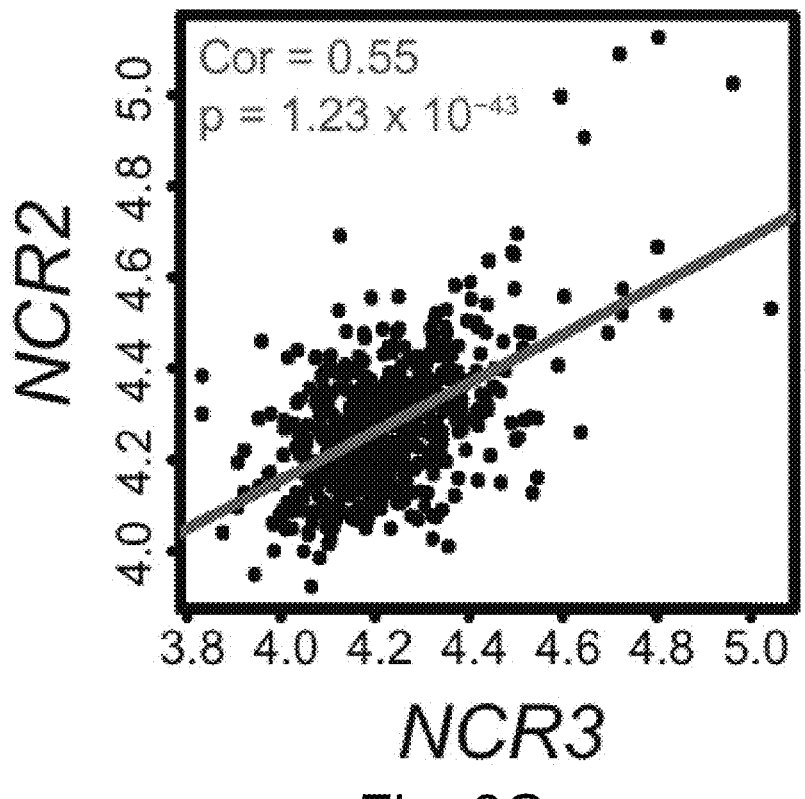

We next defined a core expression signature for the 9 most highly induced cytokine genes in PDGF-DD-activated NK cells from different donors (FIG. 6C) and a core signature of 34 most significantly downregulated cell-cycle genes in human ovarian carcinoma, breast carcinoma, and melanoma cell lines exposed to NKp44$^{DD+IgG}$ sup (FIG. 6D). We interrogated The Cancer Genome Genome Atlas (TCGA), a comprehensive map of the transcriptional changes in multiple types of cancer, for correlations between NCR2 expression and the cytokine gene signature in various human cancers. Remarkable correlations were found in the TOGA GBM cohort (539 patients); NCR2 expression positively correlated with 6 of 7 available core cytokines extracted from the GBM TOGA cohort (FIG. 6E). The canonical correlation of NCR2 with the cytokine variate was 0.60. The correlation between NCR2 expression and the NK cell cytokine gene signature in GBM suggested that NKp44+ NK cells might infiltrate GBM. Indeed, we observed numerous NKp44+ cells along with relatively few T cells infiltrating GBM in tissue sections obtained from several patients (FIG. 6F); however, a GBM variant known as gliosarcoma was infiltrated by more T cells and fewer NKp44+ cells, which suggests that lymphocytic infiltrates of GBM vary somewhat. Further supporting NK cell infiltration in GBM, NCR2 expression in the GBM TOGA cohort was positively correlated with expression of the NK cell-specific gene NCR3, which encodes the activating receptor NKp30 (FIG. 6G). These results indicate that infiltration of NKp44± NK cells is present in many, but not all, GBM and positively correlates with the expression of proinflammatory NK cell cytokine genes such as IFNG and TNF.

Figure 6I:
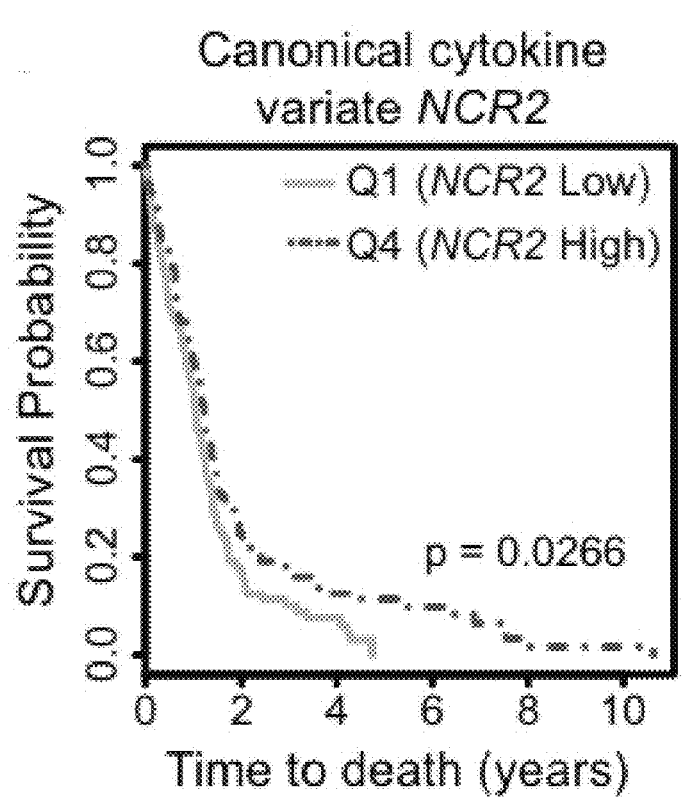
Figure 6H:
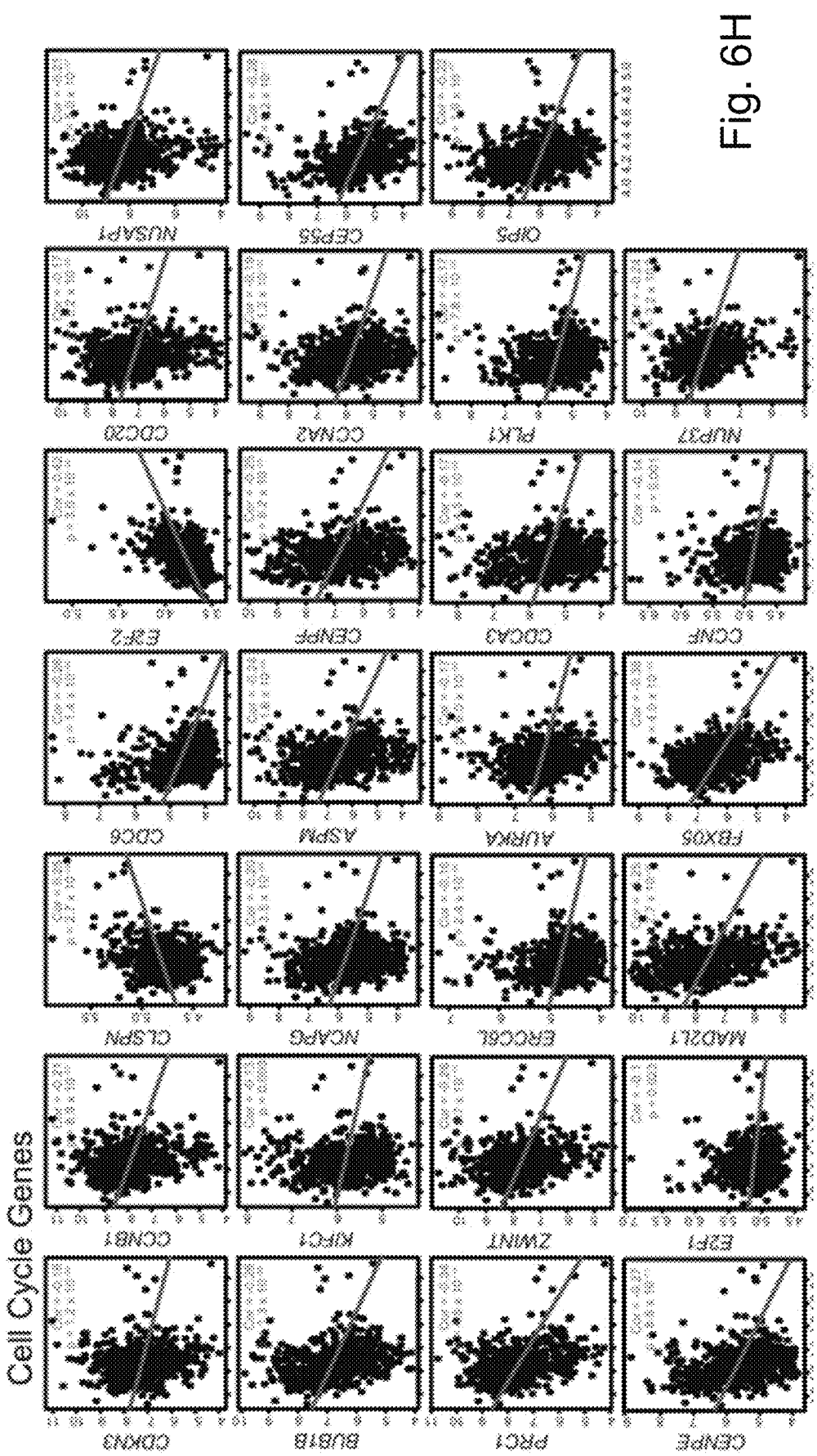
Figure 6J:
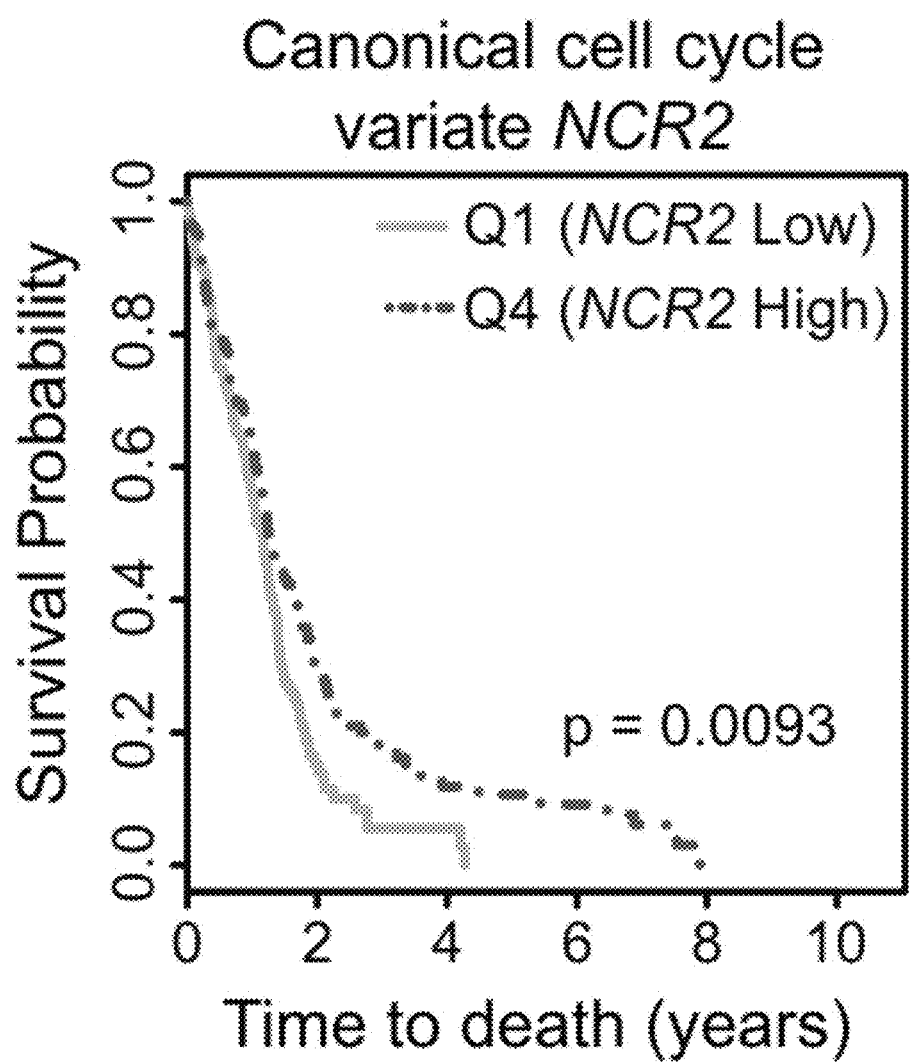

We next determined the correlation between NCR2 and the expression of the tumor cell-cycle gene signature (see FIG. 6D) for GBM. Strikingly, NCR2 expression negatively correlated with the expression of 25 of 27 available core cell-cycle genes in the GBM TOGA cohort (FIG. 6H). The canonical correlation of NCR2 with the cell-cycle variate was 0.68. We next examined if NCR2 expression was correlated with greater overall survival in the GBM cohort. GBM patients in the upper quartile (Q4) expression of the canonical cytokine (FIG. 6I) and cell-cycle (FIG. 6J) variates of NCR2 had greater overall survival compared to GBM patients in the lower quartile (Q1) (p=0.0266 and p 0.0093, respectively). We also observed a trend toward increased survival from the 1st to the 4th quartile of NCR2 expression but it was not statistically significant, probably because the dynamic range of NCR2 expression in TOGA GBM mRNA was limited (data not shown). Thus, meta-analysis of TOGA database indicates that overall survival correlates not only on the expression of NCR2 but also on the downstream effects of NKp44 engagement by PDGF-DD. While other types of tumors also showed associations of NCR2 expression with NK cell core cytokine signature, and/or down-regulation of tumor cell-cycle genes, correlations with overall survival were not significant (data not shown), suggesting that the contribution of PDGF-DD/NKp44 interaction to control of tumor progression may be context-dependent.

Example 6: PDGF-DD Binding to NKp44 Limits Tumor Growth In Vivo

Figure 7A:
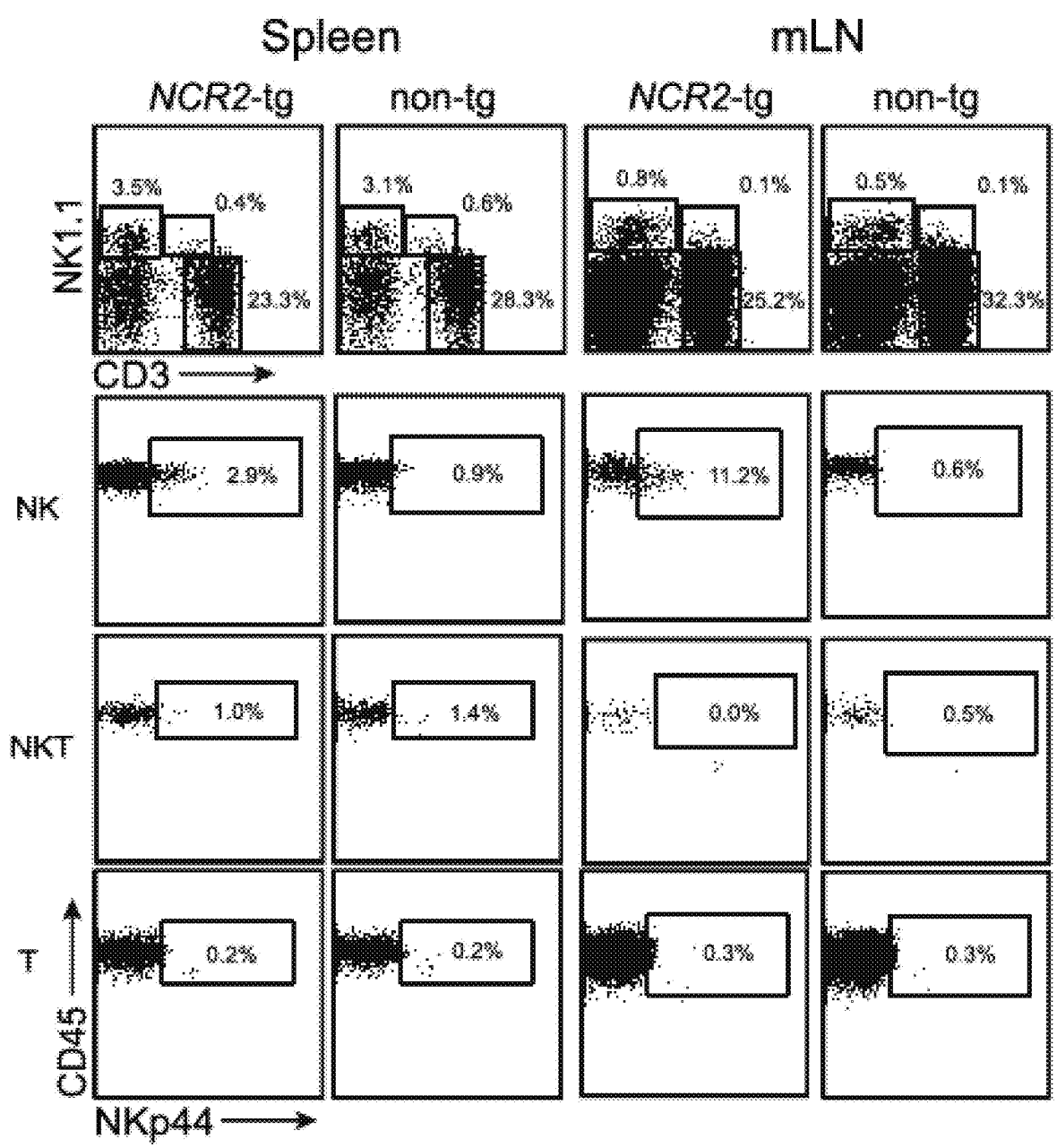
FIG. 7A, FIG. 7B, FIG. 7C, FIG. 7D, FIG. 7E, FIG. 7F, FIG. 7G, FIG. 7H, FIG. 7I, FIG. 7J and FIG. 7K SHOW NKp44 Restricts Tumor Cells Expressing PDGFD in vivo.
Figure 7B:
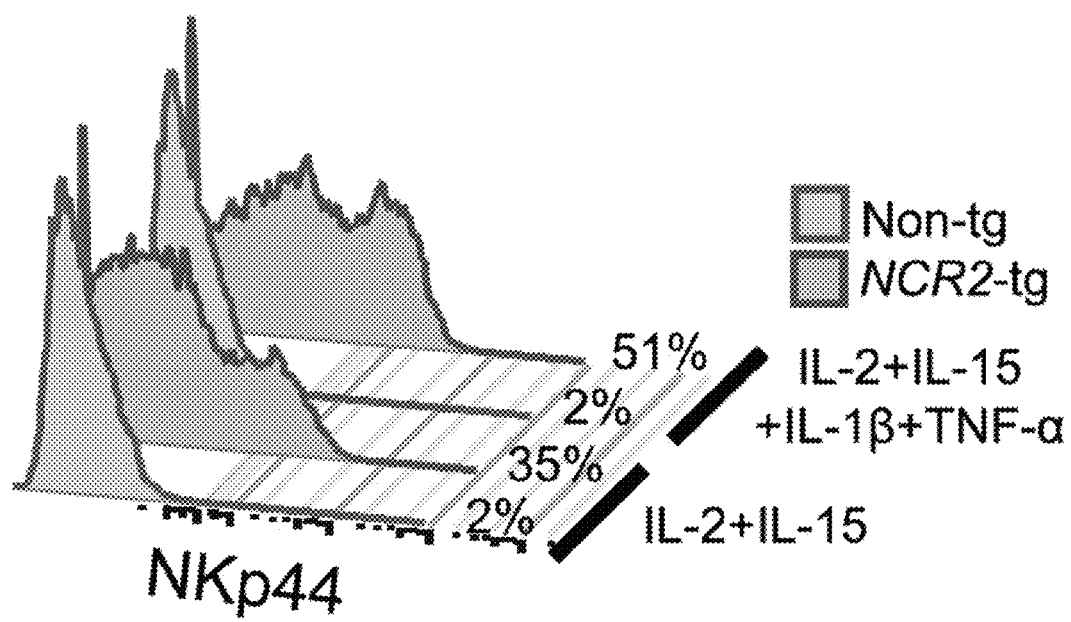
Figure 7C:
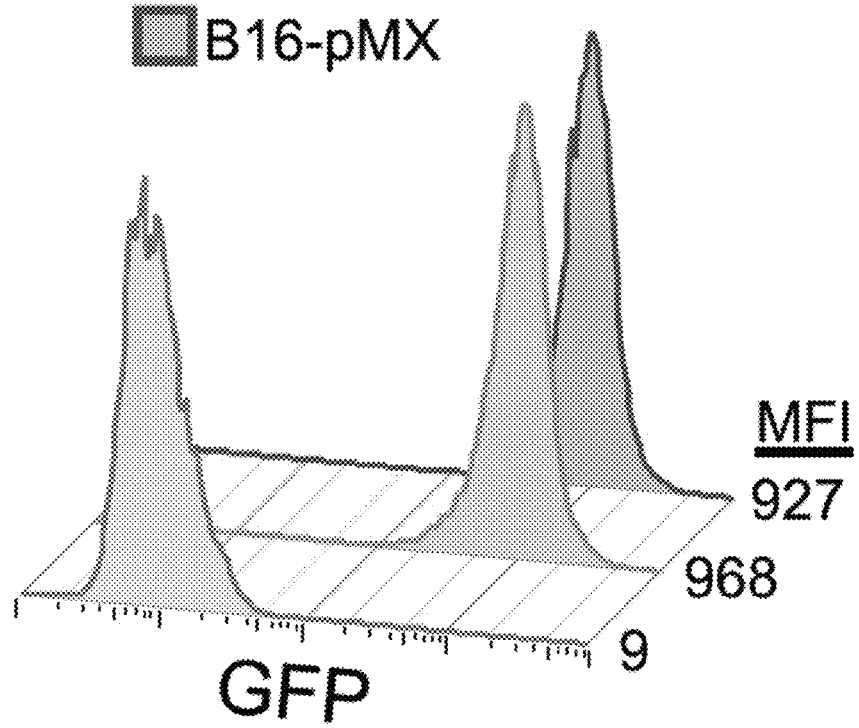
Figures 7D, 7E:
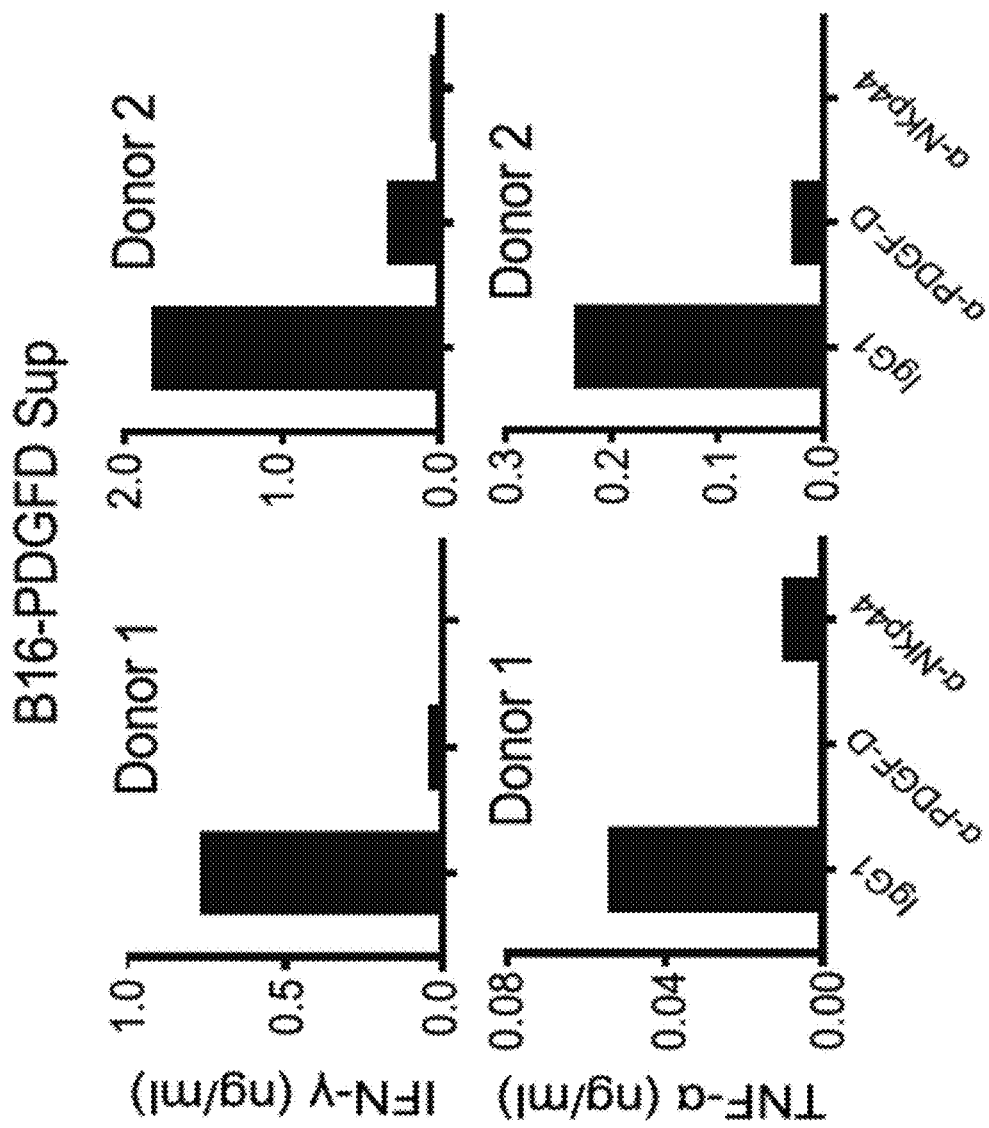
Figure 7F:
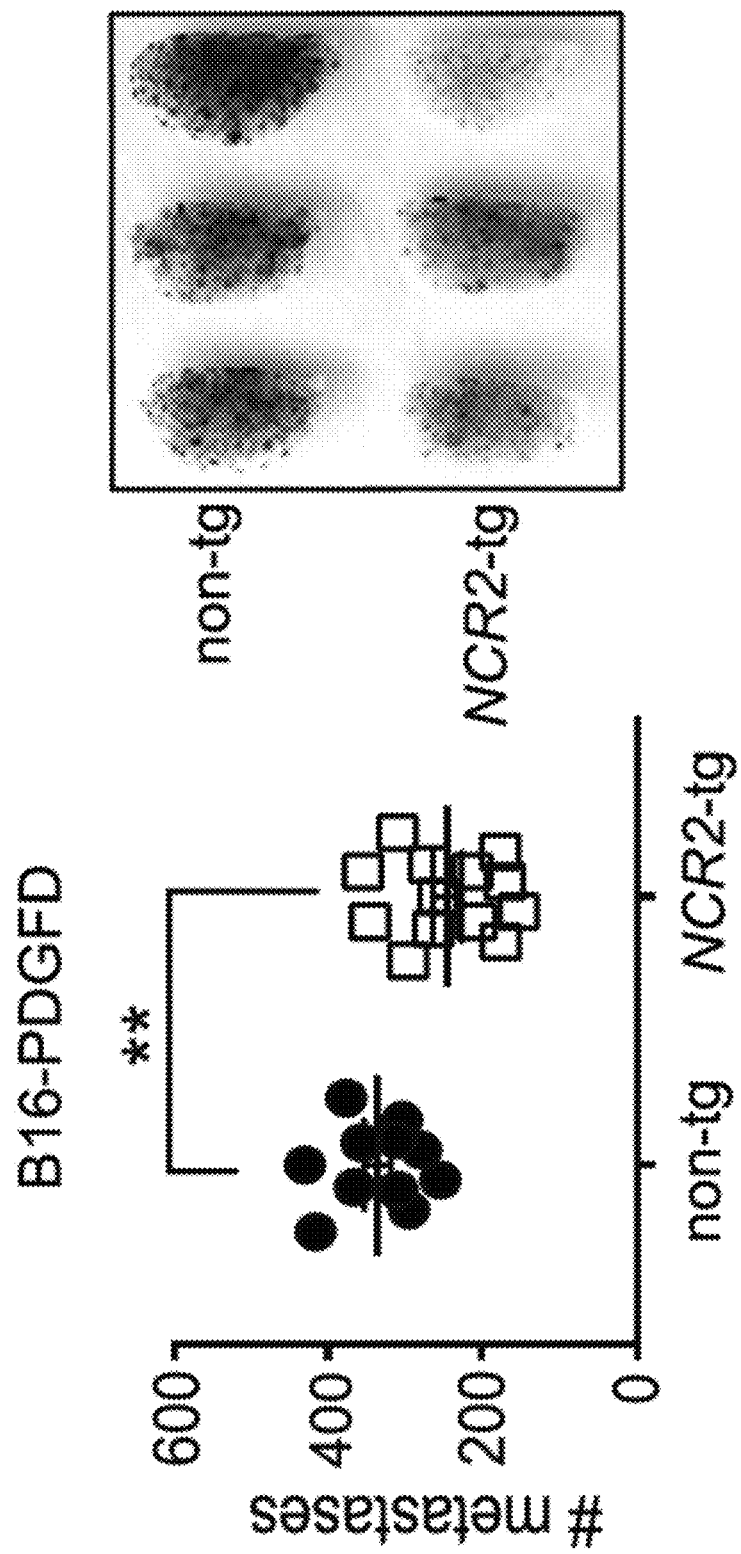
Figure 7G:
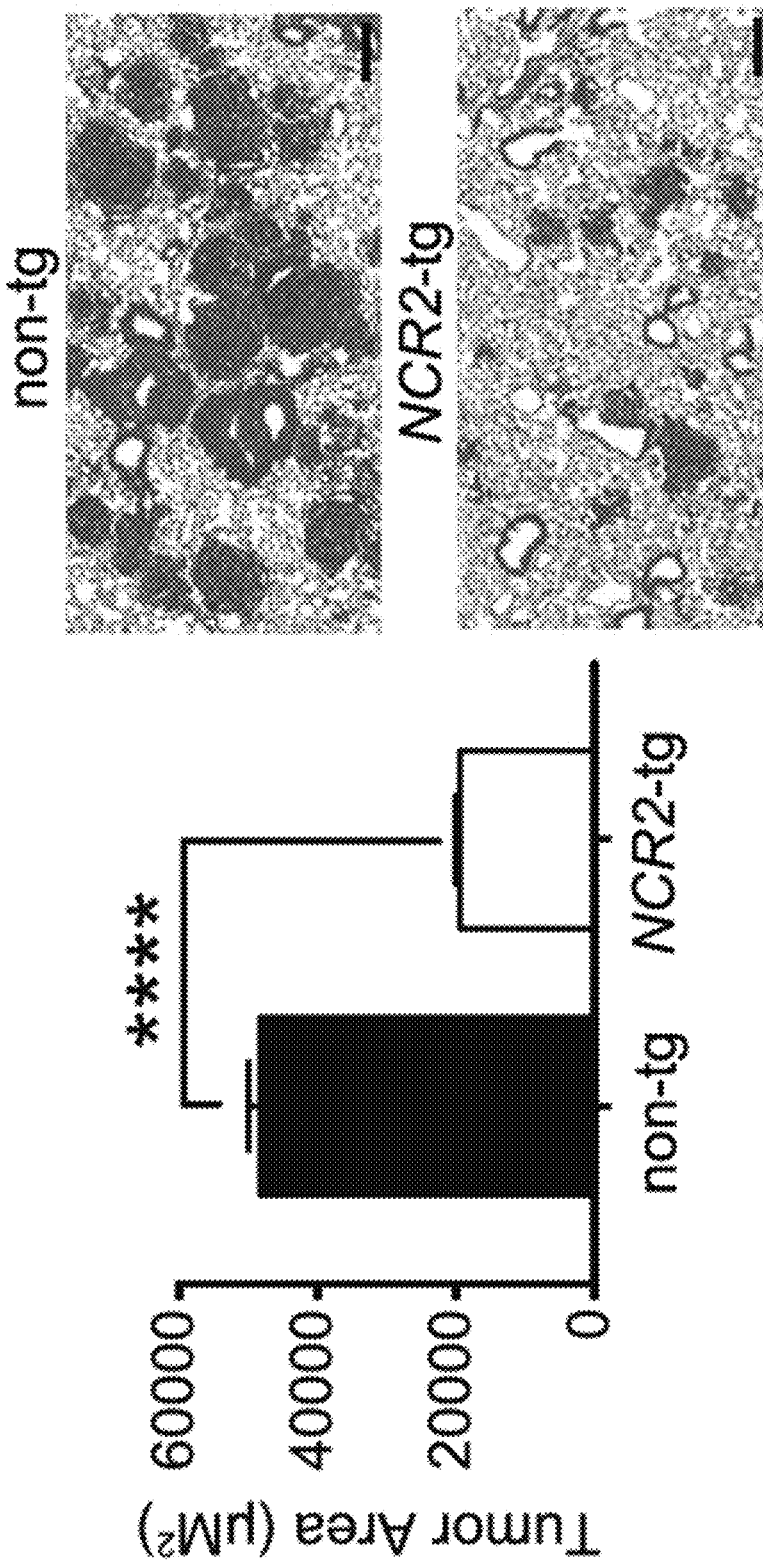
Figure 7H:
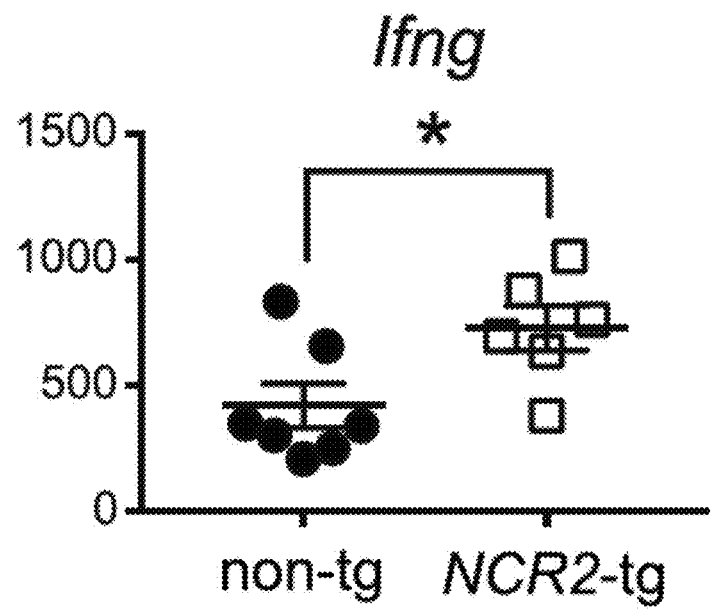
Figure 7I:
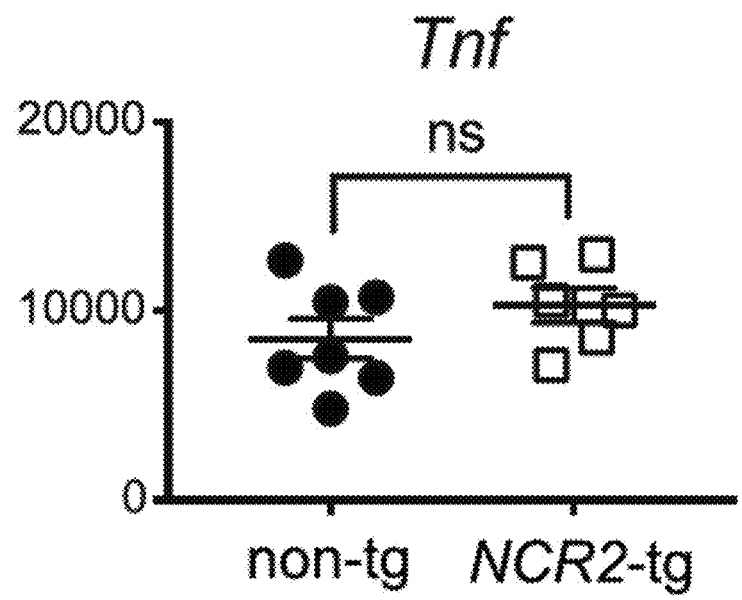
Figure 7J:
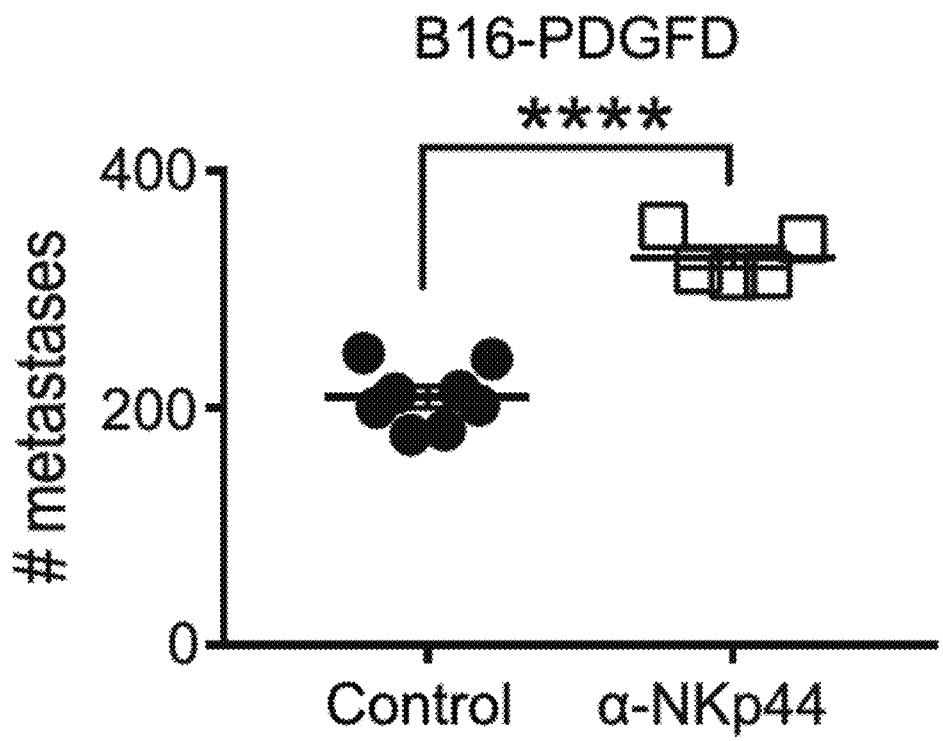
Figure 7K:
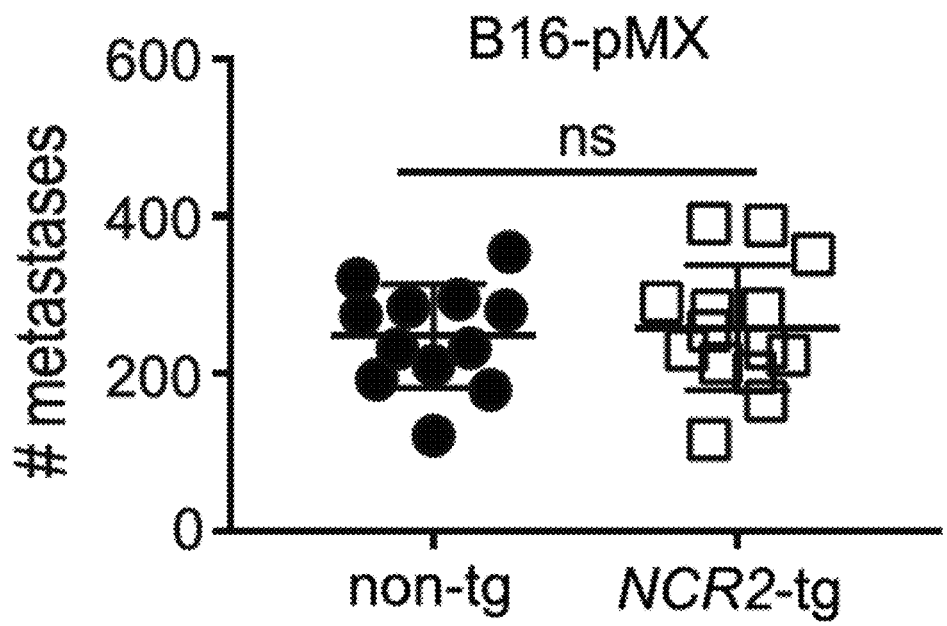
Figure 14A:
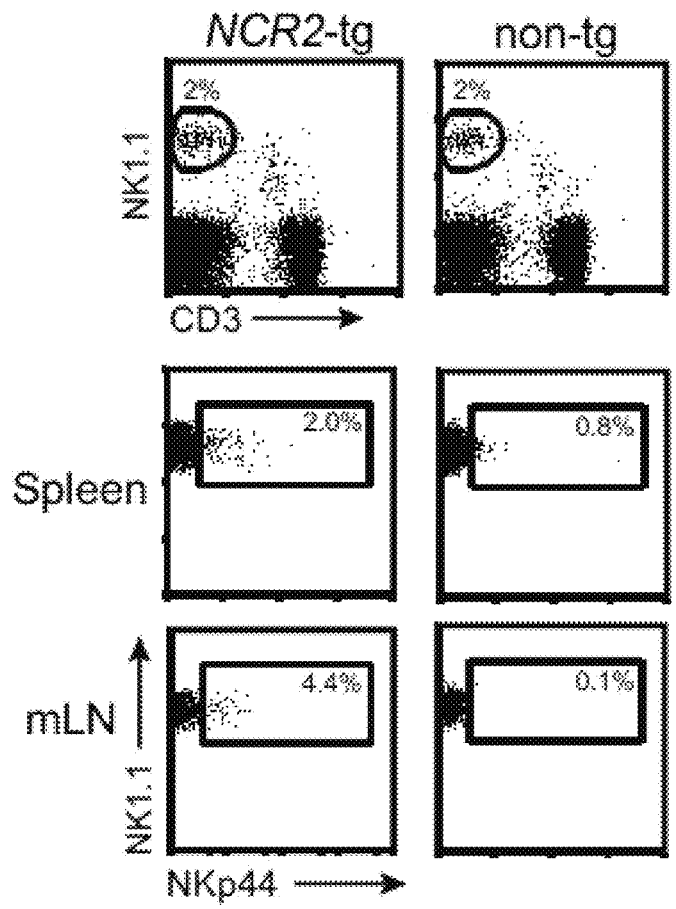
FIG. 14A, FIG. 14B, FIG. 14C, FIG. 14D, FIG. 14E, FIG. 14F, FIG. 14G and FIG. 14H show reduced dissemination of tumor cells expressing PDGFD In Vivo in a Second NCR2-tg Line.
Figure 14B:
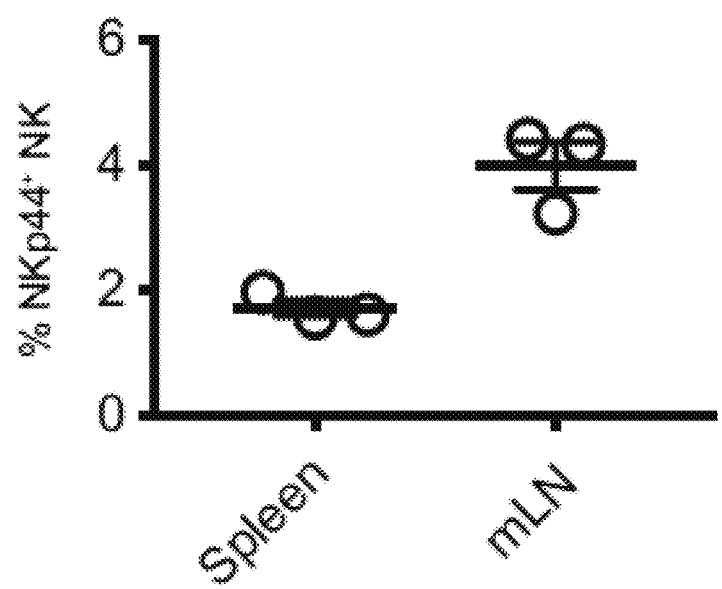
Figure 14C:
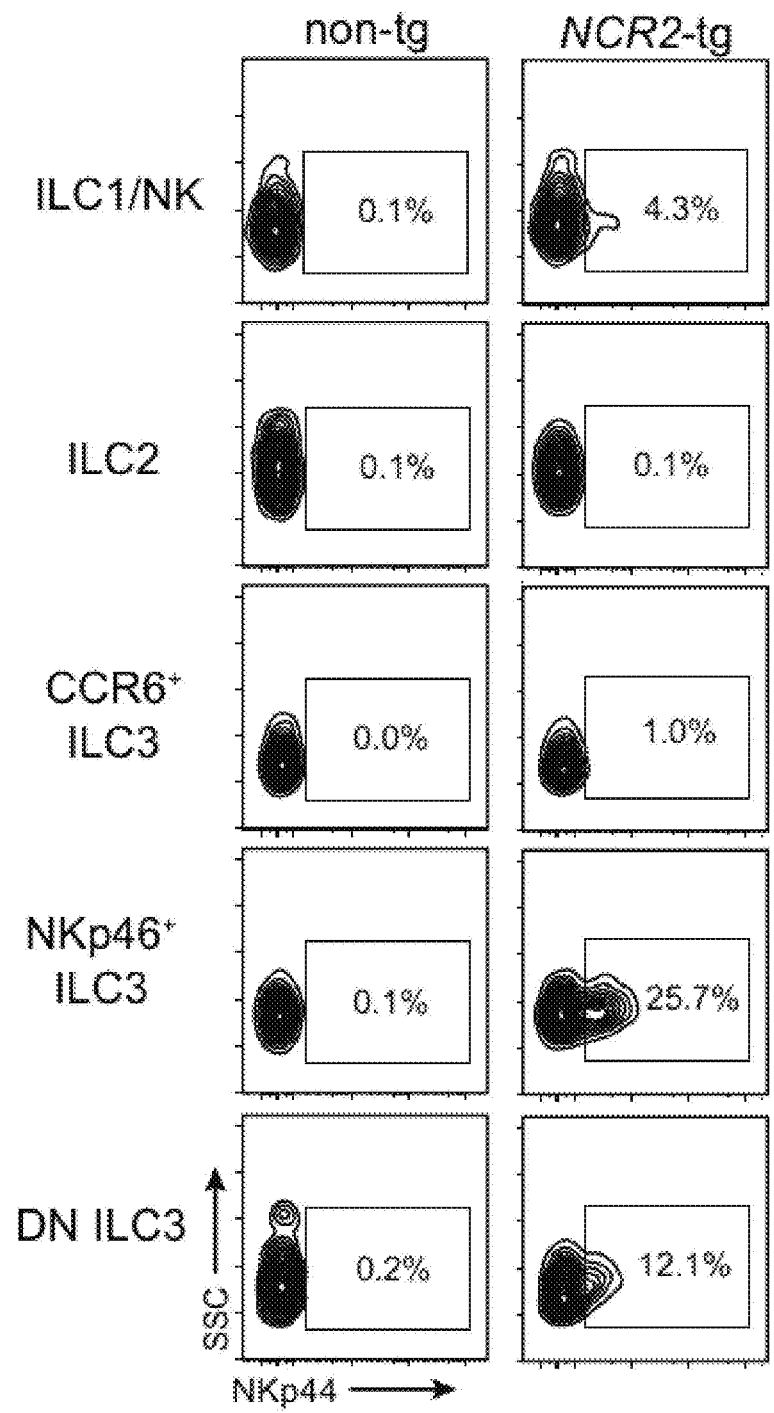
Figure 14D:
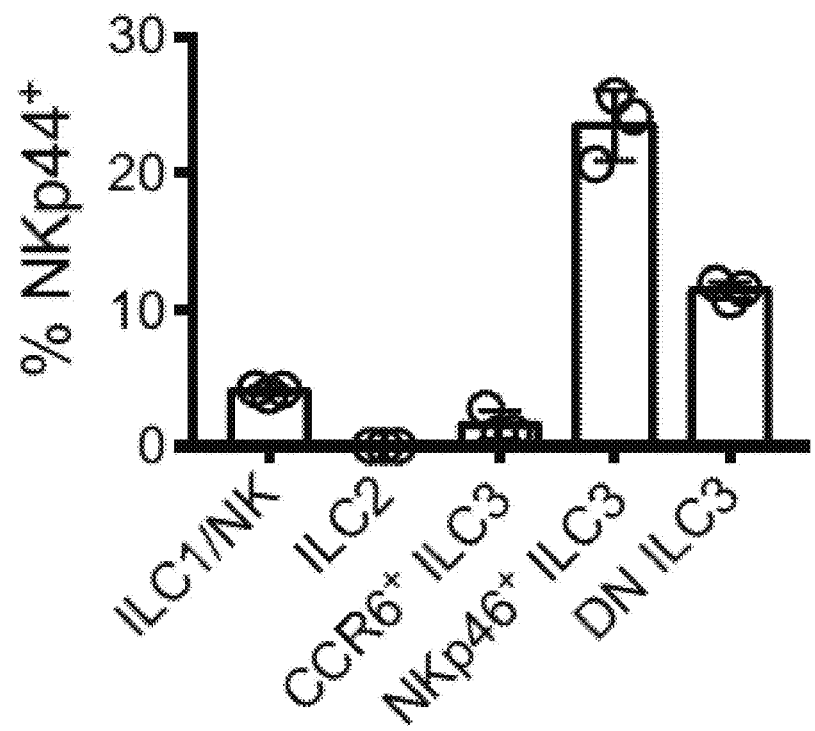
Figure 14E:
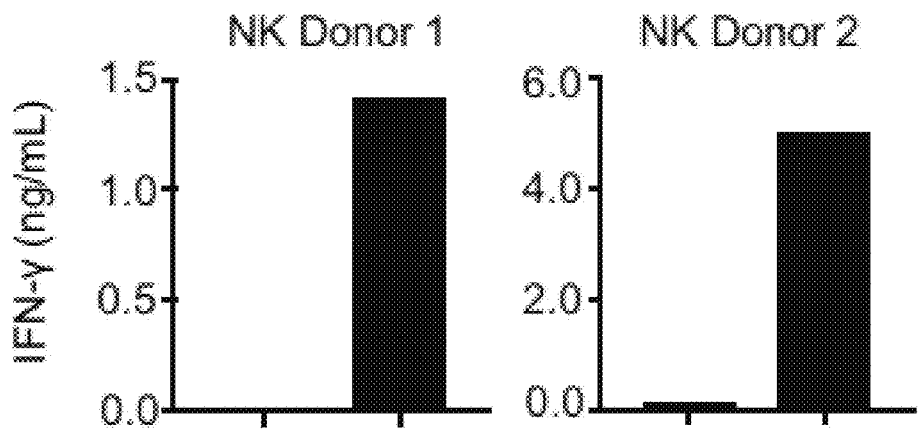
Figure 14F:
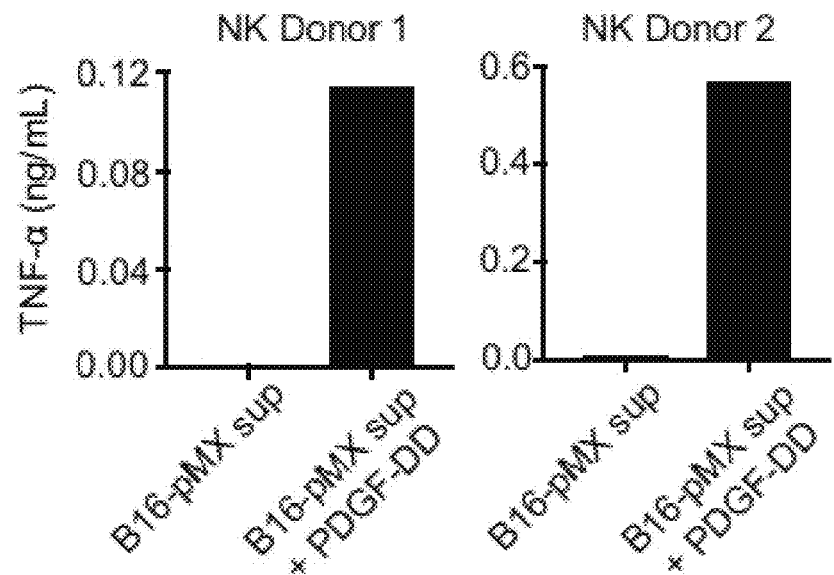
Figure 14G:
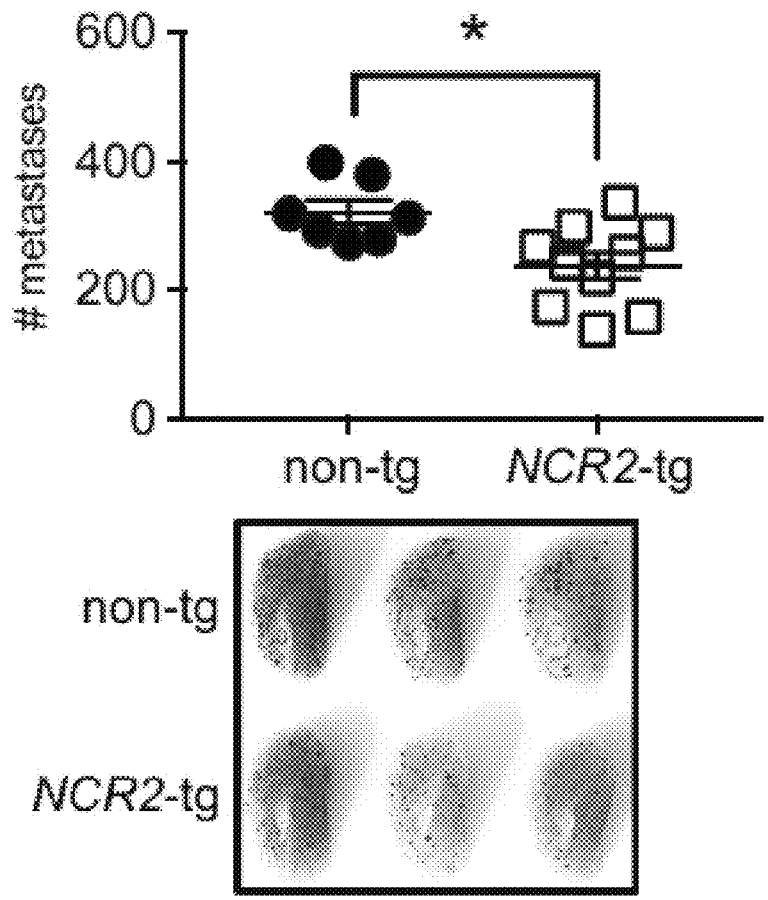
Figure 14H:
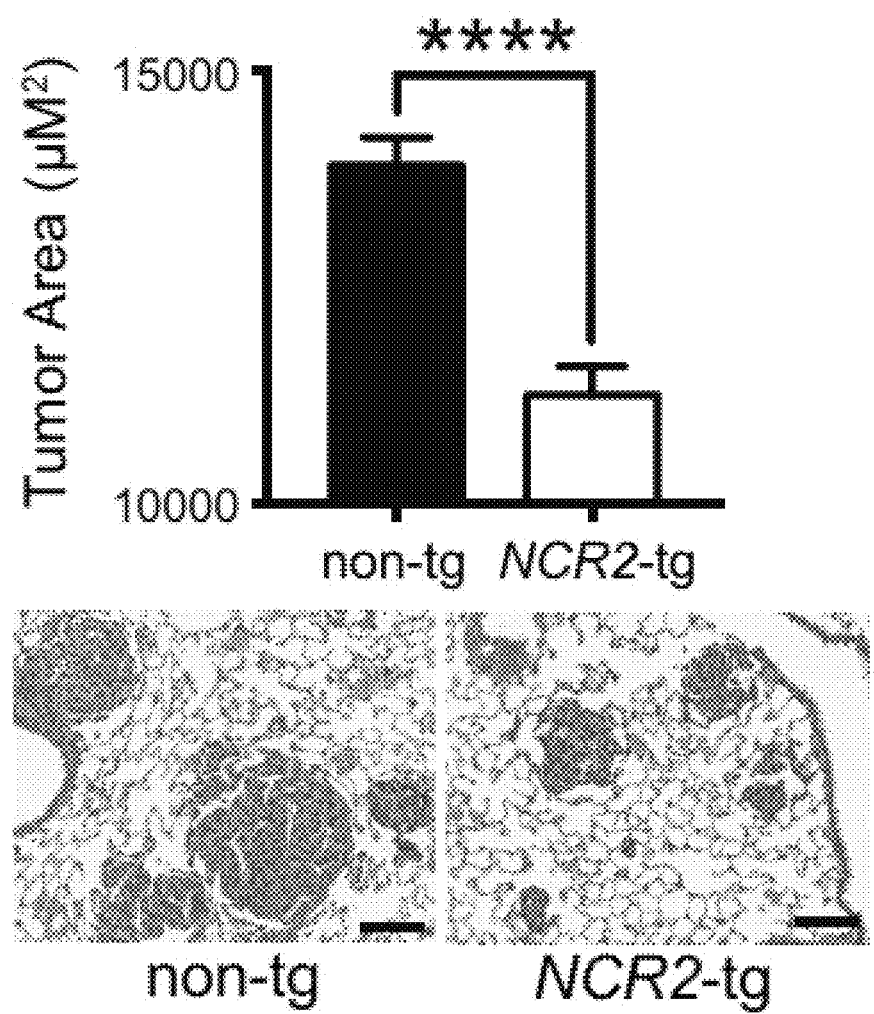
Figure 15:
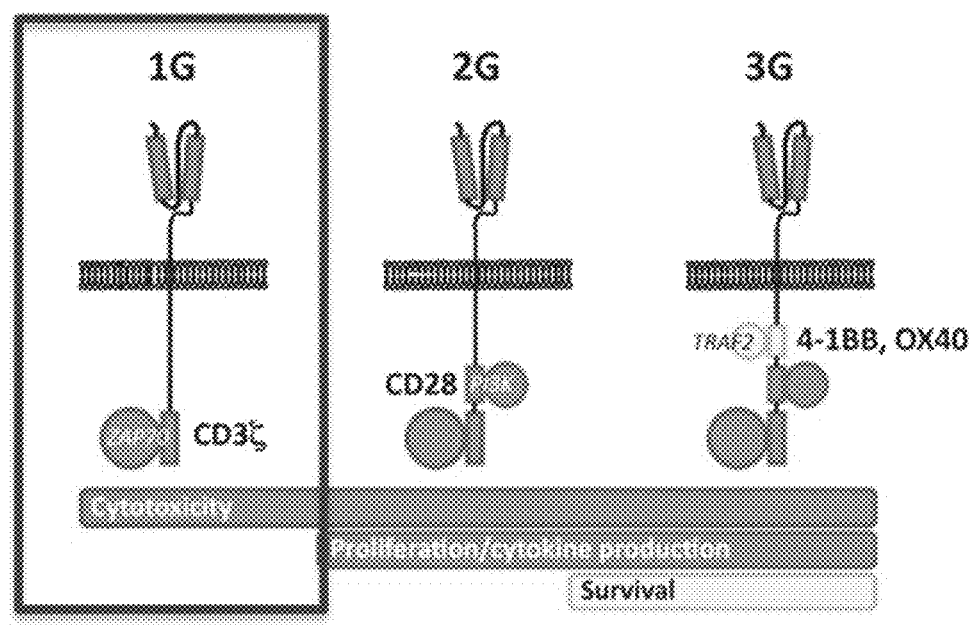
FIG. 15 shows a schematic representation of the different generations of CARs (1G, first generation, 2G, second generation, 3G, third generation). The ecotodomain is highlighted in green, whilst the different components of the T cell receptor signal transduction machinery are highlighted in red (CD3 chain/ZAP70), blue (CD28/PI3K) and yellow (4-1BB or OX40/TRAF).

Because NKp44 is encoded only in humans, we developed bacterial artificial chromosome (BAC) NCR2 transgenic (tg) mice to determine the impact of PDGF-DD/NKp44 interactions on cancer in vivo. Two NCR2-tg lines were generated; in both, expression of the NKp44 transgene mirrored NKp44 expression in the human immune system, although NKp44 was expressed at slightly higher levels in one line. In steady state, NKp44 was found on a small subset of splenic and lymph node NK cells (FIGS. 7A, 14A, and 14B). NKp44 was also expressed on a larger subset of ILC3 and few NK/ILC1 cells in the small intestine (FIGS. 14C and 14D). Upon in vitro activation with IL-2 and IL-15, NK cells showed a marked upregulation of NKp44, which was increased by further stimulation with inflammatory cytokines (FIG. 7B). To determine the impact of PDGF-DD/NKp44 interaction on anti-tumor NK cell activity in vivo, we chose the B16 metastatic tumor model, which has been shown to be sensitive to NK cells, particularly to their IFN-γ secretion capacity (Takeda et al., 2011). We generated B16F10 melanoma cells stably expressing either a bicistronic gene encoding human PDGFD and GFP (B16-PDGFD) or the backbone vector (B16-pMX) as control cells (FIG. 7C). Incubation of TC supernatants from B16-PDGFD cells (B16-PDGFD sup) with human NK cells promoted the secretion of IFN-γ and TNF-α, which was dependent on NKp44 and PDGF-DD (FIGS. 7D and 7E), whereas control TC supernatants from B16-pMX cells did not activate NK cells unless recombinant PDGF-DD was added to the cultures (FIGS. 14E and 14F). Two weeks after intravenous injection of B16-PDGFD cells, NCR2-tg mice had fewer surface metastases (FIGS. 7F and 14G), diminished mean tumor area (FIGS. 7G and 14H), as well as augmented expression of Ifng (FIG. 7H), but not Tnf (FIG. 7I), in lungs compared to non-tg littermates. B16-PDGFD cells formed more lung metastases in NCR2-tg mice treated with blocking anti-NKp44 compared to a control mAb (FIG. 7J), corroborating that higher rejection of B16-PDGFD cells in NCR2-tg mice depends on NKp44. Moreover, lung surface metastases formed by B16-pMX control cells did not differ between NCR2-tg and non-tg littermate mice, indicating that NCR2-tg mice had no inherent advantage over non-tg mice in restricting B16F10 cells (FIG. 7K). We conclude that PDGF-DD/NKp44 interactions facilitate NK cell control of tumor expansion in vivo.

Example 7: NKp44-PDGF-DD Interaction Enhances Checkpoint Blockade

Figure 8A:
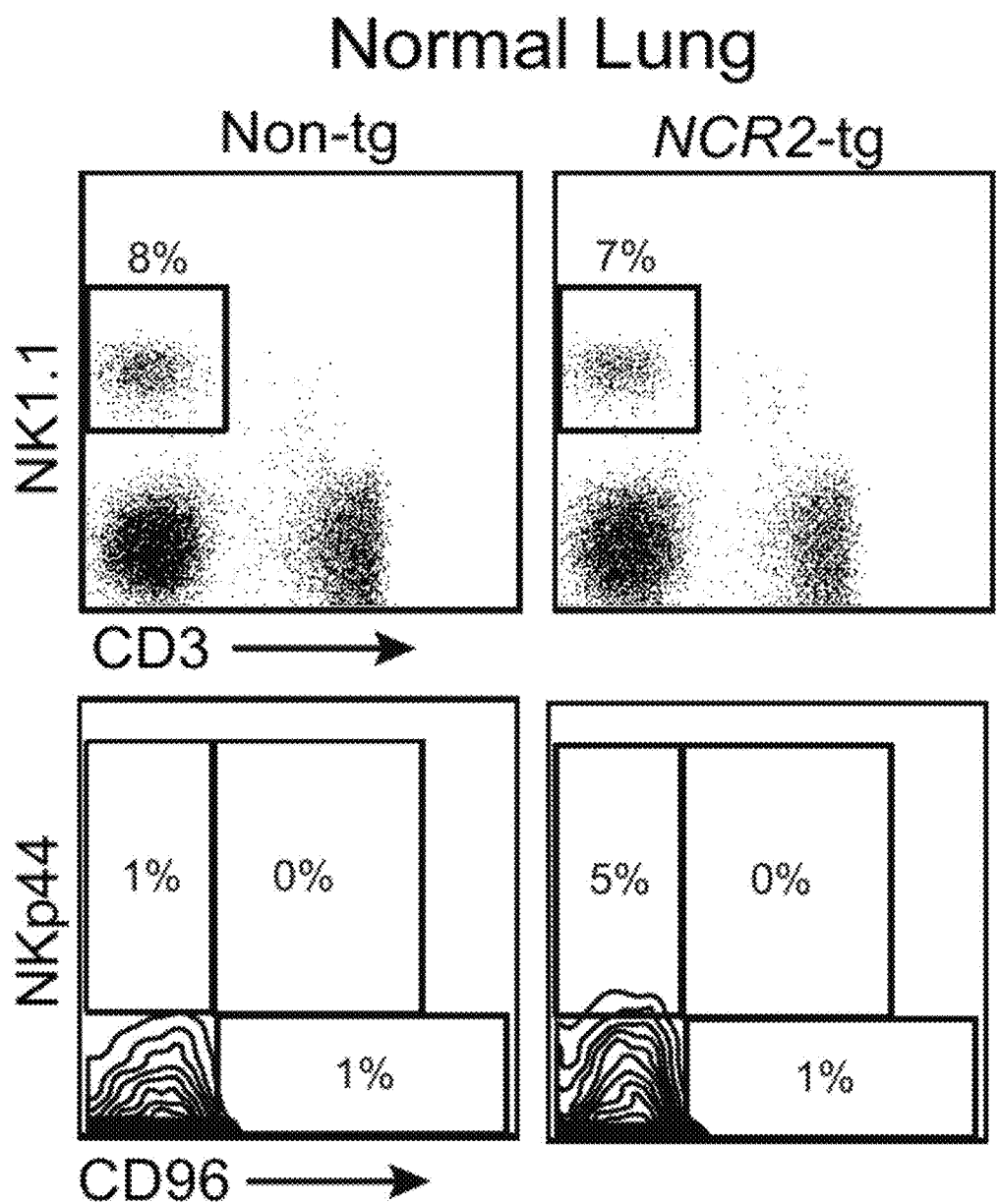
FIG. 8A, FIG. 8B, FIG. 8C, FIG. 8D, FIG. 8E, FIG. 8F, FIG. 8G and FIG. 8H show PDGF-DD binding to NKp44 augments immunotherapies.
Figure 8B:
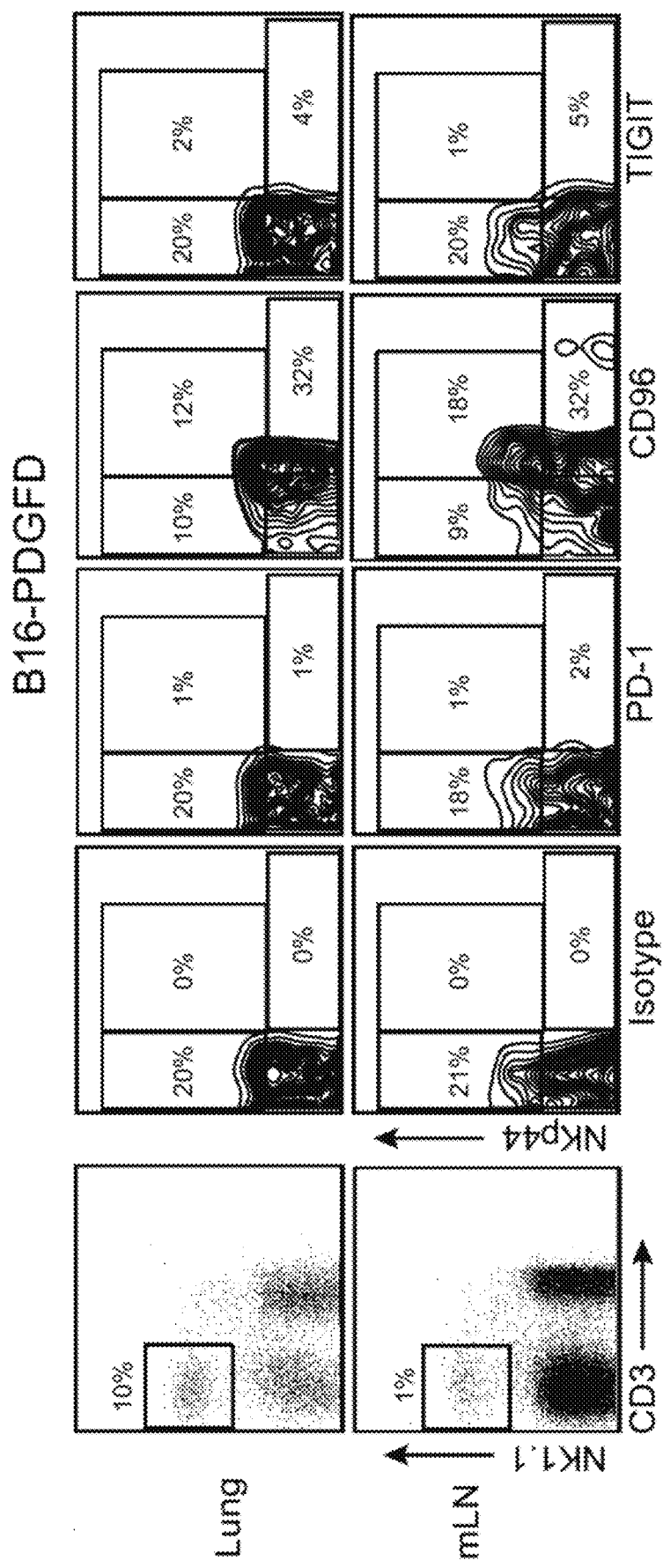
Figure 8C:
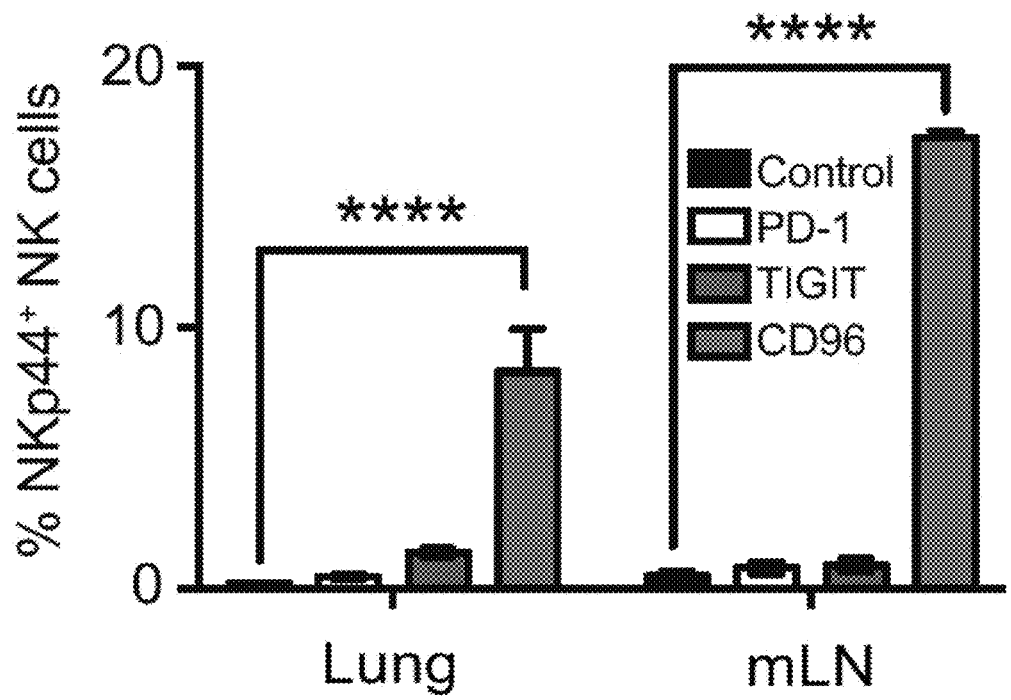
Figure 8D:
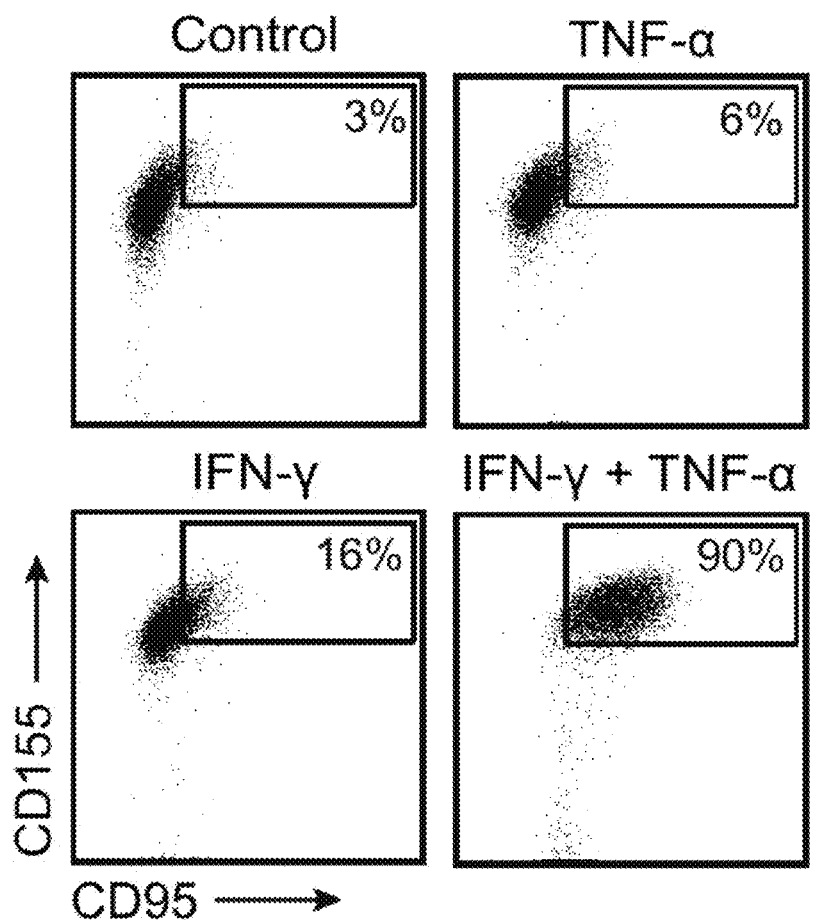
Figure 8E:
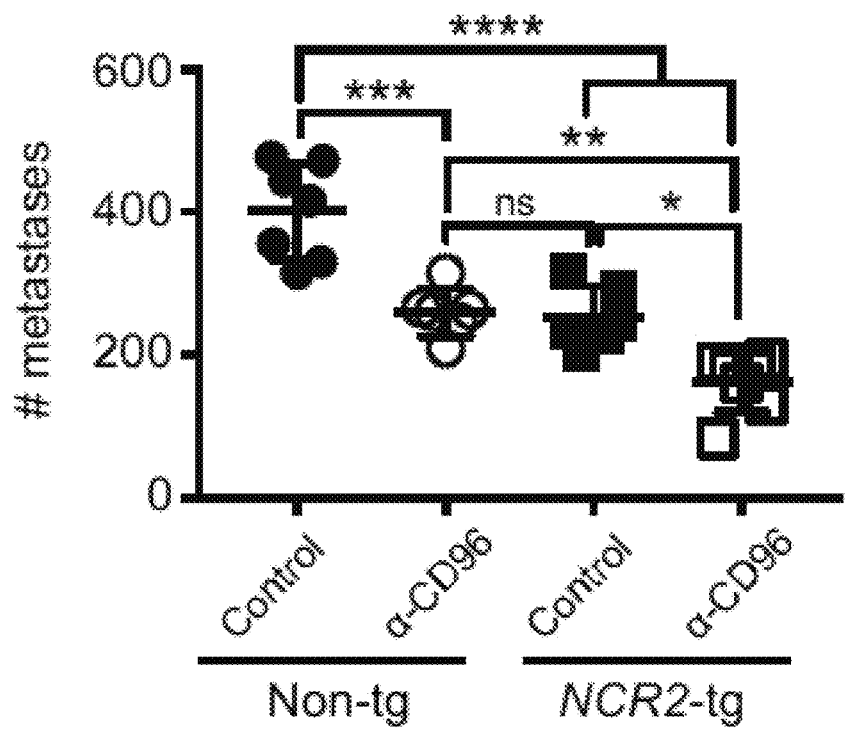

We sought to determine whether the NKp44-PDGF-DD interaction would synergize with checkpoint blockade in tumor rejection. We first examined NK cell expression of NKp44 along with the inhibitory checkpoint receptors PD-1 (Kline and Gajewski, 2010), TIGIT (Blake et al., 2016), and CD96 (Blake et al., 2016) in the lungs and lymph nodes of NCR2-tg mice. In tumor-free NCR2-tg mice, NK cells did not express NKp44, CD96, PD1, or TIGIT (FIG. 8A; data not shown). In contrast, NKp44 and CD96, but not PD-1 or TIGIT, were expressed on NK cells in the lungs and lymph nodes of NCR2-tg mice that had been intravenously injected with B16-PDGFD cells (FIGS. 8B and 8C). Moreover, the CD96 ligand, CD155, was induced on B16F10 cells by IFN-γ and TNF-α (FIG. 8D). Thus, we hypothesized that blockade of the CD96-CD155 interaction might augment NK cell activation and limit B16-PDGFD cell metastases (Blake et al., 2016). Indeed, anti-CD96 treatment lowered the number of B16-PDGFD surface lung metastases formed in NCR2-tg and non-tg littermates. Importantly, B16-PDGFD surface lung metastases were fewer in NCR2-tg mice compared to non-tg mice receiving anti-CD96 immunotherapy (FIG. 8E). Thus, PDGF-DD/NKp44 interaction and anti-CD96 immunotherapy cooperate in NK cell control of B16-PDGFD cell metastases.

Example 8: NKp44 Engagement Boosts CpG-Induced Control of Subcutaneous Melanoma

Figure 8F:
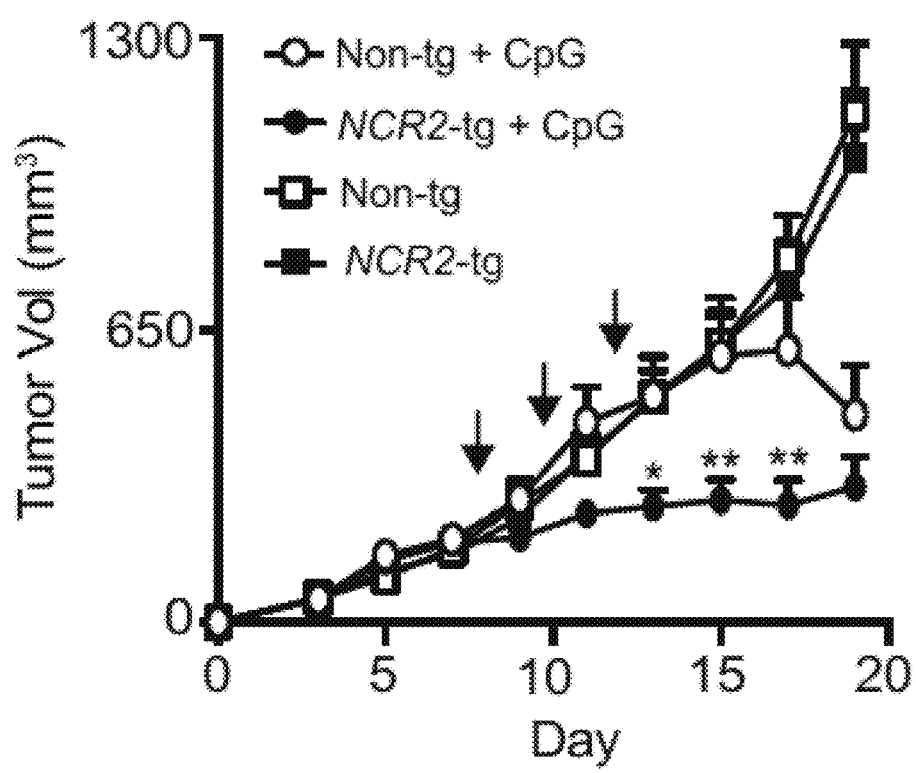
Figure 8G:
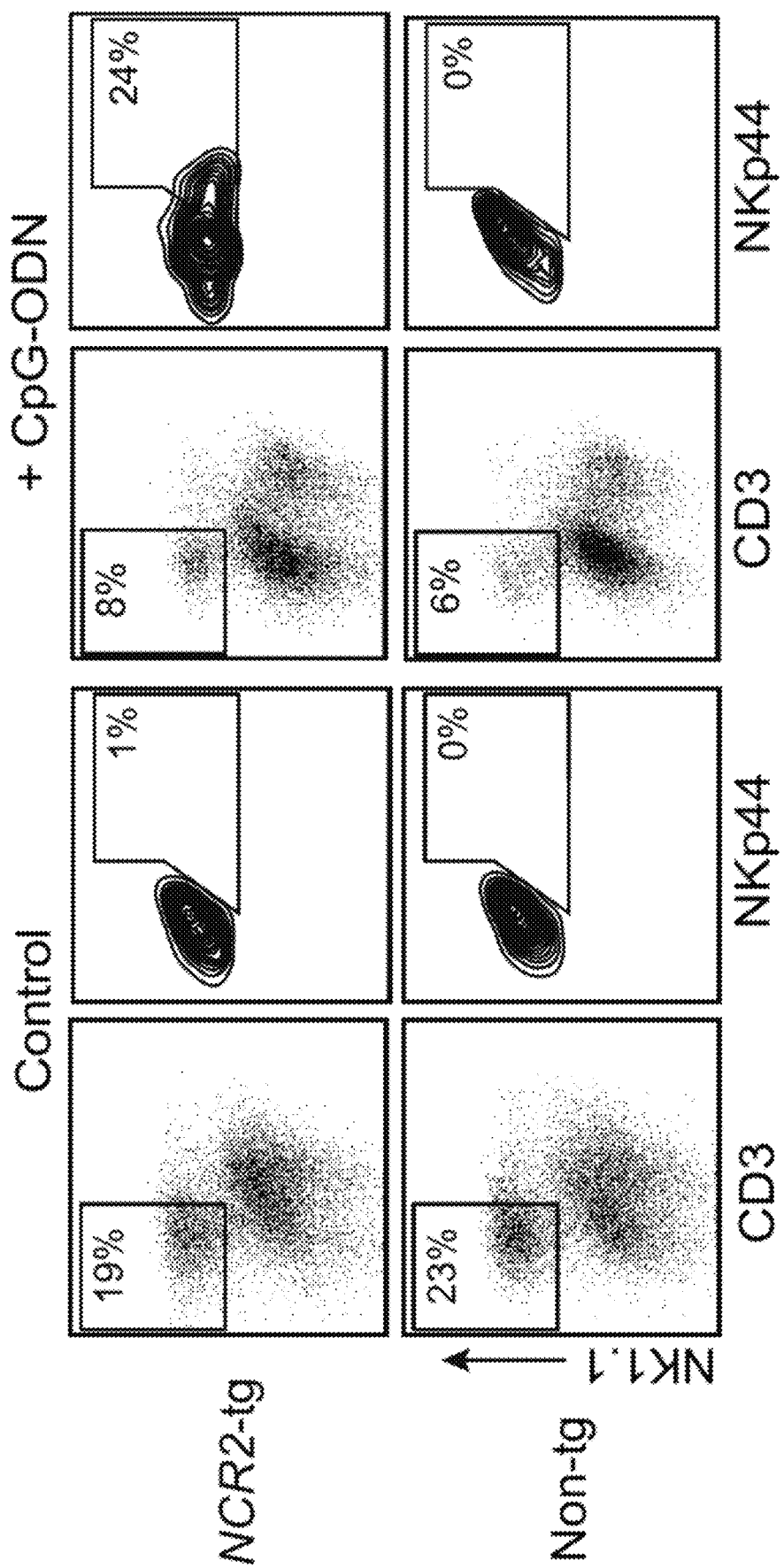
Figure 8H:
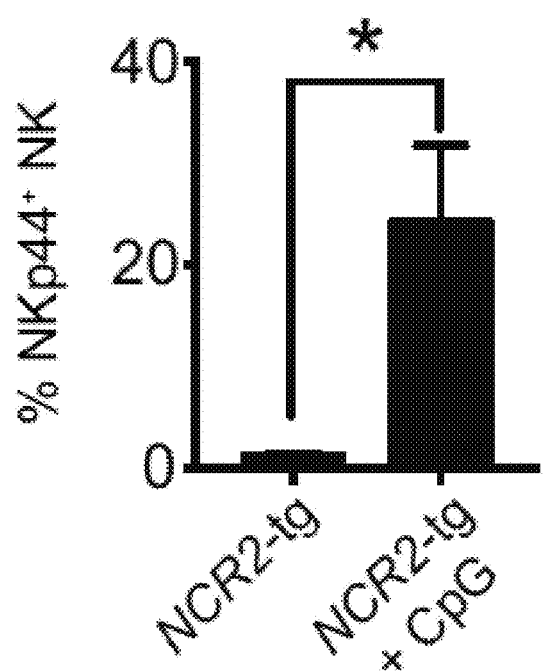

In contrast to the lung B16 metastatic model, NK cells have little impact on subcutaneous B16 melanoma, probably due a poorly immunogenic environment that prevents NK cell activation. However, it has been shown that CpG-ODN immunotherapy can stimulate NK cell recruitment, activation, and NK cell-dependent regression of subcutaneous B16 melanoma (Liu et al., 2008). We examined whether the NKp44-PDGF-DD axis can impact the ability of CpG-ODN to restrict the growth of subcutaneous melanoma. In the absence of CpG treatment, tumor growth of subcutaneous B16-PDGFD melanoma was equally unrestricted in NCR2-tg or non-tg littermates (FIG. 8F). Conversely, in mice receiving CpG-ODN, growth of B16-PDGFD tumors was restricted sooner in NCR2-tg compared to non-tg littermates (FIG. 8F). The earlier control of B16-PDGFD growth in NCR2-tg following CpG-ODN was paralleled by a marked induction of NKp44 expression in intratumoral NK cells (FIGS. 8G and 8H). These results show that CpG-ODN treatment can restrict outgrowth of a solid tumor more effectively when infiltrating NK cells are activated by tumor-expressed PDGF-DD.

Discussion Examples 1-8

We have demonstrated that NKp44 recognizes PDGF-DD, enabling NK cells, as well as ILC3 and ILC1, to detect cells secreting PDGF-DD. The identification of PDGF-DD as a ligand for NKp44 establishes a new paradigm in NK cell biology. Activating NK cell receptors have been shown to recognize cell surface ligands encoded by pathogens (Arase et al., 2002; Li et al., 2013) or induced by cellular stress during viral infections (Raulet et al., 2013). NKp44 is the first activating NK cell receptor found to recognize a cellular growth factor. In tumor settings, cancer cell production of PDGF-DD is known to stimulate tumor growth and angiogenesis through PDGFRβ. However, our data indicate that in tumors infiltrated by activated NK cells, PDGF-DD also exposes tumor cells to innate immune recognition through NKp44, inducing a proinflammatory reaction that restricts cancer cell growth in vitro and in vivo. Because the simian sarcoma virus contains a v-sis oncogene that encodes a functional homolog of PDGF (Deuel et al., 2013), NKp44-mediated recognition of PDGF-DD may reflect an evolutionary strategy for NK surveillance of transforming viruses.

Meta-analysis of TOGA datasets suggests that the PDGF-DD/NKp44 interaction may have clinical impact in the control of GBM. Higher expression of the canonical cytokine and cell-cycle variates of NCR2 correlated with greater overall survival of GBM patients. Moreover, NKp44+ NK cells infiltrated GBM, although not in all cases, and PDGF-DD protein or PDGFD mRNA were expressed in glioma cell lines and primary glioblastoma tumor tissues (Lokker et al., 2002). While PDGF-DD was shown to promote mitogenic pathways in glioblastoma cells through PDGFRβ (Lokker et al., 2002; Nazarenko et al., 2012), it may also alert tumor-infiltrating innate immune cells through engagement of NKp44. Appropriate clinical studies beyond these correlative data will be important to test this hypothesis. We envision that therapies aimed at blocking PDGFRβ may favor PDGF-DD-mediated stimulation of NKp44 and control of GBM growth. Additionally, we have shown that NKp44-PDGF-DD interactions synergized with blockade of the inhibitory receptor CD96 in controlling lung metastatic melanoma and enhanced the control of subcutaneous melanoma by CpG-ODN treatment. Thus, combination of NKp44 activation therapies with checkpoint blockade or adjuvant therapy may be a valid strategy for control of GBM and other tumors infiltrated by NK cells.

Although many tumors express PDGFD and NCR2, correlative studies of TOGA cohorts did not support a significant impact of PDGF-DD/NKp44 interactions with tumor progression beyond GBM. NK cells or ILCs may not infiltrate these tumors, the tumor environment may prevent NK cell activation or expression of NKp44. The continuing stimulation of NKp44 by PDGF-DD could result in exhaustion/anergy of innate immune cells and paradoxically promote tumor growth, as observed with chronic activation of other NK cell receptors (Groh et al.,). Sustained production of IFN-γ may also be co-opted in the tumor environment (Nirschl et al., 2017). Finally, it is possible that the PDGF-DD/NKp44 contribution is obscured by other concurrent innate and/or adaptive immune responses (Gajewski et al., 2013). Overall, the impact of PDGF-DD/NKp44 interactions may be more complex than just the control of cell growth observed in our experimental settings and may have diverse effects on tumor editing and progression in different contexts. PDGF-DD contributes to angiogenesis, embryonal development of various organs, formation of the placenta during pregnancy, and supports wound healing (Li and Eriksson 2003; Reigstad et al., 2005). In disease, PDGF-DD has been implicated in vascular diseases (Chen et al., 2005), mesangioproliferative glomerulonephritis, and fibrosis (Reigstad et al., 2005). Polymorphisms in PDGFD have even been associated with coronary artery disease (Nikpay et al., 2015) and serum levels of IFN-γ (Ahola-Olli et al., 2017). Thus, PDGF-DD/NKp44 interactions may play wider biological roles beyond cancer.

References for Examples 1-8

Ahola-Olli, A. V., Wartz, P., Havulinna, A S., Aalto, K., Pitkanen, N., Lehtimaki, T., Kahonen, M., Lyytikainen, L.-P., Raitoharju, E., Seppala, I., et al. (2017). Genome-wide association study identifies 27 loci influencing concentrations of circulating cytokines and growth factors. Am. J. Hum. Genet. 100, 40-50.

Andrae, J., Gallini, R., and Betsholtz, C. (2008). Role of platelet-derived growth factors in physiology and medicine. Genes Dev. 22, 1276-1312.

Arase, H., Mocarski, E. S., Campbell, A. E., Hill, A. B., and Lanier, L. L. (2002). Direct recognition of cytomegalovirus by activating and inhibitory NK cell receptors. Science 296, 1323-1326.

Barrow, A. D., Raynal, N., Andersen, T. L., Slatter, D. A., Bihan, D., Pugh, N., Cella, M., Kim, T., Rho, J., Negishi-Koga, T., et al. (2011). OSCAR is a collagen receptor that costimulates osteoclastogenesis in DAP12-deficient humans and mice. J. Clin. Invest. 121, 3505-3516.

Barrow, A D., Palarasah, Y., Bugatti, M., Holehouse, A S., Byers, D. E., Holtzman, M. J., Vermi, W., Skjodt, K., Crouch, E., and Colonna, M. (2015). OSCAR is a receptor for surfactant protein D that activates TNF-a release from human CCR2+ inflammatory monocytes. J. Immunol. 194, 3317-3326.

Bast, R. C., Jr., Feeney, M., Lazarus, H., Nadler, L M., Colvin, R. B., and Knapp, R. C. (1981). Reactivity of a monoclonal antibody with human ovarian carcinoma. J. Clin. Invest. 68, 1331-1337.

Baychelier, F., Sennepin, A., Ermonval, M., Dorgham, K., Debra, P., and Vieillard, V. (2013). Identification of a cellular ligand for the natural cytotoxicity receptor NKp44. Blood 122, 2935-2942.

Bergsten, E., Uutela, M., Li, X., Pietras, K., Ostman, A., Heldin, C. H., Alitalo, K., and Eriksson, U. (2001). PDGF-D is a specific, protease-activated ligand for the PDGF beta-receptor. Nat. Cell Biol. 3, 512-516.

Bezbradica, J. S., and Medzhitov, R. (2012). Role of ITAM signaling module in signal integration. Curr. Opin. Immunol. 24, 58-66. Blake, S. J., Dougall, W. C., Miles, J. J., Teng, M. W. L., and Smyth, M. J. (2016). Molecular pathways: targeting CD96 and TIGIT for cancer immunotherapy. Clin. Cancer Res. 22, 5183-5188.

Boles, K S., Barchet, W., Diacovo, T., Cella, M., and Colonna, M. (2005). The tumor suppressor TSLC1/NECL-2 triggers NK-cell and CD8+ T-cell responses through the cell-surface receptor CRTAM. Blood 106, 779-786.

Braumaller, H., Wieder, T., Brenner, E., A8mann, S., Hahn, M., Alkhaled, M., Schilbach, K., Essmann, F., Kneilling, M., Griessinger, C., et al. (2013). T-helper-1-cell cytokines drive cancer into senescence. Nature 494, 361-365.

Cantoni, C., Bottino, C., Vitale, M., Pessino, A, Augugliaro, R., Malaspina, A., Parolini, S., Moretta, L, Moretta, A., and Biassoni, R. (1999). NKp44, a triggering receptor involved in tumor cell lysis by activated human natural killer cells, is a novel member of the immunoglobulin superfamily. J. Exp. Med. 189, 787-796.

Carrega, P., Loiacono, F., Di Carlo, E., Scaramuccia, A., Mora, M., Conte, R., Benelli, R., Spaggiari, G. M., Cantoni, C., Campana, S., et al. (2015). NCR(+) ILC3 concentrate in human lung cancer and associate with intratumoral lymphoid structures. Nat. Commun. 6, 8280.

Cella, M., Fuchs, A., Vermi, W., Facchetti, F., Otero, K., Lennerz, J. K. M., Doherty, J. M., Mills, J. C., and Colonna, M. (2009). A human natural killer cell subset provides an innate source of IL-22 for mucosal immunity. Nature 457, 722-725.

Cella, M., Otero, K., and Colonna, M. (2010). Expansion of human NK-22 cells with IL-7, IL-2, and IL-Ibeta reveals intrinsic functional plasticity. Proc. Natl. Acad. Sci. USA 107, 10961-10966.

Chang, C.-C., Campoli, M., Restifo, N. P., Wang, X., and Ferrone, S. (2005). Immune selection of hot-spot beta 2-microglobulin gene mutations, HLA-A2 allospecificity loss, and antigen-processing machinery component downregulation in melanoma cells derived from recurrent metastases following immunotherapy. J. Immunol. 174, 1462-1471.

Chen, J., Han, Y., Lin, C., Zhen, Y., Song, X., Teng, S., Chen, C., Chen, Y., Zhang, Y., and Hui, R. (2005). PDGF-D contributes to neointimal hyperplasia in rat model of vessel injury. Biochem. Biophys. Res. Commun. 329, 976-983.

Dadi, S., Chhangawala, S., Whitlock, B. M., Franklin, R. A., Luo, C. T., Oh, S. A., Toure, A., Pritykin, Y., Huse, M., Leslie, C. S., and Li, M. O. (2016). Cancer immunosurveillance by tissue-resident innate lymphoid cells and innate-like T cells. Cell 164, 365-377.

Deschodt-Lanckman, M., Vanneste, Y., Loir, B., Michel, A., Libert, A, Ghanem, G., and Lejeune, F. (1990). Degradation of alpha-melanocyte stimulating hormone (alpha-MSH) by CALLA/endopeptidase 24.11 expressed by human melanoma cells in culture. Int. J. Cancer 46, 1124-1130.

Deuel, T. F., Huang, J. S., Huang, S. S., Stroobant, P., and Waterfield, M. D. (1983). Expression of a platelet-derived growth factor-like protein in simian sarcoma virus transformed cells. Science 221, 1348-1350.

Dolcetti, R., Dal Col, J., Martorelli, D., Carbone, A, and Klein, E. (2013). Interplay among viral antigens, cellular pathways and tumor microenvironment in the pathogenesis of EBV-driven lymphomas. Semin. Cancer Biol. 23, 441-456.

Fuchs, A., Cella, M., Kondo, T., and Colonna, M. (2005). Paradoxic inhibition of human natural interferon-producing cells by the activating receptor NKp44. Blood 106, 2076-2082.

Fuchs, A., Vermi, W., Lee, J. S., Lonardi, S., Gilfillan, S., Newberry, R. D., Cella, M., and Colonna, M. (2013). Intraepithelial type 1 innate lymphoid cells are a unique subset of IL-12- and IL-15-responsive IFN-y-producing cells. Immunity 38, 769-781.

Gajewski, T. F., Schreiber, H., and Fu, Y.-X. (2013). Innate and adaptive immune cells in the tumor microenvironment. Nat. Immunol. 14, 1014-1022.

Glatzer, T., Killig, M., Meisig, J., Ommert, I., Luetke-Eversloh, M., Babic, M., Paclik, D., Blathgen, N., Seidl, R., Seifarth, C., et al. (2013). RORyr innate lymphoid cells acquire a proinflammatory program upon engagement of the activating receptor NKp44. Immunity 38, 1223-1235.

Gong, J. H., Maki, G., and Klingemann, H. G. (1994). Characterization of a human cell line (NK-92) with phenotypical and functional characteristics of activated natural killer cells. Leukemia 8, 652-658.

Gonzalez, R., Jennings, L L, Knuth, M., Orth, A. P., Klock, H. E., Ou, W., Feuer-helm, J., Hull, Koesema, E., Wang, Y., et al. (2010). Screening the mammalian extracellular proteome for regulators of embryonic human stem cell pluripotency. Proc. Natl. Acad. Sci. USA 107, 3552-3557.

Gorer, P. A. (1950). Studies in antibody response of mice to tumour inoculation. Br. J. Cancer 4, 372-379.

Groh, V., Wu, J., Yee, C., and Spies, T. (2002). Tumour-derived soluble MIC ligands impair expression of NKG2D and T-cell activation. Nature 419, 734-738.

Hedrick, S. M., Matis, L A., Hecht, T. T., Samelson, L. E., Longo, D. L., Heber-Katz, E., and Schwartz, R. H. (1982). The fine specificity of antigen and Ia determinant recognition by T cell hybridoma clones specific for pigeon cytochrome c. Cell 30, 141-152.

Ho, J. W., Hershkovitz, O., Peiris, M., Zilka, A., Bar-Ilan, A., Nal, B., Chu, K., Kudelko, M., Kam, Y. W., Achdout, H., et al. (2008). H5-type influenza virus hemagglutinin is functionally recognized by the natural killer-activating receptor NKp44. J. Virol. 82, 2028-2032.

Huang, W., and Kim, H.-R. C. (2015). Dynamic regulation of platelet-derived growth factor D (PDGF-D) activity and extracellular spatial distribution by matriptase-mediated proteolysis. J. Biol. Chem. 290, 9162-9170.

Kitamura, T., Koshino, Y., Shibata, F., Oki, T., Nakajima, H., Nosaka, T., and Kumagai, H. (2003). Retrovirus-mediated gene transfer and expression cloning: powerful tools in functional genomics. Exp. Hematol. 31, 1007-1014.

Kline, J., and Gajewski, T. F. (2010). Clinical development of mAbs to block the PD1 pathway as an immunotherapy for cancer. Curr. Opin. Investig. Drugs 11, 1354-1359.

LaRochelle, W. J., Jeffers, M., Corvalan, J. R. F., Jia, X.-C., Feng, X., Vanegas, S., Vickroy, J. D., Yang, X.-D., Chen, F., Gazit, G., et al. (2002). Platelet-derived growth factor D: tumorigenicity in mice and dysregulated expression in human cancer. Cancer Res. 62, 2468-2473.

Lefrangois, L, and Lycke, N. (2001). Isolation of mouse small intestinal intraepithelial lymphocytes, Peyer's patch, and lamina propria cells. Curr. Protoc. Immunol. Chapter 3, Unit 3.19.

Li, H., and Durbin, R. (2009). Fast and accurate short read alignment with Burrows-Wheeler transform. Bioinformatics 25, 1754-1760.

Li, X., and Eriksson, U. (2003). Novel PDGF family members: PDGF-C and PDGF-D. Cytokine Growth Factor Rev. 14, 91-98.

Li, H., Handsaker, B., Wysoker, A., Fennell, T., Ruan, J., Homer, N., Marth, G., Abecasis, G., and Durbin, R.; 1000

Genome Project Data Processing Subgroup (2009). The Sequence Alignment/Map format and SAMtools. Bioinformatics 25, 2078-2079.

Li, S. S., Kyei, S. K., Timm-McCann, M., Ogbomo, H., Jones, G. J., Shi, M., Xiang, R. F., Oykhman, P., Huston, S. M., Islam, A., et al. (2013). The NK receptor NKp30 mediates direct fungal recognition and killing and is diminished in NK cells from HIV-infected patients. Cell Host Microbe 14, 387-397.

Lin, Y.-C., Boone, M., Meuris, L., Lemmens, I., Van Roy, N., Soete, A., Reumers, J., Moisse, M., Plaisance, S., Drmanac, R., et al. (2014). Genome dynamics of the human embryonic kidney 293 lineage in response to cell biology manipulations. Nat. Commun. 5, 4767.

Liu, C., Lou, Y., Lithe, G., Qin, H., Liu, S., Rabinovich, B., Kim, G. J., Wang, Y.-H., Ye, Y., Sikora, A G., et al. (2008). Plasmacytoid dendritic cells induce NK cell-dependent, tumor antigen-specific T cell cross-priming and tumor regression in mice. J. Clin. Invest. 118, 1165-1175.

Lokker, N A, Sullivan, C. M., Hollenbach, S. J., Israel, M. A., and Giese, N. A. (2002). Platelet-derived growth factor (PDGF) autocrine signaling regulates survival and mitogenic pathways in glioblastoma cells: evidence that the novel PDGF-C and PDGF-D ligands may play a role in the development of brain tumors. Cancer Res. 62, 3729-3735.

Nakamura, K., Yoshikawa, N., Yamaguchi, Y., Kagota, S., Shinozuka, K., and Kunitomo, M. (2002). Characterization of mouse melanoma cell lines by their mortal malignancy using an experimental metastatic model. Life Sci. 70, 791-798.

Nazarenko, I., Hede, S.-M., He, X., Hedren, A., Thompson, J., Lindstrom, M. S., and Nister, M. (2012). PDGF and PDGF receptors in glioma. Ups. J. Med. Sci. 117, 99-112.

Nikpay, M., Goel, A, Won, H.-H., Hall, L M., Willenborg, C., Kanoni, S., Saleheen, D., Kyriakou, T., Nelson, C. P., Hopewell, J. C., et al. (2015). A comprehensive 1,000 Genomes-based genome-wide association meta-analysis of coronary artery disease. Nat. Genet. 47, 1121-1130.

Nirschl, C. J., Suarez-Farifias, M., Izar, B., Prakadan, S., Dannenfelser, R., Tirosh, I., Liu, Y., Zhu, Q., Devi, K. S. P., Carroll, S. L., et al. (2017). IFNy-dependent tissue-immune homeostasis is co-opted in the tumor microenvironment. Cell 170, 127-141.

Oi, V. T., Morrison, S. L., Herzenberg, L A., and Berg, P. (1983). Immunoglobulin gene expression in transformed lymphoid cells. Proc. Natl. Acad. Sci. USA 80, 825-829.

Raulet, D. H., Gasser, S., Gowen, B. G., Deng, W., and Jung, H. (2013). Regulation of ligands for the NKG2D activating receptor. Annu. Rev. Immunol. 31, 413-441.

Reigstad, L. J., Varhaug, J. E., and Lillehaug, J. R. (2005). Structural and functional specificities of PDGF-C and PDGF-D, the novel members of the platelet-derived growth factors family. FEBS J. 272, 5723-5741.

Robinette, M. L., Fuchs, A., Cortez, V. S., Lee, J. S., Wang, Y., Durum, S. K., Gilfillan, S., and Colonna, M.; Immunological Genome Consortium (2015). Transcriptional programs define molecular characteristics of innate lymphoid cell classes and subsets. Nat. Immunol. 16, 306-317.

Rosental, B., Brusilovsky, M., Hadad, U., Oz, D., Appel, M. Y., Afergan, F., Yossef, R., Rosenberg, L A., Aharoni, A., Cerwenka, A., et al. (2011). Proliferating cell nuclear antigen is a novel inhibitory ligand for the natural cytotoxicity receptor NKp44. J. Immunol. 187, 5693-5702.

Schneider, U., Schwenk, H. U., and Bornkamm, G. (1977). Characterization of EBV-genome negative "null" and "T" cell lines derived from children with acute lymphoblastic leukemia and leukemic transformed non-Hodgkin lymphoma. Int. J. Cancer 19, 621-626.

Shim, A H.-R., Liu, H., Focia, P. J., Chen, X., Lin, P. C., and He, X. (2010). Structures of a platelet-derived growth factor/propeptide complex and a plateletderived growth factor/receptor complex. Proc. Natl. Acad. Sci. USA 107, 11307-11312.

Sivori, S., Parolini, S., Marcenaro, E., Castriconi, R., Pende, D., Millo, R., and Moretta, A (2000). Involvement of natural cytotoxicity receptors in human natural killer cell-mediated lysis of neuroblastoma and glioblastoma cell lines. J. Neuroimmunol. 107, 220-225.

Soule, H. D., Vazguez, J., Long, A., Albert, S., and Brennan, M. (1973). A human cell line from a pleural effusion derived from a breast carcinoma. J. Natl. Cancer Inst. 51, 1409-1416.

Studier, F. W. (2005). Protein production by auto-induction in high density shaking cultures. Protein Expr. Purif. 41, 207-234.

Takeda, K., Nakayama, M., Sakaki, M., Hayakawa, Y., Imawari, M., Ogasawara, K., Okumura, K., and Smyth, M. J. (2011). IFN-y production by lung NK cells is critical for the natural resistance to pulmonary metastasis of B16 melanoma in mice. J. Leukoc. Biol. 90, 777-785.

Ustach, C. V., and Kim, H.-R. C. (2005). Platelet-derived growth factor D is activated by urokinase plasminogen activator in prostate carcinoma cells. Mol. Cell. Biol. 25, 6279-6288.

Ustach, C. V., Huang, W., Conley-LaComb, M. K., Lin, C.-Y., Che, M., Abrams, J., and Kim, H.-R. C. (2010). A novel signaling axis of matriptase/PDGF-D/ẞ-PDGFR in human prostate cancer. Cancer Res. 70, 9631-9640. Vieillard, V., Strominger, J. L., and Debre, P. (2005). NK cytotoxicity against CD4+ T cells during HIV-1 infection: a gp41 peptide induces the expression of an NKp44 ligand. Proc. Natl. Acad. Sci. USA 102, 10981-10986.

Vitale, M., Bottino, C., Sivori, S., Sanseverino, L, Castriconi, R., Marcenaro, E., Augugliaro, R., Moretta, L, and Moretta, A. (1998). NKp44, a novel triggering surface molecule specifically expressed by activated natural killer cells, is involved in non-major histocompatibility complex-restricted tumor cell lysis. J. Exp. Med. 187, 2065-2072.

Wu, Q., Hou, X., Xia, J., Qian, X., Miele, L, Sarkar, F. H., and Wang, Z. (2013). Emerging roles of PDGF-D in EMT progression during tumorigenesis. Cancer Treat. Rev. 39, 640-646.

Xu, L, Tong, R., Cochran, D. M., and Jain, R. K. (2005). Blocking plateletderived growth factor-D/platelet-derived growth factor receptor beta signaling inhibits human renal cell carcinoma progression in an orthotopic mouse model. Cancer Res. 65, 5711-5719.

Groh, V., Wu, J., Yee, C., and Spies, T. (2002). Tumour-derived soluble MIC ligands impair expression of NKG2D and T-cell activation. Nature 419, 734-738.

Hedrick, S. M., Matis, L. A., Hecht, T. T., Samelson, L. E., Longo, D. L., Heber-Katz, E., and Schwartz, R. H. (1982). The fine specificity of antigen and Ia determinant recognition by T cell hybridoma clones specific for pigeon cytochrome c. Cell 30, 141-152.

Ho, J. W., Hershkovitz, O., Peiris, M., Zilka, A., Bar-Ilan, A., Nal, B., Chu, K., Kudelko, M., Kam, Y. W., Achdout, H., et al. (2008). H5-type influenza virus hemagglutinin is functionally recognized by the natural killer-activating receptor NKp44. J. Virol. 82, 2028-2032.

Huang, W., and Kim, H.-R. C. (2015). Dynamic regulation of platelet-derived growth factor D (PDGF-D) activity and extracellular spatial distribution by matriptase-mediated proteolysis. J. Biol. Chem. 290, 9162-9170.

Kitamura, T., Koshino, Y., Shibata, F., Oki, T., Nakajima, H., Nosaka, T., and Kumagai, H. (2003). Retrovirus-mediated gene transfer and expression cloning: powerful tools in functional genomics. Exp. Hematol. 31, 1007-1014.

Kline, J., and Gajewski, T. F. (2010). Clinical development of mAbs to block the PD1 pathway as an immunotherapy for cancer. Curr. Opin. Investig. Drugs 11, 1354-1359.

LaRochelle, W. J., Jeffers, M., Corvalan, J. R. F., Jia, X.-C., Feng, X., Vanegas, S., Vickroy, J. D., Yang, X.-D., Chen, F., Gazit, G., et al. (2002). Platelet-derived growth factor D: tumorigenicity in mice and dysregulated expression in human cancer. Cancer Res. 62, 2468-2473.

Lefrançois, L., and Lycke, N. (2001). Isolation of mouse small intestinal intraepithelial lymphocytes, Peyer's patch, and lamina propria cells. Curr. Protoc. Immunol. Chapter 3, Unit 3.19.

Li, H., and Durbin, R. (2009). Fast and accurate short read alignment with Burrows-Wheeler transform. Bioinformatics 25, 1754-1760.

Li, X., and Eriksson, U. (2003). Novel PDGF family members: PDGF-C and PDGF-D. Cytokine Growth Factor Rev. 14, 91-98.

Li, H., Handsaker, B., Wysoker, A., Fennell, T., Ruan, J., Homer, N., Marth, G., Abecasis, G., and Durbin, R.; 1000 Genome Project Data Processing Subgroup (2009). The Sequence Alignment/Map format and SAMtools. Bioinformatics 25, 2078-2079.

Li, S. S., Kyei, S. K., Timm-McCann, M., Ogbomo, H., Jones, G. J., Shi, M., Xiang, R. F., Oykhman, P., Huston, S. M., Islam, A., et al. (2013). The NK receptor NKp30 mediates direct fungal recognition and killing and is diminished in NK cells from HIV-infected patients. Cell Host Microbe 14, 387-397.

Lin, Y.-C., Boone, M., Meuris, L., Lemmens, I., Van Roy, N., Soete, A., Reumers, J., Moisse, M., Plaisance, S., Drmanac, R., et al. (2014). Genome dynamics of the human embryonic kidney 293 lineage in response to cell biology manipulations. Nat. Commun. 5, 4767.

Liu, C., Lou, Y., Lize'e, G., Qin, H., Liu, S., Rabinovich, B., Kim, G. J., Wang, Y.-H., Ye, Y., Sikora, A. G., et al. (2008). Plasmacytoid dendritic cells induce NK cell-dependent, tumor antigen-specific T cell cross-priming and tumor regression in mice. J. Clin. Invest. 118, 1165-1175.

Lokker, N. A., Sullivan, C. M., Hollenbach, S. J., Israel, M. A., and Giese, N. A. (2002). Platelet-derived growth factor (PDGF) autocrine signaling regulates survival and mitogenic pathways in glioblastoma cells: evidence that the novel PDGF-C and PDGF-D ligands may play a role in the development of brain tumors. Cancer Res. 62, 3729-3735.

Nakamura, K., Yoshikawa, N., Yamaguchi, Y., Kagota, S., Shinozuka, K., and Kunitomo, M. (2002). Characterization of mouse melanoma cell lines by their mortal malignancy using an experimental metastatic model. Life Sci. 70, 791-798.

Nazarenko, I., Hede, S.-M., He, X., Hedre'n, A., Thompson, J., Lindstro¨m, M. S., and Niste'r, M. (2012). PDGF and PDGF receptors in glioma. Ups. J. Med. Sci. 117, 99-112.

Nikpay, M., Goel, A., Won, H.-H., Hall, L. M., Willenborg, C., Kanoni, S., Saleheen, D., Kyriakou, T., Nelson, C. P., Hopewell, J. C., et al. (2015). A comprehensive 1,000 Genomes-based genome-wide association meta-analysis of coronary artery disease. Nat. Genet. 47, 1121-1130.

Nirschl, C. J., Sua'rez-Farin˜as, M., Izar, B., Prakadan, S., Dannenfelser, R., Tirosh, I., Liu, Y., Zhu, Q., Devi, K. S. P., Carroll, S. L., et al. (2017). IFNg-dependent tissue-immune homeostasis is co-opted in the tumor microenvironment. Cell 170, 127-141.

Oi, V. T., Morrison, S. L., Herzenberg, L. A., and Berg, P. (1983). Immunoglobulin gene expression in transformed lymphoid cells. Proc. Natl. Acad. Sci. USA 80, 825-829.

Raulet, D. H., Gasser, S., Gowen, B. G., Deng, W., and Jung, H. (2013). Regulation of ligands for the NKG2D activating receptor. Annu. Rev. Immunol. 31, 413-441.

Reigstad, L. J., Varhaug, J. E., and Lillehaug, J. R. (2005). Structural and functional specificities of PDGF-C and PDGF-D, the novel members of the platelet-derived growth factors family. FEBS J. 272, 5723-5741.

Robinette, M. L., Fuchs, A., Cortez, V. S., Lee, J. S., Wang, Y., Durum, S. K., Gilfillan, S., and Colonna, M.; Immunological Genome Consortium (2015). Transcriptional programs define molecular characteristics of innate lymphoid cell classes and subsets. Nat. Immunol. 16, 306-317.

Rosental, B., Brusilovsky, M., Hadad, U., Oz, D., Appel, M. Y., Afergan, F., Yossef, R., Rosenberg, L. A., Aharoni, A., Cerwenka, A., et al. (2011). Proliferating cell nuclear antigen is a novel inhibitory ligand for the natural cytotoxicity receptor NKp44. J. Immunol. 187, 5693-5702.

Schneider, U., Schwenk, H. U., and Bornkamm, G. (1977). Characterization of EBV-genome negative "null" and "T" cell lines derived from children with acute lymphoblastic leukemia and leukemic transformed non-Hodgkin lymphoma. Int. J. Cancer 19, 621-626.

Shim, A. H.-R., Liu, H., Focia, P. J., Chen, X., Lin, P. C., and He, X. (2010). Structures of a platelet-derived growth factor/propeptide complex and a plateletderived growth factor/receptor complex. Proc. Natl. Acad. Sci. USA 107, 11307-11312.

Sivori, S., Parolini, S., Marcenaro, E., Castriconi, R., Pende, D., Millo, R., and Moretta, A. (2000). Involvement of natural cytotoxicity receptors in human natural killer cell-mediated lysis of neuroblastoma and glioblastoma cell lines. J. Neuroimmunol. 107, 220-225.

Soule, H. D., Vazguez, J., Long, A., Albert, S., and Brennan, M. (1973). A human cell line from a pleural effusion derived from a breast carcinoma. J. Natl. Cancer Inst. 51, 1409-1416.

Studier, F. W. (2005). Protein production by auto-induction in high density shaking cultures. Protein Expr. Purif. 41, 207-234.

Takeda, K., Nakayama, M., Sakaki, M., Hayakawa, Y., Imawari, M., Ogasawara, K., Okumura, K., and Smyth, M. J. (2011). IFN-γ production by lung NK cells is critical for the natural resistance to pulmonary metastasis of B16 melanoma in mice. J. Leukoc. Biol. 90, 777-785.

Ustach, C. V., and Kim, H.-R. C. (2005). Platelet-derived growth factor D is activated by urokinase plasminogen activator in prostate carcinoma cells. Mol. Cell. Biol. 25, 6279-6288.

Ustach, C. V., Huang, W., Conley-LaComb, M. K., Lin, C.-Y., Che, M., Abrams, J., and Kim, H.-R. C. (2010). A novel signaling axis of matriptase/PDGF-D/β-PDGFR in human prostate cancer. Cancer Res. 70, 9631-9640.

Vieillard, V., Strominger, J. L., and Debre', P. (2005). NK cytotoxicity against CD4+ T cells during HIV-1 infection: a gp41 peptide induces the expression of an NKp44 ligand. Proc. Natl. Acad. Sci. USA 102, 10981-10986.

Vitale, M., Bottino, C., Sivori, S., Sanseverino, L., Castriconi, R., Marcenaro, E., Augugliaro, R., Moretta, L., and Moretta, A. (1998). NKp44, a novel triggering surface molecule specifically expressed by activated natural killer cells, is involved in non-major histocompatibility complex-restricted tumor cell lysis. J. Exp. Med. 187, 2065-2072.

Wu, Q., Hou, X., Xia, J., Qian, X., Miele, L., Sarkar, F. H., and Wang, Z. (2013). Emerging roles of PDGF-D in EMT progression during tumorigenesis. Cancer Treat. Rev. 39, 640-646.

Xu, L., Tong, R., Cochran, D. M., and Jain, R. K. (2005). Blocking plateletderived growth factor-D/platelet-derived growth factor receptor beta signaling inhibits human renal cell carcinoma progression in an orthotopic mouse model. Cancer Res. 65, 5711-5719.

Example 9: NKp44-CD3ζ CAR-T Cells

Figure 16:
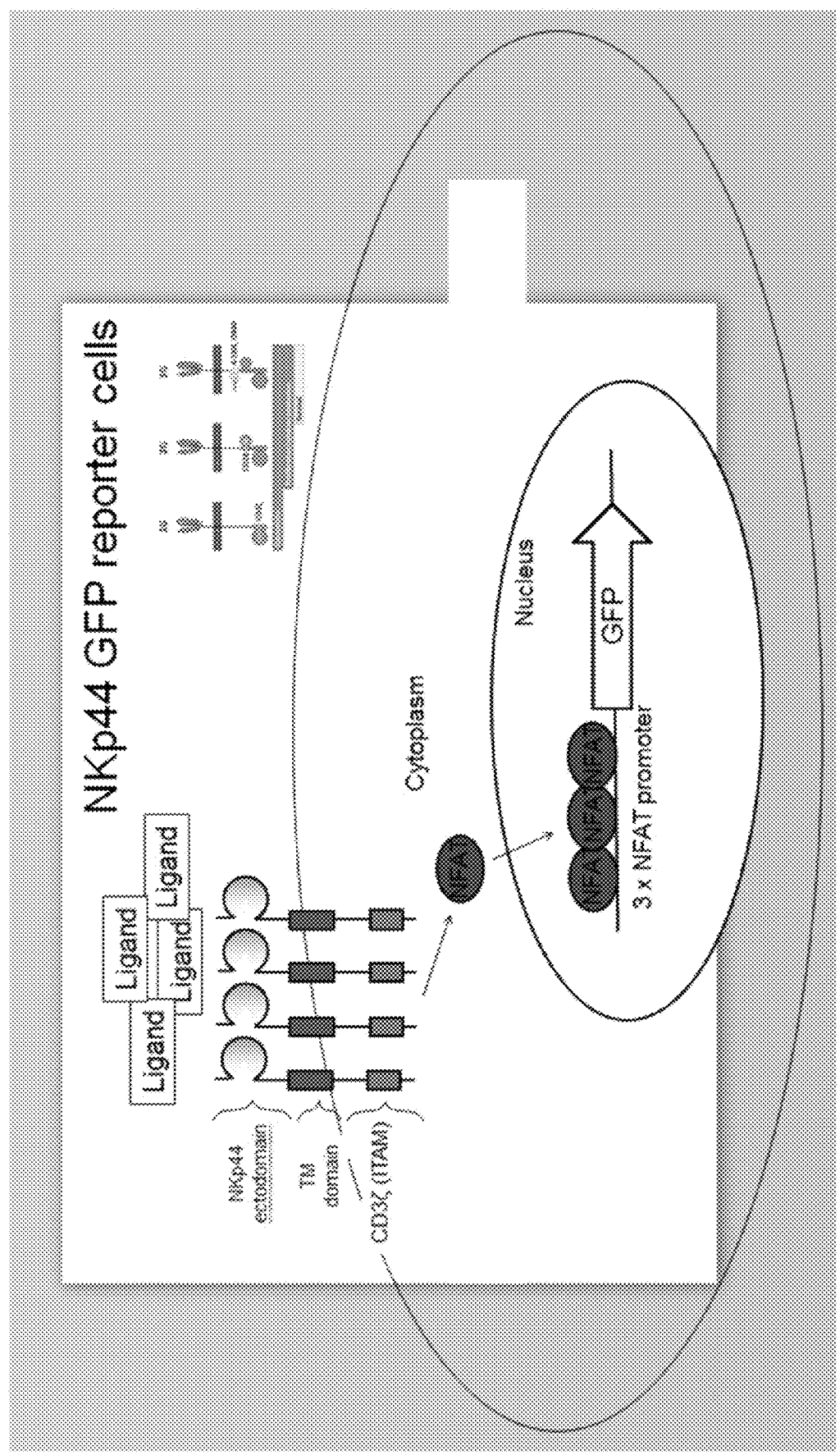
FIG. 16 shows an illustration of first generation NKp44 CAR cells
Figure 17:
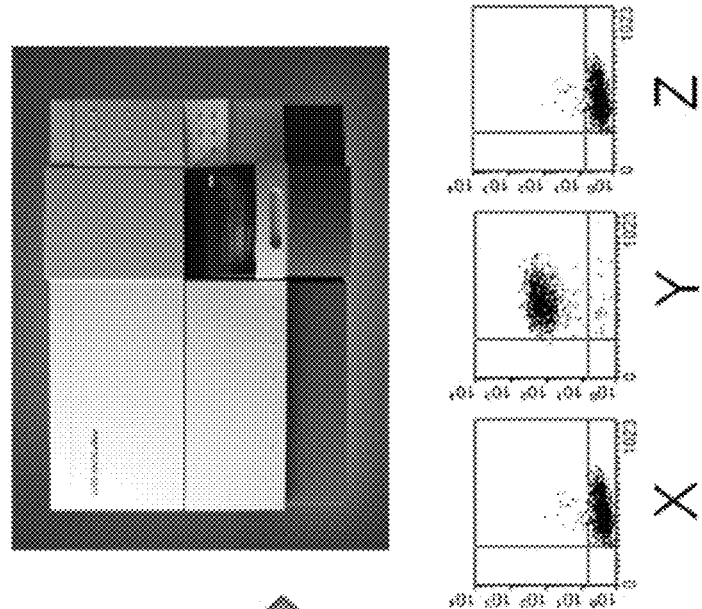
FIG. 17 shows a schematic for using NKp44 CAR cells in the secretome library screen.
Figure 17:
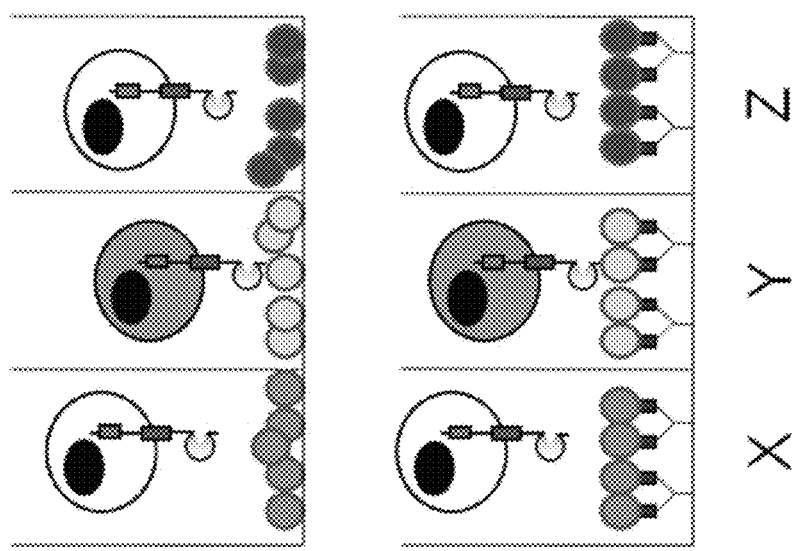
Figure 18:
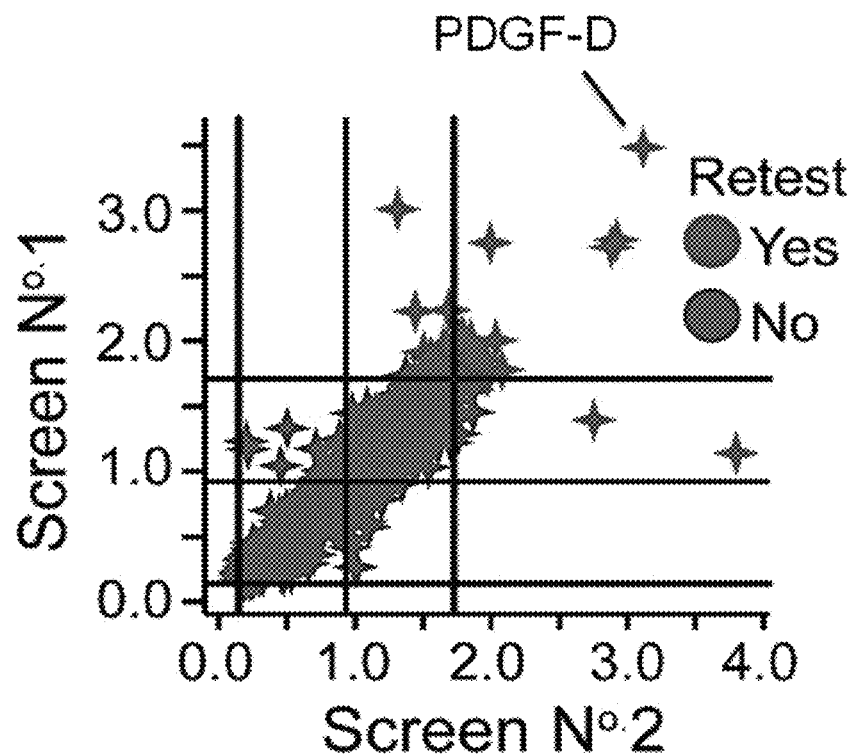
FIG. 18 depicts a graphical representation of identifying PDGF-D as a putative NKp44 ligand.
Figure 18:
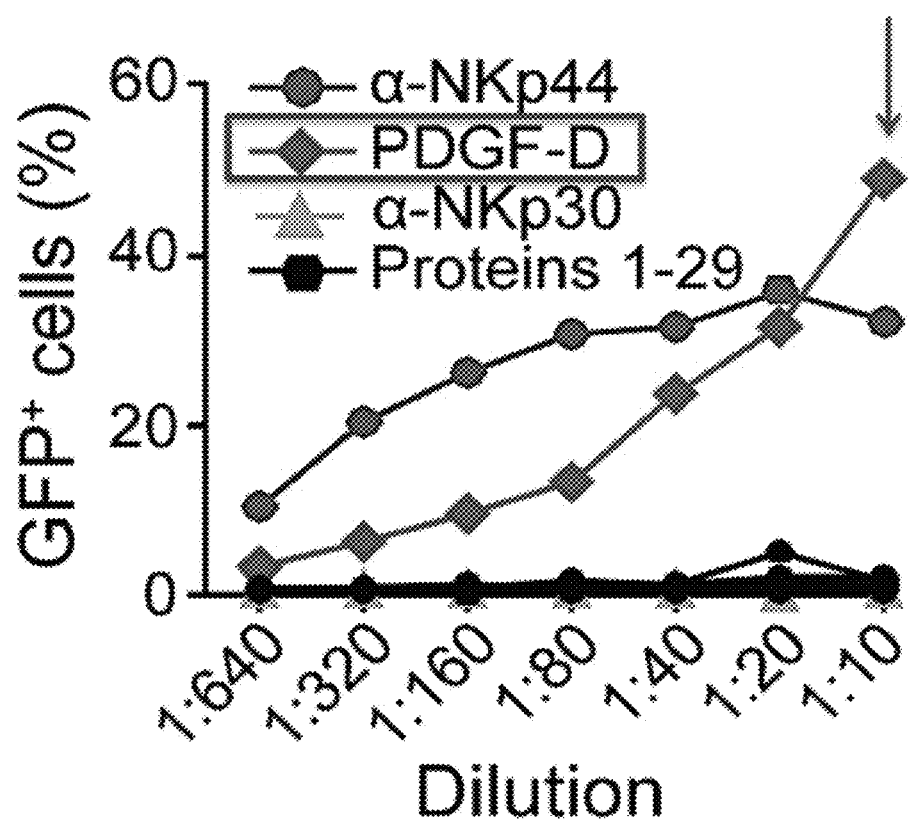

A screen was performed using the secretome protein library containing ~4,000 purified human secreted and single-pass transmembrane proteins. To perform the screen, we transfected a chimeric receptor consisting of the human NKp44 extracellular and transmembrane domains fused to the CDK intracellular signaling domain (first generation CAR; (FIG. 16)) into a reporter cell line that expresses GFP under the control of NFAT-responsive elements (FIG. 17). A schematic of the sectrome library screen is shown in FIG. 18. A functional first generation NKp44-CD3ζ CAR was used to identify PDGF-DD immobilized to tissue culture plates as the NKp44 ligand using GFP reporter 2B4 T cells.

Figure 19:
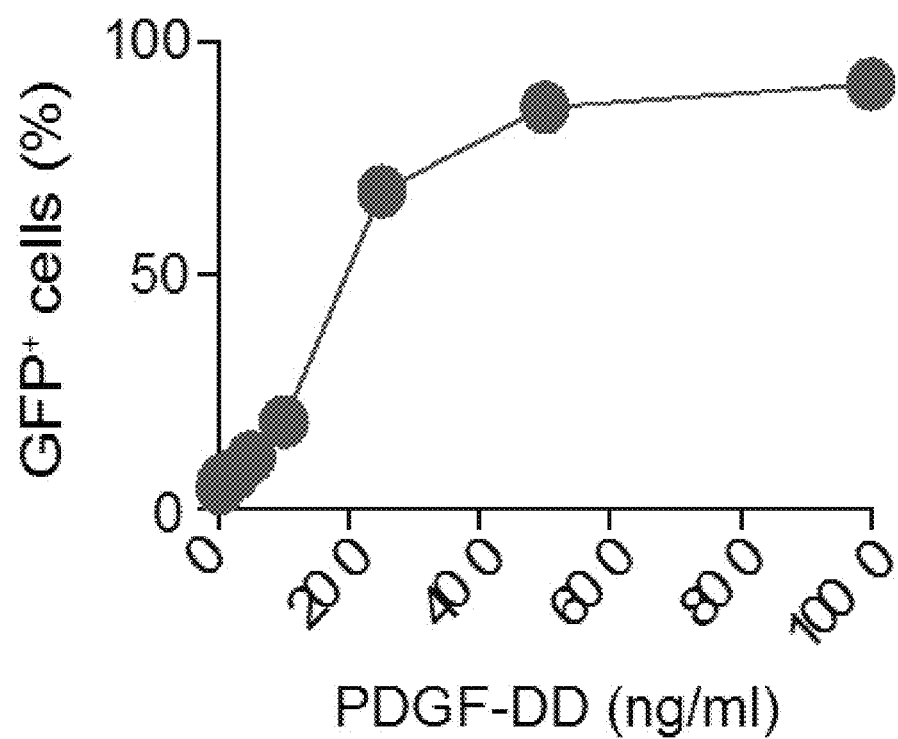
FIG. 19 shows soluble PDGF-DD activates the NKp44-CD3ζ GFP-reporter cells.
Figure 20:
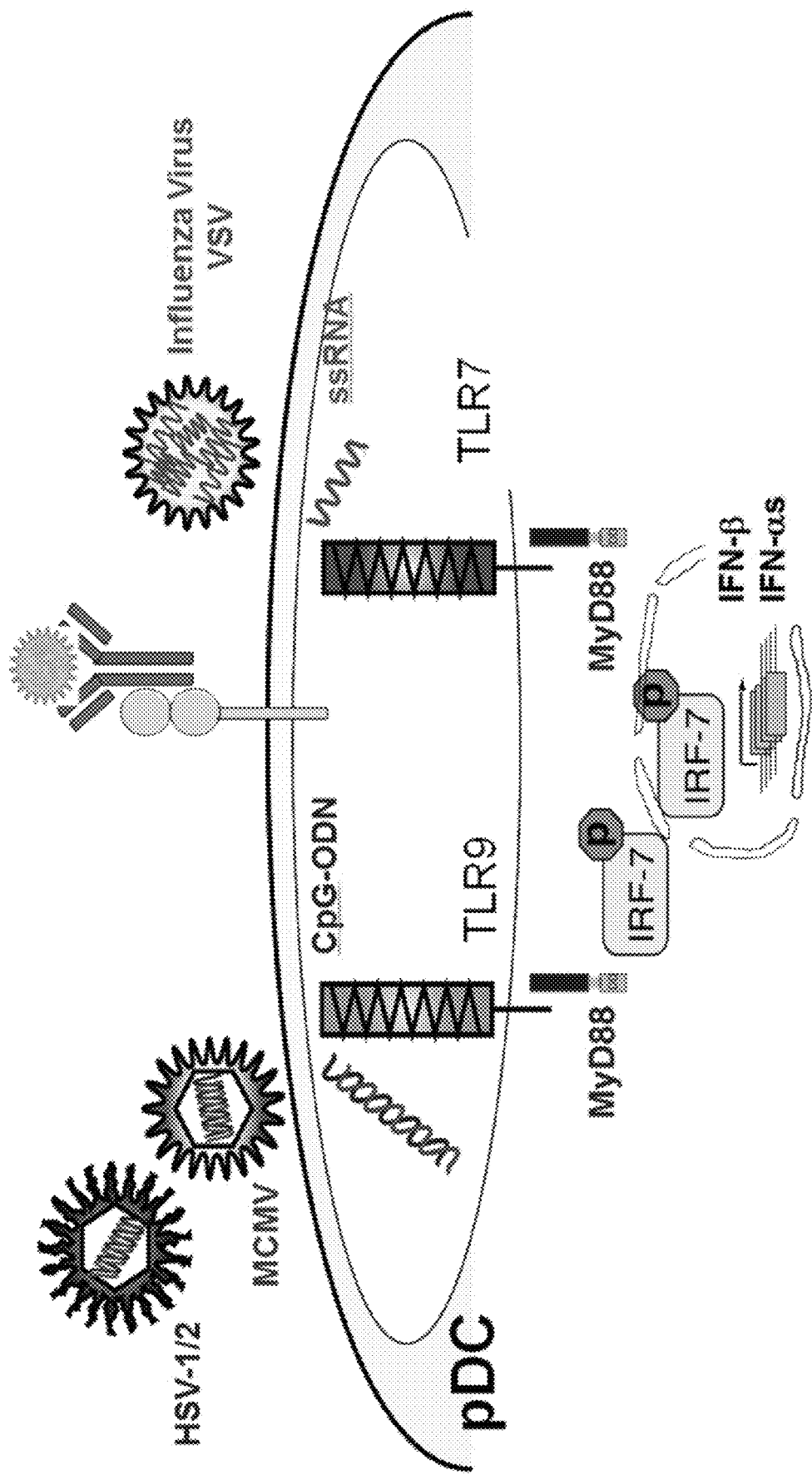
FIG. 20 shows plasmacytoid DCs (pDCs) sense viruses through TLR7 and TLR9.
Figure 21:
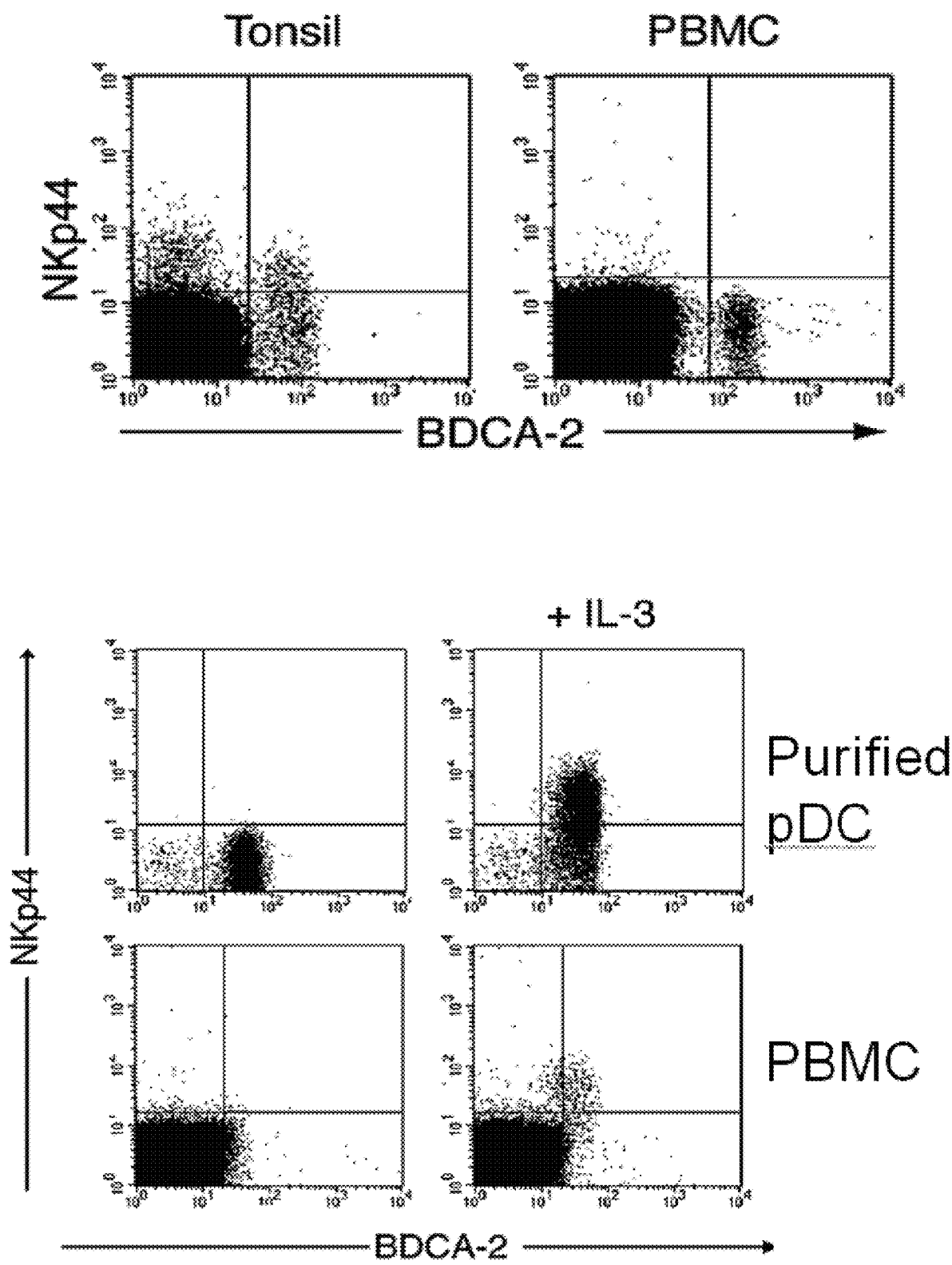
FIG. 21 shows NKp44 is expressed on pDCs in tonsils and is up-regulated by IL-3 treatment of blood pDCs.

As can be seen in FIG. 19 and FIG. 20, Platelet-derived growth factor (PDGF)-D is a putative NKp44 ligand soluble PDGF-DD also activates the NKp44-CD3ζ GFP-reporter cells. To our knowledge this is the first example of using CAR cells to detect soluble ligands. Thus the use of of this strategy to target tumor secreted ligands represents a novel strategy to cancer therapy Example 10: Plasmacytoid DCs (pDCs) Sense Viruses Through TLR7 and TLR9

Figure 22:
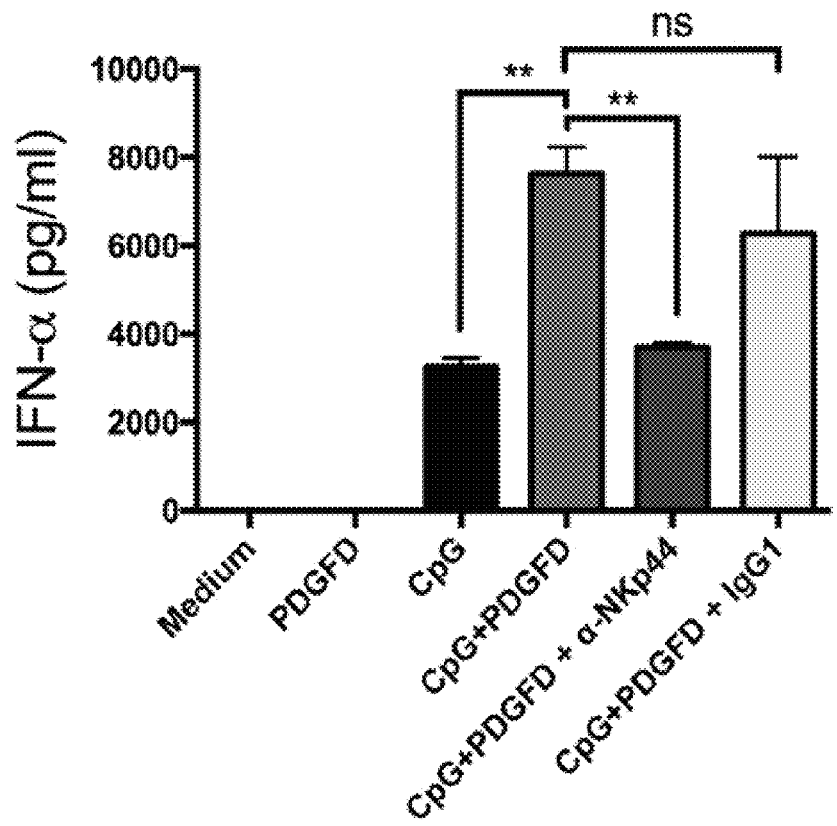
FIG. 22 shows PDGF-DD binding to NKp44 enhances IFN-α secretion in pDCs stimulated with CpG-DNA
Figure 23A:
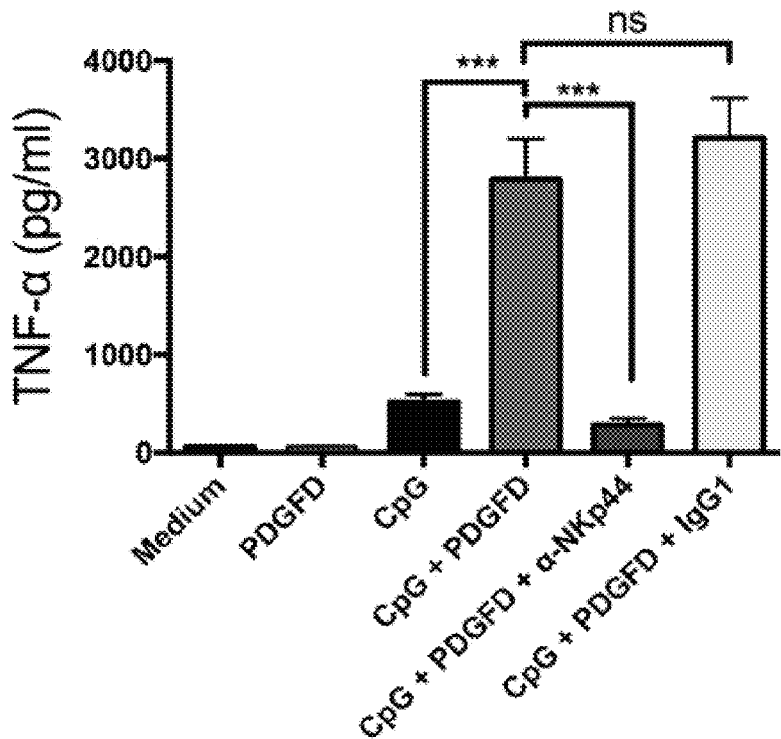
FIG. 23A, FIG. 23B, FIG. 23C and FIG. 23D show PDGF-DD binding to NKp44 induces inflammatory cytokine secretion in pDCs stimulated with CpG-DNA.
Figure 23B:
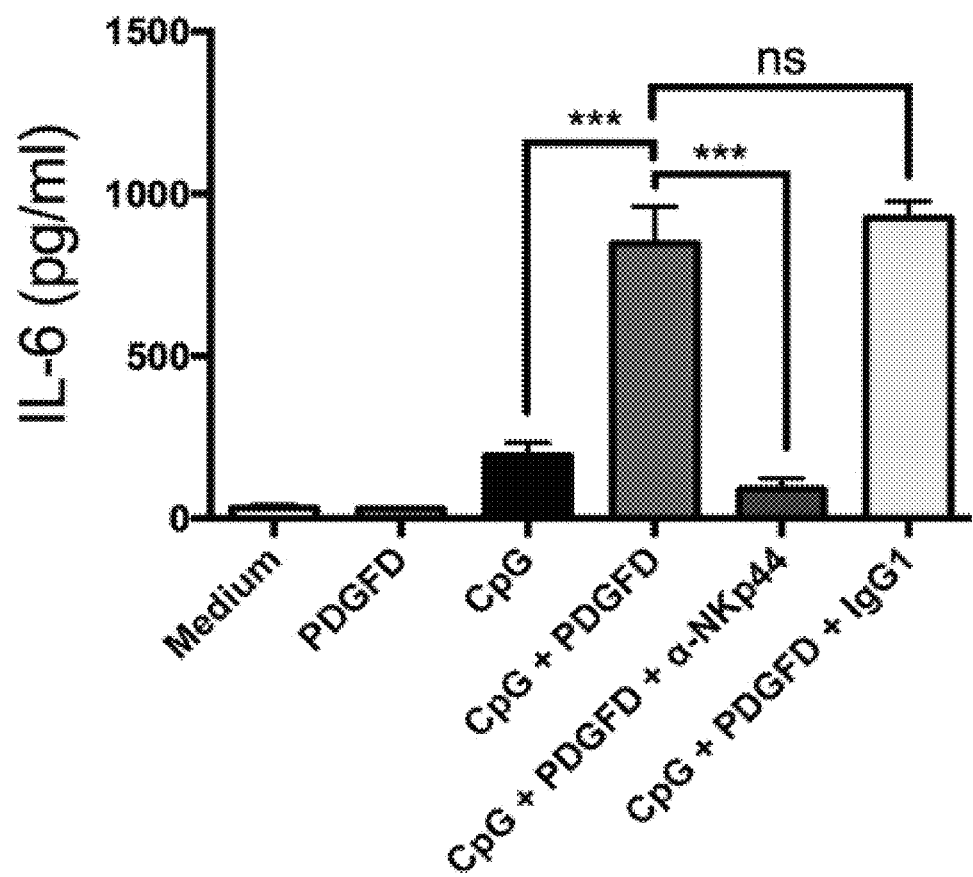
Figure 23C:
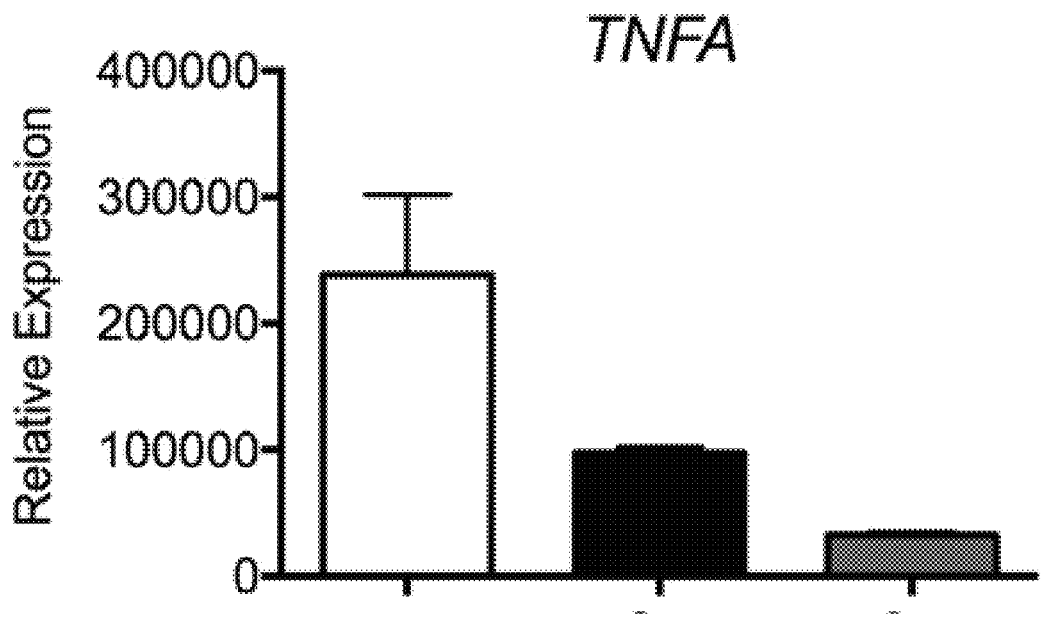
Figure 23D:
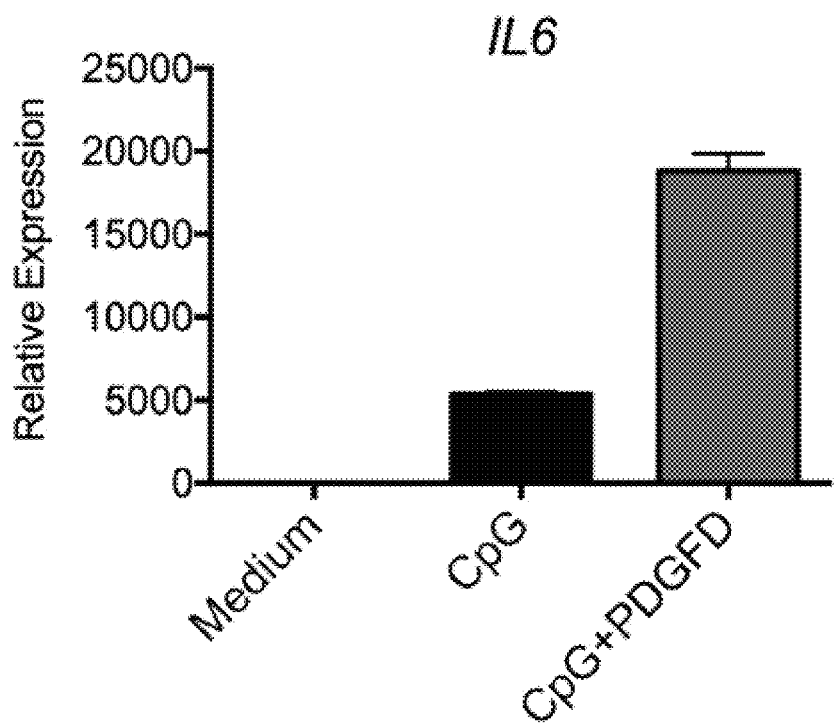

NKp44+ pDCs are found in tonsils situated adjacent to a population of IL-3 secreting T cells. As can be seen in FIG. 22, NKp44 is expressed on pDCs in tonsils and is up-regulated by IL-3 treatment of blood pDCs. CpG DNA is a ligand for Toll-like receptor 9 (TLR9) and a promising adjuvant for cancer immunotherapy. FIG. 23 shows PDGF-DD binding to NKp44 enhances IFN-α secretion in pDCs stimulated with CpG-DNA and FIG. 24 shows PDGF-DD binding to NKp44 induces inflammatory cytokine secretion in pDCs stimulated with CpG-DNA. Thus, NKp44 is expressed on tonsil pDC, PDGF-DD enhances IFN-α production (TLR9/CpG-ODN) and induces TNF-α and IL-6 secretion (TLR9/CpG-ODN)

What is claimed is:

1. A method of killing a soluble PDGF-DD ligand secreting cancer cell, the method comprising contacting the cancer cell with a chimeric antigen receptor T (CAR-T) cell, wherein the chimeric antigen receptor comprises a surface exposed soluble ligand binding moiety comprising the extracellular domain of NKp44 that specifically binds to soluble PDGF-DD ligand.

2. The method of claim 1, wherein the cancer cell is a breast cancer cell, lung cancer cell, head and neck cancer cell, prostate cancer cell, esophageal cancer cell, tracheal cancer cell, brain cancer cell, liver cancer cell, bladder cancer cell, stomach cancer cell, pancreatic cancer cell, ovarian cancer cell, uterine cancer cell, cervical cancer cell, testicular cancer cell, colon cancer cell, rectal cancer cell, leukemia cell or skin cancer cell.

3. A method of treating a mammal having a soluble PDGF-DD ligand secreting cancer cell, the method comprising administering to the mammal a composition comprising a plurality of chimeric antigen receptor T (CAR-T) cells, wherein the chimeric antigen receptor comprises a surface exposed soluble ligand binding moiety comprising the extracellular domain of NKp44 that specifically binds to soluble PDGF-DD ligand.

4. The method of claim 3, wherein the cancer cell is a breast cancer cell, lung cancer cell, head and neck cancer cell, prostate cancer cell, esophageal cancer cell, tracheal cancer cell, brain cancer cell, liver cancer cell, bladder cancer cell, stomach cancer cell, pancreatic cancer cell, ovarian cancer cell, uterine cancer cell, cervical cancer cell, testicular cancer cell, colon cancer cell, rectal cancer cell, leukemia cell or skin cancer cell.

5. A method of treating a mammal having an autoimmune disorder associated with a soluble PDGF-DD ligand, the method comprising administering to the mammal a composition comprising a plurality of chimeric antigen receptor T (CAR-T) cells, wherein the chimeric antigen receptor comprises a surface exposed soluble ligand binding moiety comprising the extracellular domain of NKp44 that specifically binds to soluble PDGF-DD ligand.

6. The method of claim 5, where in the autoimmune disease is lupus, multiple sclerosis, inflammatory bowel disease, psoriasis, celiac disease, Graves' disease, myasthenia gravis, Guillain-Barr like syndrome, Behcet's disease, Thyroiditis, cerebral vaculitis, post-infusion purpura, chronic inflammatory demyelinating polyneuropathy, Sjogren's syndrome, ticks and obsessive-compulsive disorder triggered by infection, stiff-man syndrome, Eaton-Lambert syndrome, Goodpasture syndrome, dermatomyositis, polymyositis, thrombocytopenia, warm type autoimmune hemolytic anemia, systemic vasculitic syndromes, West syndrome, Lennox-Gastaut syndrome, acute renal failure, asthma, chronic fatigue syndrome, diabetes mellitus, inclusion body myositis, rheumatoid arthritis, recurrent spontaneous abortion, euthyroid ophthalmopathy, or immune mediated neutropenia.

* * * * *